US012662478B2

(12) United States Patent
Pujala et al.

(10) Patent No.: US 12,662,478 B2
(45) Date of Patent: Jun. 23, 2026

(54) ATF6 MODULATORS AND USES THEREOF

(71) Applicant: Altos Labs, Inc., Redwood City, CA (US)

(72) Inventors: Brahmam Pujala, Greater Noida (IN); Balaji Dashrath Sathe, Greater Noida (IN); Sebastian Bernales, San Francisco, CA (US); Gonzalo Andrés Ureta Díaz, Santiago (CL); Sebastian Belmar, Santiago (CL)

(73) Assignee: Altos Labs, Inc., Redwood City, CA (US)

( * ) Notice: Subject to any disclaimer, the term of this patent is extended or adjusted under 35 U.S.C. 154(b) by 1048 days.

(21) Appl. No.: 17/767,028

(22) PCT Filed: Oct. 9, 2020

(86) PCT No.: PCT/EP2020/078507
§ 371 (c)(1),
(2) Date: Apr. 6, 2022

(87) PCT Pub. No.: WO2021/069721
PCT Pub. Date: Apr. 15, 2021

(65) Prior Publication Data

US 2023/0028584 A1 Jan. 26, 2023

Related U.S. Application Data

(60) Provisional application No. 62/913,125, filed on Oct. 9, 2019, provisional application No. 62/913,122, filed on Oct. 9, 2019.

(51) Int. Cl.
*C07D 417/14* (2006.01)
*C07D 413/14* (2006.01)

(52) U.S. Cl.
CPC ......... *C07D 417/14* (2013.01); *C07D 413/14* (2013.01)

(58) Field of Classification Search
CPC ............................ C07D 417/14; C07D 413/14
See application file for complete search history.

(56) References Cited

U.S. PATENT DOCUMENTS

| | | | |
|---|---|---|---|
| 6,458,951 | B2 | 10/2002 | Bunnage et al. |
| 7,091,215 | B2 | 8/2006 | Hibi et al. |
| 7,151,113 | B2 | 12/2006 | Dyckman et al. |
| 7,285,666 | B2 | 10/2007 | Hibi et al. |
| 8,288,419 | B2 | 10/2012 | Bur et al. |
| 8,642,660 | B2 | 2/2014 | Goldfarb |
| 8,907,306 | B2 | 12/2014 | Yoshikawa et al. |
| 10,829,485 | B2 | 11/2020 | Alfaro et al. |
| 2015/0272959 | A1 | 10/2015 | Smith et al. |
| 2017/0166552 | A1 | 6/2017 | Ban et al. |
| 2019/0241573 | A1 | 8/2019 | Axten et al. |
| 2019/0367497 | A1 | 12/2019 | Alfaro et al. |
| 2021/0221803 | A1 | 7/2021 | Alfaro et al. |
| 2022/0389001 | A1 | 12/2022 | Pujala et al. |

FOREIGN PATENT DOCUMENTS

| | | | |
|---|---|---|---|
| CN | 101384558 | A | 3/2009 |
| CN | 109789135 | A | 5/2019 |
| RU | 2308457 | C2 | 10/2007 |
| WO | 2007073300 | A1 | 6/2007 |
| WO | 2016172560 | A1 | 10/2016 |
| WO | 2017046738 | A1 | 3/2017 |
| WO | 2019195810 | A2 | 10/2019 |
| WO | 2019209962 | A1 | 10/2019 |
| WO | 2021069701 | A1 | 4/2021 |
| WO | 2021069721 | A1 | 4/2021 |

OTHER PUBLICATIONS https://aurorafinechemicals.com/ (printed Apr. 17, 2025) (Year: 2025).*
CAS Registry No. 1706080-90-1, Entered to STN May 17, 2015, Aurora Fine Chemicals (Year: 2015).*
Gallagher et. al., Elife. Jul. 20, 2016;5:e11878. (Year: 2016).*
English translation of Chinese Office Action and Search Report issued in CN Application No. 202080083441.6, mailed Nov. 6, 2023.
Adachi, Y. et al. (2008). "ATF6 Is a Transcription Factor Specializing in the Regulation of Quality Control Proteins in the Endoplasmic Reticulum," Cell Structure and Function 33(1):75-89.
Ambrose, R. et al. (Feb. 2013, e-pub. Dec. 2012). "ATF6 Signaling Is Required for Efficient West Nile Virus Replication by Promoting Cell Survival and Inhibition of Innate Immune Responses," J. Virol. 87(4):2206-2214.
Belikov, V.G. (2007). "Farmatsevticheskaya Khimiya," Pharmaceutical Chemistry: A Scholarly Manual, Moscow, MEDpress-Inform, pp. 27-29, 9 pages (English Machine Translation).
(Continued)

*Primary Examiner* — Clinton A Brooks
*Assistant Examiner* — Izabela Schmidt
(74) *Attorney, Agent, or Firm* — Meunier Carlin & Curfman LLC

(57) ABSTRACT

Compounds (1-2) as modulators of Activating Transcription Factor 6 (ATF6) are provided. The compounds may find use as therapeutic agents for the treatment of diseases or disorders mediated by ATF6 and may find particular use in the treatment of viral infections, neurodegenerative diseases, vascular diseases, or cancer. (Formula (1-2))

(I-2)

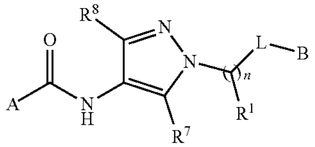

6 Claims, No Drawings

Specification includes a Sequence Listing.

(56) References Cited

OTHER PUBLICATIONS

Birdsey, G.M. et al. (Apr. 2008, e-pub. Jan. 14, 2008). "Transpcription Factor Erg Regulates Angiogenesis and Endothelial Apoptosis Though VE-cadherin," Blood, 2008, 111:3498-3506.
Cai, J.W. et al. (1993). "Induction of Glucose Regulated Proteins During Growth of a Murine Tumor," J Cell Physiol. 154(2):229-237.
Chu, W.S., et al. (Mar. 2007). "Activating Transcription Factor 6 (ATF6) Sequence Polymorphisms in Type 2 Diabetes and Pre-Diabetic Traits," Diabetes 56(3):856-862.
Dadey, D.Y. et al. (Dec. 21, 2015). "The ATF6 Pathway of the ER Stress Response Contributes to Enhanced Viability in Glioblastoma," Oncotarget 7(2):2080-2092.
Durnov, L.A. et al. (2002). "Detskaya Onkologiya," Pediatric Cancer, Moscow: Meditsina Publishing House, p. 139, 5 pages (English Machine Translation).
Fitzpatrick, J.M. et al. (Aug. 29, 2014). "Small Molecule Inhibition of the Na+/H+ Exchange Regulatory Factor 1 and Parathyroid Hormone 1 Receptor Interaction," Biochemistry 53(37):5916-5922.
Galindo I. et al. (Jul. 2012). "The ATF6 Branch of Unfolded Protein Response and Apoptosis Are Activated to Promote African Swine Fever Virus Infection," Cell Death Dis 5:3:e341, 10 pages.
Gallagher, C.M. et al. (Jul. 20, 2016). "Ceapins are a New Class of Unfolded Protein Response Inhibitors, Selectively Targeting the ATF6 [alpha] branch," eLife 5:e11878, 33 pages.
Hardy, J. et al. (Nov. 2, 1998, e-pub. Apr. 7, 2009). "Genetic Classification of Primary Neurodegenerative Disease," Science 282(5391):1075-1079.
Hensel, J.A. et al. (Jan. 2013, e-pub. Nov. 27, 2012). "Clinical opportunities and challenges in targeting tumour dormancy," Nat Rev Clin Oncol. 10(1):41-51.
International Preliminary Report on Patentability issue date of Apr. 12, 2022, mailed Jan. 25, 2021, for International Patent Application No. PCT/EP2020/078507, filed Oct. 9, 2020, 9 pages.
International Preliminary Report on Patentability issued on Apr. 12, 2022, mailed Jan. 29, 2021, for International Patent Application No. PCT/EP2020/078478, filed Oct. 9, 2020, 9 pages.
International Preliminary Report on Patentability mailed Oct. 15, 2020, for Patent Application No. PCT/US2019/026198, filed Apr. 6, 2019, 7 pages.
International Search Report and Written Opinion mailed on Jan. 25, 2021, for PCT Application No. PCT/EP2020/078507, filed on Oct. 9, 2020, 17 pages.
International Search Report mailed on Jan. 29, 2021, for PCT Application No. PCT/EP2020/078478, filed on Oct. 9, 2020, 18 pages.
Jamora, C. et al. (Jul. 1996). "Inhibition of Tumor Progression by Suppression of Stress Protein GRP78/BiP Induction in Fibrosarcoma B/C10ME," PNAS USA 93(15): 7690-7694.
Johnson, W.G. (2000). "Late-Onset Neurodegenerative Diseases the Role Of Protein Insolubility," J. Anat. 196 (part4):609-616.
Karali, E. et al. (May 22, 2014). "VEGF Signals through ATF6 and PERK to Promote Endothelial Cell Survival and Angiogenesis in the Absence of ER Stress," Molecular Cell 54:559-572.
Kümmerer, K. (2010). "Pharmaceuticals in the Environment," Annual Review of Environment and Resources 35:57-75.
Liu, C.L. et al. (2016). "High-content screening identifies inhibitors of the nuclear translocation of ATF6," Int J Mol Med 37(2):407-414.
Mashkovsky, M.D. et al. (2005). "Lekarstvennye Sredstva (Medicaments: A Guide for Doctors," p. 10-11, 6 pages (English Machine Translation).
McKimpson, W.M. et al. (Mar. 3, 2017). A New Role for the ER Unfold Protein Response Mediator ATF6: Induction of a Generalized Antioxidant Program, Circ Res. 120(5):759-761, 6 pages.
Meng, S. et al. (Dec. 15, 2004). "Circulating Tumor Cells in Patients with Breast Cancer Dormancy," Clin Cancer Res 10(24):8152-8162.
Niu, T. et al. (Dec. 2012). "Chemoselective Preparation of Unsymmetrical Bis(1,2,3-triazole) Derivatives and Application in Bis(1,2,3-trazole)-Modified Peptidomimetic Synthesis," European Journal of Organic Chemistry (34):6767-6776.
Ott, P.A. et al. (Sep. 22, 2015). "Inhibition of Immune Checkpoints and Vascular Endothelial Growth Factor as Combination Therapy for Metastatic Melanoma: An Overview of Rationale, Preclinical Evidence, and Initial Clinical Data," Front Oncol 5:202, 7 pages.
Ramaswamy, S. et al. (Dec. 18, 2001). "Multiclass Cancer Diagnosis Using Tumor Gene Expression Signatures," PNAS USA 98(26):15149-15154.
Schewe, D.M. et al. (Jul. 29, 2008). "ATF6α-Rheb-mTOR Signaling Promotes Survival of Dormant Tumor Cells In Vivo," PNAS USA 105(30):10519-10524.
Sugawara, S. et al. (Dec. 15, 1993). "Suppression of Stress Protein GRP78 Induction in Timor B/C10ME Eliminates Resistance to Cell Mediated Cytotoxicity1," Cancer Res 53(24):6001-6005.
Tay, K.H. et al. (Feb. 2014, e-pub. Nov. 12, 2013). "Sustained IRE1 and ATF6 signaling is important for survival of melanoma cells undergoing ER stress," Cell Signal 26(2):287-294.
Vekich, J. A. et al. (Aug. 2012, e-pub. May 8, 2012). "Protein Disulfide Isomerase-Associated 6 Is an ATF6-Inducible ER Stress Response Protein That Protects Cardiac Myocytes From Ischemia/Reperfusion-Mediated Cell Death," J. Mol. Cell. Cardiol. 53(2):259-267, 23 pages.
Written Opinion of the International Searching Authority mailed Sep. 30, 2019, for Patent Application No. PCT/US2019/026198, filed Apr. 6, 2019, 5 pages.
Wu, J. et al. (Sep. 2007). "ATF6a Optimizes Long-Term Endoplasmic Reticulum Function to Protect Cells from Chronic Stress," Dev Cell 13(3):351-364.
Wu, Y. et al. (Mar. 1, 2012). "Dynamic Modeling of Human 5-Llpoxygenase-Inhibitor Interactions Helps to Discovery Novel Inhibitors," Journal of Medicinal Chemistry 55(6):2597-2605.
Yang, W. et al. (2013, e-pub. Nov. 23, 2012). "Genomics of Drug Sensitivity in Cancer (GDSC): a resource for therapeutic biomarker discovery in cancer cells," Nucleic Acids Research 41(D1):D955-D961.
Ye, J. et al. (Dec. 2000). "ER Stress Induces Cleavage of Membrane-Bound ATF6 by the Same Proteases that Process SREBPs," Mol Cell 6(6):1355-1364.
Yoshida, H. et al. (Dec. 28, 2001). "XBP1 mRNA Is Induced by ATF6 and Spliced by IRE1 in Response to ER Stress to Produce a Highly Active Transcription Factor," Cell 107(7):881-891.
First Examination Report issued in AU2020365038, mailed Sep. 1, 2025.

* cited by examiner

ATF6 MODULATORS AND USES THEREOF

CROSS-REFERENCE TO RELATED APPLICATIONS

This application is a National Phase application under 35 U.S.C. § 371 of International Application No. PCT/EP2020/078507, filed Oct. 9, 2020, which claims prior benefit of U.S. Provisional Patent Application No. 62/913,125, filed Oct. 9, 2019, and U.S. Provisional Patent Application No. 62/913,122, filed Oct. 9, 2019, the disclosures of each of which are hereby incorporated herein by reference in their entirety.

FIELD OF THE INVENTION

This disclosure relates generally to therapeutic agents that may be useful as modulators of Activating Transcription Factor 6 (ATF6).

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 776352001500SEQLIST.TXT, date recorded: Apr. 6, 2022, size: 550 bytes).

BACKGROUND

The accumulation of misfolded proteins in the EP of mammalian cells causes the folding machinery to become overwhelmed and leads to a stress response. Cells attempt to decrease the ER protein load by sending signals from the ER to the nucleus, activating a vast gene expression program that increases the protein-folding capacity in the ER. However, if this system fails and homeostasis cannot be re-established, cells die by engaging apoptosis. The unfolded protein response (UPR) is an evolutionarily conserved signal transduction pathway that maintains protein homeostasis in response to ER stress.

Three intertwined signaling pathways comprise the UPR: (1) PERK (protein kinase RNA-like ER kinase); (2) IRE1 (inositol-requiring enzyme 1α); and (3) ATF6 (Activating transcription factor 6) (McKimpson, W. M. et al, Circ Res, 2017, 120(5): 759-761). Activation of the ATF6 pathway leads to the upregulation of genes, such as BIP (Grp78), CHOP or XBP-1, that enhance the capacity of the endoplasmic reticulum to fold proteins or mediate quality control. ATF6 works in partnership with IRE1, as one of the target genes of ATF6 is XBP1, the key substrate of IRE1 (Yoshida, H., et al., Cell, 2001, 107(7): 881-891). PERK performs several other roles including pausing the production of new proteins to temporarily lower the protein-folding burden.

ATF6 is a type-II transmembrane protein localized in the ER that functions as an ER stress sensor and transcription factor (Adachi, Y., et al., Cell Struct Funct, 2008, 33(1): 75-89; Wu, J., et al., Dev Cell, 2007, 13(3): 351-64). When demand exceeds the folding capacity of the ER, ATF6 is transported from the ER to the Golgi apparatus, where sequential cleavage by two Golgi-resident proteases, site-1 and site-2 proteases (SiP and S2P), releases its N-terminal domain (ATF6N) from the Golgi membrane to be imported into the nucleus where it activates transcription of its target genes (Ye, J., et al., Mol Cell, 2000, 6(6): 1355-64). This activation involves binding of ATF6 to a consensus sequence called the ER-stress responsive element (ERSE). The consensus sequence of ERSE is

```
                                       (SEQ ID NO. 1)
CCAATCGGCGGCGGCCACG.
```

Unlike the other arms of the UPR regulated by PERK and IRE1, the ATF6 arm has not been substantially linked to proapoptotic signaling (Hetz, C. and Papa, F. R. 2018; Sano, R. and Reed, J. C. 2013). Instead, ATF6 primarily functions in the so called "adaptive UPR" designed to promote protective, adaptive remodeling of cellular physiology and recovery following acute physiological and pathological insults. As part of the adaptive UPR, ATF6 integrates with multiple other stress-responsive signaling pathways to sensitively adapt cellular physiology to diverse types of ER insult.

In the context of the UPR, this integration can be achieved through heterodimerization of ATF6 with other UPR-regulated bZIP transcription factors, such as XBP1s (Yamamoto, K. et al. 2007; Shoulders, M. D. et al. 2013) or ATF6b (Thuerauf, D. J. et al. 2007; Thuerauf, D. J. et al. 2004; Forouhan, M. et al. 2018; Pieper, L. A. et al. 2017). ATF6 also has the potential to heterodimerize with other bZIP transcription factors similarly regulated through a mechanism involving S1P/S2P-dependent proteolysis, such as CREB-H (Asada, R. et al. 2011; Zhang, K. et al. 2006). Apart from heterodimerization, ATF6 signaling also integrates with other stress-responsive signaling pathways interacting with other transcription factors, such as NRF1, PGC1a, PPARa, and ERRg (Chen, X. et al. 2016; Wu, J. et al. 2011; Misra, J. et al. 2013; Baird, L. et al. 2017).

The capacity for ATF6 to integrate with other signaling pathways through multiple mechanisms reflects a unique potential for this UPR signaling arm to coordinate protective cellular responses, in addition to ER proteostasis remodeling, to a range of pathological insults that induce ER stress. The establishment of new pharmacological approaches to both inhibit and activate ATF6 signaling provides new opportunities to carefully dissect the timing and extent of ATF6 signaling involved in protecting different tissues against cancer, autoimmune diseases, neurodegeneration, metabolic diseases or I/R.

Several strategies to manipulate the UPR have been exploited to define possible links between ER stress and human disease, with great advances in cancer and neurodegeneration.

In cancer, tumor growth relies in the UPR as a selective force to drive malignant transformation (Cubillos-Ruiz, J. R. et al. 2016), in addition to remodeling the tumor microenvironment and anticancer immune responses (Song, M and Cubillos-Ruiz, J. R. 2019), as well as impacting on other central hallmarks of cancer (Urra, H. et al. 2016).

For example, multiple myeloma (MM) remains a predominantly incurable malignancy despite high-dose chemotherapy, autologous stem cell transplant and novel agents. Proteasome inhibitors (PI) such as Bortezomib have increased the response rate and survival of patients with MM. The overall patient response rate of newly diagnosed MM to Bortezomib and Dexamethasone is about 67%. In relapsed refractory MM, the response rate is reduced to about 40-60%. Therefore, there are a significant number of MM patients who are resistant to Bortezomib. MM cells are inherently sensitive to PIs because of their large volume of immunoglobulin production, which requires the constitutive expression of physiologic UPR genes. This appears to lower their threshold for the induction of a proapoptotic/terminal UPR in response to PI-induced endoplasmic reticulum (ER) stress. One of the hallmarks of UPR induction is the increased transcription and translation of ER molecular chaperones. These genes are induced by the UPR transcription factors XBP1 and ATF6. Although XBP1 splicing and its resulting activation have been shown to be inhibited in PI-treated MM cells, findings show that the high constitutive expression of 2 XBP1 target genes products, GRP78 and GRP94, is not reduced by PI treatment and the observation that the XBP1-dependent UPR target gene ERdj4 was normally induced by PIs suggest that the UPR remains functional in PI-treated MM cells. Because both XBP1 and ATF6 can bind to ER stress response elements in the promoters of UPR target genes, it has been suggested that ATF6 may compensate for decreased XBP1 activity in PI-treated MM cells. Consistent with this, it has been shown that the induction of GRP78 and GRP94 is only slightly impaired in $XBP1^{-/-}$ B cells and that the expression of GRP94 requires either, but not both, ATF6 or XBP1. Interestingly previous studies have shown that XBP1 predicts sensitivity to Bortezomib and its level correlates proportionally with sensitivity to Bortezomib. Recently Harnoss J M et al. demonstrated using genetic and pharmacologic disruption that in vitro and in vivo the IRE1a-XBP1s pathway plays a critical role in MM growth. Indeed, the inhibition of IRE1α kinase activity using a small molecule was demonstrated to be a potential effective and safe therapy for treating MM clinically.

In addition to the amount, PI sensitivity also appears to involve the efficiency of immunoglobulin folding within MM cells. The high constitutive expression of the ER resident chaperones GRP78 and GRP94 in MM cell lines is consistent with reports that physiologic UPR gene expression is required for professional secretory cell function. Elevated levels of ER chaperones are characteristic of plasma cells and their expression is essential for proper antibody assembly and secretion. GRP78 has been shown to stably bind to immunoglobulin heavy chains that have not yet associated with immunoglobulin light chains and to assist in immunoglobulin assembly. Furthermore, both GRP78 and GRP94 are important for immunoglobulin light chain folding and targeting unassembled subunits for degradation. The fact that the expression of GRP78 and GRP94 is only slightly increased in MM cells treated with PIs and classical ER stress agents suggests they already express near-maximal levels of cytoprotective UPR proteins to function as secretory cells. Thus, these cells may have a lower threshold (compared with non-secretory cells) for induction of the terminal UPR following any additional stress to the ER. Hence more resistant myeloma clones as well as other non-secretory malignancies may be sensitized to bortezomib by combining it with agents that interfere with the UPR, such as modulators of ATF6 signaling pathway.

On the other hand, the protein folding capacity of professional secretory cells is overwhelmed in several diseases, leading to cell degeneration and death through terminal UPR signaling. For example, dysregulated UPR signaling in insulin-secreting pancreatic R cells results in premature cell loss, insulin deficiency, and diabetes. Although neurons are not typically considered to be classical secretory cells, the accumulation of abnormal aggregates may nonetheless induce the terminal UPR in neurons and lead to neurodegeneration (Hetz, C. and Saxena, S. 2017). ER stress has been implicated in ocular diseases and in the death of neuronal photoreceptor cells (Kroeger, H. et al. 2019).

In addition, many diseases lead to impaired circulation, which can cause ischemic conditions in a variety of organs, including the brain, heart, and kidney (Benjamin, E. J. et al. 2018). In these settings, prolonged ischemia causes irreversible damage, which can be partially mitigated by clinical interventions that restore blood flow through reperfusion (Hausenloy, D. J. and Yellon, D. M. 2016). While reperfusion is necessary to mitigate the damage of continued ischemia, reperfusion itself is known to cause some additional damage, generally as a result of reactive oxygen species (ROS) (Murphy, E. and Steenbergen, C. 2008). The complex nature of cellular injury associated with ischemia or ischemia followed by reperfusion (I/R) has previously been shown to affect the levels and activities of numerous signaling pathways and transcription factors. One I/R-activated pathway that has been more recently studied involves the disruption of proteostasis. To protect against pathological ER stress induced by I/R, tissues activate endogenous adaptive stress-responsive signaling pathways, such as the unfolded protein response (UPR).

Recent evidence highlights a protective role for the ATF6 arm of the UPR in mitigating adverse outcomes associated with ischemia/reperfusion (I/R) injury in multiple disease models (Kudo, T. et al. 2008; Oida, Y. et al. 2008; Prachasilchai, W. et al. 2009; Oida, Y. et al. 2010; Blackwood, E. A. et al. 2019; Yu, Z. et al. 2017; Bi, X. et al. 2018), suggesting ATF6 as a potential therapeutic target for intervening pharmacologically with activator compounds in diverse ischemia-related disorders (Plate, L. et al. 2016; Glembotski, C. C. et al 2019).

ATF6-activated transcription targets play a role in the pathogenesis and development of various diseases, including viral infection, cancer, neurodegeneration, Alzheimer's disease, cerebral ischemia, hereditary cerebellar atrophy and ataxia, type 2 diabetes mellitus, and diabetic nephropathy, as well as cardiovascular diseases, such as myocardial atrophy, heart failure, ischemic heart disease and atherosclerosis (Chu, W. S., et al., Diabetes, 2007, 56(3): 856-62; Vekich, J. A., et al., J Mol Cell Cardiol, 2012, 53(2): 259-67, Liu, C. L., et al., Int J Mol Med, 2016, 37(2): 407-14). Therefore, the modulation of the ATF6-mediated transcription may provide a therapeutic strategy for these and other diseases in which ATF6 activity is implicated.

BRIEF SUMMARY

In one aspect, provided is a compound of the formula (I-1):

(I-2)

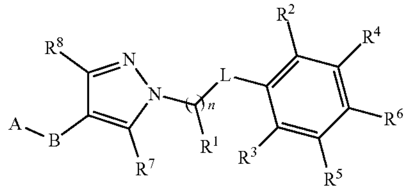

or a pharmaceutically acceptable salt thereof, wherein A, B, $R^1$, n, L, $R^2$, $R^3$, $R^4$, $R^5$, $R^6$, $R^7$, and $R^8$ are as detailed herein.

In one aspect, provided is a compound of the Formula (I-2):

(I-3)

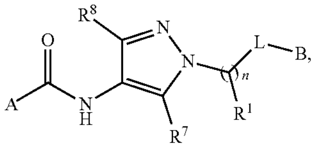

or a pharmaceutically acceptable salt thereof, wherein A, B, L, n, $R^1$, $R^7$, and $R^8$ are as defined herein.

In another aspect, provided is a method of treating a disease or disorder mediated by activating transcription factor 6 (ATF6) in an individual in need thereof, wherein the method comprises administering to the individual an effective amount of a compound of formula (I) or a pharmaceutically acceptable salt thereof or a pharmaceutical composition comprising the compound. In some embodiments, the disease or disorder mediated by activating transcription factor 6 (ATF6) is viral infection, cancer, a neurodegenerative disease, or a vascular disease. In certain embodiments, the disease or disorder is viral infection, hereditary cerebellar atrophy and ataxia, Alzheimer's disease, type 2 diabetes mellitus, diabetic nephropathy, myocardial atrophy, heart failure, atherosclerosis, ischemia, ischemic heart disease, or cerebral ischemia. In some embodiments, the disease or disorder characterized by activating transcription factor 6 (ATF6) is cancer. In some embodiments, ATF6 is ATF6a.

In another aspect, provided is a method of treating a disease or disorder characterized by activating transcription factor 6 (ATF6) in an individual in need thereof, wherein the method comprises administering to the individual an effective amount of a compound of formula (I) or a pharmaceutically acceptable salt thereof or a pharmaceutical composition comprising the compound. In some embodiments, the disease or disorder characterized by activation of ATF6 is viral infection, cancer, a neurodegenerative disease, or a vascular disease. In certain embodiments, the disease or disorder is viral infection, hereditary cerebellar atrophy and ataxia, Alzheimer's disease, type 2 diabetes mellitus, diabetic nephropathy, myocardial atrophy, heart failure, atherosclerosis, ischemia, ischemic heart disease, or cerebral ischemia. In some embodiments, the disease or disorder characterized by activating transcription factor 6 (ATF6) is cancer. In some embodiments, ATF6 is ATF6a.

In another aspect, provided is a method of treating cancer in an individual in need thereof, comprising administering to the individual a therapeutically effective amount of a compound of formula (I-1)/(I-2) or a pharmaceutically acceptable salt thereof or a pharmaceutical composition comprising the compound.

In some embodiments, the cancer is breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma. In some embodiments, one or more cancer cells in the individual are dormant cancer cells.

In some embodiments, the individual has had a prior treatment. In some embodiments, the cancer is resistant or refractory to the prior treatment. In some embodiments, the cancer is resistant to treatment with a ubiquitin-proteasome pathway inhibitor, a taxane, a Cox-2 inhibitor, a platinum-based antineoplastic drug, an anthracycline, a pyrimidine analog, a topoisomerase inhibitor, an mTOR inhibitor, an immune-check point inhibitor, or an agent that is used in immune oncology.

In some embodiments, the method further comprises administering radiation. In some embodiments, the method further comprises administering a second anticancer agent. In some embodiments, the second anticancer agent targets an immune checkpoint protein.

In another aspect, provided is a method of treating a disease or disorder associated with angiogenesis in an individual in need thereof, wherein the method comprises administering to the individual an effective amount of a compound of formula (I-1)/(I-2) or a pharmaceutically acceptable salt thereof or a pharmaceutical composition comprising the compound. In some embodiments, the method further comprises administering a second anti-angiogenesis agent.

In some embodiments of the methods disclosed herein, the method further comprises administering a second agent that modulates the Unfolded Protein Response or the Integrated Stress Response. In some embodiments, the second agent inhibits the IRE1/XBP1 pathway.

In another aspect, provided is a method of modulating (activating or inhibiting) ATF6 in an individual comprising administering to the individual a compound of formula (I-1)/(I-2) or a pharmaceutically acceptable salt thereof or a pharmaceutical composition comprising the compound.

In another aspect, provided is a method of modulating (activating or inhibiting) ATF6 in a cell comprising delivering to the cell a compound of formula (I-1)/(I-2) or a pharmaceutically acceptable salt thereof or a pharmaceutical composition comprising the compound.

Also provided are pharmaceutical compositions comprising: (A) a compound detailed herein, such as a compound of formula (I-1)/(I-2) or a pharmaceutically acceptable salt thereof, or a compound of formula (I-1)/(I-2) or a pharmaceutically acceptable salt thereof; and (B) a pharmaceutically acceptable carrier or excipient. Kits comprising a compound detailed herein or a salt thereof and optionally instructions for use are also provided. Compounds as detailed herein or a pharmaceutically acceptable salt thereof are also provided for the manufacture of a medicament for the treatment of a disease or disorder characterized by activation of ATF6. In some embodiments, the disease or disorder is cancer, a neurodegenerative disease, or a vascular disease. In certain embodiments, the disease or disorder is viral infection, hereditary cerebellar atrophy and ataxia, Alzheimer's disease, type 2 diabetes mellitus, diabetic nephropathy, myocardial atrophy, heart failure, atherosclerosis, ischemia, ischemic heart disease, or cerebral ischemia.

DETAILED DESCRIPTION

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkoxy" refers to the group R—O—, where R is alkyl; and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

The term "haloalkyl" refers to an alkyl group with one or more halo substituents, or one, two, or three halo substituents. Examples of haloalkyl groups include —$CF_3$, —$(CH_2)F$, —$CHF_2$, —$CH_2Br$, —$CH_2CF_3$, and —$CH_2CH_2F$.

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of an individual. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying recurrence, such as of unwanted cell proliferation.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

It is understood that aspects and variations described herein also include "consisting" and/or "consisting essentially of" aspects and variations.

All references throughout, such as publications, patents, patent applications and published patent applications, are incorporated herein by reference in their entireties.

Compounds

Formula (I-1)

In one aspect, provided is a compound of the formula (I-1):

(I-1)

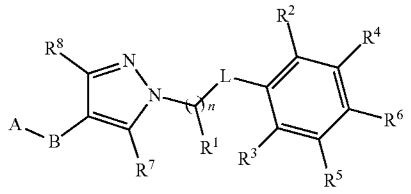

or a pharmaceutically acceptable salt thereof, wherein:

$R^1$ is H, $C_1$-$C_6$alkyl, $C_3$-$C_8$cycloalkyl, or $C_1$-$C_6$ haloalkyl;

n is 0 or 1;

L is —$CH_2$— or is absent;

B is —$CH_2CH_2$—, —CH═CH—, or —C≡C—;

$R^2$, $R^3$, $R^4$, $R^5$, and $R^6$ are each independently H, halo, CN, —OH, —$NH_2$, $C_{1-6}$alkoxy, $C_1$-$C_6$alkyl, or $C_1$-$C_6$haloalkyl;

or $R^2$, $R^4$, $R^5$, and $R^6$ are each independently H, halo, CN, —OH, —$NH_2$, $C_{1-6}$alkoxy, $C_1$-$C_6$alkyl, or $C_1$-$C_6$haloalkyl and $R^3$ is taken together with $R^1$ and the atoms to which they are attached to form a 5- or 6-membered carbocyclic ring, wherein the 5- or 6-membered carbocyclic ring is unsubstituted or substituted with one to three groups selected from the group consisting of halo, CN, —OH, $C_1$-$C_6$alkyl, and $C_1$-$C_6$haloalkyl;

A is

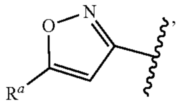, 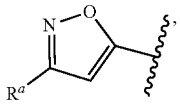, or

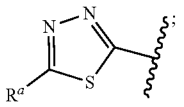;

$R^a$ is 5- or 6-membered heteroaryl, wherein the 5- or 6-membered heteroaryl is unsubstituted or substituted with one to four groups selected from the group consisting of OH, halo, $C_1$-$C_6$alkyl and $C_1$-$C_6$alkoxy, $R^7$ is H, $C_1$-$C_6$alkyl or $C_1$-$C_6$haloalkyl; and $R^8$ is H or $C_1$-$C_6$alkyl.

In one variation is provided a compound of the formula (I-1), or a salt thereof, wherein the carbon bearing $R^1$ when $R^1$ is other than H (i.e., $C_1$-$C_6$alkyl, $C_3$-$C_8$cycloalkyl or $C_1$-$C_6$haloalkyl), is in the "S" configuration. In another variation is provided a compound of the formula (I-1), or a salt thereof, wherein the carbon bearing $R^1$ when $R^1$ is other than H (i.e., $C_1$-$C_6$alkyl, $C_3$-$C_8$cycloalkyl or $C_1$-$C_6$haloalkyl), is in the "R" configuration. Mixtures of a compound of the formula (I-1) are also embraced, including racemic or non-racemic mixtures of a given compound, and mixtures of two or more compounds of different chemical formulae.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $R^1$ of formula (I-1) may be combined with every description, variation, embodiment or aspect of A of formula (I-1) the same as if each and every combination were specifically and individually listed.

In some embodiments of a compound of formula (I-1), n is 1 and $R^1$ is H. In some embodiments, n is 1 and $R^1$ is $C_1$-$C_6$alkyl. In other embodiments, n is 1 and $R^1$ is $C_3$-$C_8$cycloalkyl. In some embodiments, n is 1 and $R^1$ is $C_1$-$C_6$haloalkyl. In certain embodiments, n is 1 and $R^1$ is methyl, ethyl, n-propyl, isopropyl, n-butyl, isobutyl, sec-butyl, or tert-butyl. In some embodiments, n is 1 and $R^1$ methyl. In some embodiments, n is 1 and $R^1$ ethyl. In some embodiments, n is 1 and $R^1$ cyclopropyl, cyclobutyl, cyclopentyl, or cyclohexyl. In some embodiments, n is 1 and $R^1$ is cyclopropyl. In some embodiments of a compound of formula (I-1), n is 0.

In some embodiments of a compound of formula (I-1), L is absent. In other embodiments, L is —$CH_2$—.

In some embodiments, n is 1, L is absent, and $R^1$ is H. In some embodiments, n is 1, L is absent, and $R^1$ is $C_1$-$C_6$alkyl. In other embodiments, n is 1, L is absent, and $R^1$ is $C_3$-$C_8$cycloalkyl. In some embodiments, n is 1, L is absent, and $R^1$ is $C_1$-$C_6$haloalkyl. In certain embodiments, n is 1, L is absent, and $R^1$ is methyl, ethyl, n-propyl, isopropyl, n-butyl, isobutyl, sec-butyl, or tert-butyl. In some embodiments, n is 1, L is absent, and $R^1$ is methyl. In some embodiments, n is 1, L is absent, and $R^1$ is ethyl. In some embodiments, n is 1, L is absent, and $R^1$ is cyclopropyl, cyclobutyl, cyclopentyl, or cyclohexyl. In some embodiments, n is 1, L is absent, and $R^1$ is cyclopropyl.

In some embodiments of a compound of formula (I-1), n is 0 and L is absent.

In some embodiments of a compound of formula (I-1), n is 1, L is —$CH_2$—, and $R^1$ is H. In some embodiments, n is 1, L is —$CH_2$—, and $R^1$ is $C_1$-$C_6$alkyl. In other embodiments, n is 1, L is —$CH_2$—, and $R^1$ is $C_3$-$C_8$cycloalkyl. In some embodiments, n is 1, L is is —$CH_2$—, and $R^1$ is $C_1$-$C_6$haloalkyl. In certain embodiments, n is 1, L is —$CH_2$—, and $R^1$ is methyl, ethyl, n-propyl, isopropyl, n-butyl, isobutyl, sec-butyl, or tert-butyl. In some embodiments, n is 1, L is —$CH_2$—, and $R^1$ methyl. In some embodiments, n is 1, L is —$CH_2$—, and $R^1$ ethyl. In some embodiments, n is 1, L is —$CH_2$—, and $R^1$ is cyclopropyl, cyclobutyl, cyclopentyl, or cyclohexyl. In some embodiments, n is 1, L is —$CH_2$—, and $R^1$ is cyclopropyl.

In some embodiments of a compound of formula (I-1), n is 0 and L is —$CH_2$—.

In some embodiments of formula (I-1), $R^3$ is taken together with $R^1$ and the atoms to which they are attached to form a 5- or 6-membered carbocyclic ring. In some embodiments, $R^3$ is taken together with $R^1$ and the atoms to which they are attached to form an unsubstituted 5-membered carbocyclic ring. In some embodiments, $R^3$ is taken together with $R^1$ and the atoms to which they are attached to form an unsubstituted 6-membered carbocyclic ring. In some embodiments, $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl.

In some embodiments of a compound of formula (I-1), L is absent, and $R^3$ is taken together with $R^1$ and the atoms to which they are attached to form a 5- or 6-membered carbocyclic ring. In some embodiments, L is absent, and $R^3$ is taken together with $R^1$ and the atoms to which they are attached to form an unsubstituted 5-membered carbocyclic ring. In some embodiments, L is absent, and $R^3$ is taken together with $R^1$ and the atoms to which they are attached to form an unsubstituted 6-membered carbocyclic ring. In some embodiments, L is absent, and $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, L is absent, and $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, L is absent, and $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl. In some embodiments, L is absent, and $R^3$ is taken together with $R^1$ and the atoms to which they are attached to form a 5-membered carbocyclic ring, wherein the 5-membered carbocyclic ring is unsubstituted or substituted with halo, CN, —OH, $C_1$-$C_6$alkyl, or $C_1$-$C_6$haloalkyl and one or two of $R^2$, $R^4$, $R^5$, and $R^6$ are independently selected from halo, CN, $C_1$-$C_6$alkyl, and $C_1$-$C_6$haloalkyl. In certain embodiments, L is absent, and $R^3$ is taken together with $R^1$ and the atoms to which they are attached to form an unsubstituted 5-membered carbocyclic ring, and $R^2$, $R^4$, $R^5$, and $R^6$ are each H. In one variation, L is absent, and $R^3$ is taken together with $R^1$ and the atoms to which they are attached to form a 5-membered carbocyclic ring, when the carbon bearing $R^1$ is in the "S" configuration. In another variation, L is absent, and $R^3$ is taken together with $R^1$ and the atoms to which they are attached to form a 5-membered carbocyclic ring, when the carbon bearing $R^1$ is in the "R" configuration.

In some embodiments, L is —$CH_2$—, and $R^1$ is $C_1$-$C_6$alkyl. In other embodiments, L is —$CH_2$—, and $R^1$ is $C_3$-$C_8$cycloalkyl. In some embodiments, L is is —$CH_2$—, and $R^1$ is $C_1$-$C_6$haloalkyl. In certain embodiments, L is —$CH_2$—, and $R^1$ is methyl, ethyl, n-propyl, isopropyl, n-butyl, isobutyl, sec-butyl, or tert-butyl. In some embodiments, L is —$CH_2$—, and $R^1$ methyl. In some embodiments, L is —$CH_2$—, and $R^1$ ethyl. In some embodiments, L is —$CH_2$—, and $R^1$ is cyclopropyl, cyclobutyl, cyclopentyl, or cyclohexyl. In some embodiments, L is —$CH_2$—, and $R^1$ is cyclopropyl. In some embodiments of a compound of Formula (I-1), L is —$CH_2$—, and $R^3$ is taken together with $R^1$ and the atoms to which they are attached to form a 5- or 6-membered carbocyclic ring. In some embodiments, L is —$CH_2$—, and $R^3$ is taken together with $R^1$ and the atoms to which they are attached to form an unsubstituted 5-membered carbocyclic ring. In some embodiments, L is —$CH_2$—, and $R^3$ is taken together with $R^1$ and the atoms to which they are attached to form an unsubstituted 6-membered carbocyclic ring. In some embodiments, L is —$CH_2$—, and $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, L is —$CH_2$—, and $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, L is —$CH_2$—, and $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl. In some embodiments, L is —$CH_2$—, and $R^3$ is taken together with $R^1$ and the atoms to which they are attached to form a 5-membered carbocyclic ring, wherein the 5-membered carbocyclic ring is unsubstituted or substituted with halo, CN, —OH, $C_1$-$C_6$alkyl, or $C_1$-$C_6$haloalkyl and one or two of $R^2$, $R^4$, $R^5$, and $R^6$ are independently selected from halo, CN, $C_1$-$C_6$alkyl, and $C_1$-$C_6$haloalkyl. In certain embodiments, L is —$CH_2$—, and $R^3$ is taken together with $R^1$ and the atoms to which they are attached to form an unsubstituted 6-membered carbocyclic ring, and $R^2$, $R^4$, $R^5$, and $R^6$ are each H. In one variation, L is —$CH_2$—, and $R^3$ is taken together with $R^1$ and the atoms to which they are attached to form a 5- or 6-membered carbocyclic ring, when the carbon bearing $R^1$ is in the "S" configuration. In another variation, L is —$CH_2$—, and $R^3$ is taken together with $R^1$ and the atoms to which they are attached to form a 5- or 6-membered carbocyclic ring, when the carbon bearing $R^1$ is in the "R" configuration.

In some embodiments of a compound of formula (I-1), n is 1 and $R^1$ is H. In some embodiments, n is 1 and $R^1$ is $C_1$-$C_6$alkyl. In other embodiments, n is 1 and $R^1$ is $C_3$-$C_8$cycloalkyl. In some embodiments, n is 1 and $R^1$ is $C_1$-$C_6$haloalkyl. In certain embodiments, n is 1 and $R^1$ is methyl, ethyl, n-propyl, isopropyl, n-butyl, isobutyl, sec-butyl, or tert-butyl. In some embodiments, n is 1 and $R^1$ methyl. In some embodiments, n is 1 and $R^1$ ethyl. In some embodiments, n is 1 and $R^1$ cyclopropyl, cyclobutyl, cyclopentyl, or cyclohexyl. In some embodiments, n is 1 and $R^1$ is cyclopropyl. In some embodiments of a compound of formula (I-1), n is 1 and $R^3$ is taken together with $R^1$ and the atoms to which they are attached to form a 5- or 6-membered carbocyclic ring. In some embodiments, n is 1 and $R^3$ is taken together with $R^1$ and the atoms to which they are attached to form an unsubstituted 5-membered carbocyclic ring. In some embodiments, n is 1 and $R^3$ is taken together with $R^1$ and the atoms to which they are attached to form an unsubstituted 6-membered carbocyclic ring. In some embodiments, n is 1 and $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, n is 1 and $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, n is 1 and $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl. In some embodiments of a compound of formula (I-1), n is 0.

In some embodiments of a compound of formula (I-1), L is absent. In other embodiments, L is —$CH_2$—. In some embodiments, n is 1, L is absent, and $R^1$ is H. In some embodiments, n is 1, L is absent, and $R^1$ is $C_1$-$C_6$alkyl. In other embodiments, n is 1, L is absent, and $R^1$ is $C_3$-$C_8$cycloalkyl. In some embodiments, n is 1, L is absent, and $R^1$ is $C_1$-$C_6$haloalkyl. In certain embodiments, n is 1, L is absent, and $R^1$ is methyl, ethyl, n-propyl, isopropyl, n-butyl, isobutyl, sec-butyl, or tert-butyl. In some embodiments, n is 1, L is absent, and $R^1$ is methyl. In some embodiments, n is 1, L is absent, and $R^1$ is ethyl. In some embodiments, n is 1, L is absent, and $R^1$ is cyclopropyl, cyclobutyl, cyclopentyl, or cyclohexyl. In some embodiments, n is 1, L is absent, and $R^1$ is cyclopropyl.

In some embodiments of a compound of formula (I-1), n is 1, L is absent, and $R^3$ is taken together with $R^1$ and the atoms to which they are attached to form a 5- or 6-membered carbocyclic ring. In some embodiments, n is 1, L is absent, and $R^3$ is taken together with $R^1$ and the atoms to which they are attached to form an unsubstituted 5-membered carbocyclic ring. In some embodiments, n is 1, L is absent, and $R^3$ is taken together with $R^1$ and the atoms to which they are attached to form an unsubstituted 6-membered carbocyclic ring. In some embodiments, n is 1, L is absent, and $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, n is 1, L is absent, and $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, n is 1, L is absent, and $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl. In some embodiments, n is 1, L is absent, and $R^3$ is taken together with $R^1$ and the atoms to which they are attached to form a 5-membered carbocyclic ring, wherein the 5-membered carbocyclic ring is unsubstituted or substituted with halo, CN, —OH, $C_1$-$C_6$alkyl, or $C_1$-$C_6$haloalkyl and one or two of $R^2$, $R^4$, $R^5$, and $R^6$ are independently selected from halo, CN, $C_1$-$C_6$alkyl, and $C_1$-$C_6$haloalkyl. In certain embodiments, n is 1, L is absent, and $R^3$ is taken together with $R^1$ and the atoms to which they are attached to form an unsubstituted 5-membered carbocyclic ring, and $R^2$, $R^4$, $R^5$, and $R^6$ are each H. In one variation, n is 1, L is absent, and $R^3$ is taken together with $R^1$ and the atoms to which they are attached to form a 5-membered carbocyclic ring, when the carbon bearing $R^1$ is in the "S" configuration. In another variation, n is 1, L is absent, and $R^3$ is taken together with $R^1$ and the atoms to which they are attached to form a 5-membered carbocyclic ring, when the carbon bearing $R^1$ is in the "R" configuration.

In some embodiments of a compound of formula (I-1), n is 0 and L is absent.

In some embodiments of a compound of formula (I-1), n is 1, L is $—CH_2—$, and $R^1$ is H. In some embodiments, n is 1, L is $—CH_2—$, and $R^1$ is $C_1$-$C_6$alkyl. In other embodiments, n is 1, L is $—CH_2—$, and $R^1$ is $C_3$-$C_8$cycloalkyl. In some embodiments, n is 1, L is is $—CH_2—$, and $R^1$ is $C_1$-$C_6$haloalkyl. In certain embodiments, n is 1, L is $—CH_2—$, and $R^1$ is methyl, ethyl, n-propyl, isopropyl, n-butyl, isobutyl, sec-butyl, or tert-butyl. In some embodiments, n is 1, L is $—CH_2—$, and $R^1$ methyl. In some embodiments, n is 1, L is $—CH_2—$, and $R^1$ ethyl. In some embodiments, n is 1, L is $—CH_2—$, and $R^1$ is cyclopropyl, cyclobutyl, cyclopentyl, or cyclohexyl. In some embodiments, n is 1, L is $—CH_2—$, and $R^1$ is cyclopropyl. In some embodiments of a compound of formula (I-1), n is 1, L is $—CH_2—$, and $R^3$ is taken together with $R^1$ and the atoms to which they are attached to form a 5- or 6-membered carbocyclic ring. In some embodiments, n is 1, L is $—CH_2—$, and $R^3$ is taken together with $R^1$ and the atoms to which they are attached to form an unsubstituted 5-membered carbocyclic ring. In some embodiments, n is 1, L is $—CH_2—$, and $R^3$ is taken together with $R^1$ and the atoms to which they are attached to form an unsubstituted 6-membered carbocyclic ring. In some embodiments, n is 1, L is $—CH_2—$, and $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, n is 1, L is $—CH_2—$, and $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, n is 1, L is $—CH_2—$, and $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl. In some embodiments, n is 1, L is $—CH_2—$, and $R^3$ is taken together with $R^1$ and the atoms to which they are attached to form a 5-membered carbocyclic ring, wherein the 5-membered carbocyclic ring is unsubstituted or substituted with halo, CN, —OH, $C_1$-$C_6$alkyl, or $C_1$-$C_6$haloalkyl and one or two of $R^2$, $R^4$, $R^5$, and $R^6$ are independently selected from halo, CN, $C_1$-$C_6$alkyl, and $C_1$-$C_6$haloalkyl. In certain embodiments, n is 1, L is $—CH_2—$, and $R^3$ is taken together with $R^1$ and the atoms to which they are attached to form an unsubstituted 5-membered carbocyclic ring, and $R^2$, $R^4$, $R^5$, and $R^6$ are each H. In one variation, n is 1, L is $—CH_2—$, and $R^3$ is taken together with $R^1$ and the atoms to which they are attached to form a 5-membered carbocyclic ring, when the carbon bearing $R^1$ is in the "S" configuration. In another variation, n is 1, L is $—CH_2—$, and $R^3$ is taken together with $R^1$ and the atoms to which they are attached to form a 5-membered carbocyclic ring, when the carbon bearing $R^1$ is in the "R" configuration.

In some embodiments of a compound of formula (I-1), n is 0 and L is $—CH_2—$.

In some embodiments of a compound of formula (I-1), $R^1$ is H. In some embodiments, $R^1$ is $C_1$-$C_6$alkyl. In other embodiments, $R^1$ is $C_3$-$C_8$cycloalkyl. In some embodiments, $R^1$ is $C_1$-$C_6$haloalkyl. In certain embodiments, $R^1$ is methyl, ethyl, n-propyl, isopropyl, n-butyl, isobutyl, sec-butyl, or tert-butyl. In some embodiments, $R^1$ is methyl. In some embodiments, $R^1$ is ethyl. In some embodiments, $R^1$ is cyclopropyl, cyclobutyl, cyclopentyl, or cyclohexyl. In some embodiments, $R^1$ is cyclopropyl. In some embodiments of a compound of Formula (I-1), $R^3$ is taken together with $R^1$ and the atoms to which they are attached to form a 5- or 6-membered carbocyclic ring. In some embodiments, $R^3$ is taken together with $R^1$ and the atoms to which they are attached to form a 5-membered carbocyclic ring. In certain embodiments, $R^3$ is taken together with $R^1$ and the atoms to which they are attached to form a 5-membered carbocyclic ring, and $R^2$, $R^4$, $R^5$, and $R^6$ are each H.

In some embodiments of a compound of formula (I-1), $R^2$, $R^3$, $R^4$, $R^5$, and $R^6$ are each independently H, halo, CN, $C_1$-$C_6$alkyl, or $C_1$-$C_6$haloalkyl. In some embodiments, $R^2$, $R^3$, $R^4$, $R^5$, and $R^6$ are each independently H, Cl, CN, or $CF_3$. In some embodiments, $R^4$ and $R^5$ are each independently Cl, Br, I, CN, $C_1$-$C_6$alkyl, or $C_1$-$C_6$haloalkyl. In some embodiments, one of $R^2$, $R^3$, $R^4$, $R^5$, and $R^6$ is other than H. In some embodiments, two of $R^2$, $R^3$, $R^4$, $R^5$, and $R^6$ are other than H. In some embodiments, at least two of $R^2$, $R^3$, $R^4$, $R^5$, and $R^6$ are other than H. In some embodiments, one of $R^2$, $R^3$, $R^4$, $R^5$, and $R^6$ is CN. In some embodiments, $R^6$ is CN. In some embodiments, one of $R^2$, $R^3$, $R^4$, $R^5$, and $R^6$ is $CF_3$. In some embodiments, two of $R^2$, $R^3$, $R^4$, $R^5$, and $R^6$ are $CF_3$. In some embodiments, $R^2$ and $R^6$ are each $CF_3$, or $R^4$ and $R^5$ are each $CF_3$, or $R^3$ and $R^6$ are each $CF_3$. In some embodiments, one or two of $R^2$, $R^3$, $R^4$, $R^5$, and $R^6$ is Cl. In some embodiments, $R^4$ and $R^5$ are each Cl. In some embodiments, $R^2$, $R^4$, $R^5$, and $R^6$ are each H.

In some embodiments of formula (I-1),

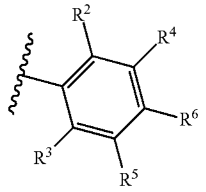 is 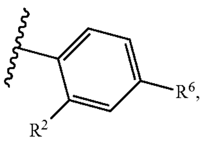

wherein $R^2$ and $R^6$ are each $C_1$-$C_6$ haloalkyl. In some embodiments of formula (I-1),

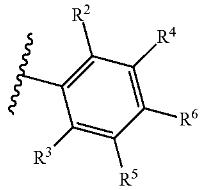 is 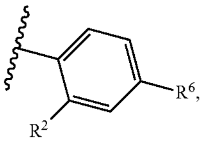

wherein $R^2$ and $R^6$ are each —$CF_3$. In some embodiments,

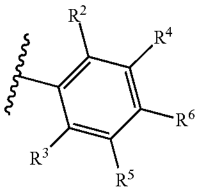 is 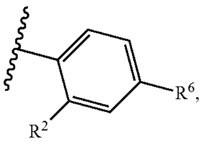

wherein $R^2$ and $R^6$ are each independently selected from the group consisting of halo, $C_1$-$C_6$alkyl, and $C_1$-$C_6$haloalkyl. In some embodiments,

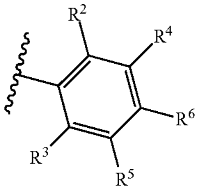 is 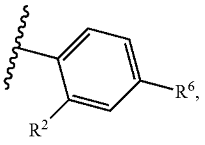

wherein $R^2$ and $R^6$ are each independently selected from the group consisting of Cl, $C_1$-$C_6$alkyl, and $C_1$-$C_6$haloalkyl. In some embodiments,

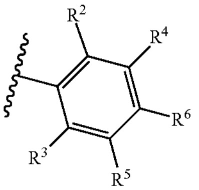 is 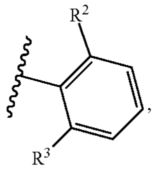

wherein $R^2$ and $R^3$ are each halo. In some embodiments,

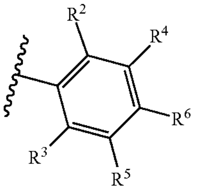 is 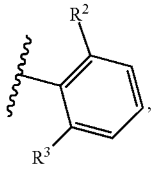

wherein $R^2$ and $R^3$ are each Cl. In some embodiments,

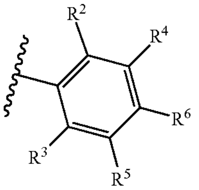 is 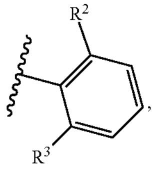

wherein one of $R^2$ and $R^3$ is Cl and one of $R^2$ and $R^3$ is F.

In some embodiments,

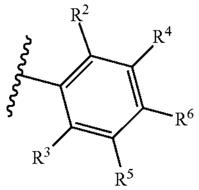 is 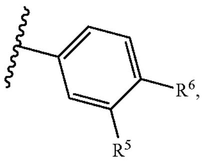

wherein $R^5$ and $R^6$ are each independently selected from the group consisting of Cl, Br, I, CN, $C_1$-$C_6$alkyl, and $C_1$-$C_6$haloalkyl. In some embodiments,

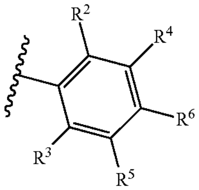 is 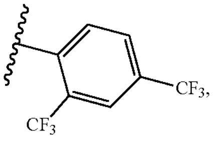

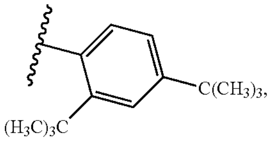 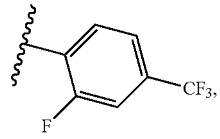

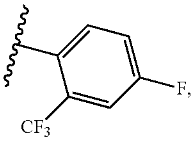 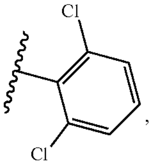, 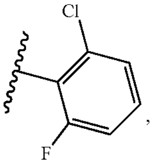,

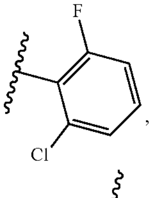, 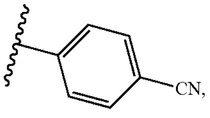 or

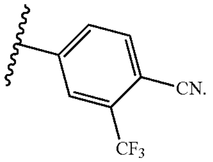

In some embodiments, provided is a compound of the formula (I-1), wherein A is

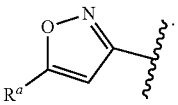

In some embodiments, provided is a compound of the formula (I-1) wherein A is

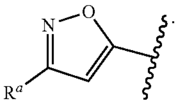

In some embodiments, provided is a compound of the formula (I-1) wherein A is

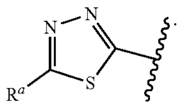

In some embodiments of a compound of formula (I-1), $R^a$ is 5- or 6-membered heteroaryl, wherein the 5- or 6-membered heteroaryl is unsubstituted or substituted with one to four groups selected from OH, halo, and $C_1$-$C_6$alkyl. In some embodiments, $R^a$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each of which is unsubstituted or is substituted with one to four groups selected from the group consisting of OH, halo, $C_1$-$C_6$alkyl, and $C_1$-$C_6$akloxy. In some embodiments, $R^a$ is selected from the group consisting of 2-furyl, 2-pyridinyl, 2-pyrimidinyl, 4-pyrimidinyl, and 2-pyrazinyl, each of which is unsubstituted or is substituted with one to four groups selected from the group consisting of OH, halo, $C_1$-$C_6$alkyl, and $C_1$-$C_6$akloxy.

In some embodiments of a compound of formula (I-1), A is

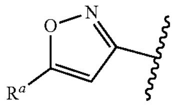

and $R^a$ is a 5- or 6-membered heteroaryl that is unsubstituted or is substituted with one to four groups selected from the group consisting of OH, halo, $C_1$-$C_6$alkyl and $C_1$-$C_6$alkoxy. In some embodiments, A is

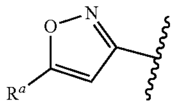

and $R^a$ is 2-furyl, 2-pyridinyl, 2-pyrimidinyl, 4-pyrimidinyl, or 2-pyrazinyl, each unsubstituted or substituted with one to four groups selected from the group consisting of OH, halo, and $C_1$-$C_6$alkyl. In some embodiments, A is

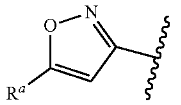

and $R^a$ is a 5- or 6-membered heteroaryl. In some embodiments, A is

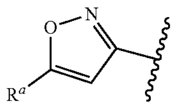

and $R^a$ is 2-furyl, 2-pyridinyl, 2-pyrimidinyl, 4-pyrimidinyl, or 2-pyrazinyl. In some embodiments of formula (I-1), A is

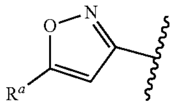

and $R^a$ is 2-furyl. In another embodiment of formula (I-1), A is

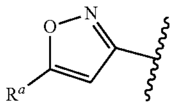

and $R^a$ is 2-pyridinyl. In some embodiments of formula (I-1), A is

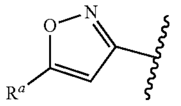

and $R^a$ is 2-pyrimidinyl. In other embodiments of formula (I-1), A is

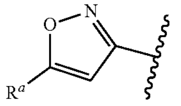

and $R^a$ is 4-pyrimidinyl. In still other embodiments of formula (I-1), A is

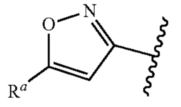

and $R^a$ is 2-pyrazinyl.

In some embodiments of a compound of formula (I-1), A is

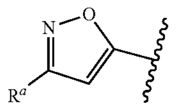

and $R^a$ is 5- or 6-membered heteroaryl, wherein the 5- or 6-membered heteroaryl of $R^a$ is unsubstituted or is substituted with one to four groups selected from the group consisting of OH, halo, and $C_1$-$C_6$alkyl. In some embodiments, A is

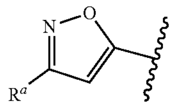

and $R^a$ is 2-furyl, 2-pyridinyl, 2-pyrimidinyl, 4-pyrimidinyl, or 2-pyrazinyl, each unsubstituted or substituted with one to four groups selected from the group consisting of OH, halo, and $C_1$-$C_6$alkyl. In some embodiments, A is

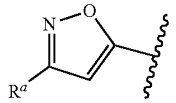

and $R^a$ is a 5- or 6-membered heteroaryl. In some embodiments, A is

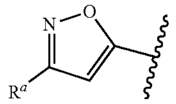

and $R^a$ is 2-furyl, 2-pyridinyl, 2-pyrimidinyl, 4-pyrimidinyl, or 2-pyrazinyl. In some embodiments of formula (I-1), A is

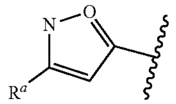

and $R^a$ is 2-furyl. In another embodiment of formula (I-1), A is

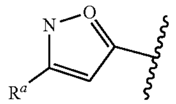

and $R^a$ is 2-pyridinyl. In some embodiments of formula (I-1), A is

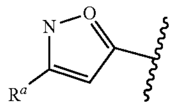

and $R^a$ is 2-pyrimidinyl. In other embodiments of formula (I-1), A is

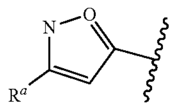

and $R^a$ is 4-pyrimidinyl. In still other embodiments of formula (I-1), A is

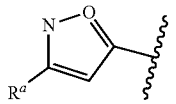

and $R^a$ is 2-pyrazinyl.

In some embodiments of a compound of formula (I-1), A is

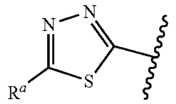

and $R^a$ is 5- or 6-membered heteroaryl, wherein the 5- or 6-membered heteroaryl of $R^a$ is unsubstituted or is substituted with one to four groups selected from the group consisting of OH, halo, and $C_1$-$C_6$alkyl. In some embodiments, A is

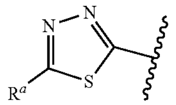

and $R^a$ is 2-furyl, 2-pyridinyl, 2-pyrimidinyl, 4-pyrimidinyl, or 2-pyrazinyl, each unsubstituted or substituted with one to four groups selected from the group consisting of OH, halo, and $C_1$-$C_6$alkyl. In some embodiments, A is

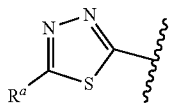

and $R^a$ is a 5- or 6-membered heteroaryl. In some embodiments, A is

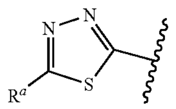

and $R^a$ is 2-furyl, 2-pyridinyl, 2-pyrimidinyl, 4-pyrimidinyl, or 2-pyrazinyl. In some embodiments of formula (I-1), A is

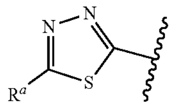

and $R^a$ is 2-furyl. In some embodiments of formula (I-1), A is

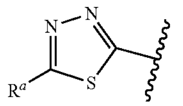

and $R^a$ is 2-pyridinyl. In other embodiments of formula (I-1), A is

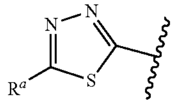

and $R^a$ is 2-pyrazinyl. In still other embodiments of formula (I-1), A is

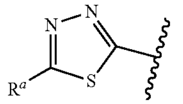

and $R^a$ is 2-pyrimidinyl. In other embodiments of formula (I-1), A is

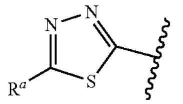

and $R^a$ is 4-pyrimidinyl.

In some embodiments of any of the formulae provided herein, $R^8$ and $R^7$ are H, A is

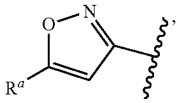, $R^a$ is 2-furyl, $R^1$ is methyl, and L is absent. In some embodiments of any of the formulae provided herein, $R^8$ is methyl, $R^7$ is H, A is

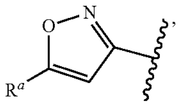, $R^a$ is 2-furyl, $R^1$ is methyl, and L is absent. In some embodiments of any of the formulae provided herein, $R^8$ is H, $R^7$ is methyl, A is

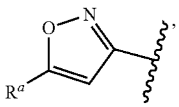, $R^a$ is 2-furyl, $R^1$ is methyl, and L is absent. In some embodiments of any of the formulae provided herein, $R^8$ and $R^7$ are H, A is

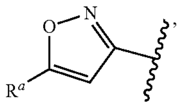, $R^a$ is 2-furyl, $R^3$ is taken together with $R^1$ and the atoms to which they are attached to form a 6-membered carbocyclic ring, unsubstituted or substituted with one to three groups selected from the group consisting of halo, CN, —OH, $C_1$-$C_6$alkyl, and $C_1$-$C_6$haloalkyl. In some embodiments of any of the formulae provided herein, $R^8$ and $R^7$ are H, A is

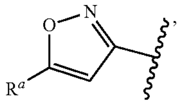, $R^a$ is 2-furyl, and $R^3$ is taken together with $R^1$ and the atoms to which they are attached to form a 5-membered carbocyclic ring, unsubstituted or substituted with one to three groups selected from the group consisting of halo, CN, —OH, $C_1$-$C_6$alkyl, and $C_1$-$C_6$haloalkyl.

In some embodiments of any of the formulae provided herein, $R^8$ and $R^7$ are H, A is

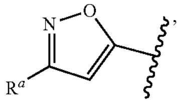, $R^a$ is 2-furyl, $R^1$ is methyl, L is absent. In some embodiments of any of the formulae provided herein, $R^8$ is methyl, $R^7$ is H, A is

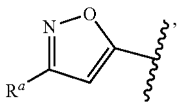, $R^a$ is 2-furyl, $R^1$ is methyl, and L is absent. In some embodiments of any of the formulae provided herein, $R^8$ is H, $R^7$ is methyl, A is

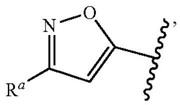, $R^a$ is 2-furyl, $R^1$ is methyl, and L is absent. In some embodiments of any of the formulae provided herein, $R^8$ and $R^7$ are H, A is

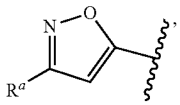, $R^a$ is 2-furyl, and $R^3$ is taken together with $R^1$ and the atoms to which they are attached to form an unsubstituted 6-membered carbocyclic ring, unsubstituted or substituted with one to three groups selected from the group consisting of halo, CN, —OH, $C_1$-$C_6$alkyl, and $C_1$-$C_6$haloalkyl. In some embodiments of any of the formulae provided herein, $R^8$ and $R^7$ are H, A is

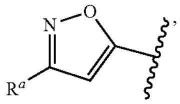, $R^a$ is 2-furyl, $R^3$ is taken together with $R^1$ and the atoms to which they are attached to form a substituted 5-membered carbocyclic ring, unsubstituted or substituted with one to three groups selected from the group consisting of halo, CN, —OH, $C_1$-$C_6$alkyl, and $C_1$-$C_6$haloalkyl.

In some embodiments of any of the formulae provided herein, $R^8$ and $R^7$ are H, A is

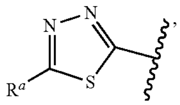, $R^a$ is 2-furyl, $R^1$ is methyl, and L is absent. In some embodiments of any of the formulae provided herein, $R^8$ and $R^7$ are H, A is

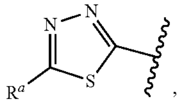, $R^a$ is 2-pyridinyl, R is methyl, and L is absent. In some embodiments of any of the formulae provided herein, $R^8$ and $R^7$ are H, A is

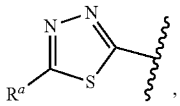, $R^a$ is 2-pyrazinyl, $R^1$ is methyl, and L is absent. In some embodiments of any of the formulae provided herein, $R^8$ is methyl, $R^7$ is H, A is

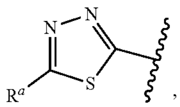, $R^a$ is 2-furyl, $R^1$ is methyl, and L is absent. In some embodiments of any of the formulae provided herein, $R^8$ is methyl, $R^7$ is H, A is

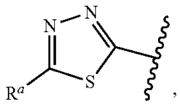, $R^a$ is 2-pyridinyl, $R^1$ is methyl, and L is absent. In some embodiments of any of the formulae provided herein, $R^8$ is H, $R^7$ is methyl, A is

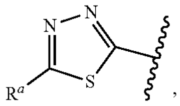, $R^a$ is 2-furyl, $R^1$ is methyl, L is absent. In some embodiments of any of the formulae provided herein, $R^8$ and $R^7$ are H, A is

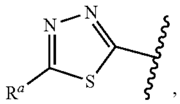, $R^a$ is 2-furyl, $R^3$ is taken together with $R^1$ and the atoms to which they are attached to form a 6-membered carbocyclic ring, unsubstituted or substituted with one to three groups selected from the group consisting of halo, CN, —OH, $C_1$-$C_6$alkyl, and $C_1$-$C_6$haloalkyl. In some embodiments of any of the formulae provided herein, $R^8$ and $R^7$ are H, A is

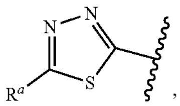, $R^a$ is 2-furyl, $R^3$ is taken together with $R^1$ and the atoms to which they are attached to form a substituted 5-membered carbocyclic ring, unsubstituted or substituted with one to three groups selected from the group consisting of halo, CN, —OH, $C_1$-$C_6$alkyl, and $C_1$-$C_6$haloalkyl.

It is understood that each description of A may be combined with each description of $R^2$, $R^3$, $R^4$, $R^5$, and/or $R^6$ the same as if each and every combination were specifically and individually listed. For example, in one aspect, it is understood that each description of A may be combined in one aspect with a variation in which $R^2$ and $R^6$ are each $CF_3$ and $R^3$, $R^4$, and $R^5$ are each hydrogen. Each description of A may also be combined with each description of $R^1$ and n the same as if each and every combination were specifically and individually listed. It is similarly understood that each description of A may be combined with each description of $R^8$ and $R^7$ the same as if each and every combination were specifically and individually listed.

In some embodiments of a compound of formula (I-1), $R^7$ is H. In some embodiments, $R^7$ is $C_1$-$C_6$alkyl. In some embodiments, $R^7$ is methyl, ethyl, n-propyl, isopropyl, n-butyl, isobutyl, sec-butyl, or tert-butyl. In certain embodiments, $R^7$ is methyl.

In some embodiments of a compound of formula (I-1), $R^8$ is H or $C_1$-$C_6$alkyl. In some embodiments of formula (I-1), $R^8$ is H. In other embodiments of formula (I-1), $R^8$ is methyl.

In some embodiments, $R^7$ and $R^8$ are both H. In some embodiments, $R^8$ is $C_1$-$C_6$alkyl and $R^7$ is H. In other embodiments, $R^8$ is H and $R^7$ is $C_1$-$C_6$alkyl. In certain embodiments, $R^8$ is methyl and $R^7$ is H. In other embodiments, $R^8$ is H and $R^7$ is methyl.

Representative compounds are listed in Table 1-2.

TABLE 1-2

| Cmpd No. | Structure | Chemical Name |
|---|---|---|
| 2-1 | 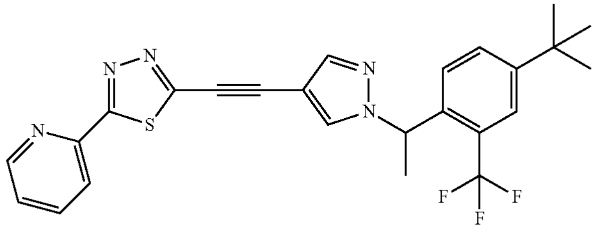 [SMILES: CC(c1ccc(C(C)(C)C)cc1C(F)(F)F)n1cc(C#Cc2nnc(-c3ccccn3)s2)cn1] | 2-((1-(1-(2,4-bis(trifluoromethyl)phenyl)ethyl)-1H-pyrazol-4-yl)ethynyl)-5-(pyridin-2-yl)-1,3,4-thiadiazole |
| 2-2 | 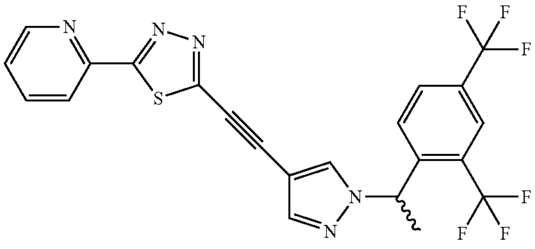 Isomer A of Compound 1 | 2-((1-(1-(2,4-bis(trifluoromethyl)phenyl)ethyl)-1H-pyrazol-4-yl)ethynyl)-5-(pyridin-2-yl)-1,3,4-thiadiazole |
| 2-3 | 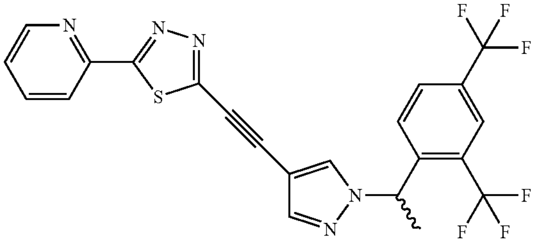 Isomer B of Compound 1 | 2-((1-(1-(2,4-bis(trifluoromethyl)phenyl)ethyl)-1H-pyrazol-4-yl)ethynyl)-5-(pyridin-2-yl)-1,3,4-thiadiazole |
| 2-4 | 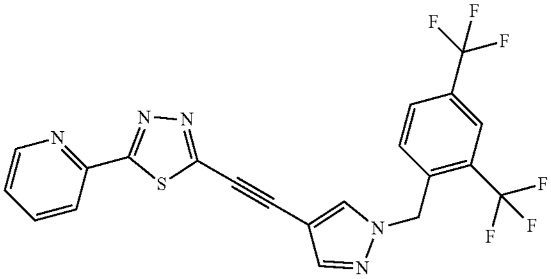 [SMILES: FC(F)(F)c1ccc(Cn2cc(C#Cc3nnc(-c4ccccn4)s3)cn2)c(C(F)(F)F)c1] | 2-((1-(2,4-bis(trifluoromethyl)benzyl)-1H-pyrazol-4-yl)ethynyl)-5-(pyridin-2-yl)-1,3,4-thiadiazole |
| 2-5 | 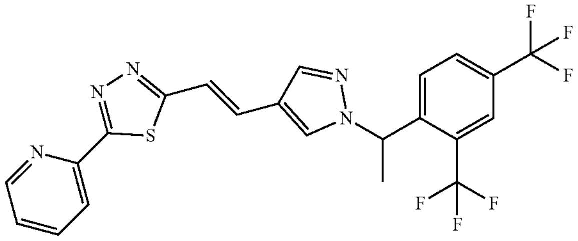 [SMILES: CC(c1ccc(C(F)(F)F)cc1C(F)(F)F)n1cc(/C=C/c2nnc(-c3ccccn3)s2)cn1] | (E)-2-(2-(1-(1-(2,4-bis(trifluoromethyl)phenyl)ethyl)-1H-pyrazol-4-yl)vinyl)-5-(pyridin-2-yl)-1,3,4-thiadiazole |

TABLE 1-2-continued

| Cmpd No. | Structure | Chemical Name |
|---|---|---|
| 2-6 | 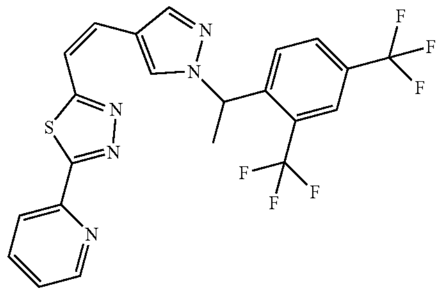 [SMILES: CC(c1ccc(C(F)(F)F)cc1C(F)(F)F)n1cc(/C=C\c2nnc(-c3ccccn3)s2)cn1] | (Z)-2-(2-(1-(1-(2,4-bis(trifluoromethyl)phenyl)ethyl)-1H-pyrazol-4-yl)vinyl)-5-(pyridin-2-yl)-1,3,4-thiadiazole |
| 2-7 | 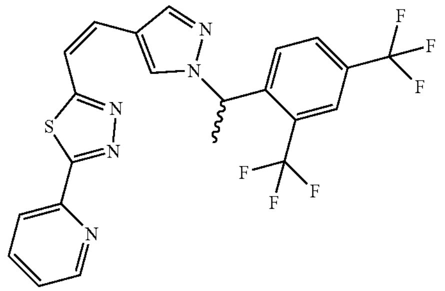 Isomer A of Compound 6 | (Z)-2-(2-(1-(1-(2,4-bis(trifluoromethyl)phenyl)ethyl)-1H-pyrazol-4-yl)vinyl)-5-(pyridin-2-yl)-1,3,4-thiadiazole |
| 2-8 | 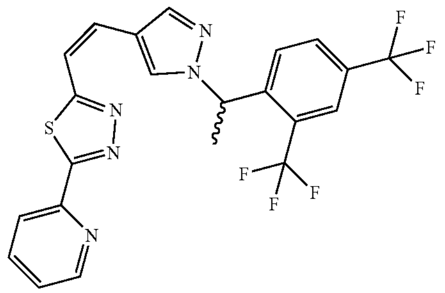 Isomer B of Compound 6 | (Z)-2-(2-(1-(1-(2,4-bis(trifluoromethyl)phenyl)ethyl)-1H-pyrazol-4-yl)vinyl)-5-(pyridin-2-yl)-1,3,4-thiadiazole |
| 2-9 | 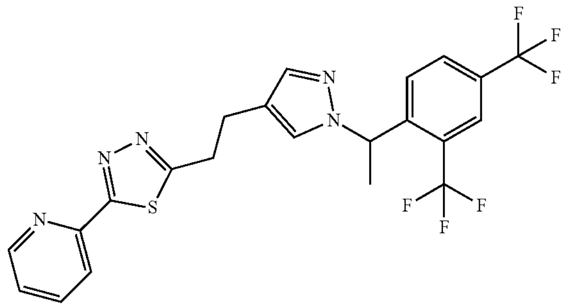 [SMILES: CC(c1ccc(C(F)(F)F)cc1C(F)(F)F)n1cc(CCc2nnc(-c3ccccn3)s2)cn1] | 2-(2-(1-(1-(2,4-bis(trifluoromethyl)phenyl)ethyl)-1H-pyrazol-4-yl)ethyl)-5-(pyridin-2-yl)-1,3,4-thiadiazole |
| 2-10 | 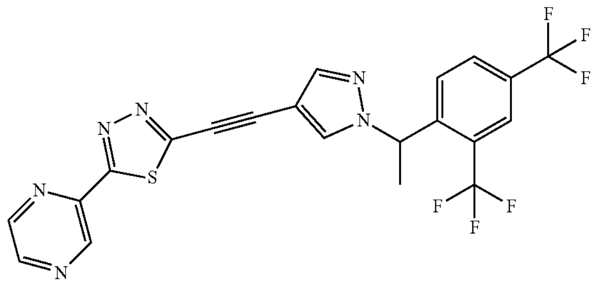 [SMILES: CC(c1ccc(C(F)(F)F)cc1C(F)(F)F)n1cc(C#Cc2nnc(-c3cnccn3)s2)cn1] | 2-((1-(1-(2,4-bis(trifluoromethyl)phenyl)ethyl)-1H-pyrazol-4-yl)ethynyl)-5-(pyrazin-2-yl)-1,3,4-thiadiazole |

TABLE 1-2-continued

| Cmpd No. | Structure | Chemical Name |
| --- | --- | --- |
| 2-11 | 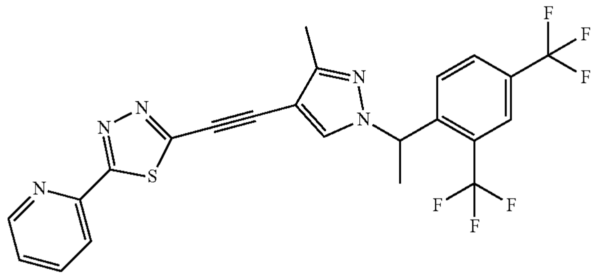 [SMILES: Cc1nn(C(C)c2ccc(C(F)(F)F)cc2C(F)(F)F)cc1C#Cc1nnc(-c2ccccn2)s1] | 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole |
| 2-12 | 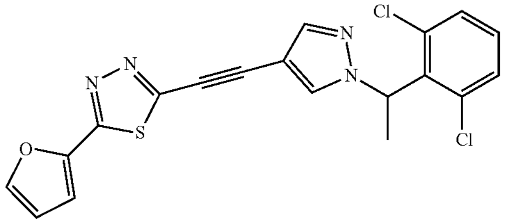 [SMILES: CC(c1c(Cl)cccc1Cl)n1cc(C#Cc2nnc(-c3ccco3)s2)cn1] | 2-((1-(1-(2,6-dichlorophenyl)ethyl)-1H-pyrazol-4-yl)ethynyl)-5-(furan-2-yl)-1,3,4-thiadiazole |
| 2-13 | 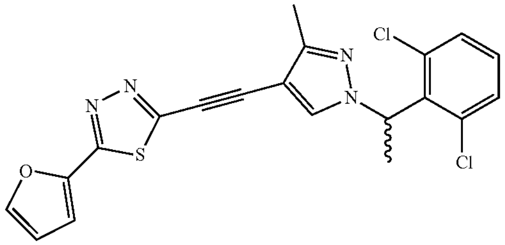 [SMILES: Cc1nn(C(C)c2c(Cl)cccc2Cl)cc1C#Cc1nnc(-c2ccco2)s1] | 2-((1-(1-(2,6-dichlorophenyl)ethyl)-3-methyl-1H-pyrazol-4-yl)ethynyl)-5-(furan-2-yl)-1,3,4-thiadiazole |
| 2-14 | 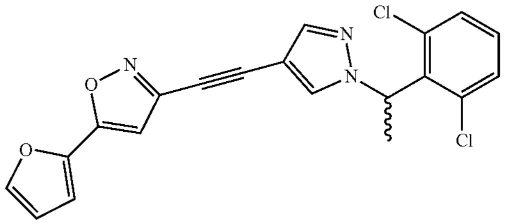 [SMILES: CC(c1c(Cl)cccc1Cl)n1cc(C#Cc2cc(-c3ccco3)on2)cn1] | 3-((1-(1-(2,6-dichlorophenyl)ethyl)-1H-pyrazol-4-yl)ethynyl)-5-(furan-2-yl)isoxazole |
| 2-15 | 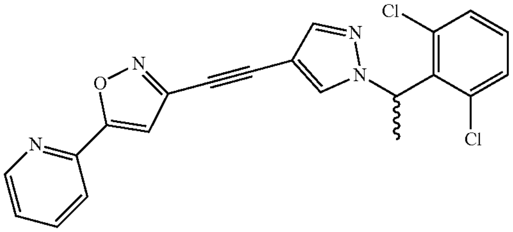 [SMILES: CC(c1c(Cl)cccc1Cl)n1cc(C#Cc2cc(-c3ccccn3)on2)cn1] | 3-((1-(1-(2,6-dichlorophenyl)ethyl)-1H-pyrazol-4-yl)ethynyl)-5-(pyridin-2-yl)isoxazole |
| 2-16 | 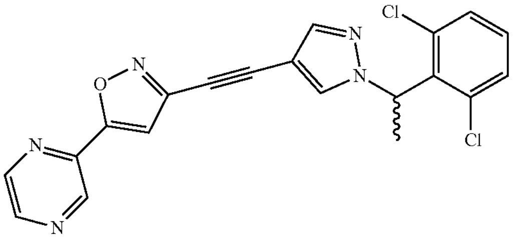 | 3-((1-(1-(2,6-dichlorophenyl)ethyl)-1H-pyrazol-4-yl)ethynyl)-5-(pyrazin-2-yl)isoxazole |

TABLE 1-2-continued

| Cmpd No. | Structure | Chemical Name |
|---|---|---|
| 2-17 | 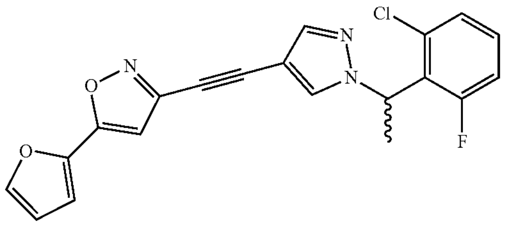 [SMILES: CC(c1c(F)cccc1Cl)n1cc(C#Cc2cc(-c3ccco3)on2)cn1] | 3-((1-(1-(2-chloro-6-fluorophenyl)ethyl)-1H-pyrazol-4-yl)ethynyl)-5-(furan-2-yl)isoxazole |
| 2-18 | 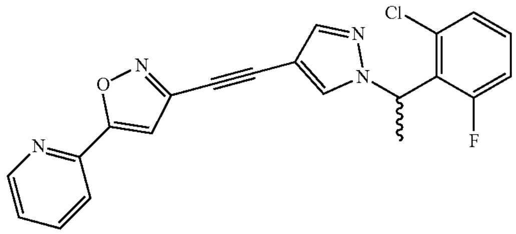 [SMILES: CC(c1c(F)cccc1Cl)n1cc(C#Cc2cc(-c3ccccn3)on2)cn1] | 3-((1-(1-(2-chloro-6-fluorophenyl)ethyl)-1H-pyrazol-4-yl)ethynyl)-5-(pyridin-2-yl)isoxazole |
| 2-19 | 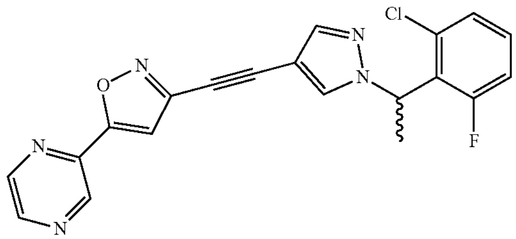 [SMILES: CC(c1c(F)cccc1Cl)n1cc(C#Cc2cc(-c3cnccn3)on2)cn1] | 3-((1-(1-(2-chloro-6-fluorophenyl)ethyl)-1H-pyrazol-4-yl)ethynyl)-5-(pyrazin-2-yl)isoxazole |
| 2-20 | 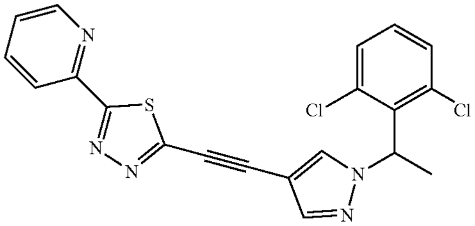 [SMILES: CC(c1c(Cl)cccc1Cl)n1cc(C#Cc2nnc(-c3ccccn3)s2)cn1] | 2-((1-(1-(2,6-dichlorophenyl)ethyl)-1H-pyrazol-4-yl)ethynyl)-5-(pyridin-2-yl)-1,3,4-thiadiazole |
| 2-21 | 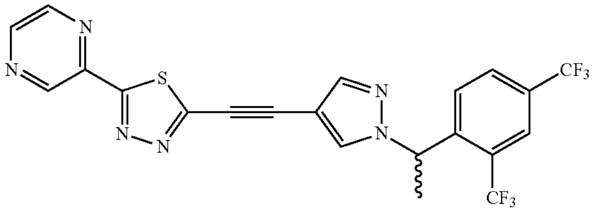 Isomer A of compound 2-10 | 2-((1-(1-(2,4-bis(trifluoromethyl)phenyl)ethyl)-1H-pyrazol-4-yl)ethynyl)-5-(pyrazin-2-yl)-1,3,4-thiadiazole |
| 2-22 | 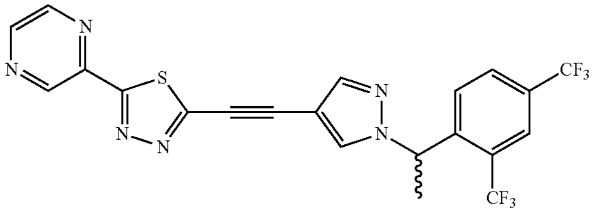 Isomer B of compound 2-10 | 2-((1-(1-(2,4-bis(trifluoromethyl)phenyl)ethyl)-1H-pyrazol-4-yl)ethynyl)-5-(pyrazin-2-yl)-1,3,4-thiadiazole |

TABLE 1-2-continued

| Cmpd No. | Structure | Chemical Name |
|---|---|---|
| 2-23 | 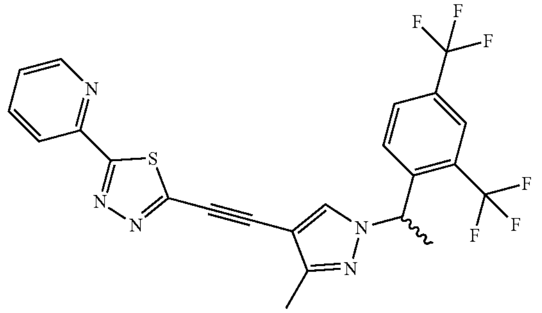 Isomer A of compound 2-11 | 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole |
| 2-24 | 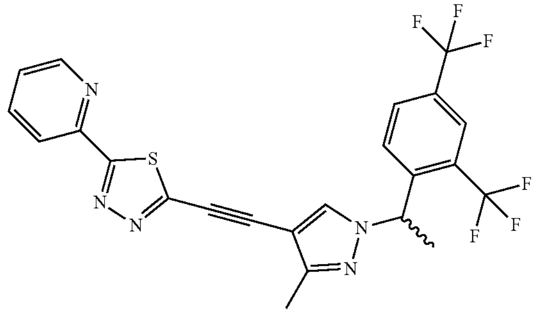 Isomer B of compound 2-11 | 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole |

In some embodiments, provided herein are compounds described in Table 1-2, or a pharmaceutically acceptable salt thereof, and uses thereof.

The embodiments and variations described herein are suitable for compounds of any formulae detailed herein, where applicable.

Provided herein is a compound selected from the group consisting of:

2-((1-(1-(2,4-bis(trifluoromethyl)phenyl)ethyl)-1H-pyrazol-4-yl)ethynyl)-5-(pyridin-2-yl)-1,3,4-thiadiazole;

2-((1-(2,4-bis(trifluoromethyl)benzyl)-1H-pyrazol-4-yl)ethynyl)-5-(pyridin-2-yl)-1,3,4-thiadiazole;

(E)-2-(2-(1-(1-(2,4-bis(trifluoromethyl)phenyl)ethyl)-1H-pyrazol-4-yl)vinyl)-5-(pyridin-2-yl)-1,3,4-thiadiazole;

(Z)-2-(2-(1-(1-(2,4-bis(trifluoromethyl)phenyl)ethyl)-1H-pyrazol-4-yl)vinyl)-5-(pyridin-2-yl)-1,3,4-thiadiazole;

2-(2-(1-(1-(2,4-bis(trifluoromethyl)phenyl)ethyl)-1H-pyrazol-4-yl)ethyl)-5-(pyridin-2-yl)-1,3,4-thiadiazole;

2-((1-(1-(2,4-bis(trifluoromethyl)phenyl)ethyl)-1H-pyrazol-4-yl)ethynyl)-5-(pyrazin-2-yl)-1,3,4-thiadiazole;

2-((1-(1-(2,4-bis(trifluoromethyl)phenyl)ethyl)-3-methyl-1H-pyrazol-4-yl)ethynyl)-5-(pyridin-2-yl)-1,3,4-thiadiazole;

2-((1-(1-(2,6-dichlorophenyl)ethyl)-1H-pyrazol-4-yl)ethynyl)-5-(furan-2-yl)-1,3,4-thiadiazole;

2-((1-(1-(2,6-dichlorophenyl)ethyl)-3-methyl-1H-pyrazol-4-yl)ethynyl)-5-(furan-2-yl)-1,3,4-thiadiazole;

3-((1-(1-(2,6-dichlorophenyl)ethyl)-1H-pyrazol-4-yl)ethynyl)-5-(furan-2-yl)isoxazole;

3-((1-(1-(2,6-dichlorophenyl)ethyl)-1H-pyrazol-4-yl)ethynyl)-5-(pyridin-2-yl)isoxazole;

3-((1-(1-(2,6-dichlorophenyl)ethyl)-1H-pyrazol-4-yl)ethynyl)-5-(pyrazin-2-yl)isoxazole;

3-((1-(1-(2-chloro-6-fluorophenyl)ethyl)-1H-pyrazol-4-yl)ethynyl)-5-(furan-2-yl)isoxazole;

3-((1-(1-(2-chloro-6-fluorophenyl)ethyl)-1H-pyrazol-4-yl)ethynyl)-5-(pyridin-2-yl)isoxazole;

3-((1-(1-(2-chloro-6-fluorophenyl)ethyl)-1H-pyrazol-4-yl)ethynyl)-5-(pyrazin-2-yl)isoxazole;

and 2-((1-(1-(2,6-dichlorophenyl)ethyl)-1H-pyrazol-4-yl)ethynyl)-5-(pyridin-2-yl)-1,3,4-thiadiazole, or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, or mixtures thereof in any ratio, including racemic mixtures.

Formula (I-2)

In one aspect, provided is a compound of the formula (I-2):

(I-2)

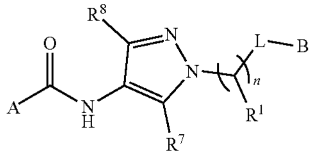

$R^1$ is H, $C_1$-$C_6$alkyl, $C_3$-$C_8$cycloalkyl, or $C_1$-$C_6$ haloalkyl;

n is 0 or 1;

L is —$CH_2$— or is absent;

B is $C_3$-$C_6$cycloalkyl, 3-6 membered heterocyclyl, or 5-6 membered heteroaryl, wherein the $C_3$-$C_6$cycloalkyl and 5-6 membered heteroaryl are each independently optionally substituted with one or more groups selected from the group consisting of halo, CN, —OH, —$NH_2$, $C_{1-6}$alkyl, $C_{1-6}$alkoxy and $C_1$-$C_6$ haloalkyl;

A is

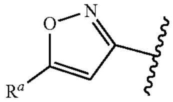

,

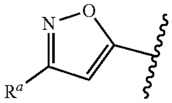

, or

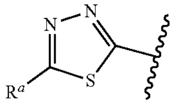

;

$R^a$ is 5- or 6-membered heteroaryl optionally substituted with one to four halo;

provided that, when A is

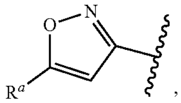

, one of (i.)-(vii.) applies:

(i) B is $C_3$-$C_6$cycloalkyl, optionally substituted with one or more groups selected from the group consisting of halo, CN, —OH, —$NH_2$, $C_{1-6}$alkyl, $C_{1-6}$alkoxy and $C_1$-$C_6$ haloalkyl;

(ii) B is 3-6 membered heterocyclyl having one or more annular heteroatoms, wherein the 3-6 membered heterocyclyl is optionally substituted with one or more groups selected from the group consisting of halo, CN, —OH, —$NH_2$, $C_{1-6}$alkoxy and $C_1$-$C_6$ haloalkyl, and wherein the one or more annular heteroatoms are nitrogen;

(iii) B is

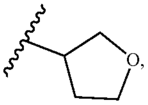

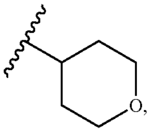

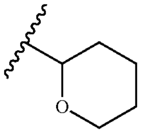

or

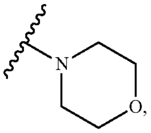

each of which is optionally substituted with one or more groups selected from the group consisting of halo, CN, —OH, —$NH_2$, $C_{1-6}$alkyl, $C_{1-6}$alkoxy and $C_1$-$C_6$ haloalkyl, n is 1, $R^1$ is $CH_3$, and L is absent;

(iv) B is

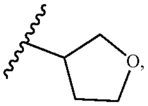

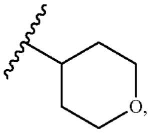

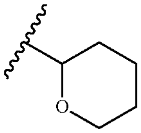

or

-continued

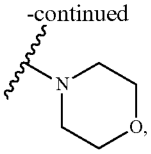

each of which is substituted with one or more groups selected from the group consisting of halo, CN, —OH, —$NH_2$, $C_{1-6}$alkyl, $C_{1-6}$alkoxy and $C_1$-$C_6$ haloalkyl;

(v) B is

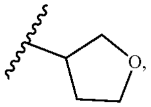

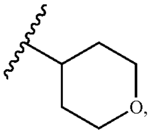

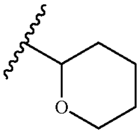

or

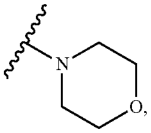

each of which is optionally substituted with one or more groups selected from the group consisting of halo, CN, —OH, —$NH_2$, $C_{1-6}$alkyl, $C_{1-6}$alkoxy and $C_1$-$C_6$ haloalkyl, and $R^a$ is

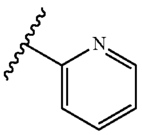

,

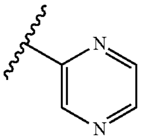

, or

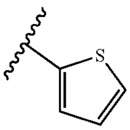

, each of which optionally substituted with one to four halo;

(vi) B is 4-6 membered bridged heterocyclyl, optionally substituted with one or more groups selected from the group consisting of halo, CN, —OH, —$NH_2$, $C_{1-6}$alkyl, $C_{1-6}$alkoxy and $C_1$-$C_6$ haloalkyl;

or (vii) B is 5-membered heteroaryl or

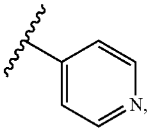

each of which is optionally substituted with one or more groups selected from the group consisting of halo, CN, —OH, —$NH_2$, $C_{1-6}$alkyl, $C_{1-6}$alkoxy and $C_1$-$C_6$ haloalkyl;

$R^7$ is H, $C_1$-$C_6$alkyl or or $C_1$-$C_6$haloalkyl; and $R^8$ is H or $C_1$-$C_6$alkyl.

In some embodiments, the pharmaceutically acceptable salt of the compound of formula (I-2) is a hydrochloride salt. In some embodiments, the pharmaceutically acceptable salt of the compound of formula (I-2) is an acetate salt.

In one variation is provided a compound of the formula (I-2), or a salt thereof, wherein the carbon bearing $R^1$ when $R^1$ is other than H (i.e., $C_1$-$C_6$alkyl, $C_3$-$C_8$cycloalkyl or $C_1$-$C_6$haloalkyl), is in the "S" configuration. In another variation is provided a compound of the formula (I-2), or a salt thereof, wherein the carbon bearing $R^1$ when $R^1$ is other than H (i.e., $C_1$-$C_6$alkyl, $C_3$-$C_8$cycloalkyl or $C_1$-$C_6$haloalkyl), is in the "R" configuration. Mixtures of a compound of the formula (I-2) are also embraced, including racemic or non-racemic mixtures of a given compound, and mixtures of two or more compounds of different chemical formulae.

It is also understood that the descriptions of any variable of formula (I-2) may, where applicable, be combined with one or more descriptions of any other variable, the same as if each and every combination of variables were specifically and individually listed. For example, every description of $R^1$ may be combined with every description of A the same as if each and every combination were specifically and individually listed. Likewise, every description of $R^1$ may be combined with every description of A, $R^7$ and $R^8$ the same as if each and every description were specifically and individually listed.

In some embodiments of a compound of formula (I-2), B is $C_3$-$C_6$cycloalkyl. In other embodiments of a compound of formula (I-2), B is 3-6 membered heterocyclyl. In still other embodiments of a compound of formula (I-2), B is 5-6 membered heteroaryl. In certain embodiments of a compound of formula (I-2), B is unsubstituted. In other embodiments of a compound of formula (I-2), B is substituted with one or more groups. In certain embodiments of a compound of formula (I-2), B is substituted with one or more groups selected from the group consisting of halo, CN, —OH, —$NH_2$, $C_{1-6}$alkyl, $C_{1-6}$alkoxy and $C_1$-$C_6$ haloalkyl. In some embodiments, B is $C_3$-$C_6$cycloalkyl unsubstituted or substituted with one or more groups selected from the group consisting of halo, CN, —OH, —$NH_2$, $C_{1-6}$alkyl, $C_{1-6}$alkoxy and $C_1$-$C_6$ haloalkyl. In some embodiments, B is 5-6 membered heteroaryl unsubstituted or substituted with one or more groups selected from the group consisting of halo, CN, —OH, —$NH_2$, $C_{1-6}$alkoxy and $C_1$-$C_6$ haloalkyl. In certain embodiments, B is not

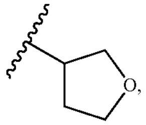 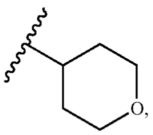 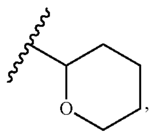 , or

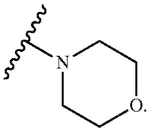

In some embodiments, B is $C_3$-$C_6$cycloalkyl, optionally substituted with one or more groups selected from the group consisting of halo, CN, —OH, —$NH_2$, $C_{1-6}$alkyl, $C_{1-6}$alkoxy and $C_1$-$C_6$ haloalkyl. In some embodiments, B is 3-6 membered heterocyclyl having one or more annular heteroatoms, wherein the 3-6 membered heterocyclyl is optionally substituted with one or more groups selected from the group consisting of halo, CN, —OH, —$NH_2$, $C_{1-6}$alkoxy and $C_1$-$C_6$ haloalkyl, and wherein the one or more annular heteroatoms are nitrogen. In some embodiments, B is

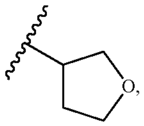 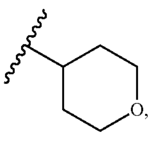 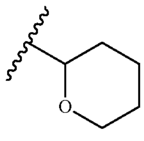 or

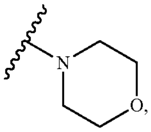

each of which is optionally substituted with one or more groups selected from the group consisting of halo, CN, —OH, —$NH_2$, $C_{1-6}$alkyl, $C_{1-6}$alkoxy and $C_1$-$C_6$ haloalkyl, n is 1, $R^1$ is $CH_3$, and L is absent. In some embodiments, (iv) B is

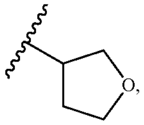 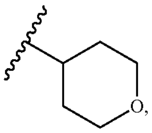 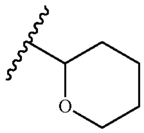 or

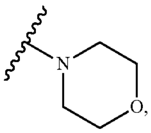

each of which is substituted with one or more groups selected from the group consisting of halo, CN, —OH, —$NH_2$, $C_{1-6}$alkyl, $C_{1-6}$alkoxy and $C_1$-$C_6$ haloalkyl. In some embodiments, B is

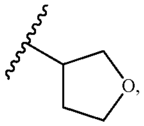 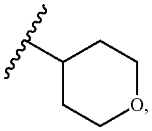 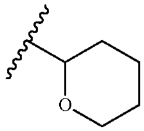 or

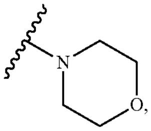

each of which is optionally substituted with one or more groups selected from the group consisting of halo, CN, —OH, —$NH_2$, $C_{1-6}$alkyl, $C_{1-6}$alkoxy and $C_1$-$C_6$ haloalkyl, and $R^a$ is

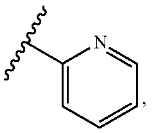 , 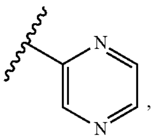 , or 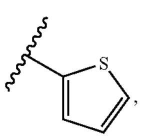 , each of which optionally substituted with one to four halo. In some embodiments, B is 4-6 membered bridged heterocyclyl, optionally substituted with one or more groups selected from the group consisting of halo, CN, —OH, —$NH_2$, $C_{1-6}$alkyl, $C_{1-6}$alkoxy and $C_1$-$C_6$ haloalkyl. In some embodiments, B is 5-membered heteroaryl or

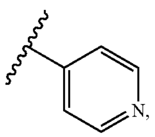 [SMILES: *c1ccncc1]

each of which is optionally substituted with one or more groups selected from the group consisting of halo, CN, —OH, —$NH_2$, $C_{1-6}$alkyl, $C_{1-6}$alkoxy and $C_1$-$C_6$ haloalkyl.

In some embodiments of a compound of formula (I-2), n is 1 and $R^1$ is H. In some embodiments, n is 1 and $R^1$ is $C_1$-$C_6$alkyl. In other embodiments, n is 1 and $R^1$ is $C_3$-$C_8$cycloalkyl. In some embodiments, n is 1 and $R^1$ is $C_1$-$C_6$haloalkyl. In certain embodiments, n is 1 and $R^1$ is methyl, ethyl, n-propyl, isopropyl, n-butyl, isobutyl, sec-butyl, or tert-butyl. In some embodiments, n is 1 and $R^1$ methyl. In some embodiments, n is 1 and $R^1$ ethyl. In some embodiments, n is 1 and $R^1$ cyclopropyl, cyclobutyl, cyclopentyl, or cyclohexyl. In some embodiments, n is 1 and $R^1$ is cyclopropyl. In some embodiments of a compound of formula (I-2), n is 0.

In some embodiments of a compound of formula (I-2), L is absent. In other embodiments, L is —$CH_2$—.

In some embodiments, n is 1, L is absent, and $R^1$ is H. In some embodiments, n is 1, L is absent, and $R^1$ is $C_1$-$C_6$alkyl. In other embodiments, n is 1, L is absent, and $R^1$ is $C_3$-$C_8$cycloalkyl. In some embodiments, n is 1, L is absent, and $R^1$ is $C_1$-$C_6$haloalkyl. In certain embodiments, n is 1, L is absent, and $R^1$ is methyl, ethyl, n-propyl, isopropyl, n-butyl, isobutyl, sec-butyl, or tert-butyl. In some embodiments, n is 1, L is absent, and $R^1$ is methyl. In some embodiments, n is 1, L is absent, and $R^1$ is ethyl. In some embodiments, n is 1, L is absent, and $R^1$ is cyclopropyl, cyclobutyl, cyclopentyl, or cyclohexyl. In some embodiments, n is 1, L is absent, and $R^1$ is cyclopropyl.

In some embodiments of a compound of formula (I-2), n is 0 and L is absent.

In some embodiments of a compound of formula (I-2), n is 1, L is —$CH_2$—, and $R^1$ is H. In some embodiments, n is 1, L is —$CH_2$—, and $R^1$ is $C_1$-$C_6$alkyl. In other embodiments, n is 1, L is —$CH_2$—, and $R^1$ is $C_3$-$C_8$cycloalkyl. In some embodiments, n is 1, L is is —$CH_2$—, and $R^1$ is $C_1$-$C_6$haloalkyl. In certain embodiments, n is 1, L is —$CH_2$—, and $R^1$ is methyl, ethyl, n-propyl, isopropyl, n-butyl, isobutyl, sec-butyl, or tert-butyl. In some embodiments, n is 1, L is —$CH_2$—, and $R^1$ methyl. In some embodiments, n is 1, L is —$CH_2$—, and $R^1$ ethyl. In some embodiments, n is 1, L is —$CH_2$—, and $R^1$ is cyclopropyl, cyclobutyl, cyclopentyl, or cyclohexyl. In some embodiments, n is 1, L is —$CH_2$—, and $R^1$ is cyclopropyl.

In some embodiments of a compound of formula (I-2), n is 0 and L is —$CH_2$—.

In some embodiments of a compound of formula (I-2), $R^a$ is 5- or 6-membered heteroaryl. In some embodiments, $R^a$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each of which is unsubstituted or is substituted with one to four groups selected from the group consisting of OH, halo, $C_1$-$C_6$alkyl, and $C_1$-$C_6$akloxy. In some embodiments, $R^a$ is selected from the group consisting of 2-furyl, 2-pyridinyl, 2-pyrimidinyl, 4-pyrimidinyl, and 2-pyrazinyl.

In some embodiments, provided is a compound of the formula (I-2) wherein A is

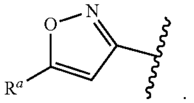

In some embodiments, provided is a compound of the formula (I-2) wherein A is

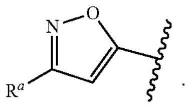

In some embodiments, provided is a compound of the formula (I-2) wherein A is

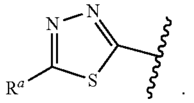

In some embodiments of a compound of formula (I-2), A is

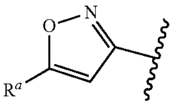

and $R^a$ is a 5- or 6-membered heteroaryl. In some embodiments, A is

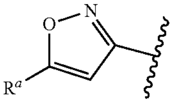

and $R^a$ is 2-furyl, 2-pyridinyl, 2-pyrimidinyl, 4-pyrimidinyl, or 2-pyrazinyl. In some embodiments, A is

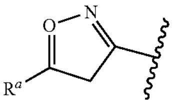

and $R^a$ is 2-furyl. In some embodiments, A is

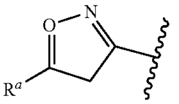

and $R^a$ is 2-pyridinyl. In other embodiments, A is

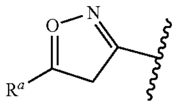

and $R^a$ is 2-pyrazinyl. In other embodiments, A is

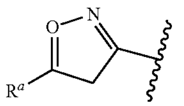

and $R^a$ is 2-pyrimidinyl. In still other embodiments, A is

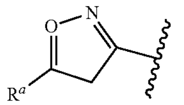

and $R^a$ is 4-pyrimidinyl.

In some embodiments of a compound of formula (I-2), A is

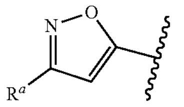

and $R^a$ is a 5- or 6-membered heteroaryl. In some embodiments, A is

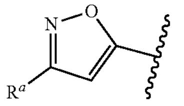

and $R^a$ is 2-furyl, 2-pyridinyl, 2-pyrimidinyl, 4-pyrimidinyl, or 2-pyrazinyl. In some embodiments, A is

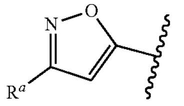

and $R^a$ is 2-furyl. In some embodiments, A is

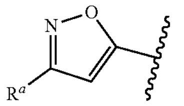

and $R^a$ is 2-pyridinyl.

In other embodiments, A is

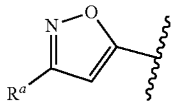

and $R^a$ is 2-pyrazinyl. In other embodiments, A is

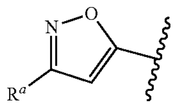

and $R^a$ is 2-pyrimidinyl. In still other embodiments, A is

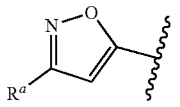

and $R^a$ is 4-pyrimidinyl.

In some embodiments of a compound of formula (I-2), A is

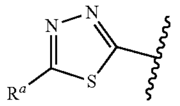

and $R^a$ is a 5- or 6-membered heteroaryl. In some embodiments, A is

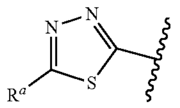

and $R^a$ is 2-furyl, 2-pyridinyl, 2-pyrimidinyl, 4-pyrimidinyl, or 2-pyrazinyl. In some embodiments, A is

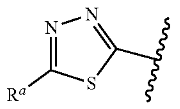

and $R^a$ is 2-furyl. In some embodiments, A is

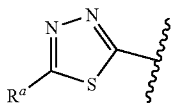

and $R^a$ is 2-pyridinyl. In other embodiments, A is

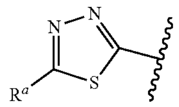

and $R^a$ is 2-pyrazinyl. In other embodiments, A is

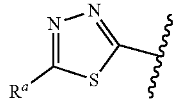

and $R^a$ is 2-pyrimidinyl. In still other embodiments, A is

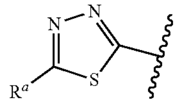

and $R^a$ is 4-pyrimidinyl.

In some embodiments of a compound of formula (I-2), A is

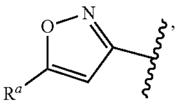, 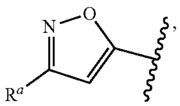, or 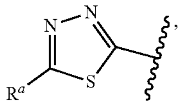, and B is $C_3$-$C_6$cycloalkyl. In other embodiments of a compound of formula (I-2), A is

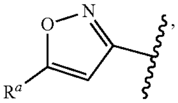, 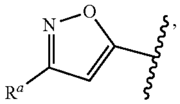, or 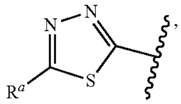, and B is 3-6 membered heterocyclyl. In still other embodiments of a compound of formula (I-2), A is

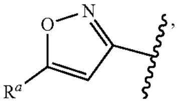, 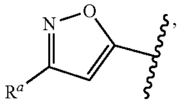, or 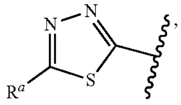, and B is 5-6 membered heteroaryl. In certain embodiments of a compound of formula (I-2), A is

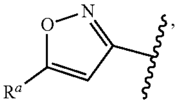, 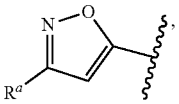, or 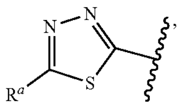, and B is unsubstituted. In some embodiments, A is

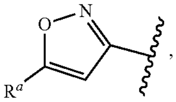, 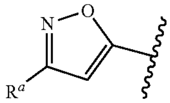, or 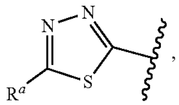, and B is $C_3$-$C_6$cycloalkyl unsubstituted or substituted with one or more groups selected from the group consisting of halo, CN, —OH, —$NH_2$, $C_{1-6}$alkoxy and $C_1$-$C_6$ haloalkyl. In some embodiments, A is

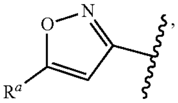, 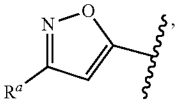, or 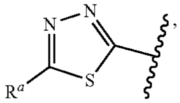, and B is 5-6 membered heteroaryl unsubstituted or substituted with one or more groups selected from the group consisting of halo, CN, —OH, —$NH_2$, $C_{1-6}$alkyl, $C_{1-6}$alkoxy and $C_1$-$C_6$ haloalkyl. In certain embodiments, A is

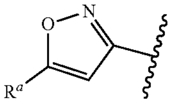

and B is not

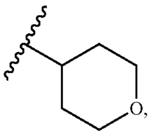, 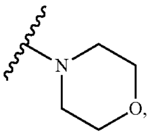,

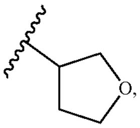, or 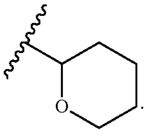.

In some embodiments of a compound of formula (I-2), $R^7$ is H. In some embodiments, $R^7$ is $C_1$-$C_6$alkyl. In some embodiments, $R^7$ is $C_1$-$C_6$haloalkyl. In some embodiments, $R^7$ is methyl, ethyl, n-propyl, isopropyl, n-butyl, isobutyl, sec-butyl, or tert-butyl. In certain embodiments, $R^7$ is methyl.

In some embodiments of a compound of formula (I-2), $R^8$ is H. In some embodiments, $R^8$ is $C_1$-$C_6$alkyl. In some embodiments, $R^8$ is methyl, ethyl, n-propyl, isopropyl, n-butyl, isobutyl, sec-butyl, or tert-butyl. In certain embodiments, $R^8$ is methyl.

In some embodiments of a compound of formula (I-2), $R^7$ and $R^8$ are both H. In some embodiments, $R^8$ is $C_1$-$C_6$alkyl and $R^7$ is H. In other embodiments, $R^8$ is H and $R^7$ is $C_1$-$C_6$alkyl. In some embodiments, $R^8$ and $R^7$ are $C_1$-$C_6$alkyl. In certain embodiments, $R^8$ is methyl and $R^7$ is H. In other embodiments, $R^8$ is H and $R^7$ is methyl. In some embodiments, $R^8$ and $R^7$ are H.

In some embodiments of any of the formulae provided herein, $R^8$ and $R^7$ are H, A is

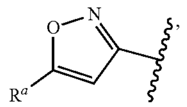

$R^a$ is 2-furyl, $R^1$ is methyl, L is absent. In some embodiments of any of the formulae provided herein, $R^8$ is methyl, $R^7$ is H, A is

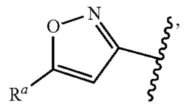

$R^a$ is 2-furyl, $R^1$ is methyl, L is absent. In some embodiments of any of the formulae provided herein, $R^8$ is H, $R^7$ is methyl, A is

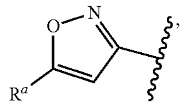

$R^a$ is 2-furyl, $R^1$ is methyl, L is absent.

In some embodiments of any of the formulae provided herein, $R^8$ and $R^7$ are H, A is

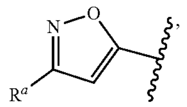

$R^a$ is 2-furyl, $R^1$ is methyl, L is absent. In some embodiments of any of the formulae provided herein, $R^8$ is methyl, $R^7$ is H, A is

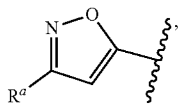

$R^a$ is 2-furyl, $R^1$ is methyl, L is absent. In some embodiments of any of the formulae provided herein, $R^8$ is H, $R^7$ is methyl, A is

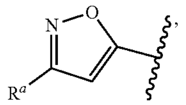

$R^a$ is 2-furyl, $R^1$ is methyl, L is absent.

In some embodiments of any of the formulae provided herein, $R^8$ and $R^7$ are H, A is

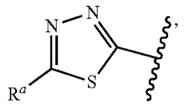

$R^a$ is 2-furyl, $R^1$ is methyl, L is absent. In some embodiments of any of the formulae provided herein, $R^8$ is methyl, $R^7$ is H, A is

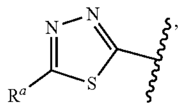

$R^a$ is 2-furyl, $R^1$ is methyl, L is absent. In some embodiments of any of the formulae provided herein, $R^8$ is H, $R^7$ is methyl, A is

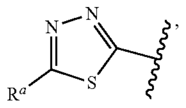

$R^a$ is 2-furyl, $R^1$ is methyl, L is absent.

Representative compounds are listed in Table 1-3.

TABLE 1-3

| Cmpd No. | Structure | Chemical Name |
|---|---|---|
| 3-1 | 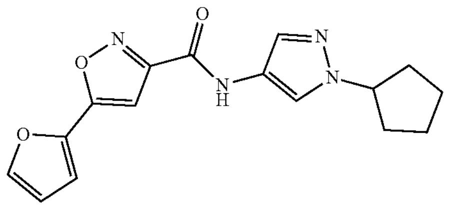 [SMILES: O=C(Nc1cnn(C2CCCC2)c1)c1cc(-c2ccco2)on1] | N-(1-cyclopentyl-1H-pyrazol-4-yl)-5-(furan-2-yl)isoxazole-3-carboxamide |

TABLE 1-3-continued

| Cmpd No. | Structure | Chemical Name |
|---|---|---|
| 3-2 | 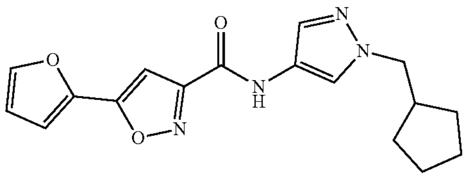 [SMILES: O=C(Nc1cnn(CC2CCCC2)c1)c1cc(-c2ccco2)on1] | N-(1-(cyclopentylmethyl)-1H-pyrazol-4-yl)-5-(furan-2-yl)isoxazole-3-carboxamide |
| 3-3 | 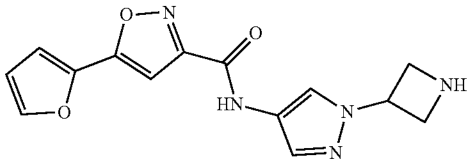 [SMILES: O=C(Nc1cnn(C2CNC2)c1)c1cc(-c2ccco2)on1] | N-(1-(azetidin-3-yl)-1H-pyrazol-4-yl)-5-(furan-2-yl)isoxazole-3-carboxamide |
| 3-4 | 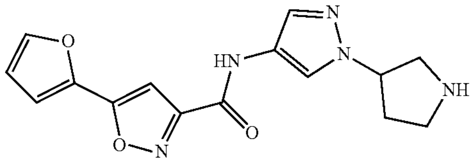 [SMILES: O=C(Nc1cnn(C2CCNC2)c1)c1cc(-c2ccco2)on1] | 5-(furan-2-yl)-N-(1-(pyrrolidin-3-yl)-1H-pyrazol-4-yl)isoxazole-3-carboxamide |
| 3-5 | 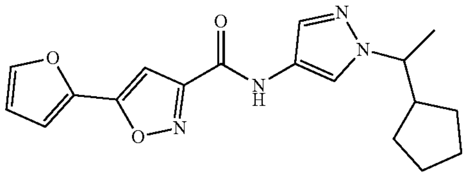 [SMILES: CC(C1CCCC1)n1cc(NC(=O)c2cc(-c3ccco3)on2)cn1] | N-(1-(1-cyclopentylethyl)-1H-pyrazol-4-yl)-5-(furan-2-yl)isoxazole-3-carboxamide |
| 3-6 | 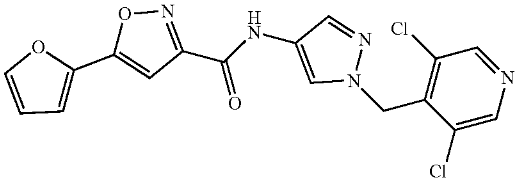 [SMILES: O=C(Nc1cnn(Cc2c(Cl)cncc2Cl)c1)c1cc(-c2ccco2)on1] | N-(1-((3,5-dichloropyridin-4-yl)methyl)-1H-pyrazol-4-yl)-5-(furan-2-yl)isoxazole-3-carboxamide |
| 3-7 | 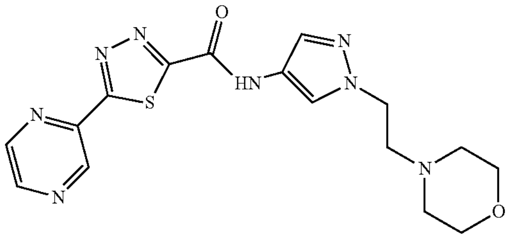 [SMILES: O=C(Nc1cnn(CCN2CCOCC2)c1)c1nnc(-c2cnccn2)s1] | N-(1-(2-morpholinoethyl)-1H-pyrazol-4-yl)-5-(pyrazin-2-yl)-1,3,4-thiadiazole-2-carboxamide |
| 3-8 | 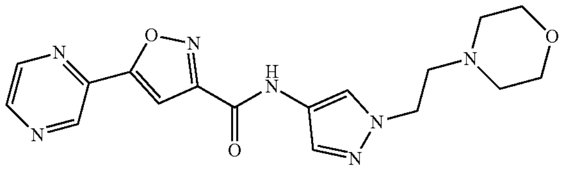 [SMILES: O=C(Nc1cnn(CCN2CCOCC2)c1)c1cc(-c2cnccn2)on1] | N-(1-(2-morpholinoethyl)-1H-pyrazol-4-yl)-5-(pyrazin-2-yl)isoxazole-3-carboxamide |

TABLE 1-3-continued

| Cmpd No. | Structure | Chemical Name |
|---|---|---|
| 3-9 | 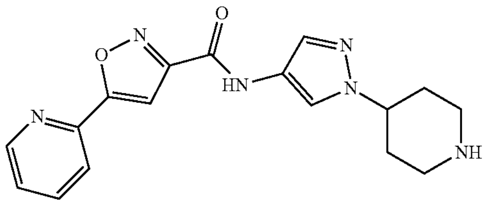 [SMILES: O=C(Nc1cnn(C2CCNCC2)c1)c1cc(-c2ccccn2)on1] | N-(1-(piperidin-4-yl)-1H-pyrazol-4-yl)-5-(pyridin-2-yl)isoxazole-3-carboxamide |
| 3-10 | 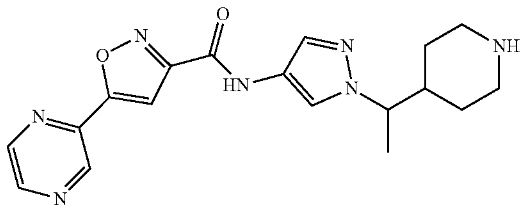 [SMILES: CC(C1CCNCC1)n1cc(NC(=O)c2cc(-c3cnccn3)on2)cn1] | N-(1-(1-(piperidin-4-yl)ethyl)-1H-pyrazol-4-yl)-5-(pyrazin-2-yl)isoxazole-3-carboxamide |
| 3-11 | 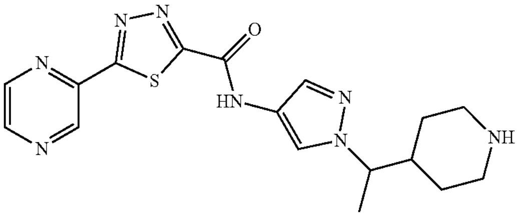 [SMILES: CC(C1CCNCC1)n1cc(NC(=O)c2nnc(-c3cnccn3)s2)cn1] | N-(1-(1-(piperidin-4-yl)ethyl)-1H-pyrazol-4-yl)-5-(pyrazin-2-yl)-1,3,4-thiadiazole-2-carboxamide |
| 3-12 | 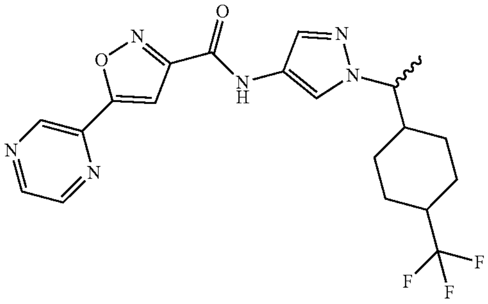 [SMILES: CC(C1CCC(C(F)(F)F)CC1)n1cc(NC(=O)c2cc(-c3cnccn3)on2)cn1] | 5-(pyrazin-2-yl)-N-(1-(1-(4-(trifluoromethyl)cyclohexyl)ethyl)-1H-pyrazol-4-yl)isoxazole-3-carboxamide |
| 3-13 | 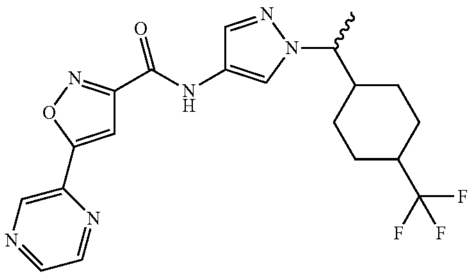 Isomer of compound 3-12 | 5-(pyrazin-2-yl)-N-(1-(1-(4-(trifluoromethyl)cyclohexyl)ethyl)-1H-pyrazol-4-yl)isoxazole-3-carboxamide |
| 3-14 | 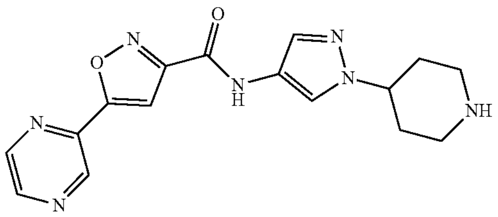 [SMILES: O=C(Nc1cnn(C2CCNCC2)c1)c1cc(-c2cnccn2)on1] | N-(1-(piperidin-4-yl)-1H-pyrazol-4-yl)-5-(pyrazin-2-yl)isoxazole-3-carboxamide |

TABLE 1-3-continued

| Cmpd No. | Structure | Chemical Name |
|---|---|---|
| 3-15 | 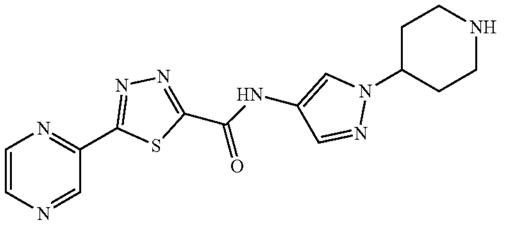 [SMILES: O=C(Nc1cnn(C2CCNCC2)c1)c1nnc(-c2cnccn2)s1] | N-(1-(piperidin-4-yl)-1H-pyrazol-4-yl)-5-(pyrazin-2-yl)-1,3,4-thiadiazole-2-carboxamide |
| 3-16 | 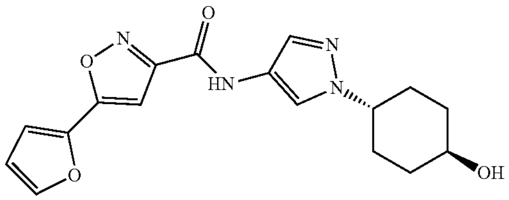 [SMILES: O=C(Nc1cnn([C@H]2CC[C@H](O)CC2)c1)c1cc(-c2ccco2)on1] | 5-(furan-2-yl)-N-(1-(trans-4-hydroxycyclohexyl)-1H-pyrazol-4-yl)isoxazole-3-carboxamide |
| 3-17 | 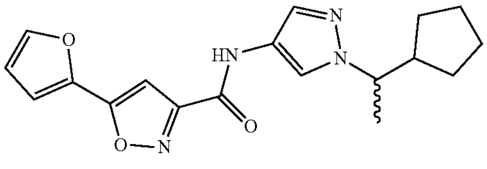 Isomer A of compound 3-5 | N-(1-(1-cyclopentylethyl)-1H-pyrazol-4-yl)-5-(furan-2-yl)isoxazole-3-carboxamide |
| 3-18 | 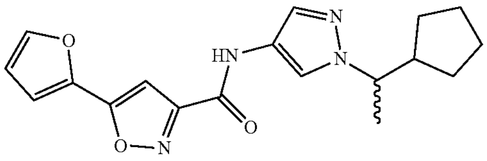 Isomer B of compound 3-5 | N-(1-(1-cyclopentylethyl)-1H-pyrazol-4-yl)-5-(furan-2-yl)isoxazole-3-carboxamide |
| 3-19 | 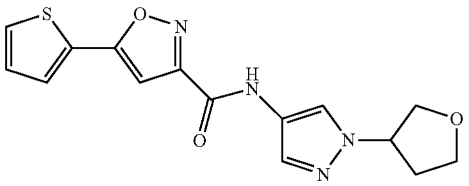 [SMILES: O=C(Nc1cnn(C2CCOC2)c1)c1cc(-c2cccs2)on1] | N-(1-(tetrahydrofuran-3-yl)-1H-pyrazol-4-yl)-5-(thiophen-2-yl)isoxazole-3-carboxamide |
| 3-20 | 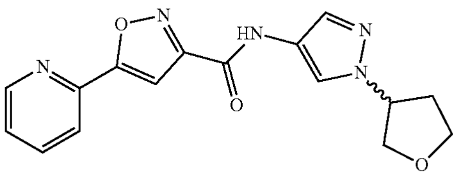 | 5-(pyridin-2-yl)-N-(1-(tetrahydrofuran-3-yl)-1H-pyrazol-4-yl)isoxazole-3-carboxamide |
| 3-21 | 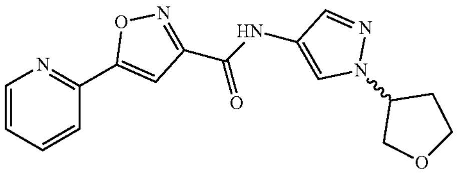 [SMILES: O=C(Nc1cnn(C2CCOC2)c1)c1cc(-c2ccccn2)on1] Isomer of compound 3-20 | 5-(pyridin-2-yl)-N-(1-(tetrahydrofuran-3-yl)-1H-pyrazol-4-yl)isoxazole-3-carboxamide |

TABLE 1-3-continued

| Cmpd No. | Structure | Chemical Name |
|---|---|---|
| 3-22 | 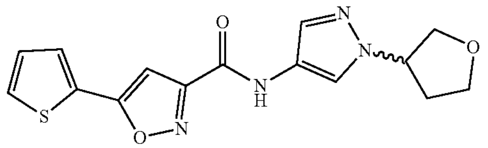 Isomer A of compound 3-19 | N-(1-(tetrahydrofuran-3-yl)-1H-pyrazol-4-yl)-5-(thiophen-2-yl)isoxazole-3-carboxamide |
| 3-23 | 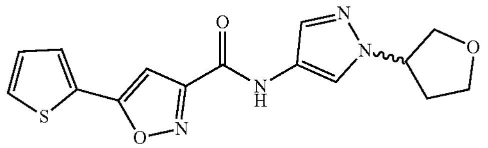 Isomer B of compound 3-19 | N-(1-(tetrahydrofuran-3-yl)-1H-pyrazol-4-yl)-5-(thiophen-2-yl)isoxazole-3-carboxamide |
| 3-24 | 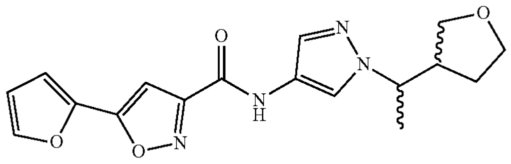 | 5-(furan-2-yl)-N-(1-(1-(tetrahydrofuran-3-yl)ethyl)-1H-pyrazol-4-yl)isoxazole-3-carboxamide |
| 3-25 | 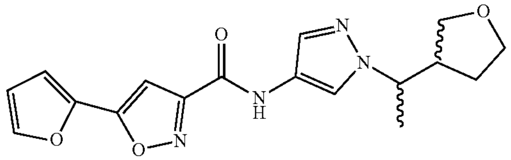 [SMILES: CC(C1CCOC1)n1cc(NC(=O)c2cc(-c3ccco3)on2)cn1] Isomer A of compound 3-24 | 5-(furan-2-yl)-N-(1-(1-(tetrahydrofuran-3-yl)ethyl)-1H-pyrazol-4-yl)isoxazole-3-carboxamide |
| 3-26 | 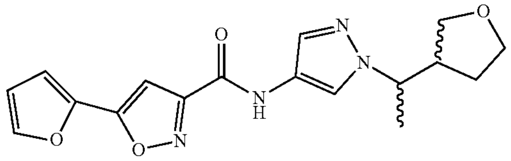 Isomer B of compound 3-24 | 5-(furan-2-yl)-N-(1-(1-(tetrahydrofuran-3-yl)ethyl)-1H-pyrazol-4-yl)isoxazole-3-carboxamide |
| 3-27 | 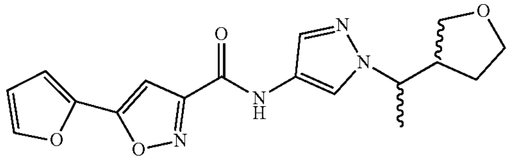 Isomer C of compound 3-24 | 5-(furan-2-yl)-N-(1-(1-(tetrahydrofuran-3-yl)ethyl)-1H-pyrazol-4-yl)isoxazole-3-carboxamide |
| 3-28 | 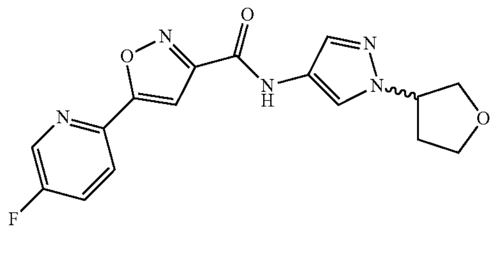 [SMILES: O=C(Nc1cnn(C2CCOC2)c1)c1cc(-c2ccc(F)cn2)on1] | 5-(5-fluoropyridin-2-yl)-N-(1-(tetrahydrofuran-3-yl)-1H-pyrazol-4-yl)isoxazole-3-carboxamide |

TABLE 1-3-continued

| Cmpd No. | Structure | Chemical Name |
|---|---|---|
| 3-29 | 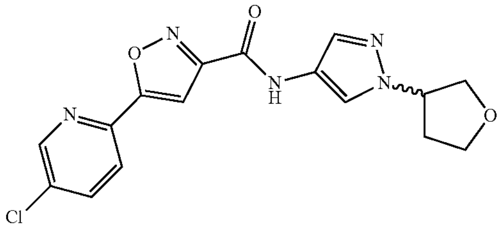 [SMILES: O=C(Nc1cnn(C2CCOC2)c1)c1cc(-c2ccc(Cl)cn2)on1] | 5-(5-chloropyridin-2-yl)-N-(1-(tetrahydrofuran-3-yl)-1H-pyrazol-4-yl)isoxazole-3-carboxamide |
| 3-30 | 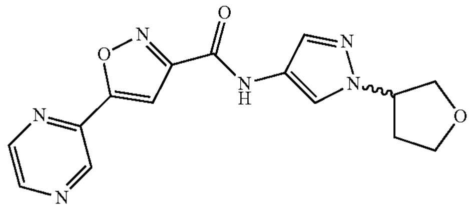 [SMILES: O=C(Nc1cnn(C2CCOC2)c1)c1cc(-c2cnccn2)on1] | 5-(pyrazin-2-yl)-N-(1-(tetrahydrofuran-3-yl)-1H-pyrazol-4-yl)isoxazole-3-carboxamide |
| 3-31 | 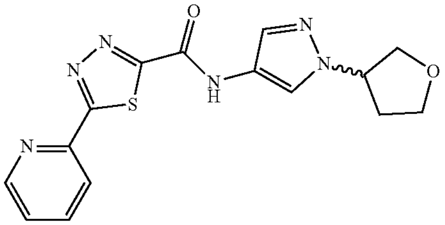 [SMILES: O=C(Nc1cnn(C2CCOC2)c1)c1nnc(-c2ccccn2)s1] | 5-(pyridin-2-yl)-N-(1-(tetrahydrofuran-3-yl)-1H-pyrazol-4-yl)-1,3,4-thiadiazole-2-carboxamide |
| 3-32 | 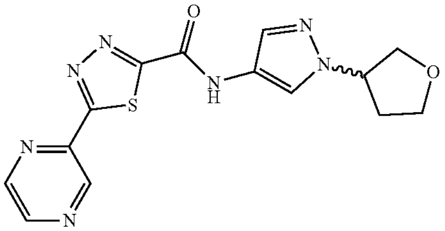 [SMILES: O=C(Nc1cnn(C2CCOC2)c1)c1nnc(-c2cnccn2)s1] | 5-(pyrazin-2-yl)-N-(1-(tetrahydrofuran-3-yl)-1H-pyrazol-4-yl)-1,3,4-thiadiazole-2-carboxamide |
| 3-33 | 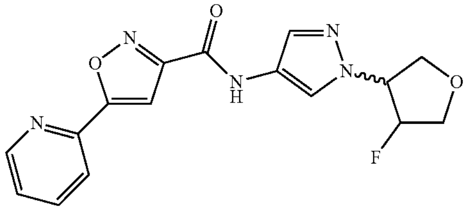 [SMILES: O=C(Nc1cnn(C2COCC2F)c1)c1cc(-c2ccccn2)on1] | N-(1-(4-fluorotetrahydrofuran-3-yl)-1H-pyrazol-4-yl)-5-(pyridin-2-yl)isoxazole-3-carboxamide |
| 3-34 | 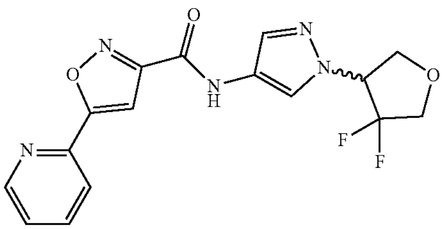 [SMILES: O=C(Nc1cnn(C2COCC2(F)F)c1)c1cc(-c2ccccn2)on1] | N-(1-(4,4-difluorotetrahydrofuran-3-yl)-1H-pyrazol-4-yl)-5-(pyridin-2-yl)isoxazole-3-carboxamide |

TABLE 1-3-continued

| Cmpd No. | Structure | Chemical Name |
|---|---|---|
| 3-35 | 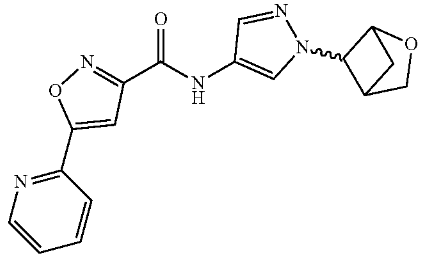 [SMILES: O=C(Nc1cnn(C2C3COC2C3)c1)c1cc(-c2ccccn2)on1] | N-(1-(2-oxabicyclo[2.1.1]hexan-5-yl)-1H-pyrazol-4-yl)-5-(pyridin-2-yl)isoxazole-3-carboxamide |
| 3-36 | 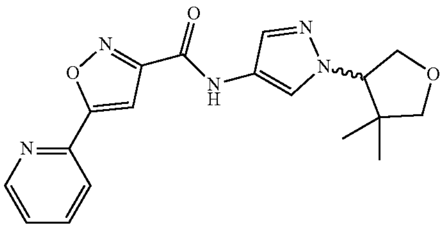 [SMILES: CC1(C)COCC1n1cc(NC(=O)c2cc(-c3ccccn3)on2)cn1] | N-(1-(4,4-dimethyltetrahydrofuran-3-yl)-1H-pyrazol-4-yl)-5-(pyridin-2-yl)isoxazole-3-carboxamide |

In some embodiments, provided herein are compounds described in Table 1-3, or a pharmaceutically acceptable salt thereof, and uses thereof. In certain variations, the pharmaceutically acceptable salt thereof is a hydrochloride salt. In one embodiment, the hydrochloride salt is N-(1-(azetidin-3-yl)-1H-pyrazol-4-yl)-5-(furan-2-yl)isoxazole-3-carboxamide hydrochloride. In another embodiment, the hydrochloride salt is 5-(furan-2-yl)-N-(1-(pyrrolidin-3-yl)-1H-pyrazol-4-yl)isoxazole-3-carboxamide hydrochloride. In one embodiment, the hydrochloride salt is N-(1-(piperidin-4-yl)-1H-pyrazol-4-yl)-5-(pyrazin-2-yl)isoxazole-3-carboxamide hydrochloride. In another embodiment, the hydrochloride salt is N-(1-(piperidin-4-yl)-1H-pyrazol-4-yl)-5-(pyridin-2-yl)isoxazole-3-carboxamide hydrochloride. In another embodiment, the hydrochloride salt is N-(1-(piperidin-4-yl)-1H-pyrazol-4-yl)-5-(pyrazin-2-yl)-1,3,4-thiadiazole-2-carboxamide hydrochloride. In other embodiments, the pharmaceutically acceptable salt thereof is an acetate salt. In one embodiment, the acetate salt is 5-(furan-2-yl)-N-(1-(pyrrolidin-3-yl)-1H-pyrazol-4-yl)isoxazole-3-carboxamide acetate. In another embodidment, the acetate salt is N-(1-(azetidin-3-yl)-1H-pyrazol-4-yl)-5-(furan-2-yl)isoxazole-3-carboxamide acetate. In some emboidments, the pharmaceutically acceptable salt thereof is a trifluoroacetate salt. In one embodiment, the trifluoroacetate salt is N-(1-(1-(piperidin-4-yl)ethyl)-1H-pyrazol-4-yl)-5-(pyrazin-2-yl)isoxazole-3-carboxamide trifluoroacetate. In another embodiment, the trifluoroacetate salt is N-(1-(1-(piperidin-4-yl)ethyl)-1H-pyrazol-4-yl)-5-(pyrazin-2-yl)-1,3,4-thiadiazole-2-carboxamide trifluoroacetate.

The embodiments and variations described herein are suitable for compounds of any formulae detailed herein, where applicable.

Provided herein is a compound selected from the group consisting of:

N-(1-cyclopentyl-1H-pyrazol-4-yl)-5-(furan-2-yl)isoxazole-3-carboxamide;
N-(1-(cyclopentylmethyl)-1H-pyrazol-4-yl)-5-(furan-2-yl)isoxazole-3-carboxamide;
N-(1-(azetidin-3-yl)-1H-pyrazol-4-yl)-5-(furan-2-yl)isoxazole-3-carboxamide;
5-(furan-2-yl)-N-(1-(pyrrolidin-3-yl)-1H-pyrazol-4-yl)isoxazole-3-carboxamide;
N-(1-(1-cyclopentylethyl)-1H-pyrazol-4-yl)-5-(furan-2-yl)isoxazole-3-carboxamide;
N-(1-((3,5-dichloropyridin-4-yl)methyl)-1H-pyrazol-4-yl)-5-(furan-2-yl)isoxazole-3-carboxamide;
N-(1-(2-morpholinoethyl)-1H-pyrazol-4-yl)-5-(pyrazin-2-yl)-1,3,4-thiadiazole-2-carboxamide;
N-(1-(2-morpholinoethyl)-1H-pyrazol-4-yl)-5-(pyrazin-2-yl)isoxazole-3-carboxamide;
N-(1-(piperidin-4-yl)-1H-pyrazol-4-yl)-5-(pyridin-2-yl)isoxazole-3-carboxamide;
N-(1-(1-(piperidin-4-yl)ethyl)-1H-pyrazol-4-yl)-5-(pyrazin-2-yl)isoxazole-3-carboxamide;
N-(1-(1-(piperidin-4-yl)ethyl)-1H-pyrazol-4-yl)-5-(pyrazin-2-yl)-1,3,4-thiadiazole-2-carboxamide;
5-(pyrazin-2-yl)-N-(1-(1-(4-(trifluoromethyl)cyclohexyl)ethyl)-1H-pyrazol-4-yl)isoxazole-3-carboxamide;
N-(1-(piperidin-4-yl)-1H-pyrazol-4-yl)-5-(pyrazin-2-yl)isoxazole-3-carboxamide;
N-(1-(piperidin-4-yl)-1H-pyrazol-4-yl)-5-(pyrazin-2-yl)-1,3,4-thiadiazole-2-carboxamide;
5-(furan-2-yl)-N-(1-(trans-4-hydroxycyclohexyl)-1H-pyrazol-4-yl)isoxazole-3-carboxamide;
N-(1-(tetrahydrofuran-3-yl)-1H-pyrazol-4-yl)-5-(thiophen-2-yl)isoxazole-3-carboxamide;
5-(pyridin-2-yl)-N-(1-(tetrahydrofuran-3-yl)-1H-pyrazol-4-yl)isoxazole-3-carboxamide;
5-(5-fluoropyridin-2-yl)-N-(1-(tetrahydrofuran-3-yl)-1H-pyrazol-4-yl)isoxazole-3-carboxamide;
5-(5-chloropyridin-2-yl)-N-(1-(tetrahydrofuran-3-yl)-1H-pyrazol-4-yl)isoxazole-3-carboxamide;
5-(pyrazin-2-yl)-N-(1-(tetrahydrofuran-3-yl)-1H-pyrazol-4-yl)isoxazole-3-carboxamide;
5-(pyridin-2-yl)-N-(1-(tetrahydrofuran-3-yl)-1H-pyrazol-4-yl)-1,3,4-thiadiazole-2-carboxamide;
5-(pyrazin-2-yl)-N-(1-(tetrahydrofuran-3-yl)-1H-pyrazol-4-yl)-1,3,4-thiadiazole-2-carboxamide;
N-(1-(4-fluorotetrahydrofuran-3-yl)-1H-pyrazol-4-yl)-5-(pyridin-2-yl)isoxazole-3-carboxamide;

N-(1-(4,4-difluorotetrahydrofuran-3-yl)-1H-pyrazol-4-yl)-5-(pyridin-2-yl)isoxazole-3-carboxamide;

N-(1-(2-oxabicyclo[2.1.1]hexan-5-yl)-1H-pyrazol-4-yl)-5-(pyridin-2-yl)isoxazole-3-carboxamide; and N-(1-(4,4-dimethyltetrahydrofuran-3-yl)-1H-pyrazol-4-yl)-5-(pyridin-2-yl)isoxazole-3-carboxamide, or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, or mixtures thereof in any ratio, including racemic mixtures.

All representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. Compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio, unless a specific stereochemistry is otherwise indicated. Where a compound of Table 1-2/1-3 is depicted with a particular stereochemical configuration, also provided herein is any alternative stereochemical configuration of the compound, as well as a mixture of stereoisomers of the compound in any ratio. For example, where a compound of any table has a stereocenter that is in an "S" stereochemical configuration, also provided herein is the enantiomer of the compound wherein that stereocenter is in an "R" stereochemical configuration. Likewise, when a compound of any table has a stereocenter that is in an "R" configuration, also provided herein is enantiomer of the compound in an "S" stereochemical configuration. Also provided are mixtures of the compound with both the "S" and the "R" stereochemical configuration. Furthermore, certain structures may exist as geometric isomers (i.e., cis and trans isomers), as tautomers, or as atropisomers. For example, compounds of any formula given herein may contain bonds with restricted rotation and therefore exist in different geometric confirgurations. Where a compound of any table is depicted as a particular geometric isomer (e.g., E or Z isomer, or cis or trans isomer), also provided herein is any alternative geometric configuration of the compound, as well as a mixture of geometric isomers of the compound in any ratio. For example, where a compound of any table is depicted as a "Z" isomer, also provided herein is the "E" isomer of the compound. Likewise, where a compound of any table is depicted as an "E" isomer, also provided herein is the "Z" isomer of the compound. Also provided are mixtures of the compound with both the "E" and the "Z" stereochemical configuration, wherein the mixtures are in any ratio. Similarly, where a compound of any table is depicted as a "cis" isomer, also provided herein is the "trans" isomer of the compound; and where a compound is depicted as a "trans" isomer, also provided herein is the "cis" isomer of the compound. Also provided are mixtures of the compound with both the "cis" and the "trans" stereochemical configuration, wherein the mixtures are in any ratio. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I-1)/(I-2) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$ $^{13}N$, $^{15}O$, $^{17}O$ $^{32}P$, $^{35}S$, $^{18}F$, $^{36}Cl$. Certain isotope labeled compounds (e.g. $^{3}H$ and $^{14}C$) are useful in compound or substrate tissue distribution study. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, I.V. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Particular examples are provided in the Example section below. It is understood that the schemes above may be modified to arrive at various compounds of the invention by selection of appropriate reagents and starting materials. For a general description of protecting groups and their use, see P. G. M. Wuts and T. W. Greene, Greene's Protective Groups in Organic Synthesis 4$^{th}$ edition, Wiley-Interscience, New York, 2006.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, PA, 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use and Uses

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In some embodiments, provided herein is a method of modulating the ATF6 pathway. In some embodiments, provided herein is a method of modualting the ATF6. In some embodiments, provided herein is a method of activating the ATF6 pathway. In some embodiments, provided herein is a method of activating the ATF6. In some embodiments, provided herein is a method of inhibiting the ATF6 pathway. In some embodiments, provided herein is a method of inhibiting the ATF6. In some embodiments, the ATF6 is ATF6α. The compounds or salts thereof described herein and compositions described herein are believed to be effective for inhibiting the ATF6 pathway, ATF6, and/or ATF6α.

In some embodiments, the method of modulating the ATF6 pathway, ATF6, or ATF6α comprises administering or delivering to a cell comprising ATF6 or ATF6α a compound described herein, or a pharmaceutically acceptable salt thereof, or a pharmaceutical composition described herein. In some embodiments, the method of activating the ATF6 pathway, ATF6, or ATF6α comprises administering or delivering to a cell comprising ATF6 or ATF6α a compound described herein, or a pharmaceutically acceptable salt thereof, or a pharmaceutical composition described herein. In some embodiments, the method of inhibiting the ATF6 pathway, ATF6, or ATF6α comprises administering or delivering to a cell comprising ATF6 or ATF6α a compound described herein, or a pharmaceutically acceptable salt thereof, or a pharmaceutical composition described herein. In some embodiments, the cell is a diseased cell, such as a cancer cell. In some embodiments, the cell has an activated ATF6 pathway. In some embodiments, the cell has been exposed to an ER stress-inducing condition. Several ER stress-inducing conditions are known in the art, such as glucose deprivation, aberrant $Ca^{2+}$ regulation, viral infection, hypoxia, and exposure to a ER stress-inducing molecule such as thapsigargin, ionomycin, or tunicamycin.

In some embodiments, the method of modulating the ATF6 pathway, ATF6, or ATF6α comprises administering or delivering a compound described herein, or a pharmaceutically acceptable salt thereof, or a pharmaceutical composition described herein to a tumor. In some embodiments, the method of activating the ATF6 pathway, ATF6, or ATF6α comprises administering or delivering a compound described herein, or a pharmaceutically acceptable salt thereof, or a pharmaceutical composition described herein to a tumor. In some embodiments, the method of inhibiting the ATF6 pathway, ATF6, or ATF6α comprises administering or delivering a compound described herein, or a pharmaceutically acceptable salt thereof, or a pharmaceutical composition described herein to a tumor.

In some embodiments, the modulation of the ATF6 pathway, ATF6, or ATF6α comprises modulating expression of an ATF6 and/or ATF6α target gene. In some embodiments, the modulation of the ATF6 pathway, ATF6, or ATF6α comprises modulating expression of an ATF6α target gene. In some embodiments, the expression of the ATF6 and/or ATF6α target gene is modulated by at least about 10%, 20%, 30%, 40%, 50%, 60%, 70%, 80%, 90%, 95%, or 98%. In some embodiments, the activation of the ATF6 pathway, ATF6, or ATF6α comprises activating expression of an ATF6 and/or ATF6α target gene. In some embodiments, the activation of the ATF6 pathway, ATF6, or ATF6α comprises activating expression of an ATF6α target gene. In some embodiments, the expression of the ATF6 and/or ATF6α target gene is activated by at least about 10%, 20%, 30%, 40%, 50%, 60%, 70%, 80%, 90%, 95%, or 98%. In some embodiments, the inhibition of the ATF6 pathway, ATF6, or ATF6α comprises inhibiting expression of an ATF6 and/or ATF6α target gene. In some embodiments, the inhibition of the ATF6 pathway, ATF6, or ATF6α comprises inhibiting expression of an ATF6α target gene. In some embodiments, the expression of the ATF6 and/or ATF6α target gene is inhibited by at least about 10%, 20%, 30%, 40%, 50%, 60%, 70%, 80%, 90%, 95%, or 98%.

In some embodiments, the ATF6 and/or ATF6α target gene comprises a promoter comprising a ER-stress responsive element (ERSE). In some embodiments, the promoter comprises a sequence that shares at least about 70%, 75%, 80%, 85%, 90%, 95%, 96%, 97%, 98%, or 99% sequence identity with CCAATCGGCGGCGGCCACG (SEQ ID NO. 1). In some embodiments, the promoter comprises SEQ ID NO. 1. In some embodiments, the ATF6 and/or ATF6α target gene is GRP78, HERPUD1, or ERO1B. In some embodiments, the ATF6α target gene is GRP78. Modulation, activation, or inhibition of expression of an ATF6 and/or ATF6α target gene can be determined by methods known in the art, such as by detection of the mRNA of the target gene using a techniques such as PCR, qPCR, or northern blotting, or by detection of polypeptide gene product, such as by western blotting or mass spectrometry.

In some embodiments, the compound, salt thereof, or composition modulates, activates, or inhibits the ATF6 pathway, ATF6, or ATF6α with an $IC_{50}$ of less than about 10 μM, such as less than about 5 μM, 2 μM, 1 μM, 900 nM, 800 nM, 700 nM, or 600 nM. In some embodiments, the compound, salt thereof, or composition inhibits the ATF6 pathway, ATF6, or ATF6α with an $IC_{50}$ between about 10 nM and 5 μM, such between about 50 nM and 2 μM, 100 nM and 1 μM, or 20 nM and 1 μM. The half maximal inhibitory concentration ($IC_{50}$) is a measure of the effectiveness of a substance in inhibiting a specific biological or biochemical function. The $IC_{50}$ is a quantitative measure that indicates how much of an inhibitor is needed to inhibit a given biological process or component of a process such as an enzyme, cell, cell receptor or microorganism by half Methods of determining $IC_{50}$ in vitro and in vivo are known in the art.

In some embodiments, the compounds or salts thereof described herein and compositions described herein are administered in an amount wherein ATF60 activity is not modulated (activated or inhibited) or is modulated (activated or inhibited) to a lesser extent. In some embodiments, modulation (activation or inhibition) of ATF6α is at least or at least about 2 fold greater than inhibition of ATF60 activity, for example at least or at least about 3 fold, 4 fold, 5 fold, 8 fold, 10 fold, 15 fold, 30 fold, 50 fold, 60 fold, 75 fold, or 100 fold greater.

Provided herein is a method of treating a disease in an individual comprising administering an effective amount of a compound of formula (I) or any embodiment, variation or aspect thereof (collectively, a compound of Formula (I) or the present compounds or the compounds detailed or described herein), or a pharmaceutically acceptable salt thereof, to the individual.

In some embodiments, provided herein is a method of treating a disease mediated by the ATF6 pathway in an individual comprising administering an effective amount of a compound of Formula (I), or a pharmaceutically acceptable salt thereof, to the individual. In some embodiments, provided herein is a method of treating a disease mediated by the activation of the ATF6 pathway in an individual comprising administering an effective amount of a compound of Formula (I), or a pharmaceutically acceptable salt thereof, to the individual. In some embodiments, provided herein is a method of treating a disease mediated by the activation of ATF6 in an individual comprising administering an effective amount of a compound of Formula (I), or a pharmaceutically acceptable salt thereof, to the individual. In some embodiments, provided herein is a method of treating a disease mediated by the activation of ATF6α in an individual comprising administering an effective amount of a compound of Formula (I), or a pharmaceutically acceptable salt thereof, to the individual.

In some embodiments, provided herein is a method of treating a disease characterized by activation of the ATF6 pathway in an individual comprising administering an effective amount of a compound of Formula (I), or a pharmaceutically acceptable salt thereof, to the individual. In some embodiments, provided herein is a method of treating a disease characterized by activation of ATF6 in an individual comprising administering an effective amount of a compound of Formula (I), or a pharmaceutically acceptable salt thereof, to the individual. In some embodiments, provided herein is a method of treating a disease characterized by activation of ATF6α in an individual comprising administering an effective amount of a compound of Formula (I), or a pharmaceutically acceptable salt thereof, to the individual. In some embodiments, provided herein is a method of treating a disease characterized by increased expression of an ATF6 target gene in an individual comprising administering an effective amount of a compound of Formula (I), or a pharmaceutically acceptable salt thereof, to the individual. In some embodiments, provided herein is a method of treating a disease characterized by increased expression of an ATF6α target gene in an individual comprising administering an effective amount of a compound of Formula (I), or a pharmaceutically acceptable salt thereof, to the individual. In some embodiments, the increased expression is in comparison to a non-diseased tissue or cell.

The present compounds or salts thereof are believed to be effective for treating a variety of diseases and disorders, such as diseases wherein ATF6-activated transcription targets play a role in the pathogenisis or development of the disease. For example, in some embodiments, the present compounds and compositions may be used to treat viral infection, cancer, a neurodegenerative disease, or a vascular disease, such as a cardiovascular disease. In some embodiments, the disease is viral infection, hereditary cerebellar atrophy and ataxia, or Alzheimer's disease. In some embodiments, the disease is type 2 diabetes mellitus or diabetic nephropathy. In some embodiments, the disease is myocardial atrophy, heart failure, atherosclerosis, or ischemia, such as ischemic heart disease or cerebral ischemia.

It has been demonstrated that ATF6 branch of the UPR is central for viral infection. For example, ATF6 is important for maintaining cell viability and modulating immune responses during West Nile virus infection (Ambrose R J. Virol. February 2013 vol. 87 no. 4 2206-2214). Also, African swine fever virus activates ATF6 branch to prevent early apoptosis and ensure viral replication (Galindo I, Cell Death Dis 2012 Jul. 5; 3:e341. doi: 10.1038/cddis.2012.81). Accordingly, in some embodiments, a compound or salt thereof described herein or a composition described herein may be used in a method of treating or preventing a viral infection. In some embodiments, the viral infection is an African swine fever virus, a dengue virus, an enterovirus, a hepatitis B virus, a hepatitis C virus, influenza virus, a tick-borne encephalitis virus, or a West Nile virus infection. In some embodiments, the viral infection is caused by a virus that activates ATF6 in an infected cell.

In some embodiments, a compound or salt thereof described herein or a composition described herein may be used in a method of treating cancer, such as breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma. In some embodiments, the compound, salt, or composition may be used in a method of treating metastatic kidney cancer, chronic lymphocytary leukemia, pancreatic adenocarcinoma, or non-small cell lung cancer.

ATF6α transcription targets are expressed at high levels in cancer cells. For example, a correlation exists between intracellular GRP78 level and tumor size (Cai, J. W., et al., J Cell Physiol, 1993, 154(2): 229-37). Furthermore, when GRP78/BiP expression was experimentally suppressed in cancer cells that were then injected into mice, the cells were unable to form tumors due to an increased sensitivity to cytotoxic T-cell (CTL) response and tumor necrosis factor (TNF) (Jamora, C., et al., Proc Natl Acad Sci USA, 1996, 93(15): 7690-7694; Sugawara, S., et al., Cancer Res, 1993, 53(24): 6001-6005).

Cancer cells that are cellularly dormant lack proliferative markers and exist in a quiescent state. Cells known to experience cellulary dormancy include disseminated tumor cells (DTCs) and tumor cells located within the circulation (termed circulating tumor cells (CTCs)) (Hensel, J. A., et al., Nat Rev Clin Oncol, 2013, 10(1): 41-51). Minimal residual disease caused by solitary DTCs is a well-recognized event associated with unfavorable patient prognosis. DTCs, which usually stain negative for proliferation markers (e.g., Ki67), may be the source of tumor recurrence that can develop up to decades after treatment of the primary tumor (Meng, S., et al., Clin Cancer Res, 2004, 10(24): 8152-8162). ATF6α has been reported to be a transducing survival signal through an ATF6α-Rheb-mTOR pathway for dormant carcinoma cells (Schewe, D. M. et al., Proc Natl Acad Sci USA, 2008, 105(30): 10519-10524). ATF6α signaling is important for protection against ER and low glucose stress, and the interaction between ATF6α and mTOR signaling appears to confer resistance of dormant cancer cells to doxorubicin and to the mTOR inhibitor rapamycin, revealing a potential drug resistance mechanism (Schewe, D. M. et al., Proc Natl Acad Sci USA, 2008, 105(30): 10519-10524).

In addition, a multicancer study showed higher ATF6 expression in metastases vs. primary lesions and colon cancer patients with increased expression of ATF6α in their primary tumors had higher chances of relapse (Ramaswamy, S., et al., Proc Natl Acad Sci USA, 2001, 98(26): 15149-15154).

In some embodiments, a compound or salt thereof described herein or a composition described herein may be used in a method of treating cancer in an individual, wherein one or more cancer cells in the individual are dormant cancer cells. In some embodiments, one or more of the dormant cancer cells are disseminated tumor cells or circulating tumor cells. In some embodiments, one or more of the dormant cancer cells are disseminated tumor cells.

In some embodiments, a compound or salt thereof described herein or a composition described herein may be used in a method of treating cancer in an individual, wherein the individual has had a prior treatment. In some embodiments, the cancer is resistant or refractory to the prior treatment. In some embodiments, the cancer has progressed on the prior treatment. In the embodiments, the cancer is a recurrent cancer. In some embodiments, the prior treatment was treatment with a ubiquitin-proteasome pathway inhibitor (e.g., bortezomib), a taxane (e.g., paclitaxel or docetaxel), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), an mTOR inhibitor (e.g., rapamycin), an immune-check point inhibitor, or an agent that is used in immune oncology. In some embodiments, the cancer is resistant to treatment with a ubiquitin-proteasome pathway inhibitor (e.g., bortezomib), a taxane (e.g., paclitaxel or docetaxel), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), an mTOR inhibitor (e.g., rapamycin), an immune-check point inhibitor, or an agent that is used in immune oncology. In some embodiments, the cancer is resistant to treatment with doxorubicin and/or rapamycin.

In some embodiments, the administration of the compound, salt, or composition reduces tumor growth, tumor proliferation, or tumorigenicity in the individual. In some embodiments, the compound, salt, or composition may be used in a method of reducing tumor growth, tumor proliferation, or tumorigenicity in an individual in need thereof. In some embodiments, tumor growth is slowed or arrested. In some embodiments, tumor growth is reduced at least about 10%, 20%, 30%, 40%, 50%, 60%, 70%, 80%, or 90%. In some embodiments, the tumor is reduced in size. In some embodiments, tumor size is reduced at least about 10%, 20%, 30%, 40%, 50%, 60%, 70%, 80%, or 90%. In some embodiments, tumor metastasis is prevented or slowed. In some embodiments, the tumor growth, tumor proliferation, or tumorigenicity is compared to the tumor growth, tumor proliferation, or tumorigenicity in the individual prior to the administration of the compound, salt, or composition. In some embodiments, the tumor growth, tumor proliferation, or tumorigenicity is compared to the tumor growth, tumor proliferation, or tumorigenicity in a similar individual or group of individuals. Methods of measuring tumor growth, tumor proliferation, and tumorigenicity are known in the art, for example by repeated imaging of the individual.

The present compounds or salts thereof are also believed to be effective at inhibiting angiogenesis. Activation of ATF6 and PERK contributes to the survival effect of vascular endothelial growth factor (VEGF) on endothelial cells (ECs) by positively regulating mTORC2-mediated phosphorylation of AKT on Ser473, which is required for full activity of AKT. Depletion of PLCγ, ATF6, or eIF2a dramatically inhibited VEGF-induced vascularization in vivo in mouse Matrigel plugs, a standard angiogenesis assay (Karali, E. et al, Molecular Cell, 2014, 54:559-572). Accordingly, the present compounds or salts thereof are believed to be effective for treating a variety of diseases and disorders associated with angiogenesis.

Angiogenesis has been implicated in the pathogenesis of a variety of diseases disorders including solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Accordingly, in some embodiments, the present compounds and compositions are used in a method to treat cancer, such as any cancer described herein, undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

A breakdown in gut barrier defenses in conjunction with microbial dysbiosis is emerging as a key contributor to several disorders, including inflammatory bowel disease, type 1 diabetes, Alzheimer's disease, and cancer. Particularly, in patients with colorectal cancer (CRC), high expression levels of ATF6 in tumor tissues were associated with increased tumor size and reduced disease-free survival. On the other hand, an altered microbiota has been associated with CRC. These data suggest a connection between activation of the UPR, the microbiota, and colon tumorigenesis. It has been demonstrated that a novel relationship between UPR activation via ATF6 and microbiota dependent colon tumorigenesis. Goblet cell loss and bacterial infiltration into epithelial crypts occur before tumor formation and antibiotic treatment of nATF6IEC mice significantly decreased tumor burden. In an inducible mouse model of ATF6 activation, there was 100% tumor incidence at 26 weeks. Four days after activated ATF6 induction, there was a notable increase in the proximity of bacteria to the colonic epithelium with increased cell proliferation, suggesting that these alterations are early events downstream of ATF6 activation. Some researchers found that microbial dysbiosis along with decreased microbial diversity was present in the cecal contents of nATF6IEC mice, as assessed by 16S rRNA gene amplicon sequencing at 5 weeks of age, which is before the onset of tumorigenesis. This dysbiotic microbiota enhanced tumor formation upon transfer into germ-free nATF6IEC mice as compared with transfer of control microbiota into nATF6IEC mice. These data suggest that microbial dysbiosis and subsequent STAT3 signaling in the epithelium significantly contribute to tumorigenesis in this model Accordingly, in some embodiments, a compound or salt thereof described herein or a composition described herein may be used in a method for preventing or treating CRC through inhibition of ATF6 preventing goblet cell loss and dysbiosis. In some embodiments, a compound or salt thereof described herein or a composition described herein may be used in a method for blocking ATF6 signaling and reversing dysbiosis to antagonize tumor progression in a subset of CRC patients.

The capacity of the UPR signaling arms to distinctly influence ER proteostasis and function suggests that selective activation of these pathways has significant potential to alleviate pathologic imbalances in ER proteostasis associated with etiologically diverse human diseases. In particular, activation of the ATF6 signaling arm has been shown to be useful for ameliorating disease-associated imbalances in ER proteostasis and function. The stress-independent activation of the ATF6 transcription factor using a chemical genetic approach induces protective remodeling of ER proteostasis pathways to selectively reduce secretion and extracellular aggregation of destabilized, amyloid disease-associated proteins, such as transthyretin and immunoglobulin light chain, without significantly impacting the secretion of the endogenous proteome (Shoulders et al., 2013; Chen et al., 2014; Cooley et al., 2014; Plate et al., 2016). Accordingly, a compound or salt thereof described herein or a composition described herein may be used in a method for correcting pathologic imbalances in ER proteostasis in cellular and animal models of protein misfolding and aggregation diseases.

One aspect of the present invention is based on the unexpected discovery that overexpression of ATF6 in a cell prevents cell death that would otherwise occur when an undesired accumulation of proteins occurs in that cell. Accordingly, in some embodiments, a compound or salt thereof described herein or a composition described herein may be used in a method for treating a condition such as Parkinson's disease (PD) associated with the abnormal accumulation of molecules that interact with parkin and that are not properly disposed of within a cell.

In some embodiments, a compound or salt thereof described herein or a composition described herein may be used in a method for preventing cell death. For example, preventing neuronal cell death is contemplated within the present invention, including preventing the death of nigral neurons in a mammal, including humans.

In some embodiments, a compound or salt thereof described herein or a composition described herein may be used in a method for treating neurodegenerative diseases associated with abnormal precipitation and/or aggregation of proteins. For example, the brains of patients with Alzheimer's disease exhibit neurofibrillary tangles (NFT), senile plaques, and cerebrovascular deposits of amyloid-beta; the brains of patients with prion disorders exhibit plaques comprising prion proteins; the brains of patients with Huntington's disease exhibit huntingtin precipitates; patients with dominantly inherited spinocerebellar ataxias exhibit corresponding ataxin protein precipitates; patients with multiple system atrophy exhibit alpha-synuclein deposits; patients with progressive supranuclear palsy exhibit tau precipitates; and patients with familial amyotrophic lateral sclerosis exhibit SOD1 precipitates (Johnson, W. G., J. Anat. 4:609-616 (2000)). Because these various diseases share common pathological mechanisms, it is likely that they share pathways that lead to aberrant aggregation and/or precipitation of proteins (Hardy, J. and Gwinn-Hardy, K., Science 282(5391):1075-1079 (1998)).

In some embodiments, a compound or salt thereof described herein or a composition described herein may be used in a method as either a stand-alone therapy, or as a conjunctive therapy with other agents that are either palliative (e.g., agents that relieve the symptoms of the disorder to be treated), and/or agents that target the etiology of the disorder. For example, the administration to a subject of a composition that increases the expression of ATF6 may be carried out in conjunction with the administration of L-DOPA, dopamine agonists, monoamine oxidase B inhibitors, or any other composition useful in the treatment of a neurodegenerative disease, such as Parkinson's disease.

Overexpression of the active ATF6 transcription factor in the heart also has been shown to improve cardiac performance in mouse models of ischemic heart disease, through a mechanism involving ATF6-dependent regulation of the antioxidant gene, catalase (Jin et al., 2017). Similarly, overexpression of the active ATF6 transcription factor in the liver improves insulin sensitivity in obese mice (Ozcan et al., 2016). These results indicate that ATF6 activation offers a unique therapeutic opportunity to ameliorate ER proteostasis defects implicated in diverse diseases.

In some embodiments, a compound or salt thereof described herein or a composition described herein may be used in a method for enhancing myocardial recovery from I/R damage, specifically by activating the endogenous adaptive ATF6 gene program in the heart.

The ATF6α pathway also plays a role in stress-induced lipid accumulation. p50ATF6 interacts with the nuclear form of SREBP-2, thereby antagonizing SREBP-2-regulated transcription of lipogenic genes and lipid accumulation in cultured hepatocytes and kidney cells. Moreover, Atf6α-deleted mice displayed hepatic dysfunction and steatosis much longer than wild-type mice in response to pharmacological induction of ER stress. This could be explained by chronic expression of CHOP and sustained suppression of C/EBPα and/or a failure of ATF6α-mediated induction of genes encoding protein chaperone, trafficking, and ERAD functions. When fed a HFD, $Atf6\alpha^{-/-}$ mice developed hepatic steatosis and glucose intolerance in association with increased expression of SREBP-1c. On the other hand, overexpression of a functionally active nuclear fragment of ATF6 in zebrafish caused fatty liver, suggesting that fine-tuning of ATF6α may be important to prevent liver steatosis.

In some embodiments, a compound or salt thereof described herein or a composition described herein may be used in a method of treating metabolic disorders, such as obesity, type I- and type II diabetes, pancreatitis, dyslipidemia, hyperlipidemia conditions, non-alcoholic fatty liver disease (NAFLD), non-alcoholic steatohepatitis (NASH), insulin resistance, hyperinsulinemia, glucose intolerance, hyperglycemia, metabolic syndrome, acute myocardial infarction, hypertension, cardiovascular diseases, atherosclerosis, peripheral arterial disease, apoplexy, heart failure, coronary artery heart disease, renal disease, diabetic complications, neuropathy, gastroparesis, disorder associated with a serious inactivation mutation in insulin receptor, and other metabolic disorders.

In some embodiments, a compound or salt thereof described herein or a composition described herein may be used in a method of treating ischemic heart disease or myocardial recovery from ischemia/reperfusion (I/R).

In accordance with the present disclosure, in some embodiments, the individual is a mammal. In some embodiments, the individual is a primate, bovine, ovine, porcine, equine, canine, feline, rabbit, or rodent. In some embodiments, the individual is a human. In some embodiments, the individual has any of the diseases or disorders disclosed herein. In some embodiments, the individual is a risk for developing any of the diseases or disorders disclosed herein.

Also provided herein are uses of a compound described herein or a pharmaceutically acceptable salt thereof, or a pharmaceutical composition described herein, in the manufacture of a medicament. In some embodiments, the manufacture of a medicament is for the treatment of a disorder or disease described herein. In some embodiments, the manufacture of a medicament is for the prevention and/or treatment of a disorder or disease mediated by the ATF6 pathway, ATF6, or ATF6α.

Combination Therapy

As provided herein, compounds or salts thereof described herein and compositions described herein may be administered with an agent to treat any of the diseases and disorders disclosed herein. In some embodiments, the agent modulates the Unfolded Protein Response or the Integrated Stress Response. In some embodiments, the agent is an anti-angiogenesis agent. In some embodiments, the agent is an anticancer agent. In some embodiments, the agent targets an immune checkpoint protein.

In some embodiments, (a) a compound described herein, or a pharmaceutically acceptable salt thereof, or a pharmaceutical composition described herein and (b) an agent are sequentially administered, concurrently administered or simultaneously administered. In certain embodiments, (a) a compound described herein, or a pharmaceutically acceptable salt thereof, or a pharmaceutical composition described herein and (b) an agent are administered with a time separation of about 15 minutes or less, such as about any of 10, 5, or 1 minutes or less. In certain embodiments, (a) a compound described herein, or a pharmaceutically acceptable salt thereof, or a pharmaceutical composition described herein and (b) an agent are administered with a time separation of about 15 minutes or more, such as about any of 20, 30, 40, 50, 60, or more minutes. Either (a) a compound described herein, or a pharmaceutically acceptable salt thereof, or a pharmaceutical composition described herein and (b) an agent may be administered first. In certain embodiments, (a) a compound described herein, or a pharmaceutically acceptable salt thereof, or a pharmaceutical composition described herein and (b) an agent are administered simultaneously.

In some embodiments, the agent modulates the Unfolded Protein Response or the Integrated Stress Response. In some embodiments, the agent inhibits the Unfolded Protein Response or the Integrated Stress Response. In some embodiments, the agent modulates the PERK pathway. In some embodiments, the agent inhibits the PERK pathway. In some embodiments, the agent inhibits PERK. ATF6 is known to work in partnership with IRE1, as one of the target genes of ATF6 is XBP1, the key substrate of IRE1 (Yoshida, H., et al., Cell, 2001, 107(7): 881-891), for example ATF6 and IRE1 signaling are important for survival of melanoma cells undergoing ER stress, suggesting a potential benefit in the use of ATF6 inhibitors in combination with IRE1 inhibitors (Tay, K. H., et al., Cell Signal, 2014, 26(2): 287-294). Accordingly, in some embodiments, the agent modulates the IRE1/XBP1 pathway. In some embodiments, the agent inhibits the IRE1/XBP1 pathway. In some embodiments, the agent inhibits IRE1 or XBP1.

In some embodiments, the agent is an anti-angiogenesis agent. The present compounds or salts thereof are believed to be effective at inhibiting angiogenesis and for treating diseases and disorders associated with angiogenesis. Accordingly, provided herein is a method of inhibiting angiogenesis comprising administering to an individual (a) a compound described herein, or a pharmaceutically acceptable salt thereof, or a pharmaceutical composition described herein and (b) an anti-angiogenesis agent. Also provided herein is a method of treating a disease or disorder associated with angiogenesis, such as any disease or disorder associated with angiogenesis disclosed herein, comprising administering to an individual (a) a compound described herein, or a pharmaceutically acceptable salt thereof, or a pharmaceutical composition described herein and (b) an anti-angiogenesis agent. In some embodiments, the anti-angiogenesis agent is a VEGF antagonist. In some embodiments, the anti-angiogenesis agent is bevacizumab or ranibizumab.

The role of angiogenesis as a mediator of immune regulation in the tumor microenvironment has recently come into focus. Furthermore, emerging evidence indicates that immunotherapy can lead to immune-mediated vasculopathy in the tumor, suggesting that the tumor vasculature may be an important interface between the tumor-directed immune response and the cancer itself. The introduction of immune checkpoint inhibition as an effective immunotherapeutic strategy for many cancers has led to a better understanding of this interface. Initial studies of the complex relationship between angiogenesis, VEGF signaling and the immune system suggest that the combination of immune checkpoint blockade with angiogenesis inhibition has potential and efforts to enhance immunotherapy will broadly impact the future of oncology. The effect of ATF6 over VEGF signaling reinforces the idea of the use of ATF6 inhibitors as a combination with immune checkpoint inhibitors (Ott, P. A., F. S. Hodi, and E. I. Buchbinder, Inhibition of Immune Checkpoints and Vascular Endothelial Growth Factor as Combination Therapy for Metastatic Melanoma: An Overview of Rationale, Preclinical Evidence, and Initial Clinical Data. Front Oncol, 2015. 5: p. 202).

Accordingly, in some embodiments, the agent targets an immune checkpoint protein. In some embodiments, the agent is an antibody that targets an immune checkpoint protein. In some embodiments, the agent targets PD-1, PD-L1, PD-L2, CTLA4, TIM3, LAG3, CCR4, OX40, OX40L, IDO, and A2AR. In some embodiments, the agent is an anti-PD-1 antibody, an anti-PD-L1 antibody, or an anti-CTLA-4 antibody.

Provided herein is a method of enhancing an immune response in an individual comprising administering to the individual (a) a compound described herein, or a pharmaceutically acceptable salt thereof, or a pharmaceutical composition described herein and (b) an agent that targets an immune checkpoint protein. In some embodiments, the individual has cancer. In some embodiments, the enhanced immune response is directed to a tumor or cancerous cell.

Also provided herein are methods of treating cancer in an individual in need thereof comprising administering to the individual (a) a compound described herein, or a pharmaceutically acceptable salt thereof, or a pharmaceutical composition described herein and (b) an agent that targets an immune checkpoint protein, wherein an immune response of the individual is increased.

In some embodiments, the agent is an anticancer agent. In some embodiments, anticancer agent is an ubiquitin-proteasome pathway inhibitor (e.g., bortezomib), a taxane (e.g., paclitaxel or docetaxil), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), or an agent that modulates the Unfolded Protein Response or the Integrated Stress Response (e.g. an IRE1/XBP1 inhibitor or a PERK inhibitor). In some embodiments, the anticancer agent is oxaliplatin, 5-fluorouracil, or gemcitabine. In some embodiments, the anticancer agent is an immune-check point inhibitor, or an agent that is used in immune oncology.

In some embodiments, an effective amount of a compound described herein, or a pharmaceutically acceptable salt thereof, or a pharmaceutical composition described herein is administered to an individual with cancer to increase sensitivity to one or more anticancer treatments.

Therapeutic resistance is a major barrier to improvement of outcomes for patients with cancer. Radiation can induce ER stress and its downstream signaling and appears to be linked to changes in ROS balance secondary to irradiation. Previously, knockdown of ATF6 was sufficient to enhance radiation induced cell death (Dadey, D. Y., et al., Oncotarget, 2016, 7(2): 2080-2092). This suggests ATF6 as a potential therapeutic target to enhance the efficacy of radiation therapy.

In some embodiments, an effective amount of a compound described herein, or a pharmaceutically acceptable salt thereof, or a pharmaceutical composition described herein is administered to an individual with cancer to increase sensitivity to radiation. In some embodiments, provided herein are methods of treating cancer in an individual in need thereof comprising administering to the individual (a) a compound described herein, or a pharmaceutically acceptable salt thereof, or a pharmaceutical composition described herein and (b) radiation.

In some embodiments, an effective amount of a compound described herein, or a pharmaceutically acceptable salt thereof, or a pharmaceutical composition described herein is administered to an individual with cancer to increase sensitivity to one or more anticancer agents. In some embodiments, the anticancer agent is an ubiquitin-proteasome pathway inhibitor (e.g., bortezomib), a taxane (e.g., paclitaxel or docetaxil), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), or an agent that modulates the Unfolded Protein Response or the Integrated Stress Response (e.g. an IRE1/XBP1 inhibitor or a PERK inhibitor). In some embodiments, the anticancer agent is oxaliplatin, 5-fluorouracil, or gemcitabine. In some embodiments, the anticancer agent is an immune-check point inhibitor, or an agent that is used in immune oncology.

Provided herein is a method of treating metabolic and/or fibrotic diseases in an individual comprising administering to the individual (a) a compound described herein, or a pharmaceutically acceptable salt thereof, or a pharmaceutical composition described herein and (b) an agent. In some embodiments, the agent is a proteasome inhibitor, e.g., bortezomib, carfilzomib and ixazomib. In some embodiments, the agent is a monoclonal antibody, e.g., daratumumab and elotuzumab. In some embodiments, the agent is an Inhibitors of Histone deacetylases (HDACs) protein, e.g., panobinostat, romidepsin and vorinostat. In some embodiments, the agent is an Immunomodulatory drug (IMiD), e.g., thalidomide, lenalidomide, and pomalidomide. In some embodiments, the agent is an adrenal corticosteroid, e.g., dexamethasone, prednisone, prednisolone, and methylprednisolone. In some embodiments, the agent is a therapy targeting the IRE1-XBP1.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account factors, e.g., the mode or route of administration or drug delivery, the pharmacokinetics of the agent, the severity and course of the disease to be treated, the subject's health status, condition, and weight. An exemplary dose is in the range of about from about 0.1 mg to 10 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral, and transdermal. In some embodiments, the compound or composition is administered orally. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

Also provided herein are compositions (including pharmaceutical compositions) as described herein for the use in treating, preventing, and/or delaying the onset and/or development of a disease described herein and other methods described herein. In certain embodiments, the composition comprises a pharmaceutical formulation which is present in a unit dosage form.

Articles of Manufacture and Kits

The present disclosure further provides articles of manufacture comprising a compound of the disclosure or a salt thereof, composition, and unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the disclosure, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of disease described herein, such as cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

The following examples are offered to illustrate but not to limit the present disclosure. One of skill in the art will recognize that the following synthetic reactions and schemes may be modified by choice of suitable starting materials and reagents in order to access other compounds of formula (I-1)/(I-2), or a salt thereof. The compounds are prepared using the general methods described above.

The following abbreviations are used throughout the Examples: DCM (dichloromethane), DIAD (diisopropyl azodicarboxylate), DIPEA or DIEA (N,N-diisopropylethylamine), DMF (N,N-dimethylformamide), DMSO (dimethyl sulfoxide), HATU ((1-[bis(dimethylamino)methylene]-1H-1,2,3-triazolo[4,5-b]pyridinium 3-oxid hexafluorophosphate), HPLC (high-pressure liquid chromatography), IPA (isopropyl alcohol), LCMS (liquid chromatography mass spectrometry), NMR (nuclear magnetic resonance), $PPh_3$ (triphenylphosphane), RT (room temperature), TEA (triethylamine), THF (tetrahydrofuran), and TLC (thin layer chromatography).

Example S2

Example S2-1. Synthesis of 2-((1-(1-(2,4-bis(trifluoromethyl)phenyl)ethyl)-1H-pyrazol-4-yl)ethynyl)-5-(pyridin-2-yl)-1,3,4-thiadiazole (Compound 2-1)

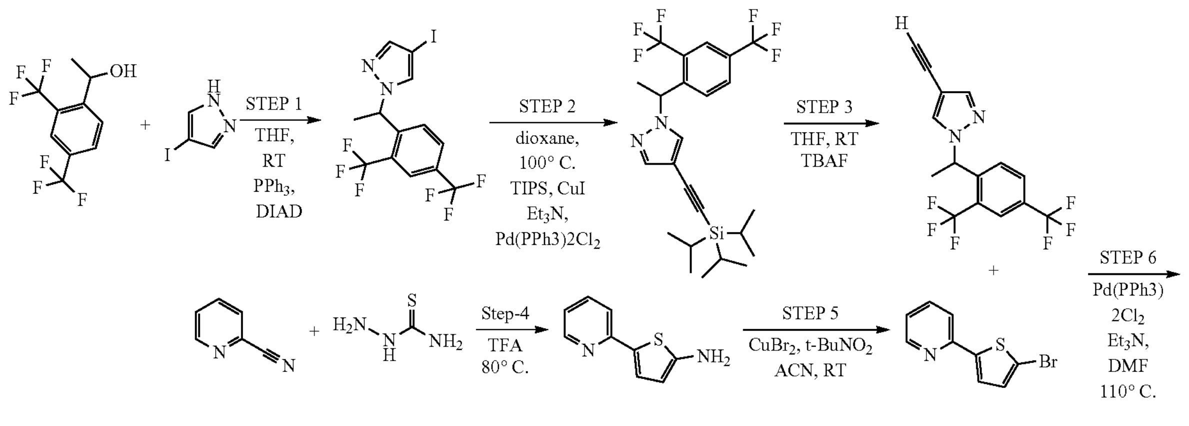

-continued

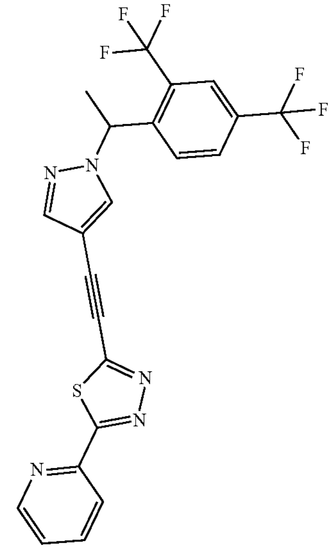

Compound 2-1

Step 1: Synthesis of 1-(1-(2,4-bis(trifluoromethyl)phenyl) ethyl)-4-iodo-1H-pyrazole. To a stirred solution of $PPh_3$ (1.52 g, 0.0057 mol, 1.5 eq.) and DIAD (1.17 g, 0.0057 mol, 1.5 eq.) in THF (10 mL), 1-(2,4-bis(trifluoromethyl)phenyl) ethan-1-ol (1 g, 0.0038 mol, 1 eq.) and 4-iodo-1H-pyrazole (0.748 g, 0.0038 mmol, 1 eq.) were added and allowed to stir at RT for 16 hr. Reaction progress was monitored by TLC and LCMS. After the reaction completion, the reaction mixture was extracted with ethyl acetate and water (2×50 mL), Organic layer was separated and evaporated under reduced pressure to give crude product which was further purified by Combi flash chromatography obtained 1-(1-(2, 4-bis(trifluoromethyl)phenyl)ethyl)-4-iodo-1H-pyrazole. Analytical Data: $^1H$ NMR (400 MHz, DMSO-$d_6$) δ ppm 8.18 (s, 1H) 8.08 (d, J=8.77 Hz, 1H) 8.04 (s, 1H) 7.67 (d, J=8.33 Hz, 1H) 7.60 (s, 1H) 5.93 (q, J=7.02 Hz, 1H) 1.84 (d, J=7.02 Hz, 3H).

Step 2: Synthesis of 1-(1-(2,4-bis(trifluoromethyl)phenyl) ethyl)-4-((triisopropylsilyl)ethynyl)-1H-pyrazole. To a solution of 1-(1-(2,4-bis(trifluoromethyl)phenyl)ethyl)-4-iodo-1H-pyrazole (900 mg, 2.078 mmol, 1 eq.), ethynyltriisopropylsilane (492.60 mg, 3.117 mmol, 1.5 eq.), CuI (39.48 mg, 0.2078 mmol, 0.1 eq.), triethylamine (629.63 mg, 6.234 mmol, 3 eq.) in 5 mL dioxane was purged with nitrogen and $Pd(PPh_3)_2C_{12}$ (72.83 mg, 0.103 mmol, 0.05 eq.) was added and heated at 110° C. for 18 hr. Reaction mixture was extracted with ethyl acetate and water (2×50 mL), Organic layer was collected and concentrated to give crude product which was purified by Combi-flash chromatography to obtain pure product 1-(1-(2,4-bis(trifluoromethyl)phenyl)ethyl)-4-((triisopropylsilyl)ethynyl)-1H-pyrazole. LCMS: 489 $[M+H]^+$.

Step 3: Synthesis of 1-(1-(2,4-bis(trifluoromethyl)phenyl) ethyl)-4-ethynyl-1H-pyrazole. To a solution of 1-(1-(2,4-bis (trifluoromethyl)phenyl)ethyl)-4-((triisopropylsilyl)ethynyl)-1H-pyrazole (200 mg, 0.461 mmol, 1 eq.) in 4 mL THF, TBAF (1 mL) was added under anhydrous condition at RT for 3H. Reaction mixture was extracted with ethylacetate and water (2×25 mL), Organic layer was collected and concentrated to give crude product which was purified by combiflash chromatography to give 1-(1-(2,4-bis(trifluoromethyl)phenyl)ethyl)-4-ethynyl-1H-pyrazole. LCMS: 333 $[M+H]^+$, $^1H$ NMR (400 MHz, DMSO-$d_6$): δ ppm 8.33 (s, 1H) 8.02-8.11 (m, 2H) 7.62-7.72 (m, 2H) 5.86-5.95 (m, 1H) 4.03 (s, 1H) 1.85 (d, J=7.02 Hz, 3H).

Step 4: Synthesis of 5-(pyridin-2-yl)-1,3,4-thiadiazol-2-amine. To a solution of picolinonitrile (500 mg, 4.807 mmol, 1 eq.) and hydrazinecarbothioamide (481.25 mg, 5.28 mmol, 1.1 eq.) in TFA (3 mL) was allowed to heat at 80° C. for 2 hr. Cold water was poured into reaction mixture, precipitate obtained was filtered off to give 5-(pyridin-2-yl)-1,3,4-thiadiazol-2-amine. $^1H$ NMR (400 MHz, DMSO-$d_6$): δ ppm 8.59 (d, J=4.82 Hz, 1H) 8.05 (d, J=8.33 Hz, 1H) 7.92 (td, J=7.78, 1.53 Hz, 1H) 7.67 (br. s., 2H) 7.43 (dd, J=7.45, 4.82 Hz, 1H).

Step 5: Synthesis of 2-bromo-5-(pyridin-2-yl)-1,3,4-thiadiazole. To a solution of 5-(pyridin-2-yl)-1,3,4-thiadiazol-2-amine (500 mg, 2.808 mmol, 1 eq.) in Acetonitrile (5 mL), $CuBr_2$ (626.40 mg, 2.808 mmol, 1 eq.) was added at 0° C. followed by tert-Butyl nitrite (0.66 mL, 5.616 mmol, 2 eq.) was added and allowed to stir at 0° C. for 3 hr. Reaction mixture was quenched with Sat.$NH_4Cl$ and extracted with ethyl acetate and water, Organic layer was evaporated to give crude product which was purified by CombiFlash chromatography to give 2-bromo-5-(pyridin-2-yl)-1,3,4-thiadiazole. 1H NMR (400 MHz, DMSO-$d_6$): δ ppm 8.72 (d, J=4.38 Hz, 1H) 8.24 (d, J=8.33 Hz, 1H) 8.07 (t, J=7.67 Hz, 1H) 7.60-7.66 (m, 1H).

Step 6: Synthesis of 2-((1-(1-(2,4-bis(trifluoromethyl) phenyl)ethyl)-1H-pyrazol-4-yl)ethynyl)-5-(pyridin-2-yl)-1, 3,4-thiadiazole. To the solution of 2-bromo-5-(pyridin-2-yl)-1,3,4-thiadiazole (50 mg, 0.205 mmol, 1 eq.) in 3 mL DMF, 1-(1-(2,4-bis(trifluoromethyl)phenyl)ethyl)-4-ethynyl-1H-pyrazole (81.97 mg, 0.246 mmol, 1.2 eq.), CuI (3.89 mg, 0.020 mmol, 0.1 eq.), $Et_3N$ (62.11 mg, 0.615 mmol, 3 eq.) was purged with nitrogen and $PdCl_2(PPh_3)_2$ (7.18 mg, 0.010 mmol, 0.05 eq.) was added and heated at 110° C. for 18 hr. Reaction mixture was extracted with ethylacetate and water (2*50 mL). Organic layer was collected and concentrated to give crude product which was purified by CombiFlash chromatography to give 2-((1-(1-(2,4-bis(trifluoromethyl) phenyl)ethyl)-1H-pyrazol-4-yl)ethynyl)-5-(pyridin-2-yl)-1, 3,4-thiadiazole (14 mg, white solid). LCMS: 494 $[M+H]^+$, $^1$H NMR (400 MHz, DMSO-$d_6$): δ ppm 8.68-8.77 (m, 2H) 8.31 (d, J=8.33 Hz, 1H) 8.05-8.14 (m, 3H) 8.00 (s, 1H) 7.71 (d, J=8.33 Hz, 1H) 7.59-7.66 (m, 1H) 5.99 (d, J=7.02 Hz, 1H) 1.90 (d, J=6.58 Hz, 3H).

Example S2-2. Synthesis of 2-((1-(1-(2,4-bis(trifluoromethyl)phenyl)ethyl)-1H-pyrazol-4-yl)ethynyl)-5-(pyridin-2-yl)-1,3,4-thiadiazole (Compound 2-2 and Compound 2-3)

Step 1: Synthesis of 1-(1-(2,4-bis(trifluoromethyl)phenyl)ethyl)-4-iodo-1H-pyrazole. To the stirred solution of $PPh_3$ (1.52 g, 0.0057 mol, 1.5 eq.) and DIAD (1.17 g, 0.0057 mol, 1.5 eq.) in THF (10 mL), 1-(2,4-bis(trifluoromethyl)phenyl)ethan-1-ol (1 g, 0.0038 mol, 1 eq.) and 4-iodo-1H-pyrazole (0.748 g, 0.0038 mmol, 1 eq.) were added and allowed to stir at RT for 16 hr. Reaction progress was monitored by TLC and LCMS. Reaction mixture was extracted with ethyl acetate and water (2×50 mL), Organic layer was separated,

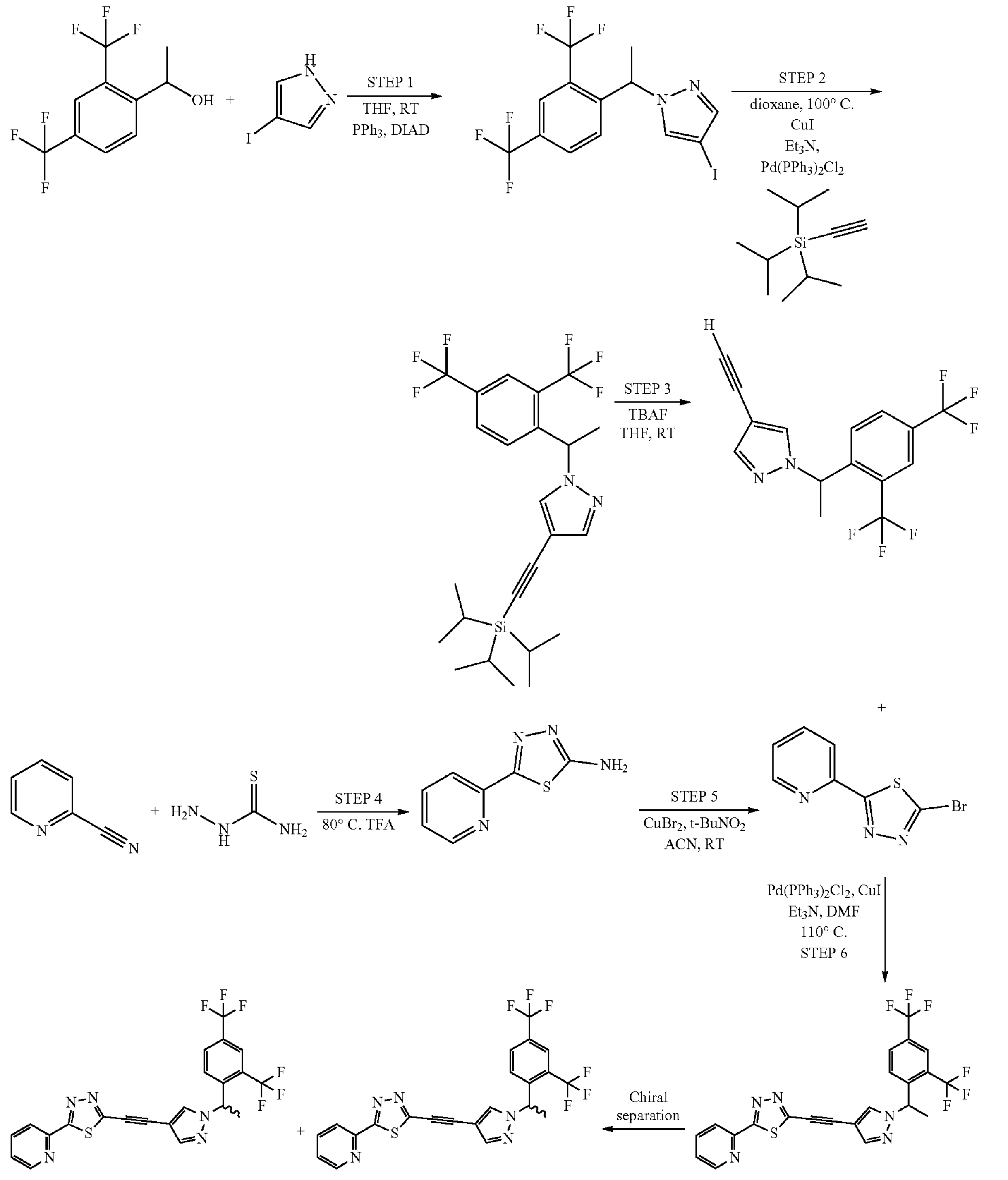

Compound 2-2

Compound 2-3 dried over anhydrous sodium sulphate, evaporated under reduced pressure to give crude product which was further purified by combiflash chromatography to yield 1-(1-(2,4-bis(trifluoromethyl)phenyl)ethyl)-4-iodo-1H-pyrazole. LCMS: 435 $[M+H]^+$. $^1$H NMR (400 MHz, DMSO-$d_6$) δ ppm 8.18 (s, 1H) 8.08 (d, J=8.77 Hz, 1H) 8.04 (s, 1H) 7.67 (d, J=8.33 Hz, 1H) 7.60 (s, 1H) 5.93 (d, J=7.02 Hz, 2H) 1.84 (d, J=7.02 Hz, 3H).

Step 2: Synthesis of 1-(1-(2,4-bis(trifluoromethyl)phenyl) ethyl)-4-((triisopropylsilyl)ethynyl)-1H-pyrazole. To the solution of 1-(1-(2,4-bis(trifluoromethyl)phenyl)ethyl)-4-iodo-1H-pyrazole (900 mg, 2.078 mmol, 1 eq.), Ethynyltriisopropylsilane (492.60 mg, 3.117 mmol, 1.5 eq.), CuI (39.48 mg, 0.2078 mmol, 0.1 eq.), triethylamine (629.63 mg, 6.234 mmol, 3 eq.) in 5 mL dioxane was purged with nitrogen and $Pd(PPh_3)_2Cl_2$ (72.83 mg, 0.103 mmol, 0.05 eq.) was added and heated at 110° C. for 18 hr. Reaction mixture was extracted with ethylacetate and water (2*50 mL). Organic layer was collected and concentrated to give crude product. Crude product was purified by combiflash chromatography to obtain pure product 1-(1-(2,4-bis(trifluoromethyl)phenyl)ethyl)-4-((triisopropylsilyl)ethynyl)-1H-pyrazole. LCMS: 489 $[M+H]^+$.

Step 3: Synthesis of 1-(1-(2,4-bis(trifluoromethyl)phenyl) ethyl)-4-ethynyl-1H-pyrazole. To the solution of 1-(1-(2,4-bis(trifluoromethyl)phenyl)ethyl)-4-((triisopropylsilyl)ethynyl)-1H-pyrazole (200 mg, 0.461 mmol, 1 eq.) in 4 mL THF, TBAF (1 mL) was added under anhydrous condition. Reaction mixture was extracted with ethylacetate and water (2×25 mL), Organic layer was collected, dried over anhydrous sodium sulphate and concentrated to give crude product which was purified by combiflash chromatography to give 1-(1-(2,4-bis(trifluoromethyl)phenyl)ethyl)-4-ethynyl-1H-pyrazole. $^1$H NMR (400 MHz, DMSO-$d_6$) δ ppm 8.33 (s, 1H) 8.02-8.11 (m, 2H) 7.62-7.72 (m, 2H) 5.86-5.95 (m, 1H) 4.03 (s, 1H) 1.85 (d, J=7.02 Hz, 3H).

Step 4: Synthesis of 5-(pyridin-2-yl)-1,3,4-thiadiazol-2-amine. To a solution of Picolinonitrile (500 mg, 4.807 mmol, 1 eq.) and hydrazinecarbothioamide (481.25 mg, 5.28 mmol, 1.1 eq.) in TFA (3 mL) was allowed to heat at 80° C. for 2 hr. After completion of reaction, reaction mixture was diluted with ice-water, precipitate obtained was filtered off to give 5-(pyridin-2-yl)-1,3,4-thiadiazol-2-amine. $^1$H NMR (400 MHz, DMSO-$d_6$) δ ppm 8.59 (d, J=4.82 Hz, 1H) 8.05 (d, J=8.33 Hz, 1H) 7.92 (td, J=7.78, 1.53 Hz, 1H) 7.67 (br. s., 2H) 7.43 (dd, J=7.45, 4.82 Hz, 1H).

Step 5: Synthesis of 2-bromo-5-(pyridin-2-yl)-1,3,4-thiadiazole. To a solution of 5-(pyridin-2-yl)-1,3,4-thiadiazol-2-amine (500 mg, 2.808 mmol, 1 eq.) in ACN (5 mL), $CuBr_2$ (626.40 mg, 2.808 mmol, 1 eq.) was added at 0° C. followed by tert-Butyl nitrite (0.66 mL, 5.616 mmol, 2 eq.) was added and allowed to stir at 0° C. for 3 hr. After completion, Reaction mixture was quenched with $NH_4Cl$ and extracted with ethyl acetate and water. Organic layer was evaporated to give crude product which was purified by combiflash chromatography to give 2-bromo-5-(pyridin-2-yl)-1,3,4-thiadiazole. $^1$H NMR (400 MHz, DMSO-$d_6$) δ ppm 8.72 (d, J=4.38 Hz, 1H) 8.24 (d, J=8.33 Hz, 1H) 8.07 (t, J=7.67 Hz, 1H) 7.60-7.66 (m, 1H).

Step 6: Synthesis of 2-((1-(1-(2,4-bis(trifluoromethyl) phenyl)ethyl)-1H-pyrazol-4-yl)ethynyl)-5-(pyridin-2-yl)-1,3,4-thiadiazole. To a solution of 2-bromo-5-(pyridin-2-yl)-1,3,4-thiadiazole (120 mg, 0.493 mmol, 1 eq.) in 3 mL DMF, 1-(1-(2,4-bis(trifluoromethyl)phenyl)ethyl)-4-ethynyl-1H-pyrazole (196.74 mg, 0.591 mmol, 1.2 eq.), CuI (9.36 mg, 0.049 mmol, 0.1 eq.), $Et_3N$ (149.37 mg, 1.479 mmol, 3 eq.) was purged with nitrogen and $PdCl_2(PPh_3)_2$ (17.27 mg, 0.024 mmol, 0.05 eq.) was added and heated at 110° C. for 18 hr. Reaction mixture was extracted with ethyl acetate and water (2×50 mL), organic layer was collected, dried over anhydrous sodium sulphate, concentrated to give crude product which was purified by combiflash chromatography. The pure fractions were concentrated to give Compound 3 (13 mg white solid) and Compound 2 (15 mg white solid). LCMS: 494 $[M+H]^+$.

Compound 2: $^1$H NMR (400 MHz, $CDCl_3$) δ ppm 8.65 (d, J=4.82 Hz, 1H) 8.37 (d, J=7.89 Hz, 1H) 7.94 (s, 1H) 7.76-7.91 (m, 4H) 7.68 (d, J=7.89 Hz, 1H) 7.36-7.44 (m, 1H) 5.95 (d, J=6.58 Hz, 1H) 1.97 (d, J=7.02 Hz, 3H). The enantiomer's elution time: 5.2 min), were separated by chiral SFC (Daicel Chiralcel®-ODH, 250×20 mm, 5 μm). Isocratic program with analytical grade liquid carbon dioxide and HPLC grade 0.2% DEA in Methanol, Total flow: 51 g/min, Co-Solvent Percentage: 18%.

Compound 3: $^1$H NMR (400 MHz, $CDCl_3$) δ ppm 8.65 (d, J=4.38 Hz, 1H) 8.37 (d, J=7.89 Hz, 1H) 7.94 (s, 1H) 7.77-7.90 (m, 4H) 7.69 (d, J=8.33 Hz, 1H) 7.36-7.44 (m, 1H) 5.95 (d, J=6.58 Hz, 1H) 1.97 (d, J=6.58 Hz, 3H). The enantiomer's elution time: 4.7 min), were separated by chiral SFC (Daicel Chiralcel®-ODH, 250×20 mm, 5 μm). Isocratic program with analytical grade liquid carbon dioxide and HPLC grade 0.2% DEA in Methanol. Total flow: 51 g/min, Co-Solvent Percentage: 18%.

Example S2-3. Synthesis of 2-((1-(2,4-bis(trifluoromethyl)benzyl)-1H-pyrazol-4-yl)ethynyl)-5-(pyridin-2-yl)-1,3,4-thiadiazole (Compound 2-4)

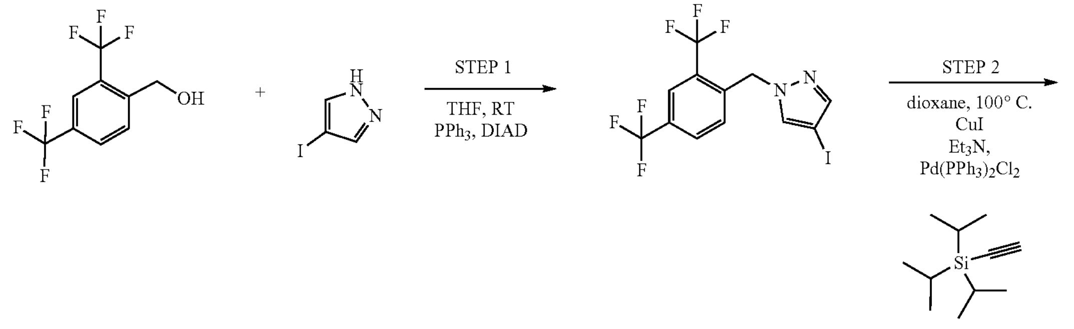

-continued

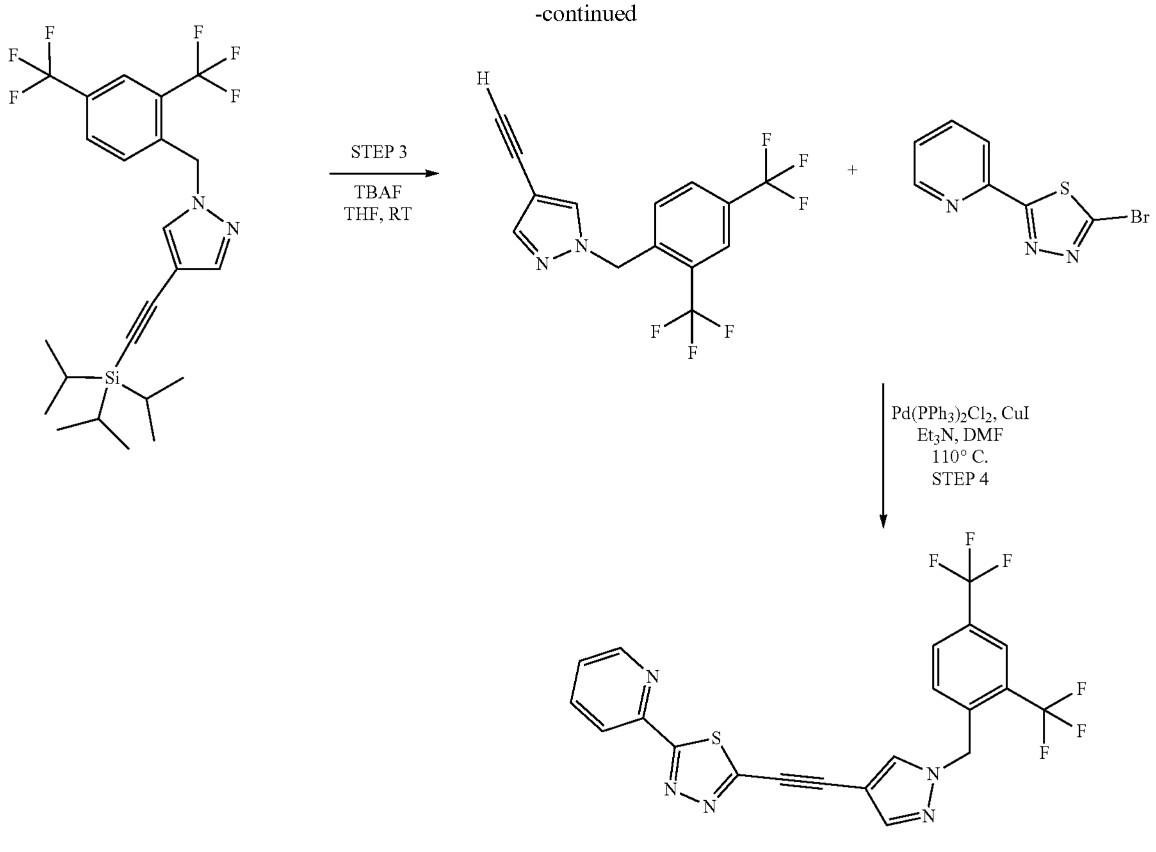

Compound 2-4

Step 1: Synthesis of 1-(2,4-bis(trifluoromethyl)benzyl)-4-iodo-1H-pyrazole. To a stirred solution of $PPh_3$ (1.57 g, 0.006 mol, 1.5 eq.) and DIAD (1.21 g, 0.006 mol, 1.5 eq.) in THF (10 mL), (2,4-bis(trifluoromethyl)phenyl)methanol (1 g, 0.0040 mol, 1 eq.) and 4-iodo-1H-pyrazole (0.790 g, 0.0040 mol, 1 eq.) were added and allowed to stir at RT for 16 hr. Reaction progress was monitored by TLC and LCMS. After completion of reaction, reaction mixture was extracted with ethyl acetate and water (2×50 mL), Organic layer was separated, dried over anhydrous sodium sulphate, evaporated under reduced pressure to give crude product which was further purified by combiflash chromatography to yield 1-(2,4-bis(trifluoromethyl)benzyl)-4-iodo-1H-pyrazole, LCMS: 421 $[M+H]^+$.

Step 2: Synthesis of 1-(2,4-bis(trifluoromethyl)benzyl)-4-((triisopropylsilyl)ethynyl)-1H-pyrazole. To a solution of 1-(2,4-bis(trifluoromethyl)benzyl)-4-iodo-1H-pyrazole (500 mg, 1.19 mmol, 1 eq.), Ethynyltriisopropylsilane (325 mg, 1.78 mmol, 1.5 eq.), CuI (22.61 mg, 0.119 mmol, 0.1 eq.), Triethylamine (360.57 mg, 3.57 mmol, 3 eq.) in 5 mL dioxane was purged with nitrogen and $Pd(PPh_3)_2Cl_2$ (41.70 mg, 0.059 mmol, 0.05 eq.) was added and heated at 110° C. for 18 hr. Reaction mixture was extracted with ethylacetate and water (2*50 mL). Organic layer was collected and concentrated to give crude product. Crude product was purified by combiflash chromatography to obtain pure product 1-(2,4-bis(trifluoromethyl)benzyl)-4-((triisopropylsilyl)ethynyl)-1H-pyrazole, LCMS: 475 $[M+H]^+$.

Step 3: Synthesis of 1-(2,4-bis(trifluoromethyl)benzyl)-4-ethynyl-1H-pyrazole. To the solution of 1-(2,4-bis(trifluoromethyl)benzyl)-4-((triisopropylsilyl)ethynyl)-1H-pyrazole (300 mg, 0.632 mmol, 1 eq.) in 4 mL THF, TBAF (1 mL) was added under anhydrous condition. Reaction mixture was extracted with Ethyl acetate and water (2×25 mL), Organic layer was collected, dried over anhydrous sodium sulphate, concentrated to give crude product which was purified by combiflash chromatography to give 1-(2,4-bis(trifluoromethyl)benzyl)-4-ethynyl-1H-pyrazole, LCMS: 319 $[M+H]^+$.

Step 4: Synthesis of 2-((1-(2,4-bis(trifluoromethyl)benzyl)-1H-pyrazol-4-yl)ethynyl)-5-(pyridin-2-yl)-1,3,4-thiadiazole. To the solution of 2-bromo-5-(pyridin-2-yl)-1,3,4-thiadiazole (80 mg, 0.330 mmol, 1 eq.) in 3 mL DMF, 1-(2,4-bis(trifluoromethyl)benzyl)-4-ethynyl-1H-pyrazole (126.14 mg, 0.396 mmol, 1.2 eq.), CuI (6.27 mg, 0.033 mmol, 0.1 eq.), $Et_3N$ (99.99 mg, 0.990 mmol, 3 eq.) was purged with nitrogen and $PdCl_2(PPh_3)_2$ (11.56 mg, 0.016 mmol, 0.05 eq.) was added and heated at 110° C. for 18 hr. Reaction mixture was extracted with ethylacetate and water (2×50 mL), Organic layer was collected and concentrated to give crude product. Crude product was purified by combiflash chromatography. The pure fractions were concentrated to give 2-((1-(2,4-bis(trifluoromethyl)benzyl)-1H-pyrazol-4-yl)ethynyl)-5-(pyridin-2-yl)-1,3,4-thiadiazole (30 mg, white solid), LCMS: 480 $[M+H]^+$, $^1H$ NMR (400 MHz, DMSO-$d_6$) δ ppm 8.74 (br. s., 1H) 8.58 (s, 1H) 8.31 (d, J=7.89 Hz, 1H) 8.06 (s, 2H) 8.11 (s, 2H) 7.64 (d, J=5.70 Hz, 1H) 7.24 (d, J=8.33 Hz, 1H) 5.72 (s, 2H).

Example S2-4. Synthesis of (E)-2-(2-(1-(1-(2,4-bis(trifluoromethyl)phenyl)ethyl)-1H-pyrazol-4-yl)vinyl)-5-(pyridin-2-yl)-1,3,4-thiadiazole (Compound 2-5)

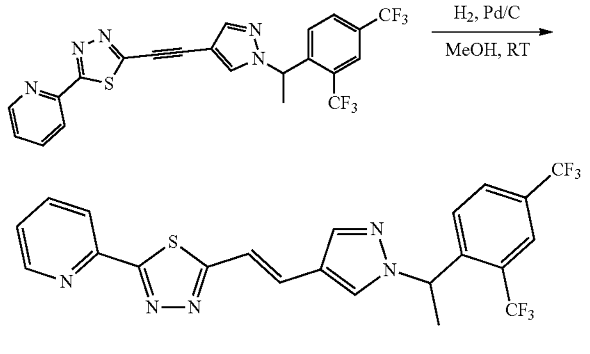

Compound 2-5

Synthesis of (E)-2-(2-(1-(1-(2,4-bis(trifluoromethyl)phenyl)ethyl)-1H-pyrazol-4-yl)vinyl)-5-(pyridin-2-yl)-1,3,4-thiadiazole. To a stirred solution of 2-((1-(1-(2,4-bis(trifluoromethyl)phenyl)ethyl)-1H-pyrazol-4-yl)ethynyl)-5-(pyridin-2-yl)-1,3,4-thiadiazole (100 mg, 0.20 mmol, 1.0 equiv.) in Methanol (20 mL) under nitrogen Palladium on Carbon[Pd/C](10 mg, 10% w/w) was added. Purge the reaction mixture with $H_2$ gas for overnight. Product formation was confirmed by TLC & LCMS. After the completion of reaction, reaction mixture was filtered through Celite bed & Filtrate was concentrate under reduced pressure to obtain crude which was further purified by flash column chromatography to obtain pure product. (E)-2-(2-(1-(1-(2,4-bis(trifluoromethyl)phenyl)ethyl)-1H-pyrazol-4-yl)vinyl)-5-(pyridin-2-yl)-1,3,4-thiadiazole (5 mg, as brown semi Solid), LCMS: 496 $[M+H]^+$, $^1H$ NMR (400 MHz, DMSO-$d_6$) δ 8.71 (d, J=4.8 Hz, 1H), 8.45 (s, 1H), 8.27 (d, J=7.9 Hz, 1H), 8.13-7.99 (m, 4H), 7.69 (d, J=8.3 Hz, 1H), 7.58 (dd, J=7.6, 4.9 Hz, 1H), 7.51 (d, J=16.3 Hz, 1H), 7.41 (d, J=16.3 Hz, 1H), 5.95 (p, J=6.8, 5.8 Hz, 2H), 1.89 (d, J=6.9 Hz, 3H).

Example S2-5. Synthesis of (Z)-2-(2-(1-(1-(2,4-bis(trifluoromethyl)phenyl)ethyl)-1H-pyrazol-4-yl)vinyl)-5-(pyridin-2-yl)-1,3,4-thiadiazole (Compound 2-6, Compound 2-7, and Compound 2-8)

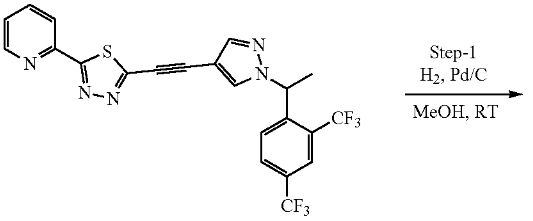

-continued

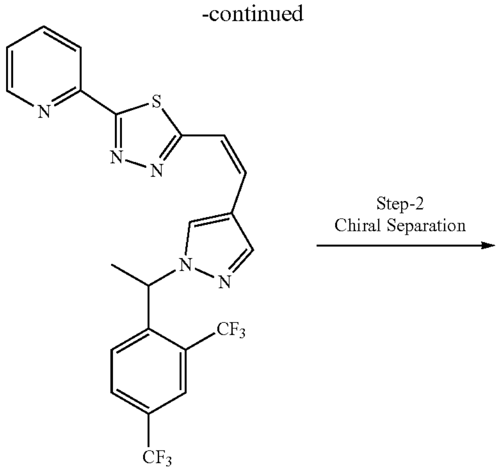

Compound 2-6

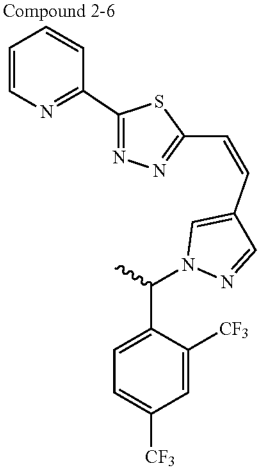

and

Compound 2-7

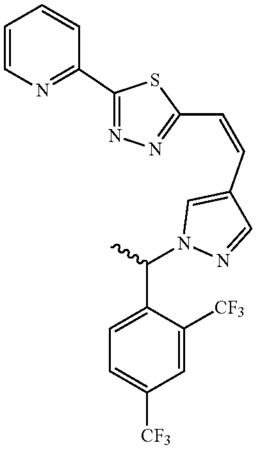

Compound 2-8

Step 1: Synthesis of (Z)-2-(2-(1-(1-(2,4-bis(trifluoromethyl)phenyl)ethyl)-1H-pyrazol-4-yl)vinyl)-5-(pyridin-2-yl)-1,3,4-thiadiazole. To a stirred solution of 2-((1-(1-(2,4-bis(trifluoromethyl)phenyl)ethyl)-1H-pyrazol-4-yl)ethynyl)-5-(pyridin-2-yl)-1,3,4-thiadiazole (100 mg, 0.20 mmol, 1.0 equiv.) in Methanol (20 mL) under nitrogen Palladium on Carbon [Pd/C](10 mg, 10% w/w) was added. Purge the reaction mixture with $H_2$ gas for overnight. Product formation was confirmed by TLC & LCMS. After the completion of reaction, reaction mixture was filtered through Celite bed & Filtrate was concentrate under reduced pressure to obtain crude. which was further purified by flash column chromatography to obtain (Z)-2-(2-(1-(1-(2,4-bis(trifluoromethyl)phenyl)ethyl)-1H-pyrazol-4-yl)vinyl)-5-(pyridin-2-yl)-1,3,4-thiadiazole (30 mg, as brown semi solid), Compound 6, LCMS: 496 $[M+H]^+$, $^1H$ NMR (400 MHz, DMSO-$d_6$): δ 8.76 (s, 1H), 8.68 (d, J=4.6 Hz, 1H), 8.30 (d, J=8.0 Hz, 1H), 8.12-7.97 (m, 4H), 7.75 (d, J=8.3 Hz, 1H), 7.63-7.55 (m, 1H), 6.92 (d, J=12.5 Hz, 1H), 6.81 (d, J=12.5 Hz, 1H), 5.99 (q, J=6.8 Hz, 1H), 1.90 (d, J=6.9 Hz, 3H).

Step 2: Synthesis of (Z)-2-(2-(1-(1-(2,4-bis(trifluoromethyl)phenyl)ethyl)-1H-pyrazol-4-yl)vinyl)-5-(pyridin-2-yl)-1,3,4-thiadiazole. The enantiomers of (Z)-2-(2-(1-(1-(2,4-bis(trifluoromethyl)phenyl)ethyl)-1H-pyrazol-4-yl)vinyl)-5-(pyridin-2-yl)-1,3,4-thiadiazole (elution time: 5.7 min & 7.06 min), were separated by chiral normal phase HPLC (Daicel Chiralpak®-IC, 250×20 mm, 5 μm). Isocratic program with HPLC grade n-Hexane and HPLC grade Isopropanol, Total flow: 56 g/min, Co-Solvent Percentage: 10% to obtain Compound 7 (10 mg) and Compound 8 (5 mg). Compound 2-7, LCMS: 496 $[M+H]^+$, $^1H$ NMR (400 MHz, DMSO-$d_6$) δ 8.76 (s, 1H), 8.68 (d, J=4.6 Hz, 1H), 8.30 (d, J=8.0 Hz, 1H), 8.12-7.97 (m, 4H), 7.75 (d, J=8.3 Hz, 1H), 7.63-7.55 (m, 1H), 6.92 (d, J=12.5 Hz, 1H), 6.81 (d, J=12.5 Hz, 1H), 5.99 (q, J=6.8 Hz, 1H), 1.90 (d, J=6.9 Hz, 3H), Compound 2-8, LCMS: 496 $[M+H]^+$, $^1H$ NMR (400 MHz, DMSO-$d_6$) δ 8.76 (s, 1H), 8.68 (d, J=4.6 Hz, 1H), 8.30 (d, J=8.0 Hz, 1H), 8.12-7.97 (m, 4H), 7.75 (d, J=8.3 Hz, 1H), 7.63-7.55 (m, 1H), 6.92 (d, J=12.5 Hz, 1H), 6.81 (d, J=12.5 Hz, 1H), 5.99 (q, J=6.8 Hz, 1H), 1.90 (d, J=6.9 Hz, 3H).

Example S2-6. Synthesis of 2-(2-(1-(1-(2,4-bis(trifluoromethyl)phenyl)ethyl)-1H-pyrazol-4-yl)ethyl)-5-(pyridin-2-yl)-1,3,4-thiadiazole (Compound 2-9)

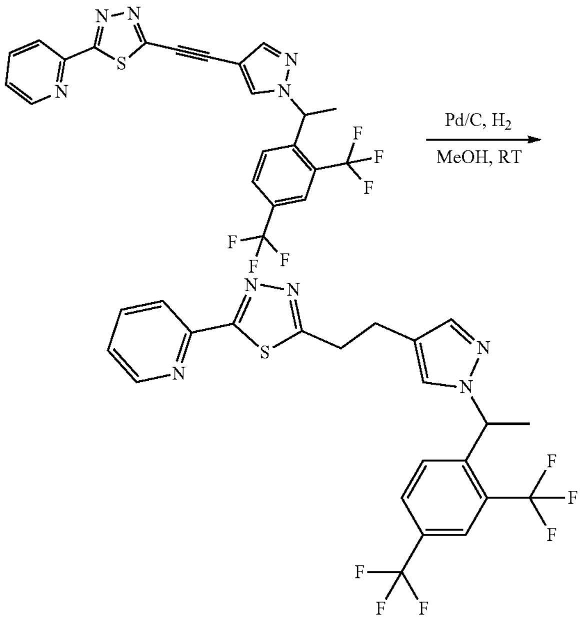

Compound 2-9

Step 1: Synthesis of 2-(2-(1-(1-(2,4-bis(trifluoromethyl)phenyl)ethyl)-1H-pyrazol-4-yl)ethyl)-5-(pyridin-2-yl)-1,3,4-thiadiazole. To a solution of 2-((1-(1-(2,4-bis(trifluoromethyl)phenyl)ethyl)-1H-pyrazol-4-yl)ethynyl)-5-(pyridin-2-yl)-1,3,4-thiadiazole (100 mg, 0.202 mmol, 1 Eq.) in 20 mL MeOH, Pd/C (15.02 mg, 0.141 mmol, 0.7 Eq.) was added and allowed to purge hydrogen gas for 24 hr at RT. After completion of reaction, reaction mixture was filtered through Celite pad and extracted with ethyl acetate and water, Organic layer was evaporated and concentrated to give product. LCMS: 498 $[M+H^+]$, $^1H$ NMR (400 MHz, DMSO-$d_6$): δ ppm 8.67 (d, J=4.39 Hz, 1H) 8.22 (d, J=7.89 Hz, 1H) 7.91-8.08 (m, 3H) 7.85 (s, 1H) 7.51-7.60 (m, 2H) 7.42 (s, 1H) 5.84 (d, J=6.58 Hz, 1H) 3.42 (t, J=7.45 Hz, 2H) 2.94 (t, J=7.24 Hz, 2H) 1.81 (d, J=7.02 Hz, 3H).

Example S2-7. Synthesis of 2-((1-(1-(2,4-bis(trifluoromethyl)phenyl)ethyl)-1H-pyrazol-4-yl)ethynyl)-5-(pyrazin-2-yl)-1,3,4-thiadiazole (Compound 2-10)

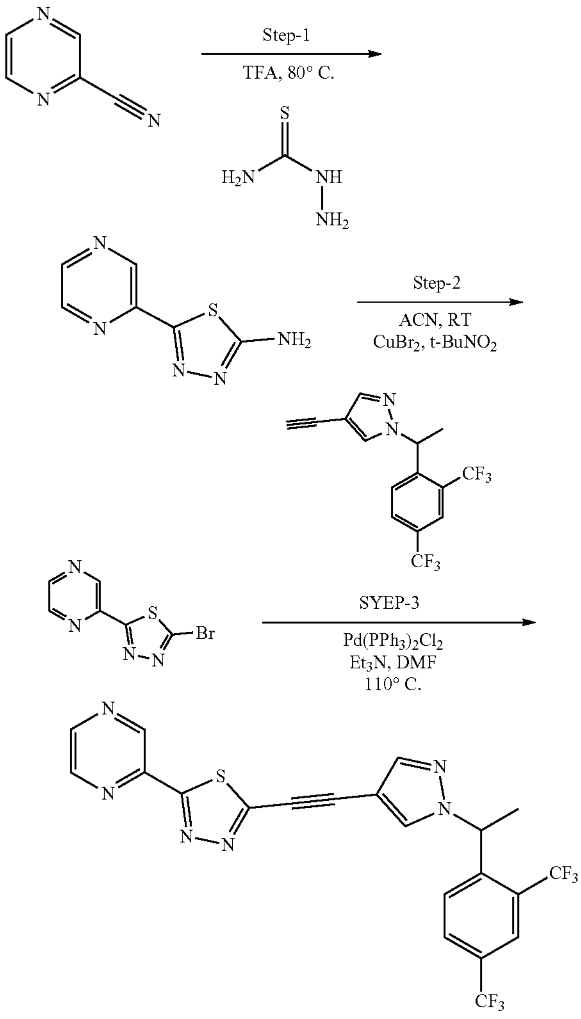

Compound 2-10

Step 1: Synthesis of 5-(pyrazin-2-yl)-1,3,4-thiadiazol-2-amine. To a solution of pyrazine-2-carbonitrile (2 g, 0.019 mmol, 1 equiv.) and hydrazinecarbothioamide (1.90 g, 0.020 mmol, 1.1 equiv.) in TFA (3 mL) was allowed to heat at 80° C. for 2 hr. Cold water was poured into reaction mixture, precipitate obtained was filtered off to give 5-(pyrazin-2-yl)-1,3,4-thiadiazol-2-amine (1.8 g). LCMS: 180 $[M+H]^+$.

Step 2: Synthesis of 2-bromo-5-(pyrazin-2-yl)-1,3,4-thiadiazole. To a solution of 5-(pyrazin-2-yl)-1,3,4-thiadiazol-2-amine (500 mg, 2.793 mmol, 1 equiv.) in ACN (5 mL), $CuBr_2$ (747 mg, 3.351 mmol, 1 equiv.) was added at 0° C. followed by t-$BuNO_2$ (431 mg, 4.189 mmol, 1.5 equiv.) was added and allowed to stir at 0° C. for 3 hr. Reaction mixture was quenched with $NH_4Cl$ and extracted with ethylacetate and water. Organic layer was evaporated to give crude product which was purified by combiflash chromatography to give 2-bromo-5-(pyrazin-2-yl)-1,3,4-thiadiazole (200 mg). LCMS: 244 $[M+H]^+$.

Step 3: Synthesis of 2-((1-(1-(2,4-bis(trifluoromethyl)phenyl)ethyl)-1H-pyrazol-4-yl)ethynyl)-5-(pyrazin-2-yl)-1,3,4-thiadiazole. To a solution of 2-bromo-5-(pyrazin-2-yl)-1,3,4-thiadiazole (72 mg, 0.30 mmol, 1 equiv.) in DMF (3 mL), 1-(1-(2,4-bis(trifluoromethyl)phenyl)ethyl)-4-ethynyl-1H-pyrazole (100 mg, 0.30 mmol, 1.0 equiv.), CuI (5.7 mg, 0.030 mmol, 0.1 equiv.), $Et_3N$ (90 mg, 0.900 mmol, 3 equiv.) was purged with nitrogen and $PdCl_2(PPh_3)_2$ (10 mg, 0.015 mmol, 0.05 equiv.) was added and heated at 110'C for overnight. Reaction mixture was diluted water (30 mL) and extracted with EtOAc (100 mL) again washed with water (30 mL×4). The reaction mixture was concentrated under reduced pressure to give a crude product. Crude product was purified by combi-flash chromatography. The pure fractions were concentrated to give 2-((1-(1-(2,4-bis(trifluoromethyl)phenyl)ethyl)-1H-pyrazol-4-yl)ethynyl)-5-(pyrazin-2-yl)-1,3,4-thiadiazole (15 mg, white solid). LCMS: 495 $[M+H]^+$, $^1H$ NMR (400 MHz, DMSO-$d_6$): δ ppm 9.48 (s, 1H) 8.86 (s, 1H) 8.81 (br. s., 1H) 8.71 (s, 1H) 8.03-8.12 (m, 2H) 7.99 (s, 1H) 7.70 (d, J=8.33 Hz, 1H) 5.97 (d, J=6.58 Hz, 1H) 1.88 (d, J=7.02 Hz, 3H).

Example S2-8. Synthesis of 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole (Compound 2-11)

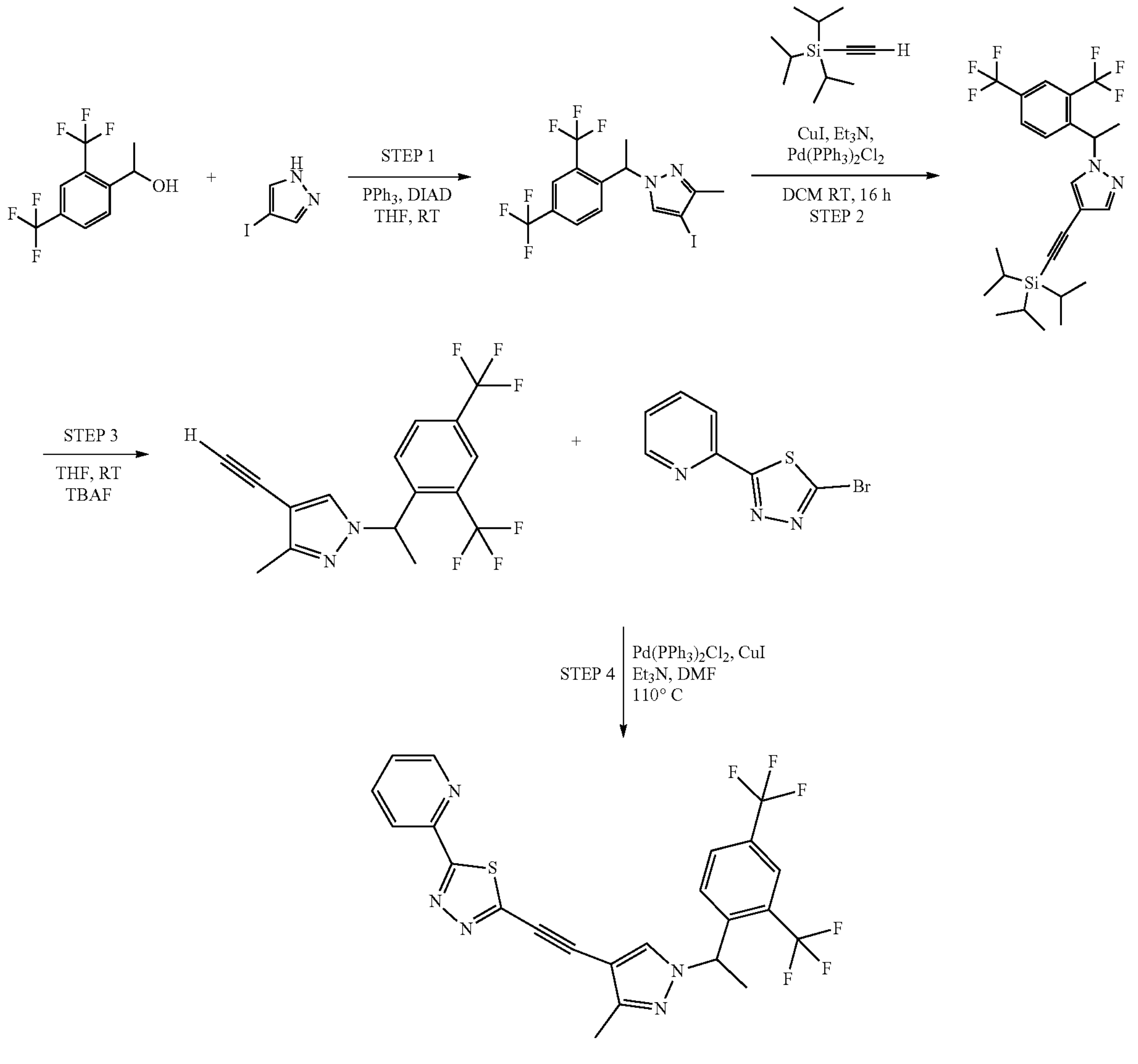

Compound 2-11

Step 1: Synthesis of 1-(1-(2,4-bis(trifluoromethyl)phenyl)ethyl)-4-iodo-3-methyl-1H-pyrazole. To a stirred solution of $PPh_3$ (0.20 g, 1.20 mmol, 1.5 eq.) and DIAD (0.264 g, 1.31 mmol, 1.6 eq.) in THE (5 mL), 1-(2,4-bis(trifluoromethyl)phenyl)ethan-1-ol (0.200 g 0.81 mmol, 1 eq.) and 4-iodo-3-methyl-1H-pyrazole (0.213 g, 1.20 mmol, 1.5 eq.) were added and allowed to stir at RT for 16 hr. Reaction progress was monitored by TLC and LCMS. After reaction completion, the reaction mixture was extracted with ethyl acetate and water (2×50 mL). Organic layer was separated and evaporated under reduced pressure to give crude product which was further purified by combiflash chromatography to yiled 1-(1-(2,4-bis(trifluoromethyl)phenyl)ethyl)-4-iodo-3-methyl-1H-pyrazole (50 mg), LCMS: 449 [M+1].

Step 2: Synthesis of 1-(1-(2,4-bis(trifluoromethyl)phenyl)ethyl)-4-((triisopropylsilyl)ethynyl)-1H-pyrazole. To a solution of 1-(1-(2,4-bis(trifluoromethyl)phenyl)ethyl)-4-iodo-3-methyl-1H-pyrazole (200 mg, 0.82 mmol, 1 eq.), $Pd(PPh_3)_2Cl_2$ (60 mg, 0.082 mmol, 0.1 eq.) in DCM (10 ml) was added triethylamine (0.3 ml, 2.48 mmol, 3 eq.) was purged with nitrogen 2-3 times was added ethynyltriisopropylsilane (0.196 mg, 1.07 mmol, 1.3 eq.), CuI (31 mg, 0.165 mmol, 0.2 eq.) Reaction mixture stirred at RT for 16 h. Reaction progress was monitored by TLC and LCMS Reaction mixture was quench water (2*50 mL) and extracted with ethylacetate and Organic layer was collected and concentrated to give crude product was purified by combiflash chromatography to obtain pure product 1-(1-(2,4-bis(trifluoromethyl)phenyl)ethyl)-4-((triisopropylsilyl)ethynyl)-1H-pyrazole (50 mg). LCMS: 489 $[M+H]^+$.

Step 3: Synthesis of 1-(1-(2,4-bis(trifluoromethyl)phenyl)ethyl)-4-ethynyl-3-methyl-1H-pyrazole. To a solution of 1-(1-(2,4-bis(trifluoromethyl)phenyl)ethyl)-4-((triisopropylsilyl)ethynyl)-1H-pyrazole (1.0 g, 1.99 mmol, 1 eq.) in THF (12 ml), was added TBAF (4 mL) was added under anhydrous condition. Reaction mixture quenched water (2×25 mL), Extracted with ethyl acetate, Organic layer was collected and concentrated to give crude product which was purified by combiflash chromatography to give 1-(1-(2,4-bis(trifluoromethyl)phenyl)ethyl)-4-ethynyl-3-methyl-1H-pyrazole (300 mg). LCMS: 347 $[M+H]^+$.

Step 4: Synthesis of 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole. To a solution of 2-bromo-5-(pyridin-2-yl)-1,3,4-thiadiazole (100 mg, 0.28 mmol, 1 eq.), $Pd(PPh_3)_2Cl_2$ (20 mg, 0.028 mmol, 0.1 eq.) in DCM (15 ml) was added triethylamine (0.12 ml, 0.86 mmol, 3 eq.) was purged with nitrogen 2-3 times was added 1-(1-(2,4-bis(trifluoromethyl)phenyl)ethyl)-4-ethynyl-3-methyl-1H-pyrazole (69 mg, 1.07 mmol, 1.0 eq.), CuI (11 mg, 0.057 mmol, 0.2 eq.). Reaction mixture stirred at RT for 16 h. Reaction progress was monitored by TLC and LCMS Reaction mixture was quench water (2×50 mL) and Extracted with ethyl acetate and Organic layer was collected and dried overs sodium sulphate and concentrated to give crude product which was purified by combi flash chromatography by using Hexane. Ethyl acetate to obtain product was further purified by revers phase chromatography to obtain pure product 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole (15 mg), LCMS: 507 $[M+H]^+$, $^1H$ NMR (400 MHz, DMSO-$d_6$) δ ppm 8.73 (d, J=4.82 Hz, 1H) 8.61 (s, 1H) 8.31 (d, J=7.89 Hz, 1H) 8.01-8.12 (m, 3H) 7.8 (d, J=7.89 Hz, 1H) 7.57-7.67 (m, 1H)) 5.9 (br. s., 1H) 2.27 (s, 3H) 1.82-1.94 (m, 3H).

Example S2-9. Synthesis of 2-((1-(1-(2,6-dichlorophenyl)ethyl)-1H-pyrazol-4-yl)ethynyl)-5-(furan-2-yl)-1,3,4-thiadiazole (Compound 2-12)

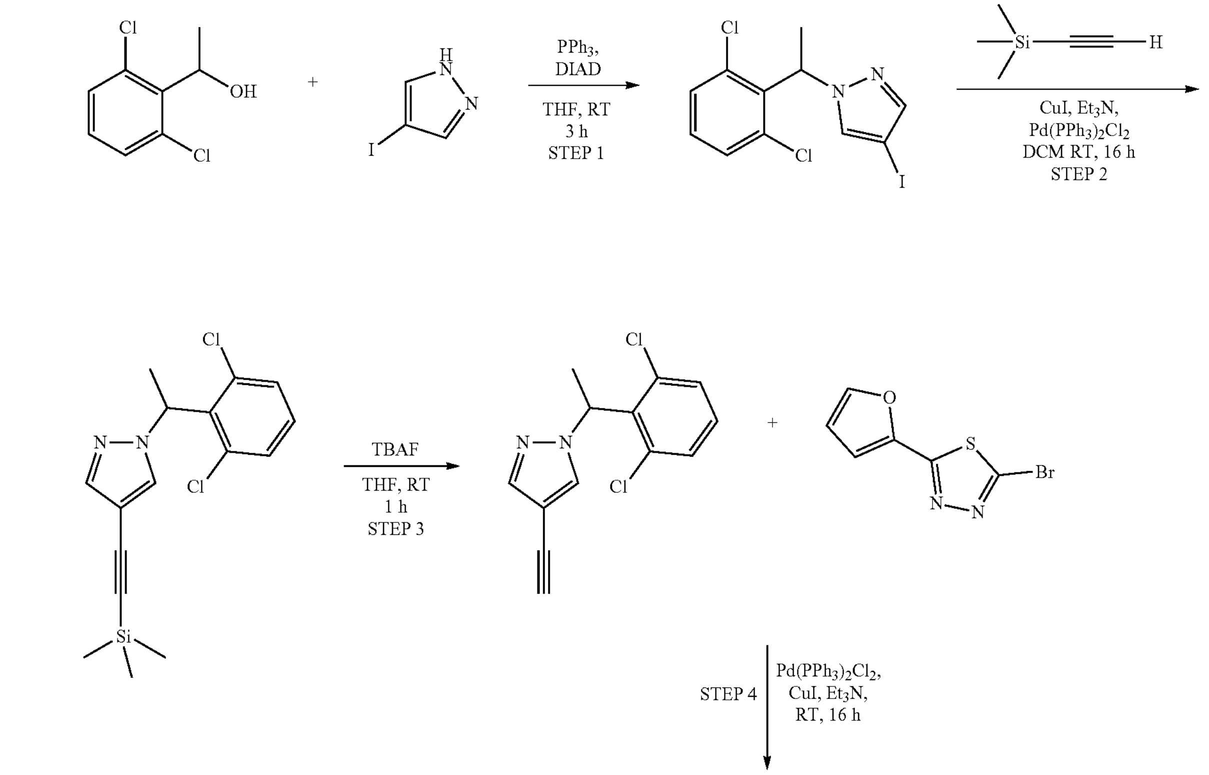

-continued

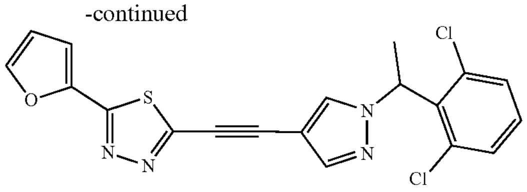

Compound 2-12

Step 1: Synthesis of 1-(1-(2,6-dichlorophenyl)ethyl)-4-iodo-1H-pyrazole. To a stirred solution of $PPh_3$ (3.0 g, 11.78 mmol, 1.5 eq.) & DIAD (2.38 g, 11.78 mmol, 1.5 eq.) in THF (10 mL) at 0 deg C. was added 1-(2,6-dichlorophenyl) ethanol (1.5 g, 7.85 mmol, 1.0 eq.) and 4-iodo-1H-pyrazole (3.04 g, 15.70, 2.0 eq.). After addition reaction mixture was allowed to stir at RT for 3 hr. Reaction progress was monitored by TLC and LCMS. After completion of the reaction, the reaction mixture quenched water (2×30 mL) and ethyl acetate (2×100 mL) Organic layer was separated and evaporated under reduced vacuum pressure to give crude product was further purified by combi flash chromatography to yield 1-(1-(2,6-dichlorophenyl)ethyl)-4-iodo-1H-pyrazole (1.6 g), Analytical Data: LCMS: 367 [M+H].

Step 2: Synthesis of 1-(1-(2,6-dichlorophenyl)ethyl)-4-((trimethylsilyl)ethynyl)-1H-pyrazole. To a solution of 1-(1-(2,6-dichlorophenyl)ethyl)-4-iodo-1H-pyrazole (1.1 g, 3.00 mmol, 1 eq.), ethynyltrimethylsilane (442 mg, 4.50 mmol, 1.5 eq.), CuI (57 mg, 0.300 mmol, 0.1 eq.), TEA (1.25 mL, 9.01 mmol, 3 eq.) in dioxane (10 ml) was purged nitrogen gas for degased 15 min. was added $Pd(PPh_3)_2Cl_2$ (110 mg, 0.150 mmol, 0.05 eq.) and heated at 110° C. for 18 hr. after complication reaction, mixture quenched water (2×50 mL) and ethyl acetate (2×100 mL), Organic layer was separated and concentrated under reduce vacuum pressure to give crude product was obtained and purified by Combi flash column chromatography to obtained product 1-(1-(2,6-dichlorophenyl)ethyl)-4-((trimethylsilyl)ethynyl)-1H-pyrazole (0.710 g), Analytical Data: LCMS: 337 [M+H].

Step 3: Synthesis of 1-(1-(2,6-dichlorophenyl)ethyl)-4-ethynyl-1H-pyrazole. To a solution of 1-(1-(2,6-dichlorophenyl)ethyl)-4-((trimethylsilyl)ethynyl)-1H-pyrazole (700 mg, 2.07 mmol, 1 eq.) in THF (15 ml), was added TBAF (4 mL) drop wise under anhydrous condition. reaction mixture stirred RT for 2 h. after complication reaction mixture diluted EtOAC (50 mL) and washed with water (2×10 mL), Organic layer was separated, concentrated to give crude product which was purified by combi flash chromatography to 1-(1-(2,6-dichlorophenyl)ethyl)-4-ethynyl-1H-pyrazole (500 mg), Analytical Data: LCMS: 265 [M+H].

Step 4: Synthesis of 2-((1-(1-(2,6-dichlorophenyl)ethyl)-1H-pyrazol-4-yl)ethynyl)-5-(furan-2-yl)-1,3,4-thiadiazole. To a solution of 2-bromo-5-(furan-2-yl)-1,3,4-thiadiazole (300 mg, 1.30 mmol, 1 eq.) in DCM (10 mL), purged Nitrogen gas for 10 min was added PdCl2(PPh3)2 (91 mg 0.130 mmol, 0.1 eq.) and purged Nitrogen gas additional 15 min. was added TEA (0.54 mL, 3.91 mmol, 3.0 eq.) CuI (49 mg 0.260 mmol, 0.2 eq.) and 1-(1-(2,6-dichlorophenyl) ethyl)-4-ethynyl-1H-pyrazole (344 mg, 1.30 mmol, 1.0 eq) and the RM was stirred at RT for overnight. after complication reaction mixture quenched water (40 mL) and extracted with DCM (2×50 mL), Organic layer was separated and concentrated under reduce vacuum pressure to give crude product was obtained and purified by combi flash column chromatography to obtained product 2-((1-(1-(2,6-dichlorophenyl)ethyl)-1H-pyrazol-4-yl)ethynyl)-5-(furan-2-yl)-1,3,4-thiadiazole (100 mg), LCMS: 415 $[M+H]^+$; $^1H$ NMR (400 MHz, DMSO-$d_6$) δ ppm 8.70 (d, J=4.82 Hz, 1H) 8.10 (s, 1H) 7.90 (d, J=3.95 Hz, 1H) 7.52 (d, J=7.89 Hz, 2H) 7.41 (d, J=7.89 Hz, 2H) 6.82 (d, J=7.89 Hz, 1H) 6.28 (d, J=7.02 Hz, 1H) 1.98 (d, J=7.02 Hz, 3H).

Example S2-10. Synthesis of 2-((1-(1-(2,6-dichlorophenyl)ethyl)-1H-pyrazol-4-yl)ethynyl)-5-(pyridin-2-yl)-1,3,4-thiadiazole (Compound 2-20)

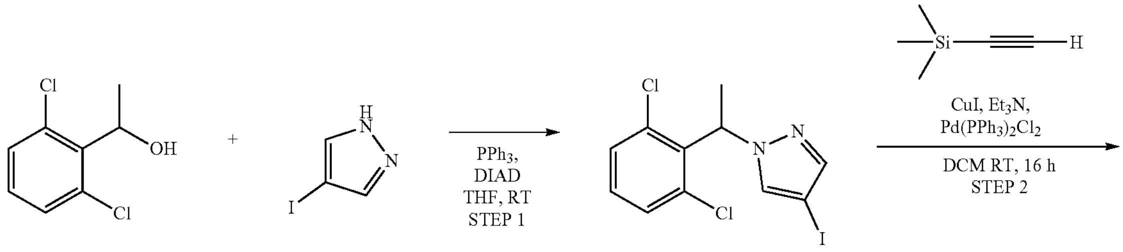

-continued

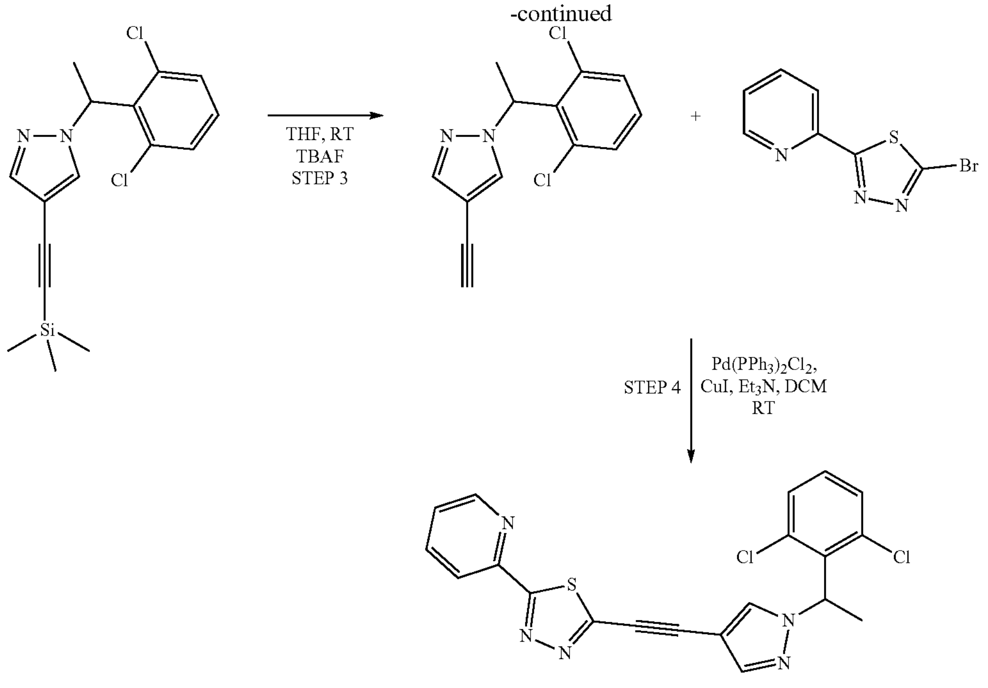

Compound 2-20

Step 1: Synthesis of 1-(1-(2,6-dichlorophenyl)ethyl)-4-iodo-1H-pyrazole. To a stirred solution of $PPh_3$ (3.0 g, 0.0117 mmol, 1.5 eq.) and DIAD (2.38 g, 0.0117 mmol, 1.5 eq.) in THF (10 mL), 1-(2,6-dichlorophenyl)ethan-1-ol (1.5 g, 0.007 mmol, 1.0 eq.) and 4-iodo-1H-pyrazole (3.0 g, 0.0157 mmol, 3.0 eq.) were added and allowed to stir at RT for 1 hr. Reaction progress was monitored by TLC and LCMS. After the reaction completion, the reaction mixture was extracted with ethyl acetate and water (2×500 mL). Organic layer was separated and evaporated under reduced pressure to give crude product which was further purified by Combi flash chromatography to yield 1-(1-(2,6-dichlorophenyl)ethyl)-4-iodo-1H-pyrazole (1.6 g), LCMS: 366.92 $[M+1]^+$ Step 2: Synthesis of 1-(1-(2,6-dichlorophenyl)ethyl)-4-((trimethylsilyl)ethynyl)-1H-pyrazole. To a solution of 1-(1-(2,6-dichlorophenyl)ethyl)-4-iodo-1H-pyrazole (1.1 g, 0.003 mmol, 1 eq.), ethynyltrimethylsilane (0.700 mg, 0.0045 mmol, 1.5 eq.), CuI (60 mg, 3.006 mmol, 0.1 eq.), triethylamine (1.7 mL, 0.0090 mmol, 3 eq.) in 10 mL dioxane was purged with nitrogen and $Pd(PPh_3)_2Cl_2$ (110 mg, 0.0090 mmol, 0.05 eq.) was added and heated at 120° C. for 18 hr. Reaction mixture was extracted with ethyl acetate and water (2×50 mL). Organic layer was collected and concentrated to give crude product. Crude product was purified by combi flash chromatography to obtain product 1-(1-(2,6-dichlorophenyl)ethyl)-4-((trimethylsilyl)ethynyl)-1H-pyrazole (0.710 g), LCMS: 337.06.

Step 3: Synthesis of 1-(1-(2,6-dichlorophenyl)ethyl)-4-ethynyl-1H-pyrazole. To a solution of 1-(1-(2,6-dichlorophenyl)ethyl)-4-((trimethylsilyl)ethynyl)-1H-pyrazole (700 mg, 6.516 mmol, 1 eq.) in 5 mL THF, TBAF (4 mL) was added under anhydrous condition & stirred at RT. Reaction mixture was extracted with ethyl acetate and water (2×25 mL). Organic layer was collected and concentrated to give crude product which was purified by combi flash chromatography to give 1-(1-(2,6-dichlorophenyl)ethyl)-4-ethynyl-1H-pyrazole (500 mg), LCMS: 265.02 $[M+1]^+$ Step 4: Synthesis of 2-((1-(1-(2,6-dichlorophenyl)ethyl)-1H-pyrazol-4-yl)ethynyl)-5-(pyridin-2-yl)-1,3,4-thiadiazole. To a solution of 2-bromo-5-(pyridin-2-yl)-1,3,4-thiadiazole (90 mg, 3.7 mmol, 1 eq.) in DCM (5 mL), $PdCl_2(PPh_3)_2$ (26 mg, 3.75 mmol, 0.1 eq.) was added and purged with Nitrogen gas for 10 min. After purging, TEA (0.2 mL, 0.00112 mmol, 3.0 eq.) CuI (20 mg 7.5 mmol, 0.2 eq.) was added to the reaction mixture, followed by the addition of 1-(1-(2,6-dichlorophenyl)ethyl)-4-ethynyl-1H-pyrazole (100 mg, 3.75 mmol, 1.0 eq) and the RM was stirred at RT for overnight. Reaction mixture was extracted with ethyl acetate and water (2×50 mL). Organic layer was collected and concentrated to give crude product. crude product which was purified by combi-flash chromatography to give as a product 2-((1-(1-(2,6-dichlorophenyl)ethyl)-1H-pyrazol-4-yl)ethynyl)-5-(pyridin-2-yl)-1,3,4-thiadiazole (21 mg), LCMS: 426 $[M+H]^+$; $^1H$ NMR (400 MHz, DMSO-$d_6$) δ ppm 8.73 (d, J=4.82 Hz, 1H) 8.68 (s, 1H) 8.31 (d, J=7.89 Hz, 1H) 8.08 (s, 1H) 7.93 (s, 1H) 7.64 (d, J=3.95 Hz, 1H) 7.49 (d, J=7.89 Hz, 1H) 7.32-7.40 (m, 1H) 6.23 (d, J=7.02 Hz, 1H) 1.98 (d, J=7.02 Hz, 3H).

Example S2-11. Synthesis of 2-((1-(1-(2,4-bis(trifluoromethyl)phenyl)ethyl)-1H-pyrazol-4-yl)ethynyl)-5-(pyrazin-2-yl)-1,3,4-thiadiazole (Compound 2-21 and Compound 2-22)

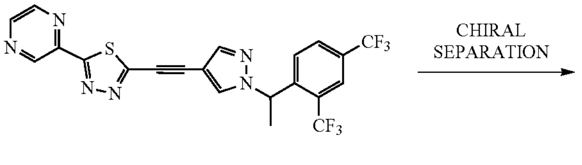

-continued

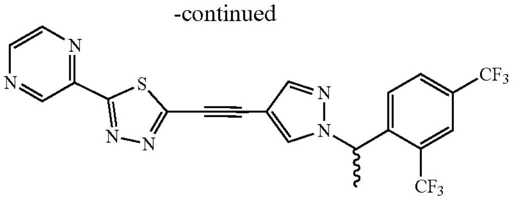

Compound 2-21

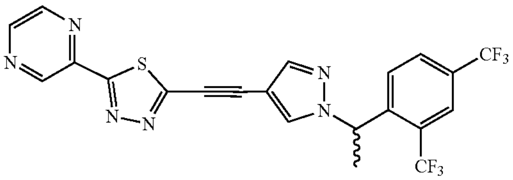

Compound 2-22

The racemic mixture of 2-((1-(1-(2,4-bis(trifluoromethyl)phenyl)ethyl)-1H-pyrazol-4-yl)ethynyl)-5-(pyrazin-2-yl)-1, 3,4-thiadiazole (260 mg,) was purified by chiral HPLC to obtain a first-eluting isomer (Compound 2-21) and a second-eluting isomer (Compound 2-22). The isomers were separated by chiral SFC (Daicel Chiralpak®-IG, 250×21 mm, 5 μm). Isocratic program with analytical grade liquid carbon dioxide and HPLC grade Methanol:Acetonitrile (1:1), Total flow: 56 g/min, Co-Solvent Percentage: 35%.

Compound 2-21: yield=62 mg; elution time=4.2 min. Compound 2-22: yield=60 mg; elution time=7.2 min Compound 2-21: LCMS: 495.07 $[M+H]^+$, $^1H$ NMR (400 MHz, DMSO-$d_6$) δ ppm 9.50 (d, J=1.32 Hz, 1H) 8.80-8.95 (m, 2H) 8.73 (s, 1H) 8.06-8.18 (m, 2H) 8.01 (s, 1H) 7.71 (d, J=8.33 Hz, 1H) 5.99 (d, J=6.58 Hz, 1H) 1.90 (d, J=7.02 Hz, 3H). Compound 2-22: LCMS: 495.07 $[M+H]^+$; $^1H$ NMR (400 MHz, DMSO-$d_6$) δ ppm 9.51 (d, J=1.32 Hz, 1H) 8.82-8.95 (m, 2H) 8.70 (s, 1H) 8.01-8.18 (m, 2H) 8.00 (s, 1H) 7.73 (d, J=8.33 Hz, 1H) 5.97 (d, J=6.58 Hz, 1H) 1.92 (d, J=7.02 Hz, 3H).

Example S2-12. Synthesis of 2-((1-(1-(2,4-bis(trifluoromethyl)phenyl)ethyl)-1H-pyrazol-4-yl)ethynyl)-5-(pyrazin-2-yl)-1,3,4-thiadiazole (Compound 2-23 and Compound 2-24)

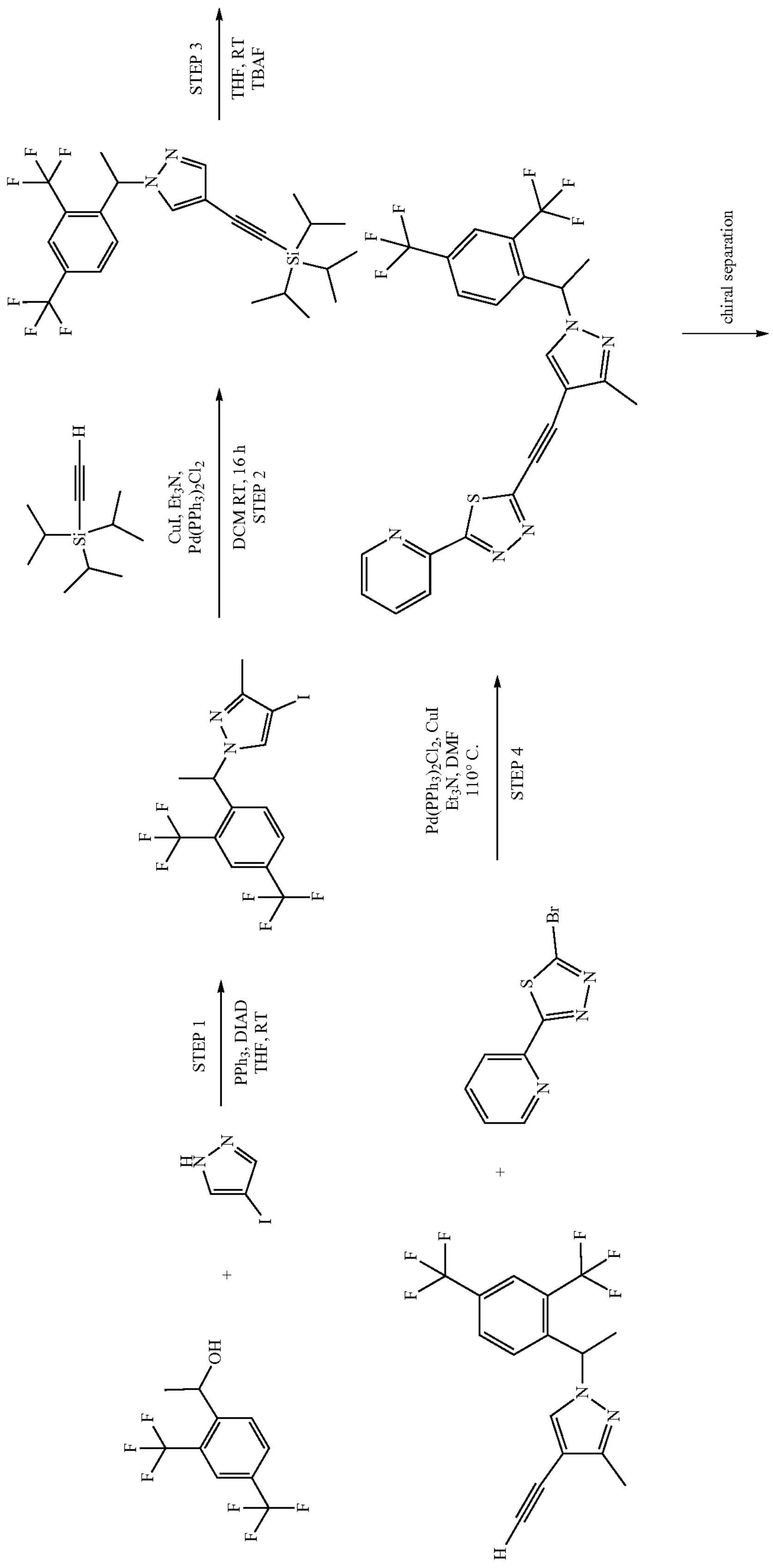
STEP 1
$PPh_3$, DIAD
THF, RT
CuI, $Et_3N$,
$Pd(PPh_3)_2Cl_2$
DCM RT, 16 h
STEP 2
STEP 3
THF, RT
TBAF
$Pd(PPh_3)_2Cl_2$, CuI
$Et_3N$, DMF
110° C.
STEP 4
chiral separation -continued
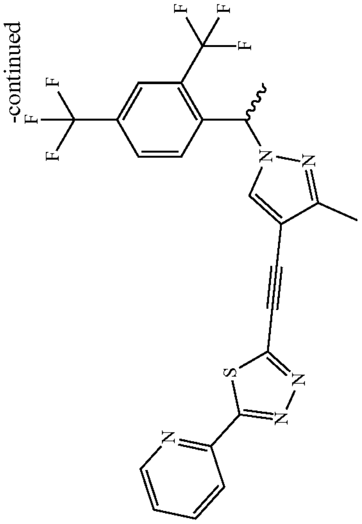
Compound 2-24
+
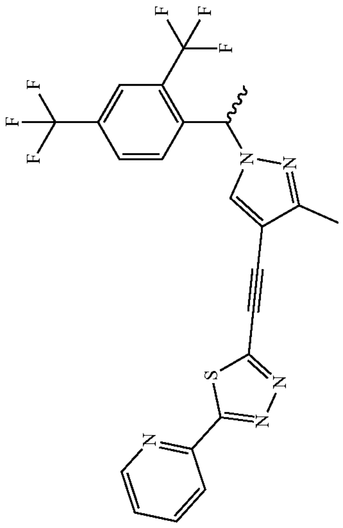
Compound 2-23

Step 1: Synthesis of 1-(1-(2,4-bis(trifluoromethyl)phenyl)ethyl)-4-iodo-3-methyl-1H-pyrazole. To a stirred solution of 1-(2,4-bis(trifluoromethyl)phenyl)ethanol (1.00 g, 3.875 mmol, 1.0 eq.) and 4-iodo-3-methyl-1H-pyrazole (886 mg, 4.2635 mmol, 1.1 eq.) & TPP (1.52 g, 5.813 mmol, 1.5 eq.) in THF (10 mL) cooled to 0° C. & was added DIAD (1.17 ml, 5.813 mmol, 1.5 eq.) drop wise, after addition stir at RT for 16 hr. Reaction progress was monitored by TLC and LCMS. After reaction completion, the reaction mixture was extracted with ethyl acetate and water (2×15 ml). Organic layer was separated and evaporated under reduced pressure to give crude product which was further purified by combiflash chromatography to obtain 1-(1-(2,4-bis(trifluoromethyl)phenyl)ethyl)-4-iodo-3-methyl-1H-pyrazole (700 mg), LCMS: 448.9 [M+1].

Step 2: Synthesis of 1-(1-(2,4-bis(trifluoromethyl)phenyl)ethyl)-3-methyl-4-((trimethylsilyl)ethynyl)-1H-pyrazole. To a solution of 1-(1-(2,4-bis(trifluoromethyl)phenyl)ethyl)-4-iodo-3-methyl-1H-pyrazole (900 mg, 2.013 mmol, 1.0 eq.) & ethynyltrimethylsilane (0.42 ml, 3.020 mmol, 1.5 eq.) in DCM (10 ml) was added triethylamine (0.82 ml, 6.040 mmol, 3 eq.) & CuI (40 mg, 0.201 mmol, 0.1 eq.) was purged with nitrogen for 10 min & was added $Pd(PPh_3)_2Cl_2$ (90 mg, 0.201 mmol, 0.1 eq.), Reaction mixture stirred at RT for 16 h. Reaction progress was monitored by TLC and LCMS, After reaction completion, the reaction mixture was extracted with DCM and water (2×15 ml). Organic layer was separated and evaporated under reduced pressure to give crude product which was further purified by combiflash chromatography to yiled 1-(1-(2,4-bis(trifluoromethyl)phenyl)ethyl)-3-methyl-4-((trimethylsilyl)ethynyl)-1H-pyrazole. (50 mg), LCMS: 489.21 [M+H].

Step 3: Synthesis 1-(1-(2,4-bis(trifluoromethyl)phenyl)ethyl)-4-ethynyl-3-methyl-1H-pyrazole. To a solution of 1-(1-(2,4-bis(trifluoromethyl)phenyl)ethyl)-3-methyl-4-((trimethylsilyl)ethynyl)-1H-pyrazole (700 mg, 1.6706 mmol, 1.0 eq.) in THE (10 ml), cool to 0° C. & was added TBAF (0.43 ml, 0.835 mmol, 0.5 eq.) drop wise under anhydrous condition. Reaction progress was monitored by TLC and LCMS. After reaction completion, the reaction mixture was extracted with ethyl acetate and water (2×15 ml). Organic layer was separated and evaporated under reduced pressure to give crude product which was further purified by combiflash chromatography to yiled 1-(1-(2,4-bis(trifluoromethyl)phenyl)ethyl)-4-ethynyl-3-methyl-1H-pyrazole (300 mg), LCMS: 347 [M+H].

Step 4: Synthesis of 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole. To a solution of 2-bromo-5-(pyridin-2-yl)-1,3,4-thiadiazole (312 mg, 1.3005 mmol, 1.0 eq.), & $Pd(PPh_3)_2C_{12}$ (80 mg, 0.1300 mmol, 0.1 eq.) in DCM (10 ml) was added triethylamine (0.53 ml, 3.9017 mmol, 3.0 eq.) & was purged with nitrogen for 10 min & was added 1-(1-(2,4-bis(trifluoromethyl)phenyl)ethyl)-4-ethynyl-3-methyl-1H-pyrazole (450 mg, 1.3005 mmol, 1.0 eq.), & CuI (50 mg, 0.2601 mmol, 0.2 eq.), After all addition, reaction mixture stirred at RT for 16 h. Reaction progress was monitored by TLC and LCMS, After completion of reaction, the reaction mixture was extracted with DCM & water (2×15 mL) and Organic layer was collected and dried overs sodium sulphate and concentrated to give crude product which was purified by combi flash chromatography to obtain product was further purified by revers phase chromatography to obtain pure product 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole (130 mg), LCMS: 507 [M+H], $^1$H NMR (400 MHz, DMSO-$d_6$) δ ppm 8.73 (d, J=4.82 Hz, 1H) 8.61 (s, 1H) 8.31 (d, J=7.89 Hz, 1H) 8.01-8.12 (m, 3H) 7.8 (d, J=7.89 Hz, 1H) 7.57-7.67 (m, 1H)) 5.9 (br. s., 1H) 2.27 (s, 3H) 1.82-1.94 (m, 3H).

Step 5: Separation of isomers of 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole. The enantiomers of 2-((1-(1-(2,4-bis(trifluoromethyl)phenyl)ethyl)-3-methyl-1H-pyrazol-4-yl)ethynyl)-5-(pyridin-2-yl)-1,3,4-thiadiazole were separated by chiral SFC (Daicel Chiralpak®-IC, 250×20 mm, 5 μm). Isocratic program with analytical grade liquid carbon dioxide and HPLC grade isopropanol, Total flow: 52 g/min, Co-Solvent Percentage: 20% to obtain a first-eluting isomer (Compound 2-23) and a second-eluting isomer (Compound 2-24).

Compound 2-23: yield=30 mg; elution time=4.2 min; Compound 2-24: yield=28 mg; elution time=6.5 min.

Compound 2-23: $^1$H NMR (400 MHz, Chloroform-d) δ 8.69 (d, J=1.9 Hz, 1H), 8.11 (dd, J=8.7, 1.7 Hz, 1H), 8.01-7.92 (m, 3H), 7.88 (dd, J=8.8, 2.4 Hz, 2H), 7.65-7.57 (m, 3H), 7.54 (td, J=7.5, 6.8, 1.4 Hz, 1H), 7.49-7.36 (m, 5H), 7.08 (s, 1H). LCMS 401 $[M+H]^+$.

Compound 2-24: $^1$H NMR (400 MHz, Chloroform-d) δ 8.69 (d, J=1.9 Hz, 1H), 8.11 (dd, J=8.7, 1.7 Hz, 1H), 8.01-7.92 (m, 3H), 7.88 (dd, J=8.8, 2.4 Hz, 2H), 7.65-7.57 (m, 3H), 7.54 (td, J=7.5, 6.8, 1.4 Hz, 1H), 7.49-7.36 (m, 5H), 7.08 (s, 1H), 401 $[M+H]^+$.

Example S3

Example S3-1. Synthesis of N-(1-cyclopentyl-1H-pyrazol-4-yl)-5-(furan-2-yl)isoxazole-3-carboxamide (Compound 3-1)

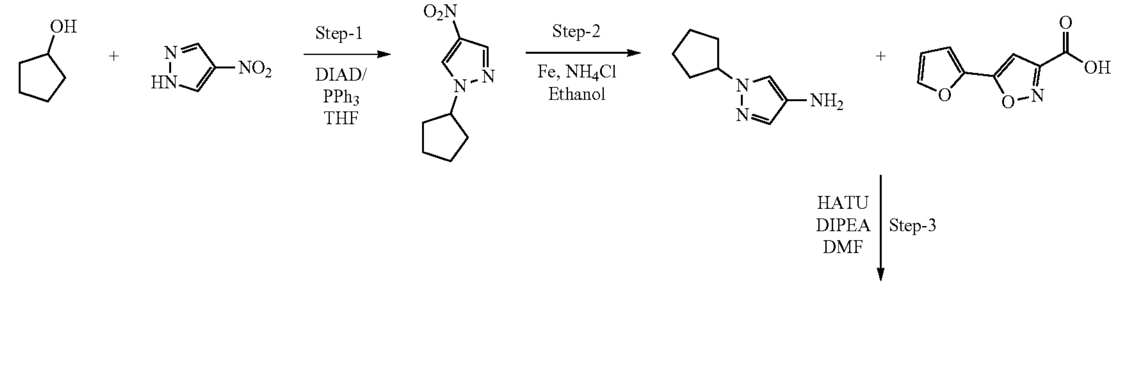

-continued

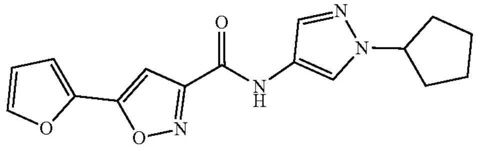

Compound 3-1

Step 1: Synthesis of 1-cyclopentyl-4-nitro-1H-pyrazole. To a stirred solution of $PPh_3$ (2.14 g, 8.71 mmol, 1.5 equiv.) in THF (10 mL), DIAD (1.75 g, 8.71 mmol, 1.5 equiv.) was added and allowed to stir at RT for 15 min. Then cyclopentanol (500 mg, 5.813 mmol, 1 equiv.) and 4-nitro-1H-pyrazole (656.86 mg, 5.813 mmol, 1 equiv.) was added and allowed to stir at RT for 16 hr. Reaction progress was monitored by TLC and LCMS. After the reaction completion, the reaction mixture was extracted with ethyl acetate and water 2 times. Organic layer was separated and evaporated under reduced pressure to give crude product which was further purified by using combiflash chromatography to yield 1-cyclopentyl-4-nitro-1H-pyrazole, $^{1}H$ NMR (400 MHz, DMSO-$d_6$) δ ppm 8.92 (s, 1H) 8.26 (s, 1H) 4.78 (t, J=6.80 Hz, 1H) 2.04-2.16 (m, 2H) 1.86-2.01 (m, 2H) 1.71-1.85 (m, 2H) 1.54-1.71 (m, 2H).

Step 2: Synthesis of 1-cyclopentyl-1H-pyrazol-4-amine. To a stirred solution of 1-cyclopentyl-4-nitro-1H-pyrazole (500 mg, 2.762 mmol, 1 equiv.) in 10 mL EtOH/water (1:1), Fe (759.66 mg, 13.81 mmol, 5 equiv.) and ammonium chloride (731.53 mg, 13.81 mmol, 5 equiv.) was added and allowed to heat at 80° C. for 2 hr. Reaction progress was monitored by TLC and LCMS. After reaction completion, reaction mixture was filtered through celite pad and filtrate was evaporated and extracted with DCM/water 2 times. Organic layer was collected and evaporated under reduced pressure to give 1-cyclopentyl-1H-pyrazol-4-amine, LCMS: 152 $[M+H]^+$.

Step 3: Synthesis of N-(1-cyclopentyl-1H-pyrazol-4-yl)-5-(furan-2-yl) isoxazole-3-carboxamide. To a stirred solution of 5-(furan-2-yl) isoxazole-3-carboxylic acid (118.54 mg, 0.662 mmol, and 1 equiv.) in DMF (4 mL), HATU (251.56 mg, 0.662 mmol, 1 equiv.) was added and allowed to stir at RT for 15 min. Then, stirred solution of 1-cyclopentyl-1H-pyrazol-4-amine (100 mg, 0.662 mmol, 1 equiv.) and DIPEA (256.19 mg, 1.986 mmol, 3 equiv.) was added. Reaction mixture was allowed to stir at RT for 18 hr. After reaction completion, reaction mixture was extracted with ethyl acetate and water 2 times. Organic layer was collected and evaporated to give crude product. Crude product was purified by using combiflash chromatography and further triturated using diethyl ether and pentane to yield N-(1-cyclopentyl-1H-pyrazol-4-yl)-5-(furan-2-yl) isoxazole-3-carboxamide. (70 mg white solid), LCMS 313 $[M+H]^+$, $^{1}H$ NMR (400 MHz, DMSO-$d_6$) δ ppm 10.96 (s, 1H) 7.98-8.07 (m, 2H) 7.63 (s, 1H) 7.29 (d, J=3.51 Hz, 1H) 7.15 (s, 1H) 6.77 (br. s., 1H) 4.66-4.74 (m, 1H) 2.05 (br. s., 2H) 1.89 (d, J=5.26 Hz, 2H) 1.77 (br. s., 2H) 1.63 (br. s., 2H).

Example S3-2. Synthesis of N-(1-(cyclopentylmethyl)-1H-pyrazol-4-yl)-5-(furan-2-yl)isoxazole-3-carboxamide (Compound 3-2)

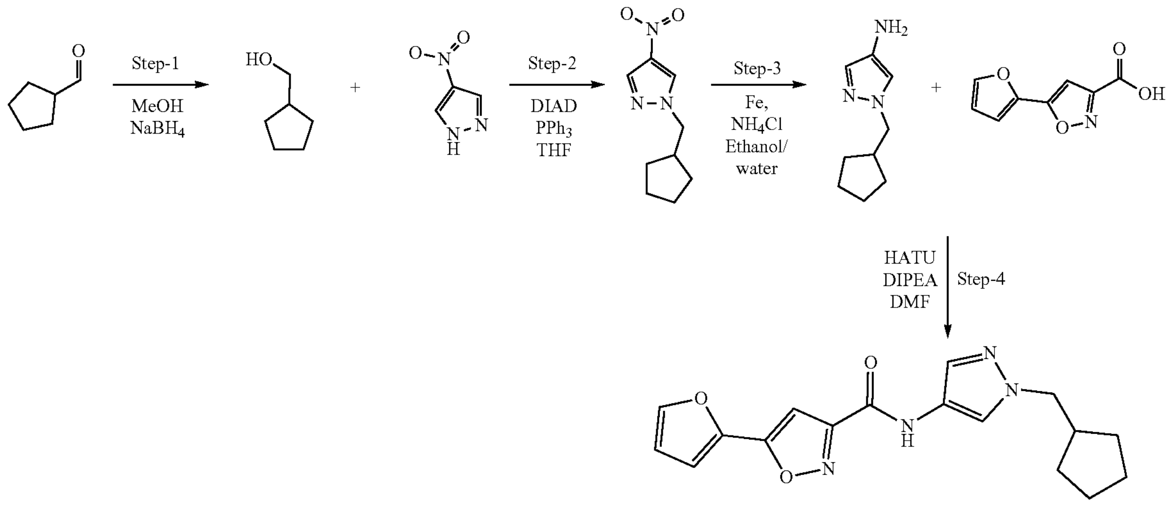

Compound 3-2

Step 1: Synthesis of cyclopentylmethanol. To a stirred solution of cyclopentanecarbaldehyde (500 mg, 5.10 mmol, 1.0 equiv) in Methanol (5 mL) was added $NaBH_4$ (298 mg, 7.65 mmol, 1.5 eq.) portion wise at 0° C. and stirred for 10 minutes. The reaction mixture was allowed to stir for 1 hour at RT. Product formation was confirmed by TLC & LCMS. After completion of reaction, reaction mixture was quenched with water and extracted with ethyl acetate (50 mL×3). Combined organic extracts were washed with water (50 mL×2), dried over anhydrous $Na_2SO_4$ and concentrated under reduced pressure to obtain cyclopentylmethanol (500 mg, as colourless liquid).

Step 2: Synthesis of 1-(cyclopentylmethyl)-4-nitro-1H-pyrazole. To a stirred solution of $PPh_3$ (1.45 g, 5.1 mmol, 1.1 eq.) and DIAD (1.09 ml, 5.1 mmol, 1.1 eq.) in THF (10 mL), cyclopentylmethanol (500 mg, 5.05 mmol, 1 eq.) and 4-nitro-1H-pyrazole (570 mg, 5.05 mmol, 1 eq.) were added and allowed to stir at RT for 16 hr. Reaction progress was monitored by TLC and LCMS. After the reaction completion, the reaction mixture was extracted with ethyl acetate and water (2×25 mL). Organic layer was separated and evaporated under reduced pressure to give crude product which was further purified by using Combiflash chromatography to obtain 1-(cyclopentylmethyl)-4-nitro-1H-pyrazole (270 mg).

Step 3: Synthesis of 1-(cyclopentylmethyl)-1H-pyrazol-4-amine. To a stirred solution of 1-(cyclopentylmethyl)-4-nitro-1H-pyrazole (200 mg, 1.025 mmol, 1 eq.) in 10 mL EtOH/water (1:1), Fe (287.17 mg, 5.128 mmol, 5 eq.) and ammonium chloride (276.9 mg, 5.128 mmol, 5 eq.) was added and allowed to heat at 80° C. for 12 hr. Reaction progress was monitored by TLC and LCMS. After reaction completion, reaction mixture was filtered through Celite pad and filtrate was evaporated and extracted with DCM/water (2×25 mL). Organic layer was collected and evaporated under reduced pressure to give 1-(cyclopentylmethyl)-1H-pyrazol-4-amine (180 mg), LCMS: 166 $[M+H]^+$.

Step 4: Synthesis of N-(1-(cyclopentylmethyl)-1H-pyrazol-4-yl)-5-(furan-2-yl)isoxazole-3-carboxamide. To a stirred solution of 5-(furan-2-yl) isoxazole-3-carboxylic acid (50 mg, 0.279 mmol, 1 eq.) in DMF (4 mL), HATU (106 mg, 0.279 mmol, 1 eq.) was added and allowed to stir at RT for 15 min. Then, stirred solution of 1-(cyclopentylmethyl)-1H-pyrazol-4-amine (55 mg, 0.279 mmol, 1 eq.) and DIPEA (0.145 ml, 0.837 mmol, 3 eq.) was added. Reaction mixture was allowed to stir at RT for 18 hr. After the reaction completion, reaction mixture was poured into ice cold water; precipitate obtained was filtered off to obtain crude product which was purified by using combiflash chromatography to yield N-(1-(cyclopentylmethyl)-1H-pyrazol-4-yl)-5-(furan-2-yl) isoxazole-3-carboxamide. (20 mg white solid), 1H NMR (400 MHz, DMSO-$d_6$) δ 10.97 (s, 1H), 8.05 (s, 1H), 8.01 (d, J=1.32 Hz, 1H), 7.62 (s, 1H), 7.28 (d, J=3.51 Hz, 1H), 7.15 (s, 1H), 6.77 (dd, J=1.75, 3.51 Hz, 1H), 4.01 (d, J=7.45 Hz, 2H), 2.34 (quin, J=7.34 Hz, 2H), 1.59 (br. s., 4H), 1.51 (d, J=8.33 Hz, 2H), 1.16-1.30 (m, 3H), LCMS 327 $[M+H]^+$.

Example S3-3. Synthesis of N-(1-(azetidin-3-yl)-1H-pyrazol-4-yl)-5-(furan-2-yl)isoxazole-3-carboxamide (Compound 3)

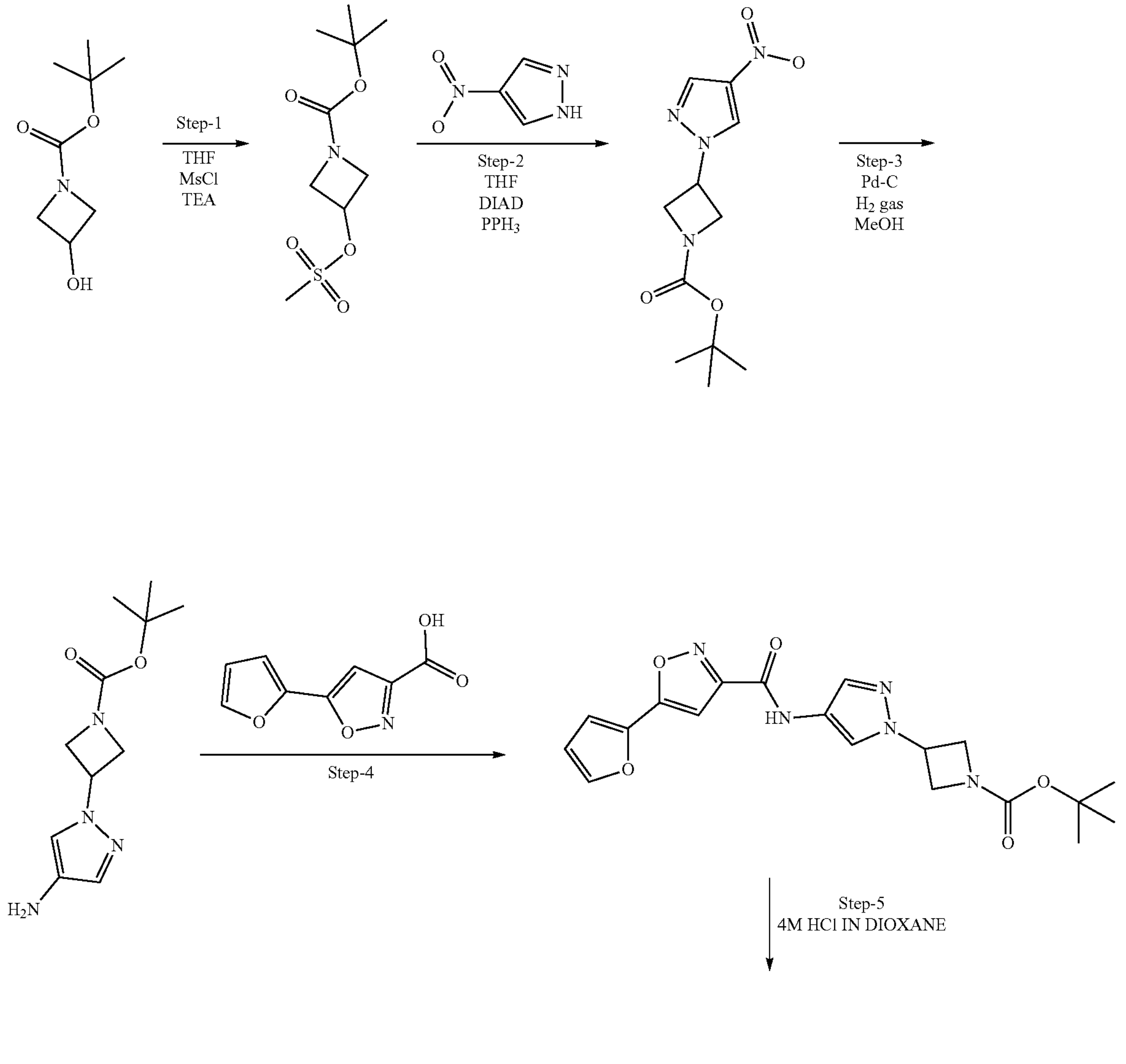

-continued

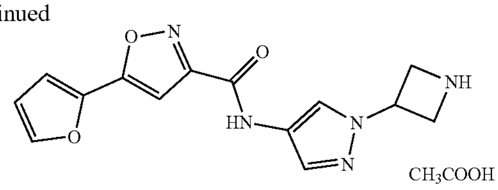

Compound 3-3

Step 1: Synthesis of tert-butyl 3-((methylsulfonyl)oxy) azetidine-1-carboxylate. To a stirred solution of tert-butyl 3-hydroxyazetidine-1-carboxylate (500 mg, 2.67 mmol, 1 equiv.) in THE (10 mL) at 0° C. was added triethylamine (0.446 mL, 3.24 mmol, and 1.2 equiv.). After stirring the reaction mixture at 0° C. for 10 min at same temperature, the reaction mixture was added mesyl chloride (0.218 ml, 3.2 mmol, and 1.2 equiv.) The reaction mixture was stirred for another 3 hrs. The progress of the reaction was monitored by TLC. After completion of reaction, the reaction mixture was added water and the aqueous layers were extracted with ethyl acetate (3x30 mL). The combined organic layers were dried over anhydrous $Na_2SO_4$ and concentrate under reduced pressure to obtained tert-butyl 3-((methylsulfonyl) oxy) azetidine-1-carboxylate (509 mg).

Step 2: Synthesis of tert-butyl 3-(4-nitro-1H-pyrazol-1-yl) azetidine-1-carboxylate. To a stirred solution 4-nitro-1H-Pyrazole (225 mg, 1.99 mmol, 1 equiv.) in DMF (10 mL) under nitrogen atmosphere was added $Cs_2CO_3$ (980 mg, 2.98 mmol, 1.5 equiv.) and TBAI (1.10 g, 2.98 mmol, 1.5 equiv.) followed by the addition of tert-butyl 3-((methylsulfonyl)oxy)azetidine-1-carboxylate (500 mg, 1.99 mmol, 1.0 equiv.). The reaction mixture was heated at 100° C. for overnight. After completion of reaction, ice-water was added to the reaction mixture and was extracted with ethyl acetate (2x25 mL). Organic layers were combined, washed with cold water, collected, dried over anhydrous $Na_2SO_4$ and concentrated under reduced pressure to obtain tert-butyl 3-(4-nitro-1H-pyrazol-1-yl) azetidine-1-carboxylate which was purified by flash column chromatography (290 mg), LCMS: 269 [M+H$^+$].

Step 3: Synthesis of tert-butyl 3-(4-amino-1H-pyrazol-1-yl)azetidine-1-carboxylate. To a stirred solution of tert-butyl 3-(4-nitro-1H-pyrazol-1-yl)azetidine-1-carboxylate (250 mg,) in MeOH (10 mL) under nitrogen atmosphere was added Pd/C (25 mg, 10% by wt). The resulting mixture was stirred under hydrogen atmosphere for 2-3 hours. The reaction mixture was carefully filtered through celite bed and was washed with methanol (2x20 mL). The methanol layers was collected and was evaporated under reduced pressure to obtain tert-butyl 3-(4-amino-1H-pyrazol-1-yl)azetidine-1-carboxylate (210 mg), LCMS: 239 [M+H]$^+$.

Step 4: Synthesis of tert-butyl 3-(4-(5-(furan-2-yl)isoxazole-3-carboxamido)-1H-pyrazol-1-yl)azetidine-1-carboxylate. To the stirred solution of 5-(furan-2-yl)isoxazole-3-carboxylic acid, 1 eq.) in DMF (4 mL), HATU (210.4 mg, 0.552 mmol, 1 eq.) was added and allowed to stir at RT for 15 min. Then, stirred solution of tert-butyl 3-(4-amino-1H-pyrazol-1-yl)azetidine-1-carboxylate (131 mg, 0.552 mmol, 1 eq.) and DIPEA (0.286 ml, 1.656 mmol, 3 eq.) was added. Reaction mixture was allowed to stir at RT for 18 hr. After the reaction completion, reaction mixture was poured into ice cold water, precipitate obtained was filtered off to obatain crude product. Crude product was purified by using combi-flash chromatography to yield tert-butyl 3-(4-(5-(furan-2-yl) isoxazole-3-carboxamido)-1H-pyrazol-1-yl)azetidine-1-carboxylate. (120 mg, white solid), LCMS: 400 [M+H]$^+$.

Step 5: Synthesis of N-(1-(azetidin-3-yl)-1H-pyrazol-4-yl)-5-(furan-2-yl) isoxazole-3-carboxamide acetate. To solution of tert-butyl 3-(4-(5-(furan-2-yl)isoxazole-3-carboxamido)-1H-pyrazol-1-yl)pyrrolidine-1-carboxylate (120 mg) was dissolved in dioxane (5 mL) and treated with 4M HCl in dioxane (1 mL). A precipitate formed after 2 h. The solvent was removed in vacuum and the resultant solid was dissolved was washed with diethyl ether and dried under vacuum to obtain crude which was purified by reverse phase HPLC N-(1-(azetidin-3-yl)-1H-pyrazol-4-yl)-5-(furan-2-yl) isoxazole-3-carboxamide acetate (25 mg), LCMS: 300 [M+H]$^+$, $^1$H NMR (400 MHz, DMSO-$d_6$) δ 11.15 (br. s., 1H), 8.20 (s, 1H), 8.01 (s, 2H), 7.84 (s, 1H), 7.29 (d, J=3.07 Hz, 1H), 7.20-7.23 (m, 1H), 6.78 (dd, J=1.75, 3.51 Hz, 1H), 5.25 (t, J=7.67 Hz, 1H), 4.06-4.13 (m, 1H), 3.93-4.01 (m, 2H), 3.78 (m, J=6.14 Hz, 2H).

Example S3-4. Synthesis of 5-(furan-2-yl)-N-(1-(pyrrolidin-3-yl)-1H-pyrazol-4-yl)isoxazole-3-carboxamide (Compound 3-4)

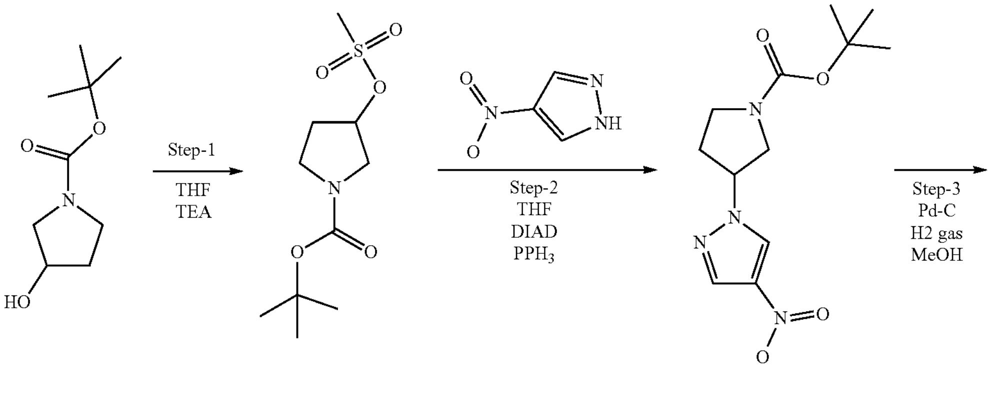

-continued

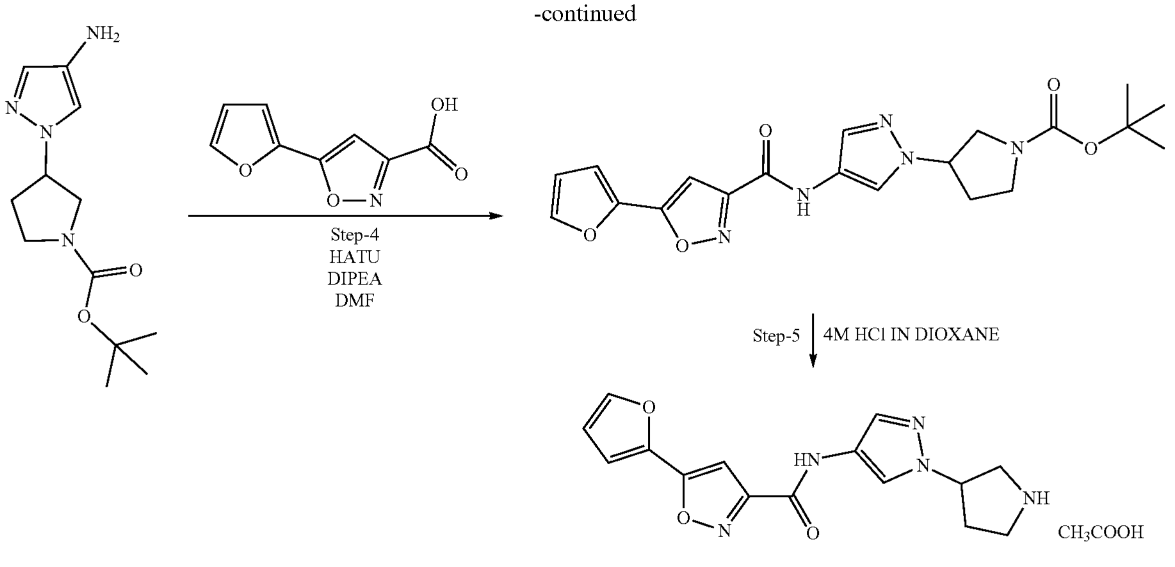

Compound 3-4

Step 1: Synthesis of tert-butyl 3-((methylsulfonyl)oxy) pyrrolidine-1-carboxylate. To a stirred solution of tert-butyl 3-hydroxypyrrolidine-1-carboxylate (500 mg, 2.67 mmol, 1 equiv.) in THE (10 mL) at 0° C. was added Triethylamine (0.446 mL, 3.24 mmol, 1.2 equiv.). After stirring reaction mixture at 0° C. for 10 min, was added mesyl chloride (0.218 ml, 3.2 mmol, 1.2 equiv.) The reaction mixture was stirred for another 3 hrs at RT. The progress of the reaction was monitored by TLC. After completion of reaction, the reaction mixture was added water and the aqueous layer was extracted with ethyl acetate (3x30 mL). The combined organic layers were dried over anhydrous $Na_2SO_4$ and concentrate under reduced pressure to obtained tert-butyl 3-((methylsulfonyl)oxy)pyrrolidine-1-carboxylate (520 mg).

Step 2: Synthesis of tert-butyl 3-(4-nitro-1H-pyrazol-1-yl)pyrrolidine-1-carboxylate. To a stirred solution 4-nitro-1H-Pyrazole (191 mg, 1.69 mmol, 0.9 equiv.) in DMF (10 mL) under nitrogen atmosphere was added $Cs_2CO_3$ (928.3 mg, 2.83 mmol, 1.5 equiv.) and TBAI (1.04 g, 2.83 mmol, 1.5 equiv.) followed by the addition of tert-butyl 3-((methylsulfonyl)oxy)pyrrolidine-1-carboxylate (500 mg, 1.88 mmol, 1.0 equiv.). The reaction mixture was heated at 100° C. for overnight. After completion of reaction, ice-water was added to the reaction mixture and was extracted with ethyl acetate (2x25 mL). The organic layers were combined, washed with cold water, collected, dried over anhydrous $Na_2SO_4$ and concentrate under reduced pressure to obtain tert-butyl 3-(4-nitro-1H-pyrazol-1-yl)pyrrolidine-1-carboxylate which was purified by flash column chromatography (420 mg), LCMS 283 $[M+H]^+$.

Step 3: Synthesis of tert-butyl 3-(4-amino-1H-pyrazol-1-yl)pyrrolidine-1-carboxylate. To a stirred solution of tert-butyl 3-(4-nitro-1H-pyrazol-1-yl)pyrrolidine-1-carboxylate (300 mg, 0.551 mmol) in MeOH (10 mL) under nitrogen atmosphere was added Pd/C (30 mg, 10% by wt). The resulting mixture was stirred under Hydrogen atmosphere for 2-3 hours. The reaction mixture was carefully filtered through celite bed and was washed with methanol (2x20 mL). The methanol layers was collected and was evaporated under reduced pressure to obtain tert-butyl 3-(4-amino-1H-pyrazol-1-yl)pyrrolidine-1-carboxylate (240 mg), LCMS 253 $[M+H^+]$.

Step 4: Synthesis of tert-butyl 3-(4-(5-(furan-2-yl)isoxazole-3-carboxamido)-1H-pyrazol-1-yl)pyrrolidine-1-carboxylate. To a stirred solution of 5-(furan-2-yl)isoxazole-3-carboxylic acid (50 mg, 0.27 mmol, 1 eq.) in DMF (4 mL), HATU (102.8 mg, 0.27 mmol, 1 eq.) was added and allowed to stir at RT for 15 min. Then, stirred solution of tert-butyl 3-(4-amino-1H-pyrazol-1-yl)pyrrolidine-1-carboxylate (70 mg, 0.27 mmol, 1 eq.) and DIPEA (0.14 ml, 0.833 mmol, 3 eq.) was added. Reaction mixture was allowed to stir at RT for 18 hr. After the reaction completion, reaction mixture was poured into ice cold water, precipitate obtained was filtered off to obtain crude product. Crude product was purified by using combiflash chromatography to yield tert-butyl 3-(4-(5-(furan-2-yl)isoxazole-3-carboxamido)-1H-pyrazol-1-yl)pyrrolidine-1-carboxylate. (52 mg white solid). LCMS: 414 $[M+H]^+$.

Step 5: Synthesis of 5-(furan-2-yl)-N-(1-(pyrrolidin-3-yl)-1H-pyrazol-4-yl)isoxazole-3-carboxamide acetate. To a stirred solution of tert-butyl tert-butyl 3-(4-(5-(furan-2-yl) isoxazole-3-carboxamido)-1H-pyrazol-1-yl)pyrrolidine-1-carboxylate (50 mg) in dioxane (5 mL) and treated with 4M HCl in dioxane (1 mL). A precipitate formed after 2 h. The solvent was removed in vacuo and the resultant solid was washed with diethyl ether and dried under vacuum to obtain crude which was purified by reverse phase HPLC to obtain 5-(furan-2-yl)-N-(1-(pyrrolidin-3-yl)-1H-pyrazol-4-yl) isoxazole-3-carboxamide acetate (24 mg), LCMS: 314 $[M+H]^+$, $^1H$ NMR (400 MHz, DMSO-$d_6$): δ 10.99 (br. s., 1H), 8.09 (s, 1H), 8.01 (s, 1H), 7.61-7.70 (m, 1H), 7.28 (d, J=3.51 Hz, 1H), 7.17 (s, 1H), 6.77 (dd, J=1.75, 3.51 Hz, 1H), 4.81 (br. s., 1H), 3.12 (m, J=6.58 Hz, 2H), 1.92-2.01 (m, 2H), 1.75-1.83 (m, 2H).

Example S3-5. Synthesis of N-(1-(1-cyclopentyl-ethyl)-1H-pyrazol-4-yl)-5-(furan-2-yl)isoxazole-3-carboxamide (Compound 3-5)

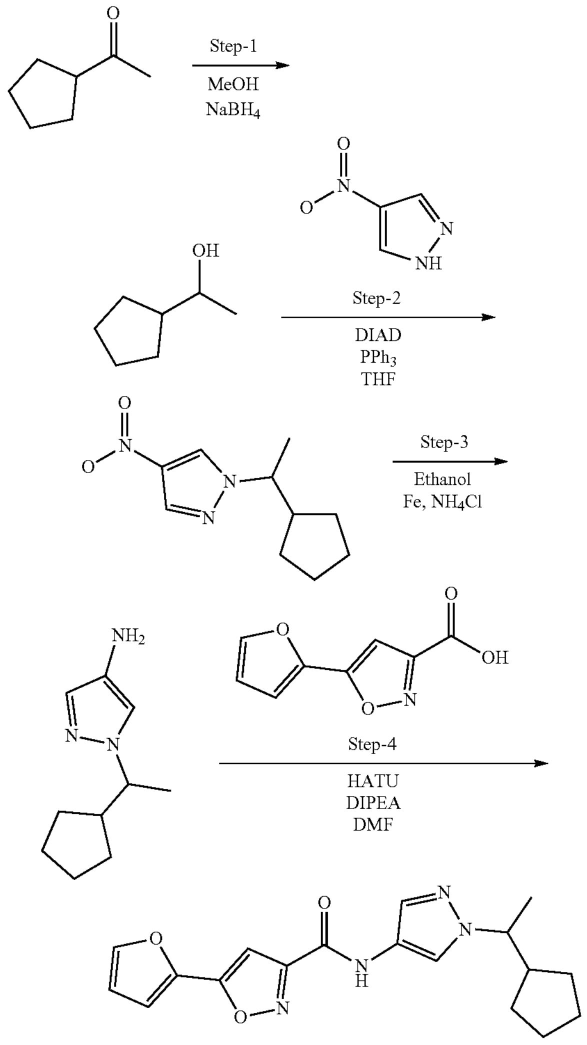

Compound 3-5

Step 1: Synthesis of 1-cyclopentylethan-1-ol. To a stirred solution of 1-cyclopentylethan-1-one (500 mg, 4.46 mmol, 1.0 equiv) in methanol (5 mL) was added $NaBH_4$ (262 mg, 6.69 mmol, 1.2 equiv) portion wise at 0° C. and stirred for 10 minutes. The reaction mixture was allowed to stir for 1 hour at RT. Product formation was confirmed by TLC & LCMS. After completion of reaction, reaction mixture was quenched with water and extracted with ethyl acetate (50 mL×3), Combined organic extracts were washed with water (50 mL×2), dried over anhydrous $Na_2SO_4$ and concentrated under reduced pressure to obtain 1-cyclopentylethan-1-ol (499 mg, as colourless liquid).

Step 2: Synthesis of 1-(1-cyclopentylethyl)-4-nitro-1H-pyrazole. To a stirred solution of $PPh_3$ (1.264 g, 4.82 mmol, 1.1 eq.) and DIAD (0.9 ml, 4.82 mmol, 1.1 eq.) in THE (10 mL), 1-cyclopentylethan-1-ol (500 mg, 4.38 mmol, 1 eq.) and 4-nitro-1H-pyrazole (495 mg, 4.38 mmol, 1 eq.) were added and allowed to stir at RT for 16 hr. Reaction progress was monitored by TLC and LCMS. After completion of reaction, the reaction mixture was extracted with ethyl acetate and water (2×25 mL). Organic layer was separated and evaporated under reduced pressure to give crude product which was further purified by using combiflash chromatography to obtain 1-(1-cyclopentylethyl)-4-nitro-1H-pyrazole (230 mg), LCMS: 210 $[M+H]^+$, $^1H$ NMR (400 MHz, DMSO-$d_6$): δ 8.92 (s, 1H), 8.30 (s, 1H), 5.11 (dd, J=5.48, 8.11 Hz, 1H), 3.89-4.03 (m, 1H), 2.28-2.47 (m, 1H), 1.5-1.8 (m, 1H), 1.4 (d, 3H), 1.1-1.25 (m, 4H).

Step 3: Synthesis of 1-(1-cyclopentylethyl)-1H-pyrazol-4-amine. To a stirred solution of 1-(1-cyclopentylethyl)-4-nitro-1H-pyrazole (250 mg, 0.717 mmol, 1 eq.) in 10 mL EtOH/water (1:1), Fe (194 mg, 3.58 mmol, 5 eq.) and ammonium chloride (200 mg, 3.58 mmol, 5 eq.) was added and allowed to heat at 80° C. for 12 hr. Reaction progress was monitored by TLC and LCMS. After reaction completion, reaction mixture was filtered through celite pad and filtrate was evaporated and extracted with DCM/water (2×25 mL). Organic layer was collected and evaporated under reduced pressure to give 1-(1-cyclopentylethyl)-1H-pyrazol-4-amine (210 mg), LCMS: 180 $[M+H]^+$.

Step 4: Synthesis of N-(1-(1-cyclopentylethyl)-1H-pyrazol-4-yl)-5-(furan-2-yl)isoxazole-3-carboxamide. To a stirred solution of 5-(furan-2-yl)isoxazole-3-carboxylic acid (50 mg, 0.27 mmol, 1 eq.) in DMF (4 mL), HATU (106 mg, 0.27 mmol, 1 eq.) was added and allowed to stir at RT for 15 min. Then, stirred solution of 1-(1-cyclopentylethyl)-1H-pyrazol-4-amine (59 mg, 0.27 mmol, 1 eq.) and DIPEA (0.14 ml, 0.83 mmol, 3 eq.) was added. Reaction mixture was allowed to stir at RT for 18 hr. After the reaction completion, reaction mixture was poured into ice cold water; precipitate obtained was filtered off to obtain crude product which was purified by using combiflash chromatography to yield N-(1-(1-cyclopentylethyl)-1H-pyrazol-4-yl)-5-(furan-2-yl)isoxazole-3-carboxamide (17 mg white solid), LCMS 341 $[M+H]^+$, $^1H$ NMR (400 MHz, DMSO-$d_6$) δ 10.96 (s, 1H), 8.04 (s, 1H), 8.01 (d, J=1.75 Hz, 1H), 7.62 (s, 1H), 7.29 (d, J=3.51 Hz, 1H), 7.15 (s, 1H), 6.78 (dd, J=1.75, 3.51 Hz, 1H), 4.10 (dd, J=6.80, 9.43 Hz, 1H), 2.23 (d, J=8.33 Hz, 1H), 1.42-1.62 (m, 4H), 1.40 (d, J=6.58 Hz, 3H), 1.19-1.31 (m, 2H), 1.11 (d, J=7.89 Hz, 2H).

Example S3-6. Synthesis of N-(1-((3,5-dichloro-pyridin-4-yl)methyl)-1H-pyrazol-4-yl)-5-(furan-2-yl) isoxazole-3-carboxamide (Compound 3-6)

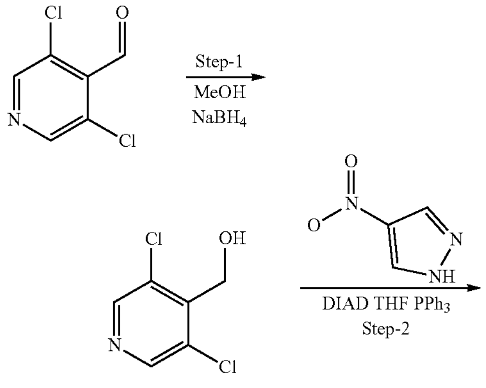

-continued

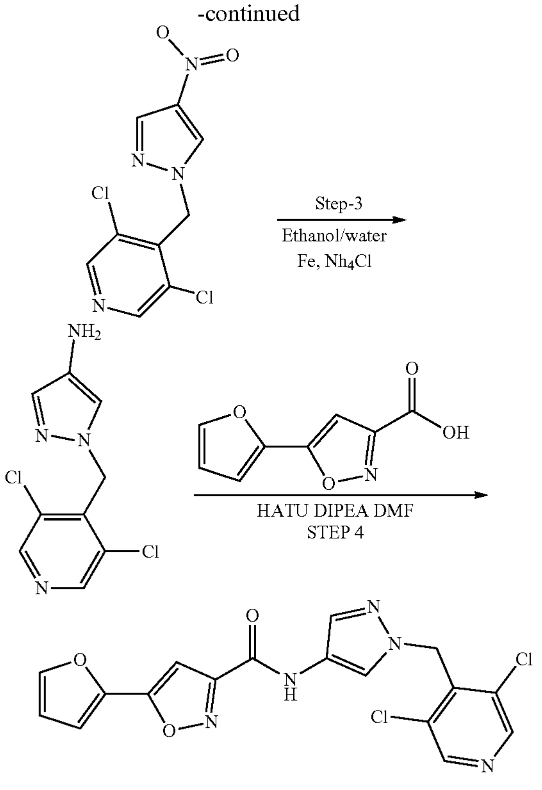

Compound 3-6

Step 1: Synthesis of (3,5-dichloropyridin-4-yl)methanol. To a stirred solution of 3,5-dichloroisonicotinaldehyde (500 mg, 2.808 mmol, 1.0 equiv) in methanol (5 mL) was added $NaBH_4$ (165 mg, 4.213 mmol, 1.5 equiv) portion wise at 0° C. and stirred for 10 minutes. The reaction mixture was allowed to stir for 1 hour at RT. Product formation was confirmed by TLC & LCMS. After completion of reaction, reaction mixture was quenched with water and extracted with ethyl acetate (50 mL×3). Combined organic extracts were washed with water (50 mL×2), dried over anhydrous $Na_2SO_4$ and concentrated under reduced pressure to obtain (3,5-dichloropyridin-4-yl)methanol (390 mg, as colourless liquid), $^1$H NMR (400 MHz, DMSO-$d_6$) δ 8.62 (s, 2H), 5.53 (t, J=5.48 Hz, 1H), 4.66 (d, J=5.26 Hz, 2H)

Step 2: Synthesis of 3,5-dichloro-4-((4-nitro-1H-pyrazol-1-yl)methyl)pyridine. To a stirred solution of $PPh_3$ (520 g, 1.94 mmol, 1 eq.) and DIAD (391.8 mg, 1.94 mmol, 1 eq.) in THE (10 mL), 3,5-dichloroisonicotinaldehyde (350 mg, 1.94 mmol, 1 eq.) and 4-nitro-1H-pyrazole (220 mg, 1.94 mmol, 1 eq.) were added and allowed to stir at RT for 16 hr. Reaction progress was monitored by TLC and LCMS. After the reaction completion, the reaction mixture was extracted with ethyl acetate and water (2×25 mL). Organic layer was separated and evaporated under reduced pressure to give crude product which was further purified by using combiflash chromatography to obtain 3,5-dichloro-4-((4-nitro-1H-pyrazol-1-yl)methyl)pyridine (220 mg), $^1$H NMR (400 MHz, DMSO-$d_6$) δ 9.15 (s, 1H), 8.88 (s, 1H), 8.71 (s, 2H),), 5.66 (s, 2H).

Step 3: Synthesis of 1-((3,5-dichloropyridin-4-yl) methyl)-1H-pyrazol-4-amine. To a stirred solution of 3,5-dichloro-4-((4-nitro-1H-pyrazol-1-yl)methyl)pyridine (100 mg, 0.369 mmol, 1 eq.) in 10 mL EtOH/water (1:1), Fe (101.47 mg, 1.845 mmol, 5 eq.) and ammonium chloride (104 mg, 1.845 mmol, 5 eq.) was added and allowed to heat at 80° C. for 12 hr. Reaction progress was monitored by TLC and LCMS. After completion of reaction, reaction mixture was filtered through celite pad and filtrate was evaporated and extracted with DCM/water (2×25 mL). Organic layer was collected and evaporated under reduced pressure to give 1-((3,5-dichloropyridin-4-yl)methyl)-1H-pyrazol-4-amine (88 mg), LCMS 243 [M+H]$^+$.

Step 4: Synthesis of N-(1-((3,5-dichloropyridin-4-yl) methyl)-1H-pyrazol-4-yl)-5-(furan-2-yl)isoxazole-3-carboxamide. To a stirred solution of 5-(furan-2-yl)isoxazole-3-carboxylic acid (50 mg, 0.206 mmol, 1 eq.) in DMF (4 mL), HATU (79 mg, 0.206 mmol, 1 eq.) was added and allowed to stir at RT for 15 min. Then, stirred solution of 1-((3,5-dichloropyridin-4-yl)methyl)-1H-pyrazol-4-amine (37 mg, 0.206 mmol, 1 eq.) and DIPEA (0.107 ml, 0.619 mmol, 3 eq.) was added. Reaction mixture was allowed to stir at RT for 18 hr. After completion of reaction, reaction mixture was poured into ice cold water, precipitate obtained was filtered off to obtain crude product which was purified by using combiflash chromatography to obtain N-(1-((3,5-dichloropyridin-4-yl)methyl)-1H-pyrazol-4-yl)-5-(furan-2-yl)isoxazole-3-carboxamide (35 mg white solid), LCMS 404 [M+H]$^+$, $^1$H NMR (400 MHz, DMSO-$d_6$) δ 11.04 (s, 1H), 8.70 (s, 1H), 8.23 (s, 1H), 8.01 (d, J=1.32 Hz, 1H), 7.63 (s, 1H), 7.28 (d, J=3.51 Hz, 1H), 7.15 (s, 1H), 6.77 (dd, J=1.75, 3.51 Hz, 1H), 5.58 (s, 2H), Example S3-7. Synthesis of N-(1-(2-morpholinoethyl)-1H-pyrazol-4-yl)-5-(pyrazin-2-yl)-1,3,4-thiadiazole-2-carboxamide (Compound 3-7)

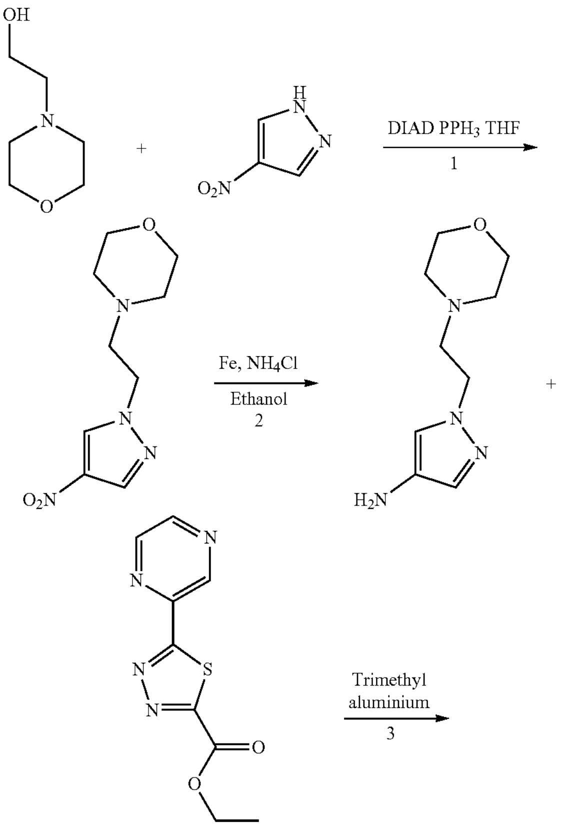

-continued

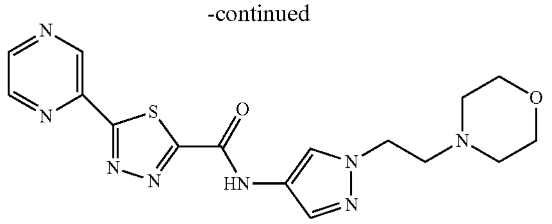

Compound 3-7

Step 1: Synthesis of 4-(2-(4-nitro-1H-pyrazol-1-yl)ethyl) morpholine. To a stirred solution of $PPh_3$ (2.98 g, 0.0114 mol, 1.5 equiv), DIAD (2.30 g, 0.0114 mol, 1.5 equiv.) in THE (10 mL) at RT was added 2-morpholinoethan-1-ol (1 g, 0.0076 mol, 1 equiv.) and 4-nitro-1H-pyrazole (0.86 g, 0.0076 mol, 1 equiv.) The reaction mixture was stirred at RT for 16 hr. Reaction progress was monitored by TLC and LCMS. After the reaction completion, the reaction mixture was extracted with ethyl acetate and water 2 times. Organic layer was separated and evaporated under reduced pressure to give crude product which was further purified by using combiflash chromatography to yield 4-(2-(4-nitro-1H-pyrazol-1-yl)ethyl)morpholine. $^1H$ NMR (400 MHz, DMSO-$d_6$) δ ppm 8.88 (s, 1H) 8.26 (s, 1H) 4.29 (t, J=6.14 Hz, 2H) 3.46-3.58 (m, 4H) 2.73 (t, J=6.36 Hz, 2H) 2.40 (d, J=3.95 Hz, 4H).

Step 2: Synthesis of 1-(2-morpholinoethyl)-1H-pyrazol-4-amine. To a stirred solution of 4-(2-(4-nitro-1H-pyrazol-1-yl)ethyl)morpholine (500 mg, 2.212 mmol, 1 equiv.) in 10 mL EtOH/water (1:1), Fe (608.40 mg, 11.06 mmol, 5 equiv.) and ammonium chloride (586.18 mg, 11.06 mmol, 5 equiv.) was added and allowed to heat at 80° C. for 2 hr. Reaction progress was monitored by TLC and LCMS. After reaction completion, reaction mixture was filtered through celite pad and filtrate was evaporated and extracted with DCM (100 ml×2), Organic layer was collected and evaporated under reduced pressure to give 1-(2-morpholinoethyl)-1H-pyrazol-4-amine. LCMS: 197 $[M+H]^+$.

Step 3: synthesis of N-(1-(2-morpholinoethyl)-1H-pyrazol-4-yl)-5-(pyrazin-2-yl)-1,3,4-thiadiazole-2-carboxamide. To the stirred solution of ethyl 5-(pyrazin-2-yl)-1,3,4-thiadiazole-2-carboxylate (100 mg, 0.510 mmol, 1 equiv.) and 1-(2-morpholinoethyl)-1H-pyrazol-4-amine (120 mg, 0.510 mmol, 1 equiv.) in 5 mL toluene, TMA (0.293 mL, 2.04 mmol, 4 equiv.) was added and allowed to heat at 120° C. for 16 hr. After reaction completion, water was added to the reaction mixture, precipitate formed was filtered off to give crude product. This crude product was further extracted with DCM and water. Organic layer was collected and evaporated to give N-(1-(2-morpholinoethyl)-1H-pyrazol-4-yl)-5-(pyrazin-2-yl)-1,3,4-thiadiazole-2-carboxamide (90 mg yellow solid). LCMS 387 $[M+H]^+$. $^1H$ NMR (400 MHz, DMSO-$d_6$) δ ppm 11.59 (s, 1H) 9.54 (s, 1H) 8.91 (d, J=2.19 Hz, 1H) 8.87 (s, 1H) 8.15 (s, 1H) 7.73 (s, 1H) 4.23 (t, J=6.58 Hz, 2H) 3.51-3.59 (m, 4H) 2.66-2.71 (m, 2H) 2.41 (br. s., 4H).

Example S3-8. Synthesis of N-(1-(2-morpholinoethyl)-1H-pyrazol-4-yl)-5-(pyrazin-2-yl)isoxazole-3-carboxamide (Compound 3-8)

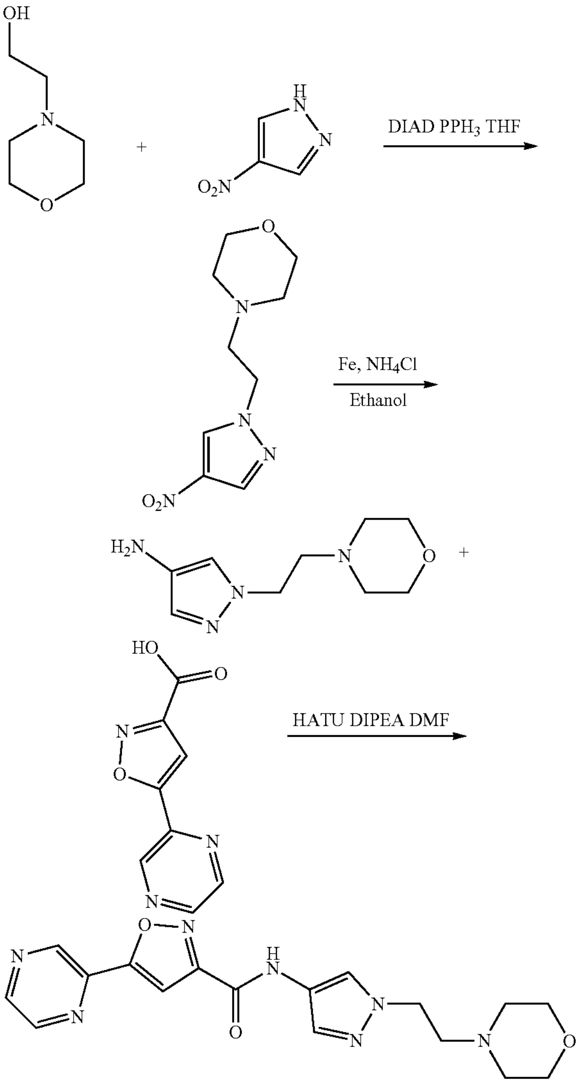

Compound 3-8

Step 1: Synthesis of 4-(2-(4-nitro-1H-pyrazol-1-yl)ethyl) morpholine. To a stirred solution of $PPh_3$ (2.98 g, 0.0114 mol, 1.5 equiv), DIAD (2.30 g, 0.0114 mol, 1.5 equiv) in THE (10 mL) was added 2-morpholinoethan-1-ol (1 g, 0.0076 mol, 1 equiv) and 4-nitro-1H-pyrazole (0.86 g, 0.0076 mol, 1 equiv) was added and allowed to stir at RT for 16 hr. Reaction progress was monitored by TLC and LCMS. The reaction mixture was diluted with water and extracted with ethyl acetate, Organic layer was separated and evaporated under reduced pressure to give crude product which was further purified by using combiflash chromatography to yield 4-(2-(4-nitro-1H-pyrazol-1-yl)ethyl)morpholine. $^1H$ NMR (400 MHz, DMSO-$d_6$) δ ppm 8.88 (s, 1H) 8.26 (s, 1H) 4.29 (t, J=6.14 Hz, 2H) 3.46-3.58 (m, 4H) 2.73 (t, J=6.36 Hz, 2H) 2.40 (d, J=3.95 Hz, 4H).

Step 2: Synthesis of 1-(2-morpholinoethyl)-1H-pyrazol-4-amine. To a stirred solution of 4-(2-(4-nitro-1H-pyrazol- 1-yl)ethyl)morpholine (500 mg, 2.212 mmol, 1 equiv.) in 10 mL EtOH/water (1:1), Fe (608.40 mg, 11.06 mmol, 5 equiv.) and ammonium chloride (586.18 mg, 11.06 mmol, 5 equiv.) was added and allowed to heat at 80° C. for 2 hr. Reaction progress was monitored by TLC and LCMS. After reaction completion, reaction mixture was filtered through celite pad and filtrate was evaporated and extracted with DCM, Organic layer was collected and evaporated under reduced pressure to give 1-(2-morpholinoethyl)-1H-pyrazol-4-amine. LCMS: 197 $[M+H]^+$.

Step 3: Synthesis of N-(1-(2-morpholinoethyl)-1H-pyrazol-4-yl)-5-(pyrazin-2-yl)isoxazole-3-carboxamide. To a stirred solution of 5-(pyrazin-2-yl)isoxazole-3-carboxylic acid (97.95 mg, 0.510 mmol, 1 equiv), HATU (193.8 mg, 0.510 mmol, 1 equiv) in DMF (4 mL) was added 1-(2-morpholinoethyl)-1H-pyrazol-4-amine hydrochloride (100 mg, 0.510 mmol, 1 equiv) and DIPEA (197.37 mg, 1.53 mmol, 3 equiv). Reaction mixture was allowed to stir at RT for 18 hr. After the reaction completion, reaction mixture was extracted with ethyl acetate. Organic layer was collected and evaporated to give crude product. Crude product was further purified by using combiflash chromatography to yield N-(1-(2-morpholinoethyl)-1H-pyrazol-4-yl)-5-(pyrazin-2-yl)isoxazole-3-carboxamide (10 mg white solid). LCMS: 370 $[M+H]^+$. $^1H$ NMR (400 MHz, DMSO-$d_6$) δ ppm 11.08 (s, 1H) 9.35 (d, J=1.32 Hz, 1H) 8.83-8.88 (m, 1H) 8.82 (d, J=2.63 Hz, 1H) 8.13 (s, 1H) 7.70 (s, 1H) 7.66 (s, 1H) 4.24 (br. s., 2H) 3.56 (br. s., 4H) 2.67 (br. s., 2H) 2.33 (br. s., 4H).

Example S3-9. Synthesis of N-(1-(piperidin-4-yl)-1H-pyrazol-4-yl)-5-(pyridin-2-yl)isoxazole-3-carboxamide (Compound 3-9)

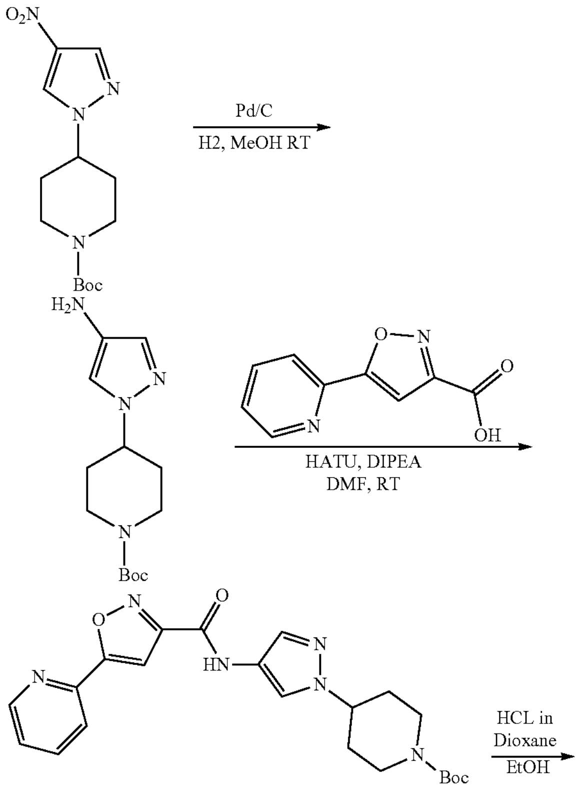

-continued

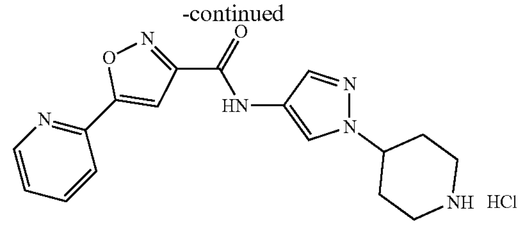

Compound 3-9

Step 1: Synthesis of tert-butyl 4-(4-amino-1H-pyrazol-1-yl)piperidine-1-carboxylate. To a stirred solution of tert-butyl 4-(4-nitro-1H-pyrazol-1-yl) piperidine-1-carboxylate (500 mg, 1.68 mmol, 1.0 equiv) in Methanol (15 mL) was added under nitrogen Palladium on Carbon (125 mg, 10% w/w). Purge the reaction mixture with $H_2$ gas for 2 h. Product formation was confirmed by LCMS. After the completion of reaction, reaction mixture was filtered through celite bed and filtrate was concentrate under reduced pressure to obtain tert-butyl 4-(4-amino-1H-pyrazol-1-yl) piperidine-1-carboxylate (300 mg, as brown colour liquid). LCMS: 211 $[M-56]^+$.

Step-2: tert-butyl4-(4-(5-(pyridin-2-yl)isoxazole-3-carboxamido)-1H-pyrazol-1yl)piperidine-1-carboxylate. To a stirred solution of 5-(pyridin-2-yl)isoxazole-3-carboxylic acid (100 mg, 0.52 mmol, 1 equiv), HATU (219 mg, 0.57 mmol, 1.1 eq) and DIPEA (217 mg, 1.68 mmol, 3.2 equiv) in DMF (1 mL) was added solution of tert-butyl 4-(4-amino-1H-pyrazol-1-yl)piperidine-1-carboxylate (139 mg, 0.52 mmol, 1 equiv) in DMF (2 mL). The reaction mixture was stirred at RT for 24 h. Product formation was confirmed with TLC and LCMS and reaction mixture was diluted water and extracted with EtOAc (50 mL) and washed with water (2×50 mL). Organic layer dried over $Na_2SO_4$ and concentrated under reduced pressure to obtain crude which was further purified by flash column chromatography to obtain pure product tert-butyl 4-(4-(5-(pyridin-2-yl)isoxazole-3-carboxamido)-1H-pyrazol-1-yl)piperidine-1-carboxylate (80 mg, as off white solid). LCMS: 439 $[M+H]^+$.

Step 3: Synthesis of N-(1-(piperidin-4-yl)-1H-pyrazol-4-yl)-5-(pyridin-2-yl)isoxazole-3-carboxamide hydrochloride. To a stirred solution of tert-butyl 4-(4-(5-(pyridin-2-yl) isoxazole-3-carboxamido)-1H-pyrazol-1-yl)piperidine-1-carboxylate (80 mg) was dissolved in dioxane (5 mL) and treated with 4M HCl in dioxane (1 mL). A precipitate formed after 2 h. The solvent was removed in vacuo and the resultant solid was washed with diethyl ether and dried under vacuum to obtain N-(1-(piperidin-4-yl)-1H-pyrazol-4-yl)-5-(pyridin-2-yl)isoxazole-3-carboxamide hydrochloride (40 mg). LCMS: 339 $[M+H]^+$. $^1H$ NMR (400 MHz, DMSO-$d_6$) δ=11.08 (s, 1H), 8.77 (d, J=4.4 Hz, 1H), 8.12-8.07 (m, 2H), 8.05 (d, J=7.0 Hz, 1H), 7.71 (s, 1H), 7.60-7.54 (m, 1H), 7.50 (s, 1H), 4.55-4.50 (m, 1H), 3.40 (d, J=13.6 Hz, 2H), 3.05 (d, J=12.3 Hz, 2H), 2.16 (br. s., 4H).

Example S3-10. Synthesis of N-(1-(1-(piperidin-4-yl)ethyl)-1H-pyrazol-4-yl)-5-(pyrazin-2-yl)isoxazole-3-carboxamide (Compound 3-10)

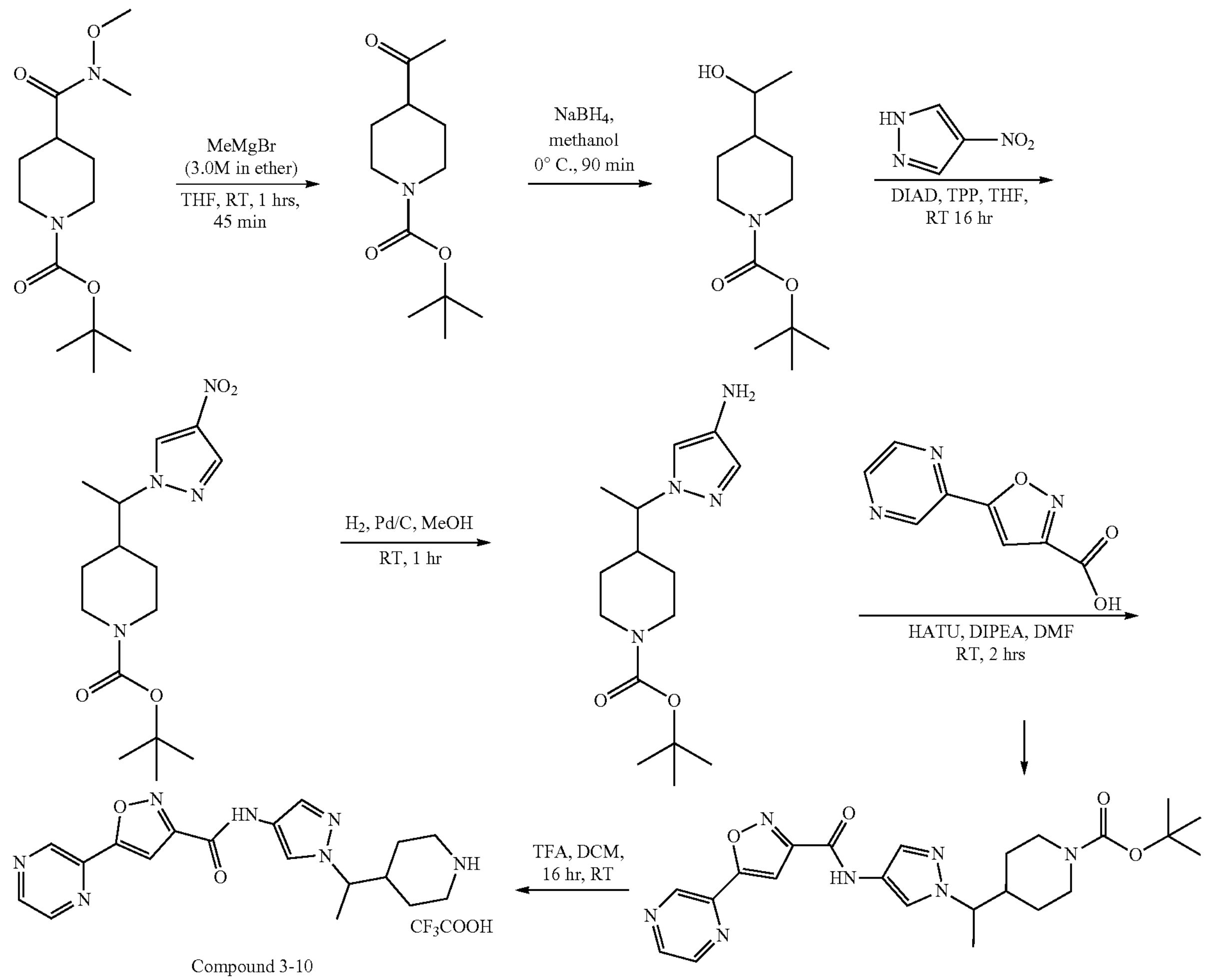

Compound 3-10

Step 1: Synthesis of tert-butyl 4-acetylpiperidine-1-carboxylate. To a stirred solution of tert-butyl 4-(methyl (methyl)carbamoyl)piperidine-1-carboxylate (600 mg, 2.20 mmol, 1.0 equiv.) in THF (5 mL), was added MeMgBr (3.0 M in ether) (1.42 mL, 4.40 mmol, 2.0 equiv.) at RT drop wise. Then, the reaction mixture was allowed to stir at RT for 1 h 45 min. The progress of reaction was monitored by TLC and NMR. After completion of reaction, the reaction was quenched by using $NH_4Cl$ solution. Product was extracted using ethyl acetate (3×50 mL). The separated organic layer was washed using brine and dried using $Na_2SO_4$, filtered and concentrated under reduced pressure to obtain tile compound as yellow liquid (470 mg).

Step 2: Synthesis of tert-butyl 4-(1-hydroxyethyl) piperidine-1-carboxylate. To a stirred solution of tert-butyl 4-acetylpiperidine-1-carboxylate (390 mg, 1.715 mmol, 1.0 equiv.) in MeOH (7 mL) was added $NaBH_4$ (97 mg, 2.57 mmol, 1.5 equiv.) portion wise at 0° C. and stirred for 10 minutes. The reaction mixture was allowed to stir for 1 hour 30 min at RT. Product formation was confirmed by TLC and LCMS. After completion of reaction, reaction mixture was quenched with water and extracted with ethyl acetate (3×50 mL). Combined organic extracts were washed with water (2×50 mL), dried over anhydrous $Na_2SO_4$ and concentrated under reduced pressure to obtain tert-butyl 4-(1-hydroxyethyl) piperidine-1-carboxylate as colorless liquid (380 mg).

Step 3: Synthesis of tert-butyl 4-(1-(4-nitro-1H-pyrazol-1-yl)ethyl)piperidine-1-carboxylate. To a stirred solution of $PPh_3$ (650 mg, 2.48 mmol, 1.5 equiv.) and DIAD (502 mg, 2.48 mmol, 1.5 equiv.) in THE (10 mL), was added 4-nitro-1H-pyrazole (227 mg, 1.98 mmol, 1.2 equiv), followed by the addition of tert-butyl 4-(1-hydroxyethyl)piperidine-1-carboxylate (380 mg, 1.65 mmol, 1.0 equiv.). The resultant reaction mixture was stirred at RT for 24 h. Product formation was confirmed with TLC and LCMS. After completion of reaction mixture were diluted with EtOAc (50 mL) and washed with water (3×50 mL). Organic layer dried over $Na_2SO_4$ and concentrated under reduced pressure to obtain crude which was further purified by flash column chromatography (EtOAc/Hexane) to obtain pure product tert-butyl 4-(1-(4-nitro-1H-pyrazol-1-yl)ethyl)piperidine-1-carboxylate (360 mg).

Step 4: Synthesis of tert-butyl 4-(1-(4-amino-1H-pyrazol-1-yl)ethyl)piperidine-1-carboxylate. To a stirred solution of tert-butyl 4-(1-(4-nitro-1H-pyrazol-1-yl)ethyl)piperidine-1-carboxylate (360 mg, 1.11 mmol, 1.0 equiv.) in Methanol (20 mL) under nitrogen was added Palladium on Carbon (50 mg, 10% w/w). Reaction mixture purged with $H_2$ gas for 2 hrs. Product formation was confirmed by LCMS. After the completion of reaction, reaction mixture was filtered through celite bed and filtrate was concentrate under reduced pressure to obtain tert-butyl 4-(1-(4-amino-1H-pyrazol-1-yl) ethyl)piperidine-1-carboxylate, as brown color liquid (350 mg). LCMS: 295 $[M+H]^+$.

Step 5: Synthesis of tert-butyl 4-(1-(4-(5-(pyrazin-2-yl) isoxazole-3-carboxamido)-1H-pyrazol-1-yl)ethyl)piperidine-1-carboxylate. To a stirred solution of 5-(pyrazin-2-yl) isoxazole-3-carboxylic acid (100 mg, 0.34 mmol, 1.0 equiv.) in DMF (1.5 mL) add HATU (193 mg, 0.34 mmol, 1.0 equiv.) and stirred the reaction mixture for 15 minute and added tert-butyl 4-(1-(4-amino-1H-pyrazol-1-yl)ethyl)piperidine-1-carboxylate (64 mg, 0.34 mmol, 1.0 equiv.) and DIPEA (131 mg, 1.02 mmol, 3.0 equiv.) stirred the resulting reaction mixture for 2 hrs at room temperature. Reaction was monitored with TLC and LCMS. Reaction mixture was diluted with ethyl acetate and washed with water, collect organic layer dried over anhydrous $Na_2SO_4$ and concentrate under reduced pressure to obtain crude product which is further purified by normal phase silica gel chromatography to obtain the title compound (30 mg). LCMS: 468 $[M+H]^+$.

Step 6: Synthesis of N-(1-(1-(piperidin-4-yl)ethyl)-1H-pyrazol-4-yl)-5-(pyrazin-2-yl)isoxazole-3-carboxamide 2,2,2-trifluoroacetate. To a stirred solution of tert-butyl 4-(1-(4-(5-(pyrazin-2-yl) isoxazole-3-carboxamido)-1H-pyrazol-1-yl) ethyl) piperidine-1-carboxylate (20 mg, 0.042 mmol, 1.0 equiv.) in DCM (2 mL), was added TFA (0.2 mL) at RT and allowed to stir the reaction mixture at RT for 16 hrs. Progress of reaction was monitored by TLC and LCMS. After completion of reaction, DCM was evaporated and washed with ether (5 mL) and pentane (5 mL) to obtain title compound as N-(1-(1-(piperidin-4-yl)ethyl)-1H-pyrazol-4-yl)-5-(pyrazin-2-yl)isoxazole-3-carboxamide (13 mg). LCMS: 368 $[M+H]^+$. $^1H$ NMR (400 MHz, METHANOL-$d_4$) δ ppm 9.23 (s, 1H) 8.73 (s, 1H) 8.77 (s, 1H) 8.16 (br. s., 1H) 7.73 (s, 1H) 7.51 (s, 1H) 4.20 (br. s., 1H) 3.44 (d, J=11.40 Hz, 1H) 3.13 (s, 1H) 3.01 (br. s., 1H) 2.90 (br. s., 2H) 1.95-2.23 (m, 4H) 1.6 (d, 3H).

Example S3-11. Synthesis of N-(1-(1-(piperidin-4-yl)ethyl)-1H-pyrazol-4-yl)-5-(pyrazin-2-yl)-1,3,4-thiadiazole-2-carboxamide (Compound 3-11)

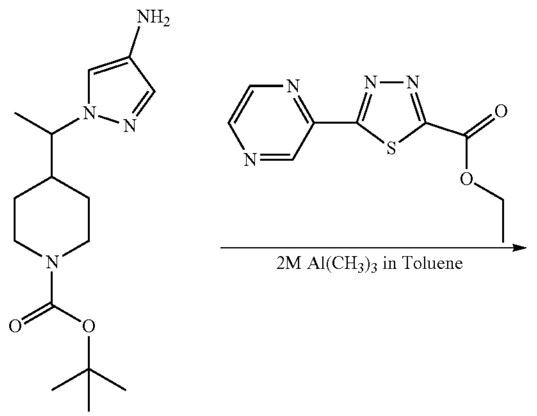

-continued

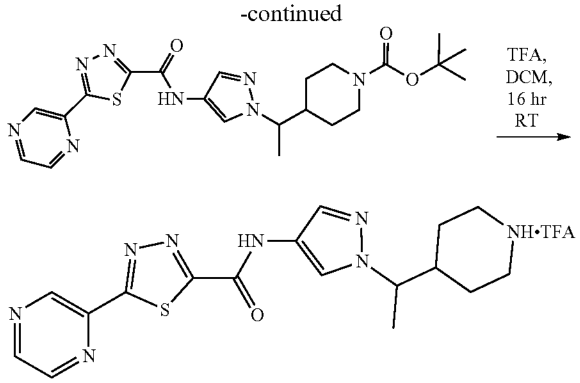

Compound 3-11

Step 1: Synthesis of tert-butyl 4-(1-(4-(5-(pyrazin-2-yl)-1,3,4-thiadiazole-2-carboxamido)-1H-pyrazol-1-yl)ethyl) piperidine-1-carboxylate. To a stirring solution of ethyl 5-(pyrazin-2-yl)-1,3,4-thiadiazole-2-carboxylate (100 mg, 0.423 mmol, 1.0 equiv.) in THE (3 mL), was added tert-butyl 4-(1-(4-amino-1H-pyrazol-1-yl)ethyl)piperidine-1-carboxylate (124 mg, 0.423 mmol, 1.0 equiv.), TMA (2.0 M in toluene) (0.4 ml, 1.35 mmol, 4.0 equiv.) at 0° C. Then, the reaction mixture was allowed to stir at RT for 30 minutes. After 30 minutes, the reaction mixture was allowed to stir at 60° C. for 1 hrs. After the completion of reaction, the reaction was quenched using $NH_4Cl$ solution. Then the reaction mixture were diluted with EtOAc (50 mL) and washed with water (3×50 mL). The organic layer was dried over $Na_2SO_4$ and concentrated under reduced pressure to obtain crude which was further purified by flash column chromatography (EtOAc/Heaxne) to obtain title compound as free base (25 mg). LCMS: 486 $[M+H]^+$.

Step 2: Synthesis of N-(1-(1-(piperidin-4-yl)ethyl)-1H-pyrazol-4-yl)-5-(pyrazin-2-yl)-1,3,4-thiadiazole-2-carboxamide 2,2,2-trifluoroacetate. To a stirred solution of tert-butyl 4-(1-(4-(5-(pyrazin-2-yl)-1,3,4-thiadiazole-2-carboxamido)-1H-pyrazol-1-yl)ethyl)piperidine-1-carboxylate (20 mg, 0.042 mmol, 1.0 equiv.) in DCM (2 mL), was added TFA (0.2 mL) at RT and allowed to stir the reaction mixture at RT for 16 hrs. Progress of reaction was monitored by TLC and LCMS. After completion of reaction, evaporated DCM solvent and washed with ether (5 mL) and pentane (5 mL) to obtain title compound as TFA salt (11 mg). LCMS: 386 $[M+H]^+$. $^1H$ NMR (400 MHz, METHANOL-$d_4$) δ ppm 9.55 (s, 1H) 8.78 (d, J=8.33 Hz, 2H) 8.18 (s, 1H) 7.78 (s, 1H) 4.21 (br. s., 1H) 3.44 (d, J=11.40 Hz, 1H) 3.13 (br. s., 2H) 2.96-3.11 (m, 2H) 2.08 (d, J=15.79 Hz, 2H) 1.57 (d, J=6.58 Hz, 3H) 1.36-1.55 (m, 2H)

Example S3-12. Synthesis of 5-(pyrazin-2-yl)-N-(1-(1-(4-(trifluoromethyl)cyclohexyl)ethyl)-1H-pyrazol-4-yl)isoxazole-3-carboxamide (Compound 3-12 and Compound 3-13)
Step 1: Synthesis of N-methoxy-N-methyl-4-(trifluoromethyl)cyclohexane-1-carboxamide. To a solution of 4-(trifluoromethyl)cyclohexane-1-carboxylic acid (1 gm, 5.1 mmol, 1 eq.) in DMF (1 mL), were added HATU (1.94 g, 5
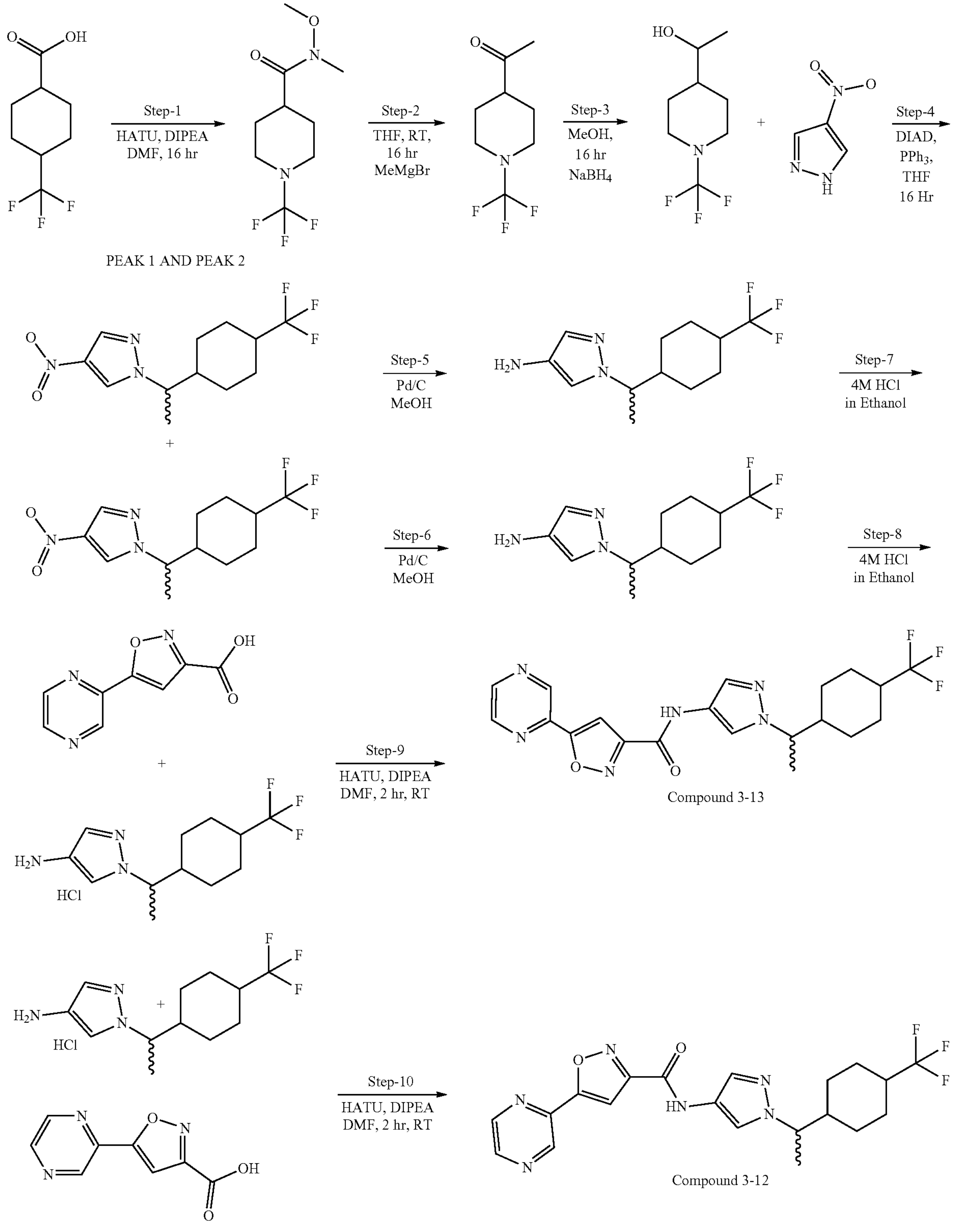
Compound 3-13
Compound 3-12 mmol, 1 eq.). The mixture was treated drop wise with DIPEA (2.65 ml, 1.5 mmol, 3 eq.) and DMAP (62 mg, 5 mmol, 0.1 eq). After stirring at RT for 15 minutes, was added a solution of the N,O-dimethylhydroxylamine hydrochloride (0.494 0 gm, 5 mmol, 1 eq.) in DMF (1 mL). The reaction mixture was kept under stirring for 24 h. Product formation was confirmed with TLC and LCMS and reaction mixture was diluted EtOAc (50 mL) and washed with water (2×50 mL). Organic layer dried over $Na_2SO_4$ and concentrated under reduced pressure to obtain crude which was further purified by flash column chromatography to obtain pure product N-methoxy-N-methyl-4-(trifluoromethyl)cyclohexane-1-carboxamide (1.2 g). LCMS: 240 $[M+H]^+$.

Step 2: Synthesis of 1-(4-(trifluoromethyl)cyclohexyl)ethan-1-one. To a solution of N-methoxy-N-methyl-4-(trifluoromethyl)cyclohexane-1-carboxamide (1.2 g, 5 mmol, 1 eq.) in THF (10 mL) was added solution of MeMgBr in THF (2M, 1.194 gm, 1 mmol, 2 eq.). The reaction mixture was kept under stirring for 24 h. Product formation was confirmed with TLC and LCMS and reaction mixture was diluted EtOAc (50 mL) and washed with $NH_4Cl$ (2×50 mL), Organic layer dried over $Na_2SO_4$ and concentrated under reduced pressure to obtain crude which was further purified by flash column chromatography to obtain pure product 1-(4-(trifluoromethyl)cyclohexyl)ethan-1-one (450 mg, as white solid). LCMS: 195 $[M+H]^+$.

Step 3: Synthesis of 1-(4-(trifluoromethyl)cyclohexyl)ethan-1-ol. To a stirred solution of 1-(4-(trifluoromethyl)cyclohexyl)ethan-1-one (0.450 g, 2.319 mmol, 1.0 eq) in methanol (20 mL) was added $NaBH_4$ (132.2 gm, 3.47 mmol, 1.5 eq) portion wise at 0° C. and stirred for 10 minutes. The reaction mixture was allowed to stir for 1 hour at RT. Product formation was confirmed by TLC and NMR. After completion of reaction, reaction mixture was quenched with water and extracted with ethyl acetate (3×50 mL), Combined organic extracts were washed with water (2×50 mL), dried over anhydrous $Na_2SO_4$ and concentrated under reduced pressure to obtain 1-(4-(trifluoromethyl)cyclohexyl)ethan-1-ol (0.375 g). 1H NMR (400 MHz, DMSO-$d_6$) δ 4.34-4.40 (m, 1H), 3.56 (dd, J=5.92, 13.81 Hz, 1H), 1.94-2.01 (m, 3H), 1.90 (br. s., 2H), 1.75 (d, J=6.58 Hz, 2H), 1.51-1.63 (m, 2H), 1.44-1.51 (m, 2H), 1.26-1.39 (m, 2H), 1.12-1.22 (m, 2H), Step 4: Synthesis of 4-nitro-1-(1-(4-(trifluoromethyl)cyclohexyl)ethyl)-1H-pyrazole and 4-nitro-1-(1-(4-(trifluoromethyl)cyclohexyl)ethyl)-1H-pyrazole. To a stirred solution of $PPh_3$ (601 mg, 2.29 mmol, 1.2 eq) and DIAD (464 mg, 2.29 mmol, 1.2 eq) in THF (2 mL) was added 1-(4-(trifluoromethyl)cyclohexyl)ethan-1-ol (375 mg, 1.913 mmol, 1.0 eq). Followed by drop wise addition of 4-nitro-1H-pyrazole (216.1 mg, 1.913 mmol, and 1 eq), the reaction mixture was stirred at RT for overnight. Product formation was confirmed with TLC and LCMS. After completion of reaction mixture were diluted with EtOAc (50 mL) and washed with water (50 mL×3). Organic layer dried over $Na_2SO_4$ and concentrated under reduced pressure to obtained crude which was further purified by flash column chromatography to obtain 4-nitro-1-(1-(4-(trifluoromethyl)cyclohexyl)ethyl)-1H-pyrazole (85 mg) and 4-nitro-1-(1-(4-(trifluoromethyl)cyclohexyl)ethyl)-1H-pyrazole (68 mg), LCMS: 292 $[M+H]^+$, Peak 1: $^1$H NMR (400 MHz, DMSO-$d_6$) δ 9.03 (s, 1H), 8.28 (s, 1H), 4.53 (dd, J=6.80, 9.87 Hz, 1H), 2.04 (br. s., 1H), 1.98 (d, J=2.63 Hz, 2H), 1.49-1.76 (m, 3H), 1.44 (d, J=6.58 Hz, 3H), 1.25 (d, J=9.21 Hz, 2H), 0.94 (br. s., 2H); Peak 2: $^1$H NMR (400 MHz, DMSO-$d_6$) δ 8.92 (s, 1H), 8.27 (s, 1H), 4.12-4.27 (m, 1H), 2.19 (br. s., 1H), 1.69-1.96 (m, 3H), 1.45 (d, J=7.02 Hz, 3H), 1.30-1.41 (m, 2H), 1.11-1.30 (m, 4H).

Step 5 and Step 6: Synthesis of 1-(1-(4-(trifluoromethyl)cyclohexyl)ethyl)-1H-pyrazol-4-amine and 1-(1-(4-(trifluoromethyl)cyclohexyl)ethyl)-1H-pyrazol-4-amine. To a stirred solution of 4-nitro-1-(1-(4-(trifluoromethyl)cyclohexyl)ethyl)-1H-pyrazole (85 mg) in methanol (10 mL) under nitrogen, palladium on carbon (10% w/w, 8 mg) was added. Purged the reaction mixture with $H_2$ gas for 2 h. Product formation was confirmed by LCMS. After the completion of reaction, reaction mixture was filtered through celite bed and filtrate was concentrate under reduced pressure to obtain 1-(1-(4-(trifluoromethyl)cyclohexyl)ethyl)-1H-pyrazol-4-amine (80 mg crude, as brown colour liquid). To a stirred solution of 4-nitro-1-(1-(4-(trifluoromethyl)cyclohexyl)ethyl)-1H-pyrazole (68 mg) in methanol (10 mL) under nitrogen, palladium on carbon (10% w/w, 7 mg) was added. Purged the reaction mixture with $H_2$ gas for 2 h. Product formation was confirmed by LCMS. After completion of reaction, reaction mixture was filtered through celite bed and filtrate was concentrate under reduced pressure to obtain 1-(1-(4-(trifluoromethyl)cyclohexyl)ethyl)-1H-pyrazol-4-amine (60 mg crude, as brown colour liquid). Composition derived from Peak 1 product of Step 4: $^1$H NMR (400 MHz, DMSO-$d_6$) δ 7.05 (s, 1H), 6.87 (s, 1H), 4.10-4.23 (m, 1H), 3.80 (br. s., 2H), 2.67 (br. s., 1H), 2.33 (br. s., 1H), 1.90 (br. s., 2H), 1.42-1.71 (m, 4H), 1.28-1.36 (m, 3H), 1.05 (d, J=6.14 Hz, 2H); Composition derived from Peak 2 product of Step 4: $^1$H NMR (400 MHz, DMSO-$d_6$) δ 7.00 (s, 1H), 6.87 (s, 1H), 4.08-4.14 (m, 1H), 3.84 (d, J=8.33 Hz, 2H), 2.15 (br. s., 1H), 1.91 (br. s., 1H), 1.79 (br. s., 2H), 1.56 (br. s., 2H), 1.32 (d, J=6.58 Hz, 3H), 1.23 (br. s., 2H), 0.98-1.12 (m, 2H).

Step 7 and Step 8: Synthesis of 1-(1-(4-(trifluoromethyl)cyclohexyl)ethyl)-1H-pyrazol-4-amine hydrochloride and 1-(1-(4-(trifluoromethyl)cyclohexyl)ethyl)-1H-pyrazol-4-amine hydrochloride. To a solution of 1-(1-(4-(trifluoromethyl)cyclohexyl)ethyl)-1H-pyrazol-4-amine (80 mg) in Ethanol (1 mL) was added solution of 2M HCl in ethanol (2 ml) for 2H at RT. Product formation was confirmed with TLC and $^1$H NMR. Reaction mixture was concentrated under reduced pressure to obtain crude which was further triturated with Diethylether and lyophilized to obtain pure 1-(1-(4-(trifluoromethyl)cyclohexyl)ethyl)-1H-pyrazol-4-amine hydrochloride (82 mg, Brown Solid). To a stirred solution of 1-(1-(4-(trifluoromethyl)cyclohexyl)ethyl)-1H-pyrazol-4-amine. (60 mg.) in Ethanol (1 mL) was added 2M HCl in Ethanol (2 ml) for 2 h at RT. Product formation was confirmed with TLC and $^1$H NMR. Reaction mixture was concentrated under reduced pressure to obtain crude which was further triturated with diethyl ether and lyophilized to obtain pure product 1-(1-(4-(trifluoromethyl)cyclohexyl)ethyl)-1H-pyrazol-4-amine hydrochloride (62 mg, Brown Solid). Composition derived from Peak 1 product of Step 4: $^1$H NMR (400 MHz, DMSO-$d_6$) δ 10.24 (br. s., 2H), 8.03 (s, 1H), 7.54 (s, 1H), 4.44-4.53 (m, 1H), 2.33 (br. s., 2H), 2.00 (br. s., 1H), 1.53-1.71 (m, 0.3H), 1.51 (br. s., 2H), 1.36-1.43 (m, 3H), 1.23 (d, J=4.38 Hz, 2H); Composition derived from Peak 2 product of Step 4: $^1$H NMR (400 MHz, DMSO-$d_6$) δ 10.03 (br. s., 2H), 7.94 (s, 1H), 7.54 (s, 1H), 4.10-4.18 (m, 1H), 2.33 (br. s., 1H), 2.16 (d, J=8.77 Hz, 1H), 1.74-1.96 (m, 3H), 1.68 (d, J=8.33 Hz, 1H), 1.40 (d, J=7.02 Hz, 2H), 1.00-1.29 (m, 5H).

Step 9 and Step 10: Synthesis of 5-(pyrazin-2-yl)-N-(1-(1-(4-(trifluoromethyl)cyclohexyl)ethyl)-1H-pyrazol-4-yl)isoxazole-3-carboxamide and 5-(pyrazin-2-yl)-N-(1-(1-(4-(trifluoromethyl)cyclohexyl)ethyl)-1H-pyrazol-4-yl)isoxazole-3-carboxamide. To a solution of 5-(pyrazin-2-yl)isoxazole-3-carboxylic acid (51 mg, 0.269 mmol, 1 eq.) in DMF (1 mL), were added HATU (102.62 mg, 0.269 mmol, 1 eq.). The mixture was treated drop wise with DIPEA (0.109 ml, 0.629 mmol, 3 eq.). After stirring at RT for 15 minutes, the mixture was treated drop wise with a solution of 1-(1-(4-(trifluoromethyl)cyclohexyl)ethyl)-1H-pyrazol-4-amine hydrochloride (80 mg, 0.269 mmol, 1 eq.) in DMF (1 mL). The reaction mixture was kept under stirring for 24 h. Product formation was confirmed with TLC and LCMS and reaction mixture was diluted EtOAc (50 mL) and washed with water (2×50 mL), Organic layer dried over $Na_2SO_4$ and concentrated under reduced pressure to obtain crude which was further purified by flash column chromatography to obtain pure product 5-(pyrazin-2-yl)-N-(1-(1-(4-(trifluoromethyl)cyclohexyl)ethyl)-1H-pyrazol-4-yl) isoxazole-3-carboxamide (40 mg, as white solid). To a solution of 5-(pyrazin-2-yl)isoxazole-3-carboxylic acid (39 mg, 0.202 mmol, 1 eq.) in DMF (1 mL), were added HATU (77 mg, 0.202 mmol, 1 eq.). The mixture was treated drop wise with DIPEA (0.104 ml, 0.606 mmol, 3 eq.). After stirring at RT for 15 minutes, the mixture was treated drop wise with a solution of the 1-(1-(4-(trifluoromethyl)cyclohexyl)ethyl)-1H-pyrazol-4-amine hydrochloride (60 mg, 0.202 mmol, 1 eq.) in DMF (1 mL). The reaction mixture was kept under stirring for 24 h. Product formation was confirmed with TLC and LCMS and reaction mixture was diluted EtOAc (50 mL) and washed with water (2×50 mL). Organic layer dried over $Na_2SO_4$ and concentrated under reduced pressure to obtain crude which was further purified by flash column chromatography to obtain 5-(pyrazin-2-yl)-N-(1-(1-(4-(trifluoromethyl)cyclohexyl)ethyl)-1H-pyrazol-4-yl)isoxazole-3-carboxamide (15 mg, as white solid). LCMS: 435 $[M+H]^+$. Composition derived from Peak 1 product of Step 4: $^1H$ NMR (400 MHz, DMSO-$d_6$) δ 11.07 (br. s., 1H), 9.35 (s, 1H), 8.83 (d, J=11.84 Hz, 2H), 8.05 (s, 1H), 7.67 (d, J=9.21 Hz, 1H), 4.04-4.16 (m, 1H), 2.17 (br. s., 1H), 1.74-1.94 (m, 3H), 1.68 (br. s., 1H), 1.41 (d, J=6.58 Hz, 2H), 1.22 (d, J=10.52 Hz, 2H), 0.91-1.17 (m, 4H); Composition derived from Peak 2 product of Step 4: $^1H$ NMR (400 MHz, DMSO-$d_6$) δ 11.07 (s, 1H), 9.35 (s, 1H), 8.78-8.88 (m, 2H), 8.12 (s, 1H), 7.66 (d, J=9.21 Hz, 2H), 4.45 (dd, J=6.58, 10.09 Hz, 1H), 2.33 (br. s., 2H), 2.01 (br. s., 1H), 1.55-1.76 (m, 5H), 1.53 (br. s., 1H), 1.41 (d, J=6.58 Hz, 3H), 1.21 (d, J=14.03 Hz, 1H).

Example S3-13. Synthesis of N-(1-(piperidin-4-yl)-1H-pyrazol-4-yl)-5-(pyrazin-2-yl)isoxazole-3-carboxamide (Compound 3-14)

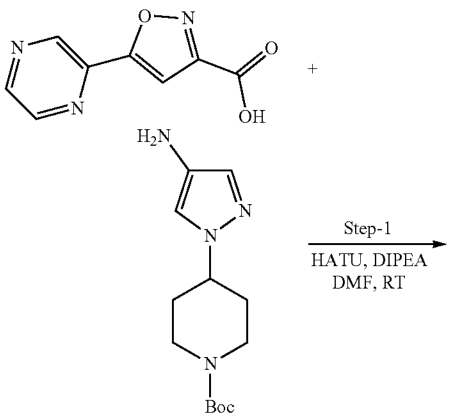

-continued

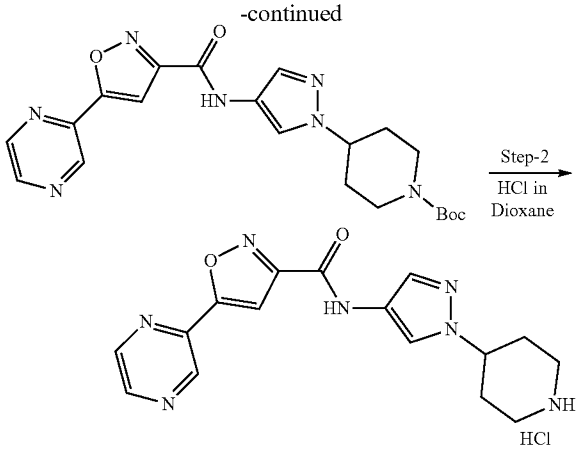

Compound 3-14

Step 1: Synthesis of tert-butyl 4-(4-(5-(pyrazin-2-yl) isoxazole-3-carboxamido)-1H-pyrazol-1-yl)piperidine-1-carboxylate To a solution of 5-(pyrazin-2-yl)isoxazole-3-carboxylic acid (100 mg, 0.52 mmol, 1 equiv) in DMF (1 mL), were added HATU (199.47 mg, 0.52 mmol, 1 eq). The mixture was treated drop wise with DIPEA (0.271 ml, 1.68 mmol, 3.2 equiv). After stirring at RT for 15 minutes, the mixture was treated drop wise with a solution of the tert-butyl 4-(4-amino-1H-pyrazol-1-yl)piperidine-1-carboxylate (139 mg, 0.52 mmol, 1 equiv) in DMF (2 mL). The reaction mixture was kept under stirring for 24 h. Product formation was confirmed with TLC & LCMS and reaction mixture was diluted EtOAc (50 mL) & washed with water (50 mL×2). Organic layer dried over $Na_2SO_4$ & concentrated under reduced pressure to obtain crude which was further purified by flash column chromatography to obtain pure product tert-butyl 4-(4-(5-(pyrazin-2-yl)isoxazole-3-carboxamido)-1H-pyrazol-1-yl)piperidine-1-carboxylate (60 mg, as off white solid). LCMS: 440 $[M+H]^+$, $^1H$ NMR (400 MHz, DMSO-$d_6$) δ 11.07 (s, 1H), 9.35 (s, 1H), 8.85 (s, 1H), 8.81 (d, J=2.19 Hz, 1H), 8.09 (s, 1H), 7.68 (d, J=2.19 Hz, 1H), 4.37 (br. s., 1H), 4.04 (d, J=10.96 Hz, 2H), 2.90 (br. s., 2H), 1.98-2.00 (m, 4H), 1.5 (s, 9H).

Step 2: Synthesis of N-(1-(piperidin-4-yl)-1H-pyrazol-4-yl)-5-(pyrazin-2-yl)isoxazole-3-carboxamide hydrochloride. To a stirred solution of tert-butyl 4-(4-(5-(pyrazin-2-yl)isoxazole-3-carboxamido)-1H-pyrazol-1-yl)piperidine-1-carboxylate (60 mg) in Dioxane (5 mL) was added 4M HCl in Dioxane (1 mL) and stirred at room temperature for 2 h. A precipitate formed after 2 h. The solvent was removed in vacuo and the resultant solid was washed with diethyl ether and dried under vacuum to obtained N-(1-(piperidin-4-yl)-1H-pyrazol-4-yl)-5-(pyrazin-2-yl)isoxazole-3-carboxamide hydrochloride (50 mg). LCMS: 340 $[M+H]^+$, $^1H$ NMR (400 MHz, DMSO-$d_6$) δ 11.19 (s, 1H), 9.31-9.43 (m, 1H), 9.25 (br. s., 2H), 8.81-8.92 (m, 1H), 8.10 (s, 1H), 7.73 (d, J=4.38 Hz, 2H), 4.43-4.61 (m, 1H), 3.38 (br. s., 2H), 2.98-3.10 (m, 2H), 2.04-2.22 (m, 4H).

Example S3-14. Synthesis of N-(1-(piperidin-4-yl)-1H-pyrazol-4-yl)-5-(pyrazin-2-yl)-1,3,4-thiadiazole-2-carboxamide (Compound 3-15)

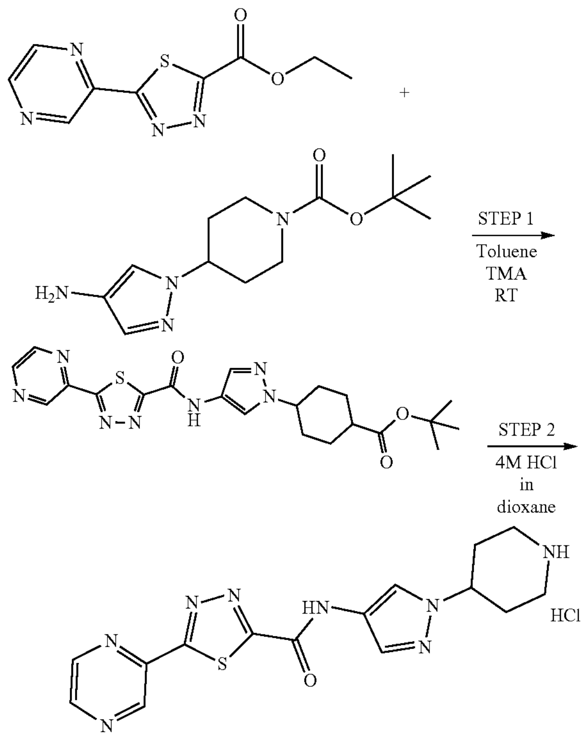

Compound 3-15

Step 1: Synthesis of tert-butyl 4-(4-(5-(pyrazin-2-yl)-1,3,4-thiadiazole-2-carboxamido)-1H-pyrazol-1-yl)piperidine-1-carboxylate). To a stirred solution of ethyl 5-(pyrazin-2-yl)-1,3,4-thiadiazole-2-carboxylate (150 mg, 0.635 mmol, 1 equiv.) and tert-butyl 4-(4-amino-1H-pyrazol-1-yl)piperidine-1-carboxylate (169.06 mg, 0.635 mmol, 1 equiv.) in Toluene (10 mL) was added 3M Trimethyl Aluminium in Toluene (365.76 mg, 2.54 mmol, 4 equiv.). Reaction mixture was stirred at RT for 24 hr. The reaction mixture was diluted with cold water and filtered to give tert-butyl 4-(4-(5-(pyrazin-2-yl)-1,3,4-thiadiazole-2-carboxamido)-1H-pyrazol-1-yl)piperidine-1-carboxylate (100 mg yellow solid). LCMS: 357 $[M-100]^+$.

Step 2: Synthesis of N-(1-(piperidin-4-yl)-1H-pyrazol-4-yl)-5-(pyrazin-2-yl)-1,3,4-thiadiazole-2-carboxamide. To the tert-butyl 4-(4-(5-(pyrazin-2-yl)-1,3,4-thiadiazole-2-carboxamido)-1H-pyrazol-1-yl)piperidine-1-carboxylate (100 mg, 0.109 mmol, 1 equiv.), 4 M HCl in dioxane was added and allowed to stir at RT for 1 h. After reaction completion, reaction mixture was concentrated to give N-(1-(piperidin-4-yl)-1H-pyrazol-4-yl)-5-(pyrazin-2-yl)-1,3,4-thiadiazole-2-carboxamide (100 mg yellow solid). LCMS: 357 $[M+H]^+$. $^1$H NMR (400 MHz, DMSO-$d_6$) δ ppm 11.63 (s, 1H) 9.54 (br. s., 1H) 8.87 (s, 2H) 8.92 (s, 1H) 8.54 (br. s., 2H) 8.12 (s, 1H) 7.79 (s, 1H) 4.52 (d, J=4.38 Hz, 1H) 3.96 (br. s., 1H) 3.07 (br. s., 3H) 2.16 (br. s., 3H).

Example S3-15. Synthesis of 5-(furan-2-yl)-N-(1-(trans4-hydroxycyclohexyl)-1H-pyrazol-4-yl)isoxazole-3-carboxamide (Compound 3-16)

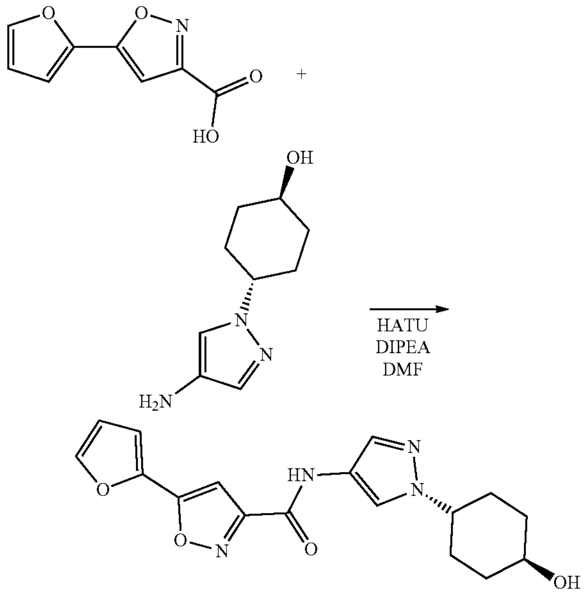

Compound 3-16

Step 1: Synthesis of 5-(furan-2-yl)-N-(1-(trans4-hydroxycyclohexyl)-1H-pyrazol-4-yl)isoxazole-3-carboxamide. To a solution of 5-(furan-2-yl)isoxazole-3-carboxylic acid (100 mg, 0.555 mmol, 1 equiv) in DMF (1 mL), were added HATU (210 g, 0.555 mmol, 1.0 equiv). The mixture was treated drop wise with DIPEA (0.192 ml, 1.111 mmol, 2.0 equiv). After stirring at RT for 15 minutes, the mixture was treated drop wise with a solution of the trans-4-(4-amino-1H-pyrazol-1-yl)cyclohexan-1-ol (100.55 mg, 0.555 mmol, 1 equiv) in DMF (1 mL). The reaction mixture was kept under stirring for 24 h. After completion of reaction mixture were diluted with EtOAc (50 mL) & washed with water (10 mLx3). Organic layer dried over $Na_2SO_4$ & concentrated under reduced pressure to obtain crude which was further purified by trituration with Acetone Hexane (8:2) ml to afford precipitate as 5-(furan-2-yl)-N-(1-(trans-4-hydroxycyclohexyl)-1H-pyrazol-4-yl)isoxazole-3-carboxamide. LCMS: 343 $[M+H]^+$, $^1$H NMR (400 MHz, DMSO-$d_6$) δ 10.96 (s, 1H), 7.91-8.15 (m, 2H), 7.62 (s, 1H), 7.28 (d, J=3.51 Hz, 1H), 7.15 (s, 1H), 6.77 (br. s., 1H), 4.65 (d, J=4.39 Hz, 1H), 4.11 (d, J=11.40 Hz, 2H), 3.49 (br. s., 1H), 1.93 (t, J=14.69 Hz, 3H), 1.61-1.82 (m, 2H), 1.19-1.44 (m, 2H).

Example S3-16. Synthesis of N-(1-(1-cyclopentylethyl)-1H-pyrazol-4-yl)-5-(furan-2-yl)isoxazole-3-carboxamide (Compound 3-17 and Compound 3-18)

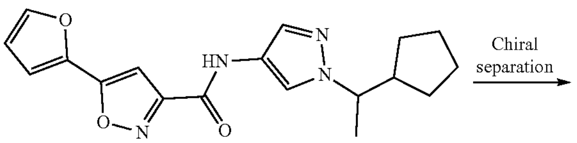

-continued

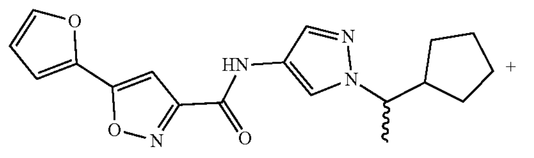

Compound 3-17

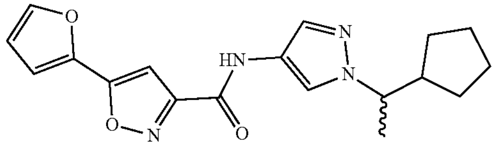

Compound 3-18

The racemic mixture of N-(1-(1-cyclopentylethyl)-1H-pyrazol-4-yl)-5-(furan-2-yl)isoxazole-3-carboxamide (160 mg) was purified by chiral HPLC to obtain a first-eluting isomer (Compound 3-17) and a second-eluting isomer (Compound 3-18). The isomers were separated by chiral SFC (Daicel Chiralpak-IC, 250×20 mm, 5 um), isocratic program with analytical grade liquid carbon dioxide and HPLC grade Methanol, Total flow: 56 gJmin, Co-Solvent Percentage: 18%.

Compound 3-17: yield=22 mg; elution time=7.9 min. Compound 3-18: yield=20 mg; elution time=10.13 min Compound 3-17: LCMS: 341 [M+H]; $^{1}$H NMR (400 MHz, DMSO-$d_6$) δ 10.95 (s, 1H), 8.02 (d, J=13.59 Hz, 2H), 7.62 (s, 1H), 7.28 (d, J=3.51 Hz, 1H), 7.15 (s, 1H), 6.69-6.85 (m, 1H), 4.02-4.24 (m, 1H), 2.23 (m, J=8.51 Hz, 1H), 1.71-1.88 (m, 2H), 1.45-1.68 (m, 2H), 1.35-1.45 (m, 3H), 1.15-1.33 (m, 2H), 1.00-1.14 (m, 2H). Compound 3-18: LCMS: 341 [M+1]; $^{1}$H NMR (400 MHz, DMSO-$d_6$) δ 10.93 (s, 1H), 8.01 (d, J=13.59 Hz, 2H), 7.61 (s, 1H), 7.28 (d, J=3.50 Hz, 1H), 7.13 (s, 1H), 6.69-6.83 (m, 1H), 4.02-4.21 (m, 1H), 2.21 (m, J=8.51 Hz, 1H), 1.71-1.87 (m, 2H), 1.45-1.63 (m, 2H), 1.35-1.43 (m, 3H), 1.15-1.31 (m, 2H), 1.00-1.11 (m, 2H).

Example S3-17. Synthesis of N-(1-(tetrahydrofuran-3-yl)-1H-pyrazol-4-yl)-5-(thiophen-2-yl)isoxazole-3-carboxamide (Compound 3-19)

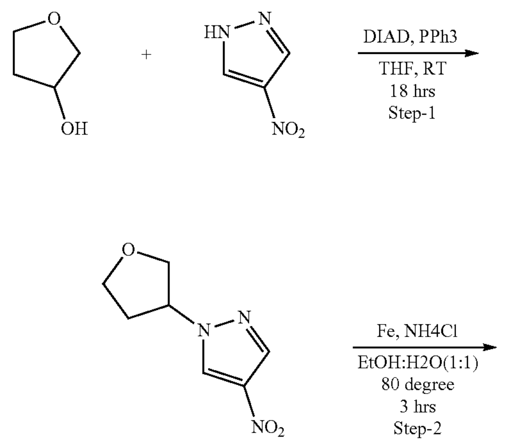

-continued

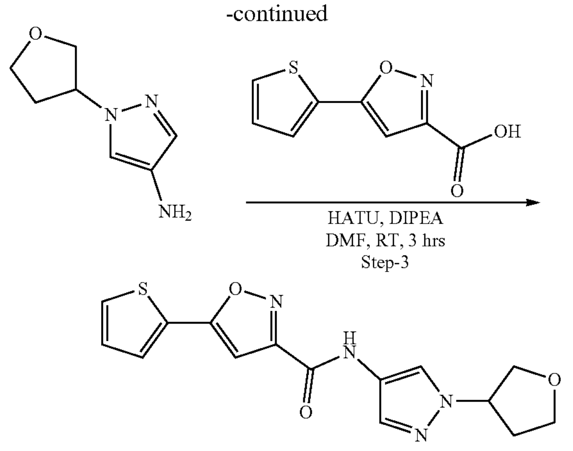

Compound 3-19

Step 1: Synthesis of 4-nitro-1-(tetrahydrofuran-3-yl)-1H-pyrazole. To a stirred solution of tetrahydrofuran-3-ol (1 g, 11.357 mmol, 1.0 eq) and 4-nitro-1H-pyrazole (1.283 g, 11.357 mmol, 1.0 eq) was added $PPh_3$ (4.46 g, 17.035 mmol, 1.5 eq) and the RM was stirred at 0° C. under nitrogen atmosphere for 10 min. Further, DIAD (2.3 mL, 17.035 mmol, 1.5 eq) was added slowly to the RM and allowed to stir at room temperature for 18 hrs. Progress of the reaction was analyzed by TLC, and LCMS. After the completion of the reaction, RM was extracted with ethyl acetate 2×times (50 mL), dried over sodium sulphate, concentrated under reduced pressure and further purified by using flash chromatography to obtain desired compound 4-nitro-1-(tetrahydrofuran-3-yl)-1H-pyrazole (1.5 g), LCMS (M+1): 184.

Step 2: Synthesis of 1-(tetrahydrofuran-3-yl)-1H-pyrazol-4-amine. To a stirred solution of 4-nitro-1-(tetrahydrofuran-3-yl)-1H-pyrazole (500 mg, 2.732 mmol, 1.0 eq) in EtOH: $H_2O$ (1:1) 5 mL was added Fe (765 mg, 13.661 mmol, 5.0 eq) and $NH_4Cl$ (738 mg, 13.661 mmol, 5.0 eq) and the RM was stirred at 80° C. for 3 hrs. Progress of the reaction was analyzed by LCMS. After the completion of the reaction, RM was passed through celite bed then concentrated under reduced pressure. Further, extraction is done by EtOAc (25 ml×2), organic layer dried over sodium sulphate and concentrated under reduced pressure to obtain the desired compound 1-(tetrahydrofuran-3-yl)-1H-pyrazol-4-amine (350 mg), LCMS (M+1): 155.

Step 3: Synthesis of N-(1-(tetrahydrofuran-3-yl)-1H-pyrazol-4-yl)-5-(thiophen-2-yl)isoxazole-3-carboxamide. To a stirred solution of 5-(thiophen-2-yl)isoxazole-3-carboxylic acid (100 mg, 0.513 mmol, 1.0 eq) in DMF (2 mL) was added HATU (195 mg, 0.513 mmol, 1.0 eq) and stirred at RT for 15 min. To the reaction mixture 1-(tetrahydrofuran-3-yl)-1H-pyrazol-4-amine (78 mg, 0.513 mmol, 1.0 eq) was added followed by the addition of DIPEA (0.3 mL, 1.538 mmol, 3.0 eq) and allowed to stir at RT for 3 hrs. Progress of the reaction was analyzed by TLC and LCMS. After the completion of the reaction, RM was poured into ice cold water, filtered, then excluding the filterate, further purification was done by using flash chromatography to obtain the desired compound N-(1-(tetrahydrofuran-3-yl)-1H-pyrazol-4-yl)-5-(thiophen-2-yl)isoxazole-3-carboxamide (24 mg), LCMS (M+1): 331.3, $^{1}$H NMR (400 MHz, DMSO-$d_6$) δ 10.98 (s, 1H), 8.10 (s, 1H), 7.89 (d, J=5.26 Hz, 1H), 7.81-7.86 (m, 1H), 7.67 (s, 1H), 7.23-7.33 (m, 2H), 5.00-

5.08 (m, 1H), 3.91-4.01 (m, 2H), 3.74-3.89 (m, 2H), 2.29-2.43 (m, 1H), 2.22 (d, J=3.95 Hz, 1H).

Example S3-18. Synthesis of 5-(pyridin-2-yl)-N-(1-(tetrahydrofuran-3-yl)-1H-pyrazol-4-yl)isoxazole-3-carboxamide (Compound 3-20 and Compound 3-21)

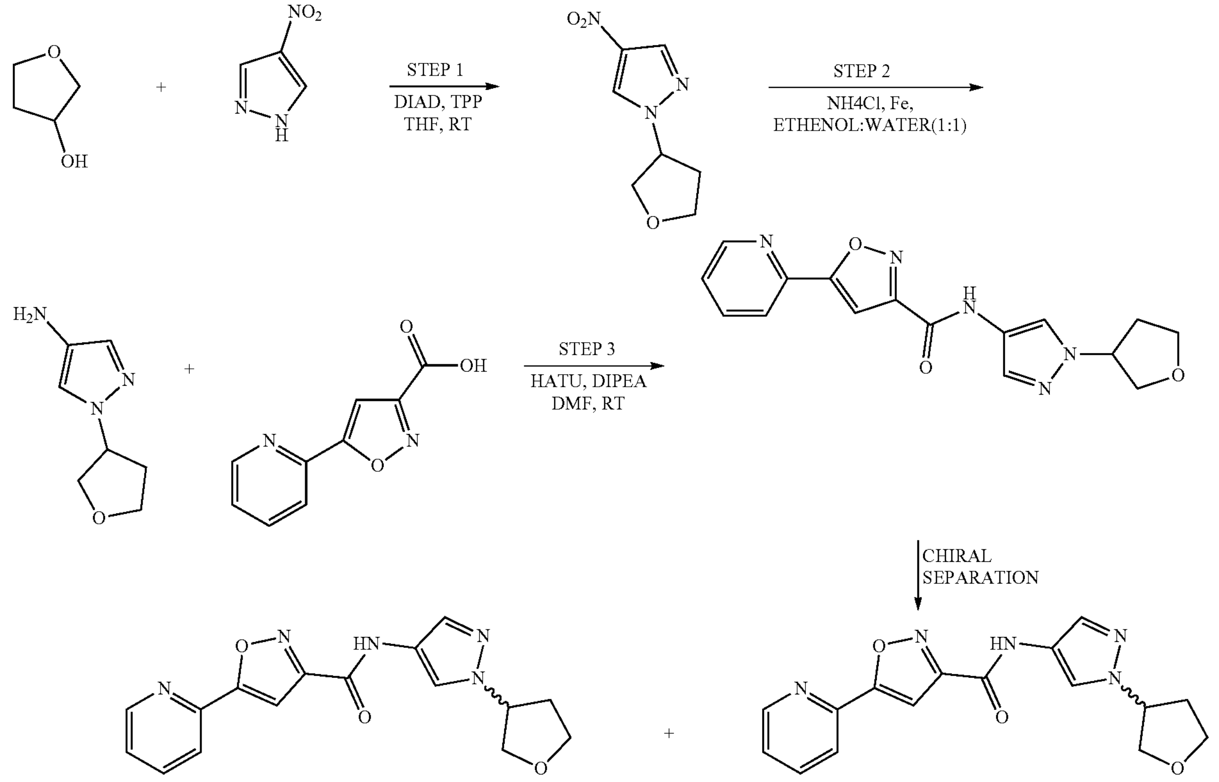

Compound 3-21

Compound 3-20

Step 1: Synthesis of 4-nitro-1-(tetrahydrofuran-3-yl)-1H-pyrazole. To a stirred solution of tetrahydrofuran-3-ol (2.00 g, 22.72 mmol, 1 eq.) and 4-nitro-1H-pyrazole (2.568 g, 22.72 mmol, 1 eq.) & TPP (8.931 gm, 34.090 mmol, 1.5 eq.) in THE (10 ml) was added DIAD (6.88 ml, 34.090 mmol, 1.5 eq.) Drop wise, and allowed to stir at RT for 4 hr. Reaction progress was monitored by TLC and LCMS. After the reaction completion, the reaction mixture was extracted with ethyl acetate and water (2×500 mL). Organic layer was separated and evaporated under reduced pressure to give crude product which was further purified by combi flash chromatography to yield 4-nitro-1-(tetrahydrofuran-3-yl)-1H-pyrazole (1.6 g), LCMS: 184.06 [M+H].

Step 2: Synthesis of 1-(tetrahydrofuran-3-yl)-1H-pyrazol-4-amine. To a solution of 4-nitro-1-(tetrahydrofuran-3-yl)-1H-pyrazole (1.0 g, 5.464 mmol, 1 eq.), in 10 ml Ethenol: Water (1:1) was added NH4Cl (1.475 g, 27.322 mmol, 5 eq.), & Fe (1.530 g, 27.322 mmol, 5 eq.), stir the resulting reaction mixture at 80° C. for 4 hr. Reaction progress was monitored by TLC and LCMS. After completion of reaction, RM was filtered through celite bed, filtrate concentrated, extracted with ethyl acetate and water (2×50 mL), organic layer was collected and concentrated to give crude product 1-(tetrahydrofuran-3-yl)-1H-pyrazol-4-amine (0.730 g), LCMS: 154.02 [M+H].

Step 3: Synthesis of 5-(pyridin-2-yl)-N-(1-(tetrahydrofuran-3-yl)-1H-pyrazol-4-yl)isoxazole-3-carboxamide. To a Solution of 5-(pyridin-2-yl)isoxazole-3-carboxylic acid (0.9189 g, 4.836 mmol, 1 eq.) & HATU (1.837 g, 4.836 mmol, 1 eq.) in DMF (5 mL), stir for 5 min & was added DIPEA (2.52 ml 14.509 mmol, 3 eq.) & 1-(tetrahydrofuran-3-yl)-1H-pyrazol-4-amine (0.740 g, 4.836 mmol, 1 eq.) stir the resulting reaction mixture at RT for 4 hr, reaction progress was monitored by TLC and LCMS, After completion of Reaction, Reaction mixture was extracted with ethyl acetate and water (2×25 mL). Organic layer was collected and concentrated to give crude product which was purified by combi flash chromatography to give 5-(pyridin-2-yl)-N-(1-(tetrahydrofuran-3-yl)-1H-pyrazol-4-yl)isoxazole-3-carboxamide (200 mg), LCMS: 326.0 [M+H], $^1$H NMR (400 MHz, DMSO-$d_6$) 11.05 (s, 1H), 8.76 (d, J=3.95 Hz, 1H), 7.97-8.20 (m, 3H), 7.68 (s, 1H), 7.54-7.49 (s, 2H), 5.05 (br. s., 1H), 3.96-3.90 (m, 4H), 2.32-2.45 (m, 2H).

Step 4: Separation of isomers of 5-(pyridin-2-yl)-N-(1-(tetrahydrofuran-3-yl)-1H-pyrazol-4-yl)isoxazole-3-carboxamide. The racemic mixture of 5-(pyridin-2-yl)-N-(1-(tetrahydrofuran-3-yl)-1H-pyrazol-4-yl)isoxazole-3-carboxamide (400 mg,) was purified by chiral HPLC to obtain a first-eluting isomer (Compound 3-20) and a second-eluting isomer (Compound 3-21). The isomers were separated using Column: Chiralcel-ODH, 250×20 mm, 5 μm, Flow rate: 56 mL/min, Column Oven Temperature: Ambient, Isocratic Program: A: Liquid Carbon dioxide food grade B: Isopropanol HPLC grade, ABPR: 100 bar, Initial (time min), B (%) composition (23%), 23 min B (%) composition (28%), Wavelength: Max plot, Sample preparation: HPLC grade Methanol, Filter with 0.22p.

Compound 3-20: yield=115 mg; Compound 3-21: yield=110 mg.

Compound 3-20: LCMS: 326 $[M+H]^+$; $^1$H NMR (400 MHz, DMSO-$d_6$) 11.05 (s, 1H), 8.76 (d, J=3.95 Hz, 1H), 7.97-8.20 (m, 3H), 7.68 (s, 1H), 7.54-7.49 (s, 2H), 5.05 (br. s., 1H), 3.96-3.90 (m, 4H), 2.32-2.45 (m, 2H). Compound 3-21: LCMS: 326 $[M+H]^+$ $^1$H NMR (400 MHz, DMSO-$d_6$) 11.05 (s, 1H), 8.76 (d, J=3.95 Hz, 1H), 7.97-8.20 (m, 3H), 7.68 (s, 1H), 7.54-7.49 (s, 2H), 5.05 (br.s., 1H), 3.96-3.90 (m, 4H), 2.32-2.45 (m, 2H).

Example S3-19. Synthesis of N-(1-(tetrahydrofuran-3-yl)-1H-pyrazol-4-yl)-5-(thiophen-2-yl)isoxazole-3-carboxamide (Compound 3-22 and Compound 3-23)

Reaction progress was monitored by TLC and LCMS. After reaction completion, reaction mixture was filtered through celite pad and filtrate was evaporated and extracted with DCM/water 2 times. Organic layer was collected and evaporated under reduced pressure to give 1-(tetrahydrofuran-3-yl)-1H-pyrazol-4-amine (1.1 g). LCMS: 154.09 [M+1].

Step 3: Synthesis of N-(1-(tetrahydrofuran-3-yl)-1H-pyrazol-4-yl)-5-(thiophen-2-yl)isoxazole-3-carboxamide. To a stirred solution 5-(thiophen-2-yl)isoxazole-3-carboxylic acid (764 mg, 3.921 mmol, 1.0 eq) in DMF (5 mL), were added HATU (1.490 g, 3.921 mmol, 1.0 eq). After stirring at RT for 15 minutes, the mixture was treated drop wise with DIPEA (2.045 ml, 11.764 mmol, 3.0 eq). After stirring at RT for 15 minutes, the mixture was treated with a solution of 1-(tetrahydrofuran-3-yl)-1H-pyrazol-4-amine (600 mg,

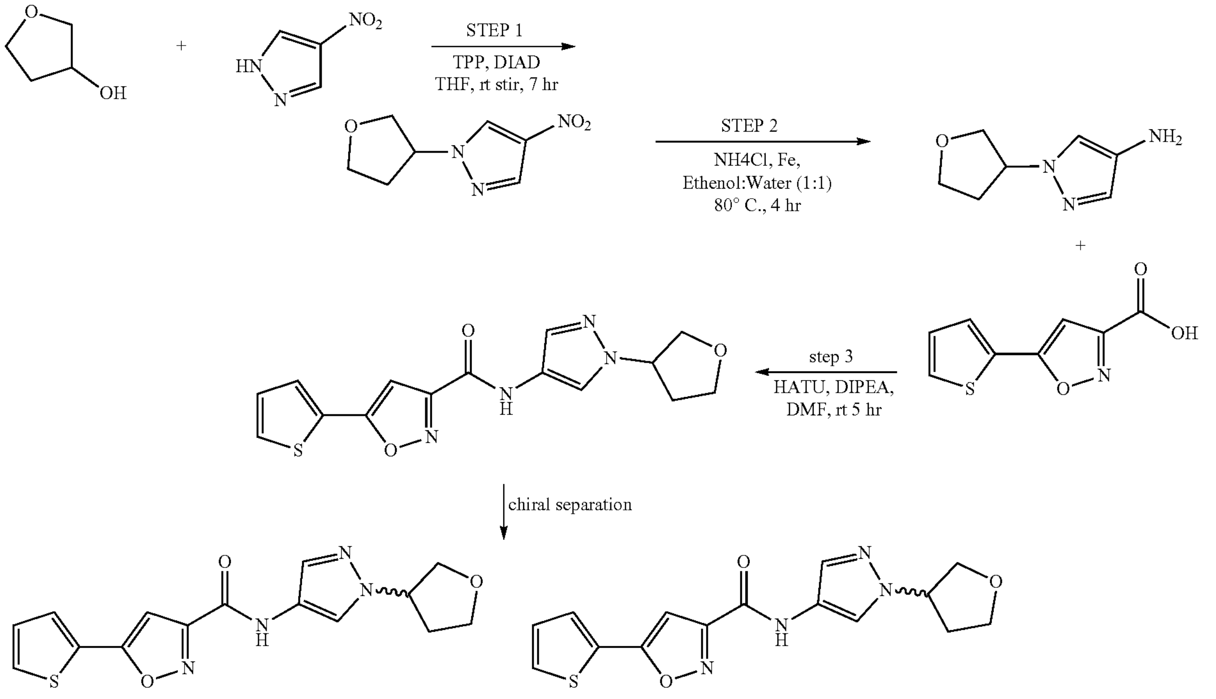

Compound 3-22

Compound 3-23

Step 1: Synthesis of 4-nitro-1-(tetrahydrofuran-3-yl)-1H-pyrazole. To a stirred solution of tetrahydrofuran-3-ol (2.00 g, 22.72 mmol, 1.0 eq.) and 4-nitro-1H-pyrazole (2.568 g, 22.72 mmol, 1.0 eq.) & TPP (8.931 g, 34.090 mmol, 1.5 eq.) in THE (10 mL), at 0° C. was added DIAD (6.88 ml, 34.090 mmol, 1.5 eq.) drop wise, after all addition reaction mixture were allowed to stir at RT for 6 hr. Reaction progress was monitored by TLC and LCMS. After reaction completion, the reaction mixture was extracted with ethyl acetate (100 ml×2) and water (100 mL). organic layer was separated and evaporated under reduced pressure to give crude product which was further purified by combiflash chromatography to obtain 4-nitro-1-(tetrahydrofuran-3-yl)-1H-pyrazole (900 mg), LCMS: 184.06 [M+1].

Step 2: Synthesis of 1-(tetrahydrofuran-3-yl)-1H-pyrazol-4-amine. To a stirred solution 4-nitro-1-(tetrahydrofuran-3-yl)-1H-pyrazole (1.00 g, 5.464 mmol, 1.0 eq) in EtOH/water (1:1, 10 ml), was added ammonium chloride (1.475 g, 27.322 mmol, 5.0 eq) & Fe (1.5300 g, 27.322 mmol, 5.0 eq) at RT was added and allowed to heat at 80° C. for 2 hr.

3.921 mmol, 1.0 eq) in DMF (1 mL). The reaction mixture was kept under stirring for 24 h. The reaction mixture was diluted with water (50 mL). The resulting precipitate was filtered off N-(1-(tetrahydrofuran-3-yl)-1H-pyrazol-4-yl)-5-(thiophen-2-yl)isoxazole-3-carboxamide (250 mg) Analytical Data: LCMS: 331.08 [M+H], $^1$H NMR (400 MHz, DMSO-$d_6$) δ ppm 8.73 (d, J=4.82 Hz, 1H) 8.61 (s, 1H) 8.31 (d, J=7.89 Hz, 1H) 8.01-8.12 (m, 3H) 7.8 (d, J=7.89 Hz, 1H) 7.57-7.67 (m, 1H)) 5.9 (br. s., 1H) 2.27 (s, 3H) 1.82-1.94 (m, 3H), Step 4: Separation of isomers of N-(1-(tetrahydrofuran-3-yl)-1H-pyrazol-4-yl)-5-(thiophen-2-yl)isoxazole-3-carboxamide. The racemic mixture of N-(1-(tetrahydrofuran-3-yl)-1H-pyrazol-4-yl)-5-(thiophen-2-yl)isoxazole-3-carboxamide was purified by chiral HPLC to obtain a first-eluting isomer (Compound 3-22) and a second-eluting isomer (Compound 3-23). The enantiomers were separated by chiral SFC (Daicel Chiralpak®-IC, 250×21 mm, 5 μm). Isocratic program with analytical grade liquid carbon dioxide and HPLC grade Methanol, Total flow: 56 g/min, Co-Solvent Percentage: 33%.

Compound 3-22: yield=29 mg; elution time=3.0 min. Compound 3-23: elution time=4.2 min.

Example S3-20. Synthesis of 5-(furan-2-yl)-N-(1-(1-(tetrahydrofuran-3-yl)ethyl)-1H-pyrazol-4-yl) isoxazole-3-carboxamide (Compound 3-24, Compound 3-25, Compound 3-26, and Compound 3-27)

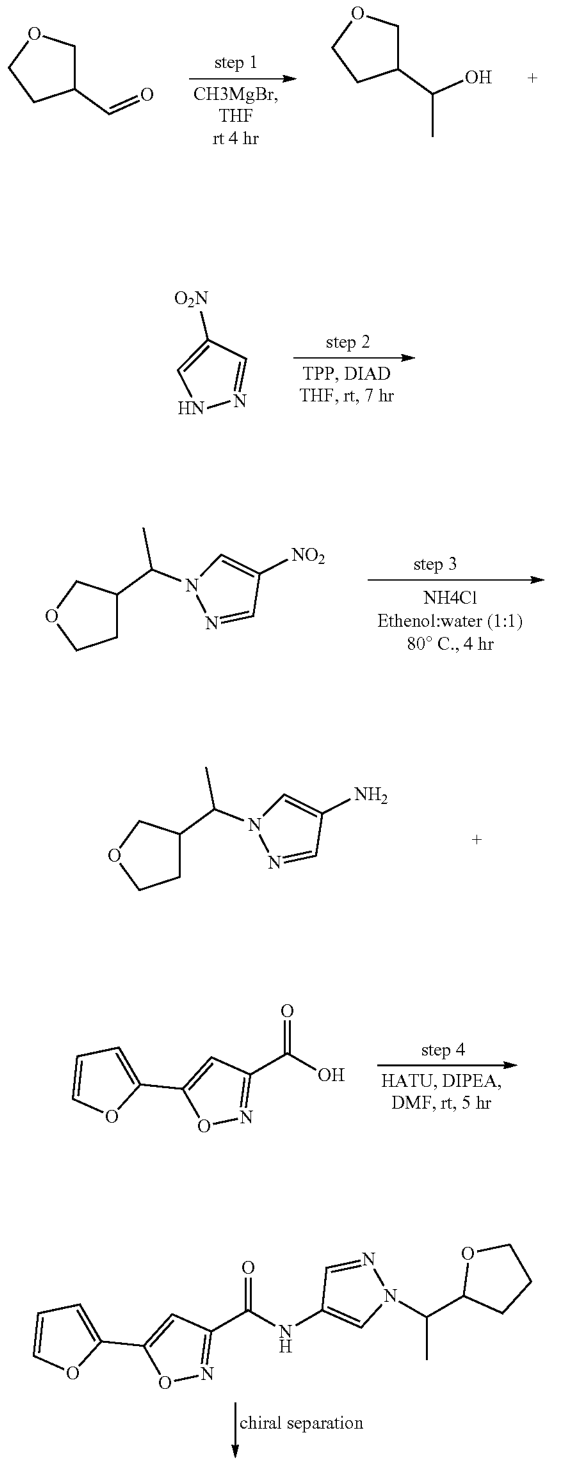

-continued

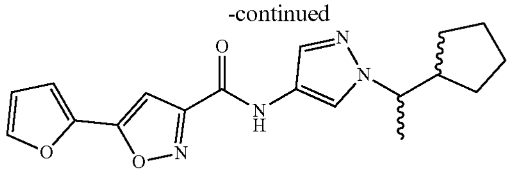

Compound 3-24

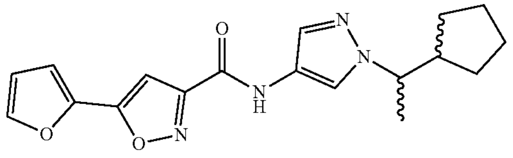

Compound 3-254

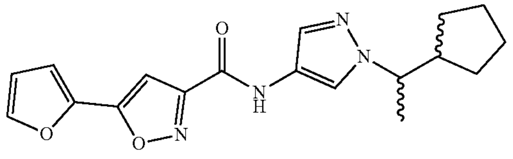

Compound 3-264

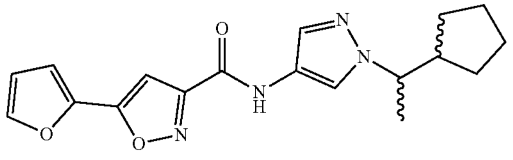

Compound 3-27

Step 1: Synthesis of 1-(tetrahydrofuran-3-yl) ethanol. To a stirred solution of tetrahydrofuran-3-carbaldehyde (2.0 g, 20.0 mmol, 1.0 eq) in THE (10 ml) at 0° C. was added Methyl magnesium bromide (10.0 ml, 30.0 mmol, 1.5 eq.)) drop wise, after all addition stir the reaction mixture at rt for 4 hr & Reaction progress was monitored by TLC and LCMS. After reaction completion the reaction mixture was extracted with ethyl acetate and water (2×20 ml). Organic layer was separated and evaporated under reduced pressure to give product which was to next step without purification 1-(tetrahydrofuran-3-yl)ethanol (1.00 g), LCMS: 117.08 (M+1).

Step 2: Synthesis of 4-nitro-1-(1-(tetrahydrofuran-3-yl) ethyl)-1H-pyrazole. To a stirred solution of 1-(tetrahydrofuran-3-yl)ethanol (900 mg, 7.758 mmol, 1.0 eq.) and 4-nitro-1H-pyrazole (876 mg, 7.758 mmol, 1.0 eq.) & TPP (2.032 g, 7.758 mmol, 1.0 eq.) in THE (10 mL), at 0° C. was added DIAD (2.350 ml, 11.637 mmol, 1.5 eq.) drop wise, after all addition reaction mixture were allowed to stir at RT for 6 hr. Reaction progress was monitored by TLC and LCMS. After reaction completion, the reaction mixture was extracted with ethyl acetate and water (2×10 mL). Organic layer was separated and evaporated under reduced pressure to give crude product which was further purified by combiflash chromatography to obtain 4-nitro-1-(1-(tetrahydrofuran-3-yl)ethyl)-1H-pyrazole (900 mg), LCMS: 212.0 [M+H]

Step 3: Synthesis of 1-(1-(tetrahydrofuran-3-yl)ethyl)-1H-pyrazol-4-amine. To a stirred solution 4-nitro-1-(1-(tetrahydrofuran-3-yl)ethyl)-1H-pyrazole (900 mg, 4.918 mmol, 1.0 eq) in EtOH/water (1:1, 10 ml), was added ammonium chloride (1.32 g, 24.59 mmol, 5.0 eq) & Fe (1.377 gm, 24.59 mmol, 5.0 eq) at rt and allowed to heat at 80° C. for 2 hr. Reaction progress was monitored by TLC and LCMS. After reaction completion, reaction mixture was filtered through celite pad and filtrate was evaporated and extracted with DCM/water 2 times. Organic layer was collected and evaporated under reduced pressure to give 1-(1-(tetrahydrofuran-3-yl)ethyl)-1H-pyrazol-4-amine (1.0 g), LCMS: 181.9 [M+H].

Step 4: Synthesis of 5-(furan-2-yl)-N-(1-(1-(tetrahydrofuran-3-yl)ethyl)-1H-pyrazol-4-yl)isoxazole-3-carboxamide. To a stirred solution 5-(furan-2-yl)isoxazole-3-carboxylic acid (1.087 gm, 6.0773 mmol, 1.0 eq) in DMF (5 mL) were added HATU (2.309 g, 6.0773 mmol, 1.0 eq). After stirring at RT for 15 minutes, the mixture was treated drop wise with DIPEA (3.169 ml, 18.232 mmol, 3.0 eq). After stirring at RT for 15 minutes, the mixture was treated drop wise with a solution of the 1-(1-(tetrahydrofuran-3-yl)ethyl)-1H-pyrazol-4-amine (1.1 g, 6.0773 mmol, 1.0 eq) in DMF (1 mL). The reaction mixture was stirred for 24 h. The reaction mixture was diluted with water (50 mL). The resulting precipitate was filtered off 5-(furan-2-yl)-N-(1-(1-(tetrahydrofuran-3-yl)ethyl)-1H-pyrazol-4-yl)isoxazole-3-carboxamide. (250 mg), LCMS: 343.3 [M+H], $^1$H NMR (400 MHz, DMSO-$d_6$) δ ppm 1.23-1.36 (s, 3H) 1.51 (m, 2H) 2.65-2.75 (m, 1H) 3.41-3.81 (4H), 4.3 (1H) 6.77 (dd, J=3.29, 1.97 Hz, 1H) 7.15 (s, 1H) 7.29 (d, J=3.51 Hz, 1H) 7.65 (d, J=3.95 Hz, 1H) 8.01 (s, 1H) 8.09 (d, J=13.59 Hz, 1H) 10.99 (s, 1H).

Step 5: Four isomers of 5-(furan-2-yl)-N-(1-(1-(tetrahydrofuran-3-yl)ethyl)-1H-pyrazol-4-yl)isoxazole-3-carboxamide were separated by chiral HPLC purification to obtain Compound 3-24, Compound 3-25, Compound 3-26, and Compound 3-27.

BIOLOGICAL EXAMPLES

Example B1. ERSE ATF6-Luciferase Assays

To understand how exemplary compounds of the invention modulate the activity of ATF6 in absence or presence of endoplasmic reticulum (ER) stress, a Human bone osteosarcoma (U2-OS)-based TRE-luciferase reporter stable cell line was generated to determine the modulation of transcription of ATF6 target genes.

U2-OS cells were obtained from the American Type Culture Collection (ATCC HTB-96, ATCC Manassas, VA) and were cultured with growing medium containing Dulbecco's Modified Eagle's Medium (DMEM) (Cat. No.: SH30023.02, HyClone) supplemented with fetal bovine serum (FBS) 10% (Cat. No.: 16000044, Gibco) and 1% penicillin-streptomycin antibiotic cocktail (Cat. No.: SV30010, Hyclone).

Cignal Lenti ATF6 luc reporter (Qiagen #CLS-6031L) was used to produce a stable cell line in U2-OS cells (U2-OS ATF6 TRE-luciferase reporter). The lenti ATF6 reporter is a preparation of replication incompetent, VSV-g pseudotyped lentivirus particles expressing the firefly luciferase gene under the control of a minimal (m)CMV promoter and tandem repeats of the ATF6 transcriptional response element (TRE). The number of response elements as well as the intervening sequence between response elements has been experimentally optimized to maximize the signal to noise ratio.

Exemplary compounds of the invention and reference compounds were prepared from powder as 10 mM stock solutions in dimethyl sulfoxide (DMSO; Cat. No. #D2650, Sigma Aldrich) and stored at −80° C. in presence of N2 neutral atmosphere.

For the primary screening, 40,000 U2-OS ATF6 TRE-luciferase reporter cells were plated in poly-D-lysine (Cat. No.: P2636, Sigma) pre-coated white 96-well plates (Thermo Scientific Nunc #136101) with 100 μL of growing medium. Cells were incubated in humidified chambers for 24 hr.

For testing exemplary compounds in presence of ER-stress, cells were pre-treated for 30 min with 50 μL growing medium containing either vehicle (DMSO), 1 or 10 μM test compound. After this pre-incubation, 50 μL of a solution containing 0.2 μM of the ER stress-inducer thapsigargin (Tg) was added to the appropriate wells. The Tg solution also contains vehicle or test compounds at 1 or 10 μM as indicated. The final concentration of DMSO in each well was kept at 0.3%. Plates were incubated for 8 hr in humidified chambers.

After the 8 hr incubation, plates were cooled down to room temperature for 10 min prior to the luciferase assays. Luciferase reactions were performed using Luciferase Assay System (Cat. No.: E4550, Promega). Briefly, each well was washed with 100 μl of PBS 1× and, then, 20 μl of lysis reagent was added into each well. Plates were shaken for 10 min and, then, 50 μl of Luciferase Assay Reagent was added to each well. Luminescence was determined by integration of 1 s with a gain of 110 in a Synergy 4 Microplate reader. All measurements were carried out in triplicate.

The average activity determined from the wells containing vehicle only (DMSO, 0% of ATF6 activity) was used as blank and subtracted from the rest of measurements. The average activity determined from the wells containing Tg only was used as 100% of ATF6 activity. The percentage of modulation of exemplary compounds was calculated by normalizing values to potential maximal activation with Tg. In this assay, exemplary compounds showing ATF6 activity higher than 100% (positive modulation) suggest an activator activity for those molecules, while compounds showing ATF6 activity less than 100% (negative modulation) suggest an inhibitory modulation.

ATF6 activities of exemplary compounds at 1 and 10 μM in presence Tg-induced ER stress tested in the U2-OS ATF6 TRE-luciferase reporter cells were determined and are shown in Table 2-2 and Table 3-2.

TABLE 2-2

ATF6 activity in presence of ER stress in ATF6-luc cell reporter.

| Compound No. | ATF6 activity @ 1 μM [%] | ATF6 activity @ 10 μM [%] |
|---|---|---|
| Ceapin-A7 | −−− | −−− |
| Ceapin-A4 | + | ++ |
| Ceapin-A8 | + | − |
| 2-1 | −− | −−− |
| 2-2 | −−− | −−− |
| 2-4 | −− | − |
| 2-5 | + | −−− |
| 2-6 | + | −− |
| 2-7 | + | − |
| 2-8 | + | −− |
| 2-9 | − | −−− |
| 2-10 | −− | − |
| 2-11 | −− | −− |
| 2-20 | − | + |
| 2-21 | − | − |
| 2-22 | −− | − |
| 2-23 | − | −− |
| 2-24 | −−− | −−− |

TABLE 2-3

| ATF6 activity in presence of ER stress in ATF6-luc cell reporter. | | |
|---|---|---|
| Compound No. | ATF6 activity @ 1 μM [%] | ATF6 activity @ 10 μM [%] |
| Ceapin-A7 | ––– | ––– |
| Ceapin-A4 | + | ++ |
| Ceapin-A8 | + | – |
| 3-1 | +++ | +++ |
| 3-2 | +++ | +++ |
| 3-3 | ++ | NT |
| 3-4 | ++ | +++ |
| 3-5 | ++ | +++ |
| 3-6 | + | ++ |
| 3-17 | ++ | ++ |
| 3-18 | + | ++ |
| 3-19 | +++ | +++ |
| 3-20 | + | +++ |
| 3-21 | +++ | +++ |
| 3-22 | ++ | +++ |
| 3-23 | +++ | +++ |
| 3-24 | + | +++ |
| 3-25 | + | +++ |
| 3-26 | +++ | +++ |
| 3-27 | + | +++ |

Ceapin-A4, Ceapin-A7, and Ceapin-A8 refer to compounds described in Gallagher et al. eLife 2016;5:e11878; for % ATF6 activity:
––– refers to <50% at 1 or 10 μM test compound;
–– refers to 50% < % activity < 75% at 1 or 10 μM test compound;
– refers to 75% < % activity < 100% at 1 or 10 μM; + refers to 100% < % activity < 125% at 1 or 10 μM;
++ refers to 125% < % activity < 150% at 1 or 10 μM test compound;
+++ refers to >150% at 1 or 10 μM test compound;
NT: not tested.

For testing exemplary compounds in absence of ER-stress, cells were treated for 8 hr with 100 μL growing medium containing either vehicle (DMSO), 1 or 10 μM test compound or 0.1 μM Tg. The final concentration of DMSO in each well was kept at 0.3%. Plates were incubated in humidified chambers.

After 8 hr of incubation, plates were cooled down to room temperature for 10 min prior to luciferase assays. Luciferase reactions were performed as above. Luminescence was read by integration of 1 s with a gain of 110 in a Synergy 4 Microplate reader. All measurements were carried out in triplicate.

The average activity determined from the wells containing vehicle only (DMSO, 0% of ATF6 activity) was used as blank and subtracted from the rest of measurements. The percentage of modulation of exemplary compound was calculated by normalizing values to potential maximal activation with Tg.

ATF6 activities of exemplary compounds at 1 and 10 μM in absence of Tg-induced ER stress in the U2-OS ATF6 TRE-luciferase reporter cells were determined and are shown in Table 3-2, and Table 3-3.

TABLE 3-2

| ATF6 activity in absence of ER stress in ATF6-luc cell reporter | | |
|---|---|---|
| Compound No. | ATF6 activity @ 1 μM [%] | ATF6 activity @ 10 μM [%] |
| Ceapin-A7 | ––– | ––– |
| Ceapin-A4 | + | ++ |
| Ceapin-A8 | + | - |
| 2-20 | + | + |

TABLE 3-3

| ATF6 activity in absence of ER stress in ATF6-luc cell reporter. | | |
|---|---|---|
| Compound No. | ATF6 activity @ 1 μM-No Tg [%] | ATF6 activity @ 10 μM - No Tg [%] |
| 3-1 | + | + |
| 3-2 | + | + |
| 3-3 | + | NT |
| 3-4 | + | + |
| 3-5 | + | + |
| 3-6 | + | + |
| 3-17 | + | + |
| 3-18 | + | + |
| 3-19 | + | ++ |
| 3-20 | + | + |
| 3-21 | + | ++ |
| 3-22 | + | ++ |
| 3-23 | ++ | +++ |
| 3-24 | + | ++ |
| 3-25 | + | + |
| 3-26 | + | +++ |
| 3-27 | + | ++ |

For % ATF6 activity:
+ refers to 0% < % activity < 25% at 1 or 10 μM test compound;
++ refers to 25% < % activity < 50% at 1 or 10 μM test compound;
+++ refers to % activity >50 % at 1 or 10 μM test compound;
NT: not tested.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of formula (I-1):

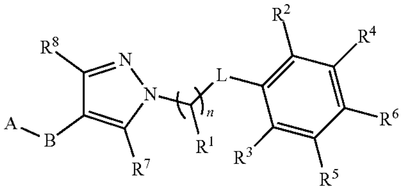

(I-1)

or a pharmaceutically acceptable salt thereof, wherein:

$R^1$ is H, $C_1$-$C_6$alkyl, $C_3$-$C_8$cycloalkyl, or $C_1$-$C_6$ haloalkyl;

n is 0 or 1;

L is —$CH_2$— or is absent;

B is —$CH_2CH_2$—, —CH═CH—, or —C≡C—;

$R^2$, $R^3$, $R^4$, $R^5$, and $R^6$ are each independently H, halo, CN, —OH, —$NH_2$, $C_{1-6}$alkoxy, $C_1$-$C_6$alkyl, or $C_1$-$C_6$haloalkyl;

or $R^2$, $R^4$, $R^5$, and $R^6$ are each independently H, halo, CN, —OH, —$NH_2$, $C_{1-6}$alkoxy, $C_1$-$C_6$alkyl, or $C_1$-$C_6$haloalkyl and $R^3$ is taken together with $R^1$ and the atoms to which they are attached to form a 5- or 6-membered carbocyclic ring, wherein the 5- or 6-membered carbocyclic ring is unsubstituted or substituted with one to three groups selected from the group consisting of halo, CN, —OH, $C_1$-$C_6$alkyl, and $C_1$-$C_6$haloalkyl;

A is

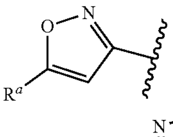

,

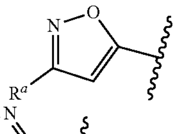

, or

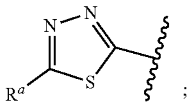

;

$R^a$ is 5- or 6-membered heteroaryl, wherein the 5- or 6-membered heteroaryl is unsubstituted or substituted with one to four groups selected from the group consisting of OH, halo, $C_1$-$C_6$alkyl and $C_1$-$C_6$alkoxy, $R^7$ is H, $C_1$-$C_6$alkyl or $C_1$-$C_6$haloalkyl; and $R^8$ is H or $C_1$-$C_6$alkyl.

2. The compound of claim 1, or a pharmaceutically acceptable salt thereof, wherein the 5- or 6-membered heteroaryl of $R^a$ is selected from the group consisting of 2-furyl, 2-pyridinyl, 2-pyrimidinyl, 4-pyrimidinyl, and 2-pyrazinyl.

3. The compound of claim 1, or a pharmaceutically acceptable salt thereof, wherein n is 1, $R^1$ is H and L is absent.

4. The compound of claim 1, or a pharmaceutically acceptable salt thereof, wherein $R^7$ and $R^8$ are H.

5. The compound of claim 1, or a pharmaceutically acceptable salt thereof, wherein B is —CH═CH—, or —C≡C—.

6. A compound selected from the group consisting of:

2-1

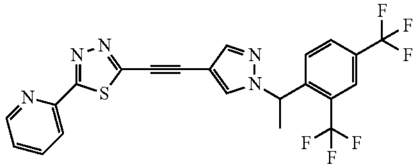 [SMILES: CC(c1ccc(C(F)(F)F)cc1C(F)(F)F)n1cc(C#Cc2nnc(-c3ccccn3)s2)cn1]

2-2

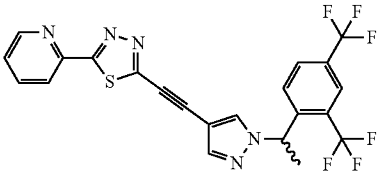 [SMILES: CC(c1ccc(C(F)(F)F)cc1C(F)(F)F)n1cc(C#Cc2nnc(-c3ccccn3)s2)cn1]

Isomer A of Compound 1

2-3

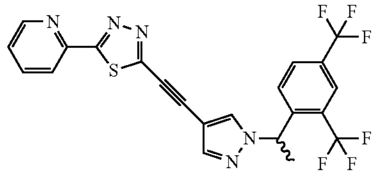 [SMILES: CC(c1ccc(C(F)(F)F)cc1C(F)(F)F)n1cc(C#Cc2nnc(-c3ccccn3)s2)cn1]

2-4

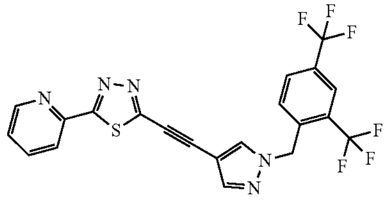 [SMILES: FC(F)(F)c1ccc(Cn2cc(C#Cc3nnc(-c4ccccn4)s3)cn2)c(C(F)(F)F)c1]

2-5

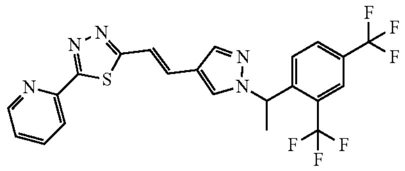 [SMILES: CC(c1ccc(C(F)(F)F)cc1C(F)(F)F)n1cc(/C=C/c2nnc(-c3ccccn3)s2)cn1]

2-6

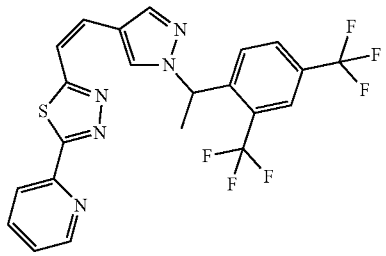 [SMILES: CC(c1ccc(C(F)(F)F)cc1C(F)(F)F)n1cc(/C=C\c2nnc(-c3ccccn3)s2)cn1]

2-7

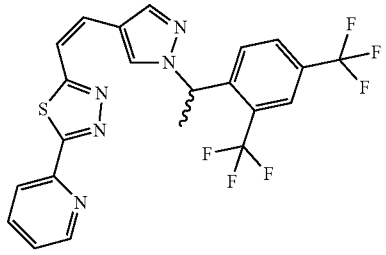 [SMILES: CC(c1ccc(C(F)(F)F)cc1C(F)(F)F)n1cc(/C=C\c2nnc(-c3ccccn3)s2)cn1]

Isomer A of Compound 6

-continued
2-8
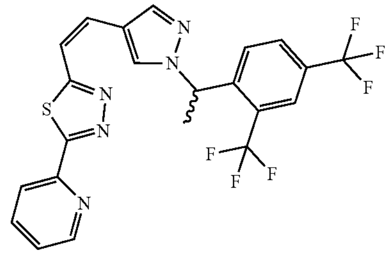 [SMILES: CC(c1ccc(C(F)(F)F)cc1C(F)(F)F)n1cc(/C=C\c2nnc(-c3ccccn3)s2)cn1]
Isomer B of Compound 6
2-9
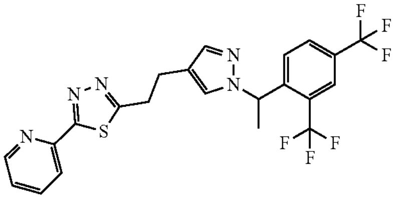 [SMILES: CC(c1ccc(C(F)(F)F)cc1C(F)(F)F)n1cc(CCc2nnc(-c3ccccn3)s2)cn1]
2-10
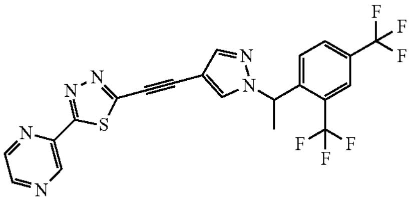 [SMILES: CC(c1ccc(C(F)(F)F)cc1C(F)(F)F)n1cc(C#Cc2nnc(-c3cnccn3)s2)cn1]
2-11
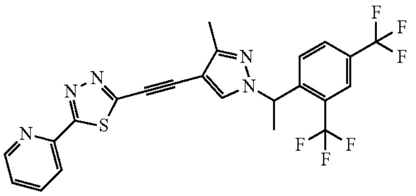 [SMILES: Cc1nn(C(C)c2ccc(C(F)(F)F)cc2C(F)(F)F)cc1C#Cc1nnc(-c2ccccn2)s1]
2-12
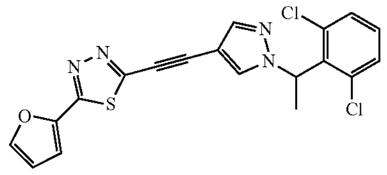 [SMILES: CC(c1c(Cl)cccc1Cl)n1cc(C#Cc2nnc(-c3ccco3)s2)cn1]
2-13
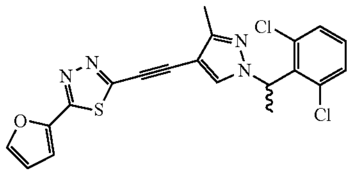 [SMILES: Cc1nn(C(C)c2c(Cl)cccc2Cl)cc1C#Cc1nnc(-c2ccco2)s1]
2-14
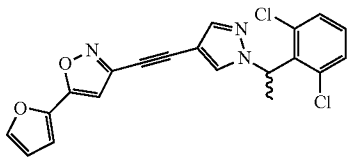 [SMILES: CC(c1c(Cl)cccc1Cl)n1cc(C#Cc2cc(-c3ccco3)on2)cn1]
2-15
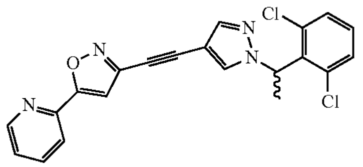 [SMILES: CC(c1c(Cl)cccc1Cl)n1cc(C#Cc2cc(-c3ccccn3)on2)cn1]
-continued
2-16
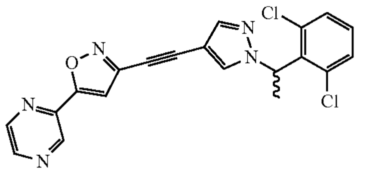 [SMILES: CC(c1c(Cl)cccc1Cl)n1cc(C#Cc2cc(-c3cnccn3)on2)cn1]
2-17
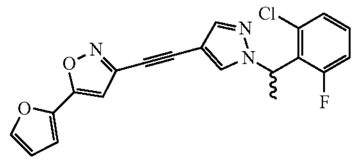 [SMILES: CC(c1c(F)cccc1Cl)n1cc(C#Cc2cc(-c3ccco3)on2)cn1]
2-18
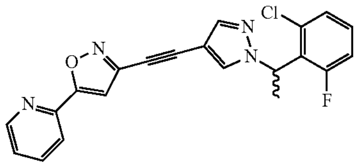 [SMILES: CC(c1c(F)cccc1Cl)n1cc(C#Cc2cc(-c3ccccn3)on2)cn1]
2-19
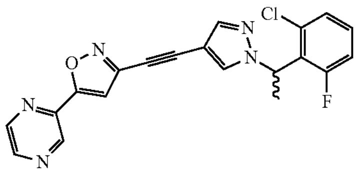 [SMILES: CC(c1c(F)cccc1Cl)n1cc(C#Cc2cc(-c3cnccn3)on2)cn1]
2-20
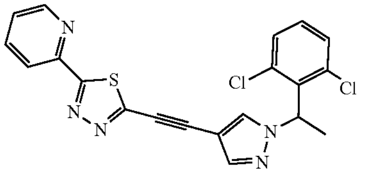 [SMILES: CC(c1c(Cl)cccc1Cl)n1cc(C#Cc2nnc(-c3ccccn3)s2)cn1]
2-21
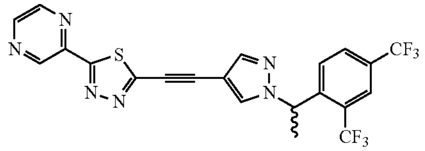 [SMILES: CC(c1ccc(C(F)(F)F)cc1C(F)(F)F)n1cc(C#Cc2nnc(-c3cnccn3)s2)cn1]
Isomer A of compound 2-10
2-22
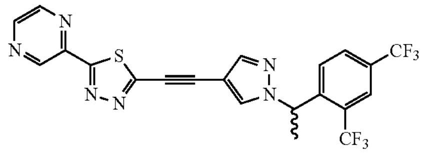 [SMILES: CC(c1ccc(C(F)(F)F)cc1C(F)(F)F)n1cc(C#Cc2nnc(-c3cnccn3)s2)cn1]
Isomer B of compound 2-10
2-23
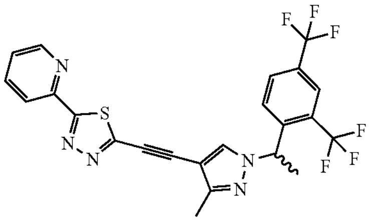 [SMILES: Cc1nn(C(C)c2ccc(C(F)(F)F)cc2C(F)(F)F)cc1C#Cc1nnc(-c2ccccn2)s1]
Isomer A of compound 2-11

-continued
2-24
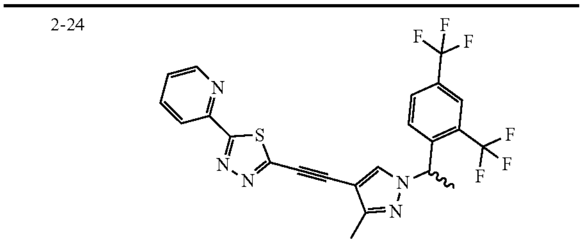
Isomer B of compound 2-11
or a pharmaceutically acceptable salt thereof.
* * * * *

SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
ccaatcggcg gcggccacg 19